US008604172B2

(12) United States Patent
Sabbadini et al.

(10) Patent No.: US 8,604,172 B2
(45) Date of Patent: Dec. 10, 2013

(54) HUMANIZED ANTIBODY COMPOSITIONS AND METHODS FOR BINDING LYSOPHOSPHATIDIC ACID

(75) Inventors: Roger A. Sabbadini, Lakeside, CA (US); William A. Garland, San Clemente, CA (US); Genevieve Hansen, San Diego, CA (US); Steven Tarran Jones, Radlett (GB); David Gareth Williams, Epsom (GB)

(73) Assignee: Lpath, Inc., San Diego, CA (US)

(*) Notice: Subject to any disclaimer, the term of this patent is extended or adjusted under 35 U.S.C. 154(b) by 450 days.

(21) Appl. No.: 12/761,584

(22) Filed: Apr. 16, 2010

(65) Prior Publication Data

US 2011/0076267 A1 Mar. 31, 2011

Related U.S. Application Data

(60) Provisional application No. 61/170,595, filed on Apr. 17, 2009.

(51) Int. Cl.
*C12P 21/08* (2006.01)

(52) U.S. Cl.
USPC .......................................................... 530/387.3

(58) Field of Classification Search
None
See application file for complete search history.

(56) References Cited

U.S. PATENT DOCUMENTS

| | | | |
|---|---|---|---|
| 4,816,397 | A | 3/1989 | Boss et al. |
| 4,816,567 | A | 3/1989 | Cabilly et al. |
| 5,225,539 | A | 7/1993 | Winter |
| 5,229,275 | A | 7/1993 | Goroff |
| 5,530,101 | A | 6/1996 | Queen et al. |
| 5,567,610 | A | 10/1996 | Borrebaeck et al. |
| 5,573,905 | A | 11/1996 | Lerner et al. |
| 5,585,089 | A | 12/1996 | Queen et al. |
| 5,624,821 | A | 4/1997 | Winter et al. |
| 5,693,761 | A | 12/1997 | Queen et al. |
| 5,693,762 | A | 12/1997 | Queen et al. |
| 5,714,350 | A | 2/1998 | Co et al. |
| 5,777,085 | A | 7/1998 | Co et al. |
| 5,834,597 | A | 11/1998 | Tso et al. |
| 5,861,155 | A | 1/1999 | Lin |
| 5,882,644 | A | 3/1999 | Chang et al. |
| 5,932,448 | A | 8/1999 | Tso et al. |
| 6,013,256 | A | 1/2000 | Light et al. |
| 6,129,914 | A | 10/2000 | Weiner et al. |
| 6,180,370 | B1 | 1/2001 | Queen et al. |
| 6,210,671 | B1 | 4/2001 | Co |
| 6,329,511 | B1 | 12/2001 | Vasquez et al. |
| 6,350,861 | B1 | 2/2002 | Co et al. |
| 6,407,213 | B1 | 6/2002 | Carter et al. |
| 6,479,284 | B1 | 11/2002 | Marasco et al. |
| 6,500,931 | B1 | 12/2002 | Tempest et al. |
| 6,548,640 | B1 | 4/2003 | Winter |
| 6,639,055 | B1 | 10/2003 | Carter et al. |
| 2002/0078757 | A1 | 6/2002 | Hines et al. |
| 2003/0000313 | A1 | 1/2003 | Bernhardi et al. |
| 2003/0166871 | A1 | 9/2003 | Barbas, III et al. |
| 2003/0229208 | A1 | 12/2003 | Queen et al. |
| 2007/0148168 | A1 | 6/2007 | Sabbadini et al. |
| 2007/0281320 | A1 | 12/2007 | Sabbadini et al. |
| 2008/0145360 | A1 | 6/2008 | Sabbadini et al. |
| 2009/0136483 | A1 | 5/2009 | Sabbadini et al. |

FOREIGN PATENT DOCUMENTS

| | | | |
|---|---|---|---|
| EP | 0125023 | B1 | 6/1991 |
| EP | 0519596 | A1 | 12/1992 |
| EP | 0120694 | B1 | 7/1993 |
| EP | 0194276 | B1 | 8/1993 |
| EP | 0239400 | B1 | 8/1994 |
| WO | 86/01533 | A1 | 3/1986 |
| WO | 96/27011 | A1 | 9/1996 |
| WO | 96/32478 | A1 | 10/1996 |
| WO | 2006/105062 | A2 | 10/2006 |
| WO | 2007/140434 | A2 | 12/2007 |
| WO | 2008/150841 | A1 | 12/2008 |

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
Winkler et al (J. Imm., 265:4505-4514, 2000).*
Berge et al., J. Pharm. Sci., 1977, 1-19, 66(1).
Carter et al., Biotechnology (NY), 1992, 163-167, 10(2).
Champe et al., J. Biol. Chem., 1995, 1388-1394, 270(3).
Chen et al., Bioorg. Med. Chem. Lett., 2000, 1691-1693, 10(15).
Chen et al., FEBS Lett., 2006, 4737-4745, 580(19).
Chothia et al., J. Mol. Biol., 1985, 651-663, 186(3).
Chothia et al., J. Mol. Biol., 1987, 901-917, 196(4).
Chun et al., Curr. Pharm. Des., 2006, 161-171, 12(2).
Foote et al., J. Mol. Biol., 1992, 487-499, 224(2).
Gardell et al., Trends Mol. Med., 2006, 65-75, 12(2).
Jones et al., Nature, 1986, 522-525, 321(6069).
Kabat et al., Sequences of Proteins of Immunological Interest, 5th Ed., 1992, 647-669, NIH Pub. Iss.: 91/3242 , U.S. Department of Health and Human Services, Public Health Service, National Institutes of Health, Bethesda, MD, USA.
Kohler et al., Nature, 1975, 495-497, 256(5517).
Lefranc, Nucleic Acids Res., 2003, 307-310, 31(1).
Martin et al., J. Mol. Biol., 1996, 800-815, 263(5).
Morea et al., Methods, 2000, 267-279, 20(3).
Morrison et al., Proc. Natl. Acad. Sci. USA, 1984, 6851-6855, 81(21).
Presta, Curr. Opin. Struct. Biol., 1992, 593-596, 2(4).
Pyne et al., Biochem. J., 2000, 385-402, 349(Pt. 2).
Queen et al., Proc. Natl. Acad. Sci. USA, 1989, 10029-10033, 86(24).
Riechmann et al., Nature, 1988, 323-327, 332(6162).

* cited by examiner

*Primary Examiner* — Brad Duffy
(74) *Attorney, Agent, or Firm* — Acuity Law Group, P.C.; Daniel M. Chambers

(57) ABSTRACT

Compositions and methods for making and using humanized anti-LPA monoclonal antibodies, and fragments and derivatives thereof, are described.

5 Claims, 7 Drawing Sheets

Synthesis of Typical Thiolated S1P-Related Antigen

6

7

8

9

10

Synthesis of Typical Thiolated S1P-Related Antigen (Continued)

6

11

12

13

Synthesis of Typical Thiolated S1P–Related Antigen (Continued)

14

15

Synthesis of Typical Protected Thiolated Fatty Acid

Synthesis of Typical Thiolated Fatty Acid

Synthesis of Typical Thiolated LPA Hapten

Synthesis of Typical Thiolated LPA Hapten (Continued)

HUMANIZED ANTIBODY COMPOSITIONS AND METHODS FOR BINDING LYSOPHOSPHATIDIC ACID

RELATED APPLICATION

This application claims the benefit of and priority to commonly owned U.S. provisional patent application Ser. No. 61/170,595, filed 17 Apr. 2009, which is herein incorporated by reference in its entirety for any and all purposes.

TECHNICAL FIELD

The present invention relates to agents that bind lysophosphatidic acid (LPA) and its variants, particularly to monoclonal antibodies, antibody fragments, and antibody derivatives specifically reactive to LPA under physiological conditions. Such agents can be used in the treatment and/or prevention of various diseases or disorders through the delivery of pharmaceutical compositions that contain such agents.

LPA is a bioactive lipid mediating multiple cellular responses including proliferation, differentiation, angiogenesis, motility, and protection from apoptosis in a variety of cell types.

LPA is involved in the establishment and progression of cancer by providing a pro-growth tumor microenvironment and promoting angiogenesis. In addition, LPA has been implicated in fibrosis, ocular diseases such as macular degeneration, and pain-related disorders. Therefore, an antibody-based approach to the neutralization of LPA offers the potential to increase the arsenal of current therapies for these indications.

Applicants have invented a family of high-affinity, specific monoclonal antibodies to LPA, one of which is known as Lpathomab or LT3000. The efficacy of Lpathomab in various animal models of cancer, fibrosis, and ocular disorders highlights the utility of this class of anti-LPA antibodies (and molecules derived therefrom), for example, in the treatment of malignancies, angiogenesis, and fibrosis-related disorders.

SEQUENCE LISTING

The instant application contains a Sequence Listing submitted via the Electronic Filing System on Dec. 1, 2010 and, is hereby incorporated by reference in its entirety. Said ASCII copy, created on May 7, 2010, is named LPT3210UT.txt, and is 98,293 bytes in size.

BACKGROUND OF THE INVENTION

1. Introduction

The following description includes information that may be useful in understanding the present invention. It is not an admission that any of the information provided herein, or any publication specifically or implicitly referenced herein, is prior art, or even particularly relevant, to the presently claimed invention.

2. Background

A. Bioactive Signaling Lipids

Lipids and their derivatives are now recognized as important targets for medical research, not as just simple structural elements in cell membranes or as a source of energy for β-oxidation, glycolysis or other metabolic processes. In particular, certain bioactive lipids function as signaling mediators important in animal and human disease. Although most of the lipids of the plasma membrane play an exclusively structural role, a small proportion of them are involved in relaying extracellular stimuli into cells. These lipids are referred to as "bioactive lipids" or, alternatively, "bioactive signaling lipids." "Lipid signaling" refers to any of a number of cellular signal transduction pathways that use cell membrane lipids as second messengers, as well as referring to direct interaction of a lipid signaling molecule with its own specific receptor. Lipid signaling pathways are activated by a variety of extracellular stimuli, ranging from growth factors to inflammatory cytokines, and regulate cell fate decisions such as apoptosis, differentiation and proliferation. Research into bioactive lipid signaling is an area of intense scientific investigation as more and more bioactive lipids are identified and their actions characterized.

Examples of bioactive lipids include the eicosanoids (including the cannabinoids, leukotrienes, prostaglandins, lipoxins, epoxyeicosatrienoic acids, and isoeicosanoids), non-eicosanoid cannabinoid mediators, phospholipids and their derivatives such as phosphatidic acid (PA) and phosphatidylglycerol (PG), platelet activating factor (PAF) and cardiolipins as well as lysophospholipids such as lysophosphatidyl choline (LPC) and various lysophosphatidic acids (LPA). Bioactive signaling lipids also include the sphingolipids such as sphingomyelin, ceramide, ceramide-1-phosphate, sphingosine, sphingosylphosphoryl choline, sphinganine, sphinganine-1-phosphate (dihydro-S1P) and sphingosine-1-phosphate. Sphingolipids and their derivatives represent a group of extracellular and intracellular signaling molecules with pleiotropic effects on important cellular processes. Other examples of bioactive signaling lipids include phosphatidylinositol (PI), phosphatidylethanolamine (PEA), diacylglyceride (DG), sulfatides, gangliosides, and cerebrosides.

1. Lysolipids

Lysophospholipids (LPLs), also known as lysolipids, are low molecular weight (typically less than about 500 dalton) lipids that contain a single hydrocarbon backbone and a polar head group containing a phosphate group. Some lysolipids are bioactive signaling lipids. Two particular examples of medically important bioactive lysolipids are LPA (glycerol backbone) and S1P (sphingoid backbone). The structures of selected LPAs, S1P, and dihydro S1P are presented below.

LPA (20:4)

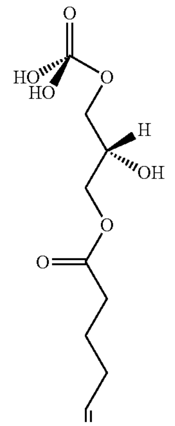

-continued
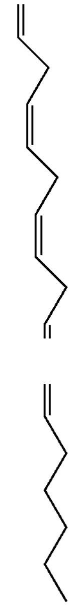
LPA (16:0)
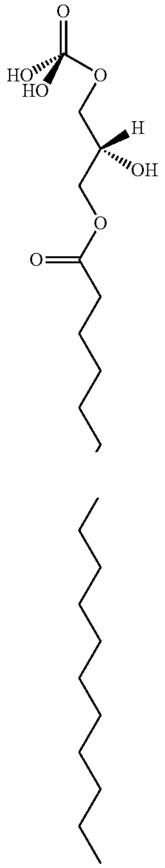
-continued
LPA (18:2)
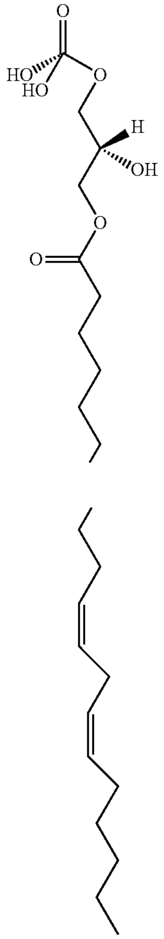
LPA (18:1)
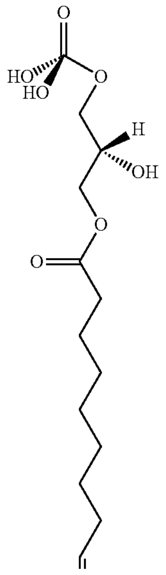

-continued
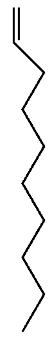
LPA (18:0)
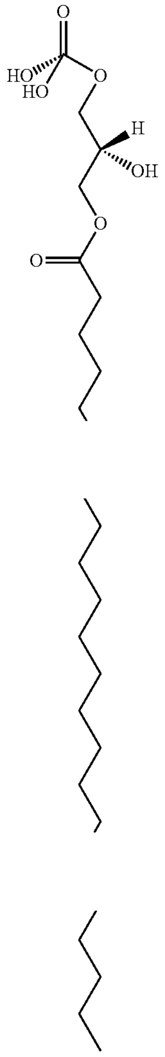
-continued
S1P
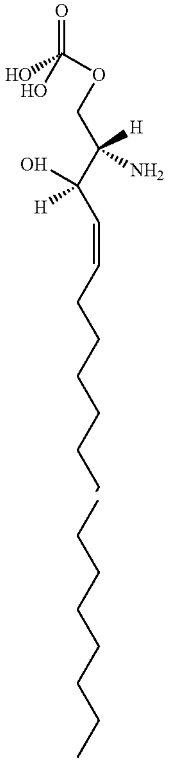
Dihydro-S1P
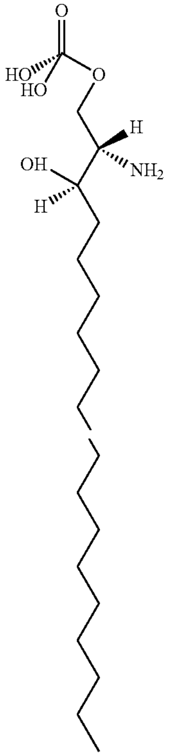
The structural backbone of LPA is derived from glycerol-based phospholipids such as phosphatidylcholine (PC) or phosphatidic acid (PA). In the case of lysosphingolipids such as S1P, the fatty acid of the ceramide backbone is missing. The structural backbone of S1P, dihydro S1P (DHS1P), and sphingosylphosphorylcholine (SPC) is based on sphingosine, which is derived from sphingomyelin.

LPA and S1P regulate various cellular signaling pathways by binding to the same class of multiple transmembrane domain G protein-coupled (GPCR) receptors. The S1P receptors are designated as S1P1, S1P2, S1P3, S1P4 and S1P5 (formerly EDG-1, EDG-5/AGR16, EDG-3, EDG-6 and EDG-8) and the LPA receptors designated as LPA1, LPA2, LPA3 (formerly, EDG-2, EDG-4, and EDG-7). A fourth LPA receptor of this family has been identified for LPA (LPA4), and other putative receptors for these lysophospholipids have also been reported.

LPA and S1P have been shown to play a role in the immune response through modulation of immune-related cells such as T- and B-lymphocytes. These lipids promote T-cell migration to sites of immune response and regulate proliferation of T cells as well as secretion of various cytokines. In particular, S1P is thought to control egress of lymphocytes into the peripheral circulation. Thus agents which bind LPA and S1P are believed to be useful in methods for decreasing an undesired, excessive or aberrant immune response, and for treating diseases and conditions, including certain hematological cancers and autoimmune disorders, that are associated with an undesired, excessive or aberrant involvement of lymphocytes and or an aberrant immune response.

a. Lysophosphatic Acid (LPA)

Lysophosphatidic acid (mono-acylglycerol-3-phosphate, <500 Dalton) consists of a single hydrocarbon backbone and a polar head group containing a phosphate group. LPA is not a single molecular entity but a collection of endogenous structural variants with fatty acids of varied lengths and degrees of saturation. Biologically relevant variants of LPA include 18:2, 18:1, 18:0, 16:0 and 20:4. LPA species with both saturated fatty acids (16:0 and 18:0) and unsaturated fatty acids (16:1, 18:1, 18:2, and 20:4) have been detected in serum and plasma. The 16:0, 18:1, 18:2 and 20:4 LPA isoforms are the predominant species in blood. Significant levels (>1 μM) of bioactive LPA are detectable in various body fluids, including serum, saliva, follicular fluid and malignant effusions.

The present invention provides among its aspects anti-LPA agents that are useful for treating or preventing hyperproliferative disorders and various other disorders, as described in greater detail below. In particular, certain embodiments of the invention is drawn to antibodies targeted to LPA including but not limited to 18:2, 18:1, 18:0, 16:0, and 20:4 variants of LPA.

LPAs have long been known as precursors of phospholipid biosynthesis in both eukaryotic and prokaryotic cells, but LPAs have emerged only recently as signaling molecules that are rapidly produced and released by activated cells, notably platelets, to influence target cells by acting on specific cell-surface receptor. Besides being synthesized and processed to more complex phospholipids in the endoplasmic reticulum, LPA can be generated through the hydrolysis of pre-existing phospholipids following cell activation; for example, the sn-2 position is commonly missing a fatty acid residue due to de-acylation, leaving only the sn-3 hydroxyl esterified to a fatty acid. Moreover, a key enzyme in the production of LPA, autotaxin (lysoPLD/NPP2), may be the product of an oncogene, as many tumor types up-regulate autotoxin. The concentrations of LPA in human plasma and serum have been reported, including determinations made using sensitive and specific LC/MS procedures. For example, in freshly prepared human serum allowed to sit at 25° C. for one hour, LPA concentrations have been estimated to be approximately 1.2 mM, with the LPA analogs 16:0, 18:1, 18:2, and 20:4 being the predominant species. Similarly, in freshly prepared human plasma allowed to sit at 25° C. for one hour, LPA concentrations have been estimated to be approximately 0.7 mM, with 18:1 and 18:2 LPA being the predominant species.

LPA mediates its biological functions predominantly by binding to a class of multiple transmembrane G protein-coupled receptors (GPCR). Five LPA-specific GPCRs, termed LPA1-5, have been identified to date; they show both overlapping and distinct signaling properties and tissue expression. The LPA1-3 receptors belong to the so-called EDG subfamily (EGD2/LPA1, EDG4/LPA2, and EDG7/LPA3) of GPCRs with 50% sequence similarity to each other. Their closest relative is the cannabinoid CB1 receptor, which binds the bioactive lipids 2-arachidonoyl-glycerol (2-AG) and arachidonoyl-ethanolamine. Two newly identified LPA receptors, termed LPA4 (formerly GPR23/p2y9) and LPA5 (formerly GPR92) are more closely related to the P2Y nucleotide receptors. In addition, LPA recognizes the intracellular receptor, PPRgamma.

LPA1 is expressed in a wide range of tissues and organs whereas LPA2 and LPA3 show more restricted expression profile. However, LPA2 and LPA3 expressions were shown to be increased in ovarian and colon cancers and inflammation, suggesting that the main role of LPA2 and LPA3 is in pathophysiological conditions.

The role of these receptors has been in part elucidated by receptor knockout studies in mice. LPA1-deficient mice show partial postnatal lethality due to a suckling defect resulting from impaired olfaction. LPA1-deficient mice are also protected from lung fibrosis in response to bleomycin-induced lung injury. Furthermore, mice lacking the LPA1 receptor gene lose the nerve injury-induced neuropathic pain behaviors and phenomena.

In contrast, mice lacking LPA2 receptors appear to be normal. LPA3 receptor knockout mice have reduced litter size due to delayed blastocyst implantation and altered embryo spacing, and LPA3-deficient uteri show reduced cyclooxygenase-2 (COX-2) expression and prostaglandin synthesis; while exogenous administration of PGE2 into LPA3-deficient female mice has been reported to rescue the implantation defect.

LPAs influence a wide range of biological responses, including induction of cell proliferation, stimulation of cell migration and neurite retraction, gap junction closure, and even slime mold chemotaxis. The body of knowledge about the biology of LPA continues to grow as more and more cellular systems are tested for LPA responsiveness. The major physiological and pathophysiological effects of LPA include, for example:

Wound healing: It is now known that, in addition to stimulating cell growth and proliferation, LPA promote cellular tension and cell-surface fibronectin binding, which are important events in wound repair and regeneration.

Apoptosis: Recently, anti-apoptotic activity has also been ascribed to LPA, and it has recently been reported that peroxisome proliferation receptor gamma is a receptor/target for LPA.

Blood vessel maturation: Autotaxin, a secreted lysophospholipase D responsible for producing LPAs, is essential for blood vessel formation during development. In addition, unsaturated LPAs were identified as major contributors to the induction of vascular smooth muscle cell dedifferentiation.

Edema and vascular permeability: LPA induces plasma exudation and histamine release in mice.

Pain: Initiation of neuropathic pain has been found to require lysophosphatidic acid receptor signaling. Nature Med. (2004) 10:712-718. As described above, mice lacking LPA1 receptors show decreases in neuropathic pain behaviors.

Inflammation: LPA acts as inflammatory mediator in human corneal epithelial cells. LPA participates in corneal wound healing and stimulates the release of ROS in lens. LPA can also re-activate HSV-1 in rabbit cornea.

The bite of the venomous spider, *Loxosceles reclusa* (brown recluse spider), causes necrotic ulcers that can cause serious and long lasting tissue damage, and occasionally death. The pathology of wounds generated from the bite of this spider consists of an intense inflammatory response mediated by AA and prostaglandins. The major component of the *L. reclusa* spider venom is the phospholipase D enzyme often referred to as sphingomyelinase D (SMase D), which hydrolyzes sphingomyelin to produce C1P. It has been found, however, that lysophospholipids with a variety of headgroups are hydrolysed by the *L. reclusa* enzyme to release LPA. It is believed that anti-LPA agents such as those of the invention will be useful in reducing or treating inflammation of various types, including but not limited to inflammation resulting from *L. reclusa* envenomation.

Fibrosis and scar formation: LPA inhibits TGF-mediated stimulation of type 1 collagen mRNA stability via an ERK-dependent pathway in dermal fibroblasts. Moreover, LPA have some direct fibrogenic effects by stimulating collagen gene expression and proliferation of fibroblasts.

Immune response: LPA, like S1P, has been shown to play a role in the immune response through modulation of immune-related cells. These lipids promote T-cell migration to sites of immune response and regulate proliferation of T cells as well as secretion of various cytokines.

Thus agents that reduce the effective concentration of LPA, such as Lpath's anti-LPA mAb, are believed to be useful in methods for treating diseases and conditions such as those associated with wound healing and fibrosis, apoptosis, angiogenesis and neovascularizaion, vascular permeability and inflammation, that are associated with an undesired, excessive or aberrant level of LPA.

Recently, the applicants have developed several monoclonal antibodies against LPAs. These anti-LPA antibodies can neutralize various LPAs and mitigate their biologic and pharmacologic action. Anti-LPA antibodies are, therefore, believed to be useful in prevention and/or treatment of various diseases and conditions associated with excessive, unwanted or aberrant levels of LPA.

Rapid and specific methods of detecting LPA are also desired. Methods for separating and semi-quantitatively measuring phospholipids such as LPA using techniques such as thin-layer chromatography (TLC) followed by gas chromatography (GC) and/or mass spectrometry (MS) are known. For example, lipids may be extracted from the test sample of bodily fluid. Alternatively, thin-layer chromatography may be used to separate various phospholipids. Phospholipids and lysophospholipids can then be visualized on plates, for example, using ultraviolet light. Alternatively, lysophospholipid concentrations can be identified by NMR or HPLC following isolation from phospholipids or as part of the phospholipid. LPA levels have also been determined in ascites from ovarian cancer patients using an assay that relies on LysoPA-specific effects on eukaryotic cells in culture. However, these prior procedures are time-consuming, expensive and variable and typically only semi-quantitative. Enzymatic methods for detecting lysophospholipids such as LPA in biological fluids, and for correlating and detecting conditions associated with altered levels of lysophospholipids, are also known. U.S. Pat. Nos. 6,255,063 and 6,248,553, originally assigned to Atairgin Technologies, Inc. and now commonly owned with the instant invention.

3. Definitions

Before describing the instant invention in detail, several terms used in the context of the present invention will be defined. In addition to these terms, others are defined elsewhere in the specification, as necessary. Unless otherwise expressly defined herein, terms of art used in this specification will have their art-recognized meanings.

"Aberrant" means excessive or unwanted, for example in reference to levels or effective concentrations of a cellular target such as a protein or bioactive lipid.

The term "antibody" ("Ab") or "immunoglobulin" (Ig) refers to any form of a peptide, polypeptide derived from, modeled after or encoded by, an immunoglobulin gene, or fragment thereof, that is capable of binding an antigen or epitope. See, e.g., Immunobiology, Fifth Edition, C. A. Janeway, P. Travers, M., Walport, M. J. Shlomchiked., ed. Garland Publishing (2001). The term "antibody" is used herein in the broadest sense, and encompasses monoclonal, polyclonal or multispecific antibodies, minibodies, heteroconjugates, diabodies, triabodies, chimeric, antibodies, synthetic antibodies, antibody fragments, and binding agents that employ the complementarity determining regions (CDRs) of the parent antibody, or variants thereof that retain antigen binding activity. Antibodies are defined herein as retaining at least one desired activity of the parent antibody. Desired activities can include the ability to bind the antigen specifically, the ability to inhibit proleration in vitro, the ability to inhibit angiogenesis in vivo, and the ability to alter cytokine profile(s) in vitro.

Native antibodies (native immunoglobulins) are usually heterotetrameric glycoproteins of about 150,000 Daltons, typically composed of two identical light (L) chains and two identical heavy (H) chains. The heavy chain is approximately 50 kD in size, and the light chain is approximately 25 kDa. Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The light chains of antibodies (immunoglobulins) from any vertebrate species can be assigned to one of two clearly distinct types, called kappa (κ) and lambda (λ), based on the amino acid sequences of their constant domains. The ratio of the two types of light chain varies from species to species. As a way of example, the average κ to λ ratio is 20:1 in mice, whereas in humans it is 2:1 and in cattle it is 1:20.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

An "antibody derivative" is an immune-derived moiety, i.e., a molecule that is derived from an antibody peptide or from nucleic acid encoding an antibody peptide. This includes any antibody (Ab) or immunoglobulin (Ig), and refers to any form of a peptide, polypeptide derived from, modeled after or encoded by, an immunoglobulin gene, or a fragment of such peptide or polypeptide that is capable of binding an antigen or epitope. This comprehends, for example, antibody variants, antibody fragments, chimeric antibodies, humanized antibodies, multivalent antibodies, antibody conjugates and the like, which retain a desired level of binding activity for antigen.

As used herein, "antibody fragment" refers to a portion of an intact antibody that includes the antigen binding site or variable regions of an intact antibody, wherein the portion can be free of the constant heavy chain domains (e.g., CH2, CH3, and CH4) of the Fc region of the intact antibody. Alternatively, portions of the constant heavy chain domains (e.g., CH2, CH3, and CH4) can be included in the "antibody fragment". Antibody fragments retain antigen-binding and include Fab, Fab', $F(ab')_2$, Fd, and Fv fragments; diabodies; triabodies; single-chain antibody molecules (sc-Fv); minibodies, nanobodies, and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen. By way of example, a Fab fragment also contains the constant domain of a light chain and the first constant domain (CH1) of a heavy chain. "Fv" is the minimum antibody fragment that contains a complete antigen-recognition and -binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site. "Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains that enables the sFv to form the desired structure for antigen binding. For a review of sFv, see Pluckthun in The Pharmacology of Monoclonal Antibodies, vol. 113, Rosenburg and Moore eds. Springer-Verlag, New York, pp. 269-315 (1994).

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

An "antibody variant," in this case generally an anti-LPA antibody variant, refers herein to a molecule which differs in amino acid sequence from a native anti-LPA antibody amino acid sequence by virtue of addition, deletion and/or substitution of one or more amino acid residue(s) in the antibody sequence and which retains at least one desired activity of the parent anti-binding antibody. Desired activities can include the ability to bind the antigen specifically, the ability to inhibit proliferation in vitro, the ability to inhibit angiogenesis in vivo, and the ability to alter cytokine profile in vitro. The amino acid change(s) in an antibody variant may be within a variable region or a constant region of a light chain and/or a heavy chain, including in the Fc region, the Fab region, the $CH_1$ domain, the $CH_2$ domain, the $CH_3$ domain, and the hinge region. In one embodiment, the variant comprises one or more amino acid substitution(s) in one or more hypervariable region(s) of the parent antibody. For example, the variant may comprise at least one, e.g. from about one to about ten, and preferably from about two to about five, substitutions in one or more hypervariable regions of the parent antibody. Ordinarily, the variant will have an amino acid sequence having at least 50% amino acid sequence identity with the parent antibody heavy or light chain variable domain sequences, more preferably at least 65%, more preferably at 80%, more preferably at least 85%, more preferably at least 90%, and most preferably at least 95%. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind LPA and preferably has desired activities which are superior to those of the parent antibody. For example, the variant may have a stronger binding affinity, enhanced ability to reduce angiogenesis and/or halt tumor progression. To analyze such desired properties (for example les immunogenic, longer half-life, enhanced stability, enhanced potency), one should compare a Fab form of the variant to a Fab form of the parent antibody or a full length form of the variant to a full length form of the parent antibody, for example, since it has been found that the format of the anti-sphingolipid antibody impacts its activity in the biological activity assays disclosed herein. The variant antibody of particular interest herein can be one which displays at least about 10 fold, preferably at least about % 5, 25, 59, or more of at least one desired activity. The preferred variant is one that has superior biophysical properties as measured in vitro or superior activities biological as measured in vitro or in vivo when compared to the parent antibody.

An "anti-LPA agent" refers to any therapeutic agent that binds LPA, and includes antibodies, antibody variants, antibody-derived molecules or non-antibody-derived moieties that bind LPA and its variants. An "anti-LPA antibody" or an "immune-derived moiety reactive against LPA" refers to any antibody or antibody-derived molecule that binds LPA. As will be understood from these definitions, antibodies or immune-derived moieties may be polyclonal or monoclonal and may be generated through a variety of means, and/or may be isolated from an animal, including a human subject.

An "anti-S1P agent" refers to any therapeutic agent that binds S1P, and includes antibodies, antibody variants, antibody-derived molecules or non-antibody-derived moieties that bind LPA and its variants.

An "anti-S1P antibody" or an "immune-derived moiety reactive against S1P" refers to any antibody or antibody-derived molecule that binds S1P. As will be understood from these definitions, antibodies or immune-derived moieties may be polyclonal or monoclonal and may be generated through a variety of means, and/or may be isolated from an animal, including a human subject.

A "bioactive lipid" refers to a lipid signaling molecule. Bioactive lipids are distinguished from structural lipids (e.g., membrane-bound phospholipids) in that they mediate extracellular and/or intracellular signaling and thus are involved in controlling the function of many types of cells by modulating differentiation, migration, proliferation, secretion, survival, and other processes. In vivo, bioactive lipids can be found in extracellular fluids, where they can be complexed with other molecules, for example serum proteins such as albumin and lipoproteins, or in "free" form, i.e., not complexed with another molecule species. As extracellular mediators, some bioactive lipids alter cell signaling by activating membrane-bound ion channels or GPCRs or enzymes or factors that, in turn, activate complex signaling systems that result in changes in cell function or survival. As intracellular mediators, bioactive lipids can exert their actions by directly interacting with intracellular components such as enzymes, ion channels or structural elements such as actin.

Examples of bioactive lipids include sphingolipids such as ceramide, ceramide-1-phosphate (C1P), sphingosine, sphinganine, sphingosylphosphorylcholine (SPC) and sphingosine-1-phosphate (S1P). Sphingolipids and their derivatives and metabolites are characterized by a sphingoid backbone (derived from sphingomyelin). Sphingolipids and their derivatives and metabolites represent a group of extracellular and intracellular signaling molecules with pleiotropic effects on important cellular processes. They include sulfatides, gangliosides and cerebrosides. Other bioactive lipids are characterized by a glycerol-based backbone; for example, lysophospholipids such as lysophosphatidyl choline (LPC) and various lysophosphatidic acids (LPA), as well as phosphatidylinositol (PI), phosphatidylethanolamine (PEA), phosphatidic acid, platelet activating factor (PAF), cardiolipin, phosphatidylglycerol (PG) and diacylglyceride (DG). Yet other bioactive lipids are derived from arachidonic acid; these include the eicosanoids (including the eicosanoid metabolites such as the HETEs, cannabinoids, leukotrienes, prostaglandins, lipoxins, epoxyeicosatrienoic acids, and isoeicosanoids), non-eicosanoid cannabinoid mediators. Other bioactive lipids, including other phospholipids and their derivatives, may also be used according to the instant invention.

In some embodiments of the invention it may be preferable to target glycerol-based bioactive lipids (those having a glycerol-derived backbone, such as the LPAs) for antibody production, as opposed to sphingosine-based bioactive lipids (those having a sphingoid backbone, such as sphingosine and S1P). In other embodiments it may be desired to target arachidonic acid-derived bioactive lipids for antibody generation, and in other embodiments arachidonic acid-derived and glycerol-derived bioactive lipids but not sphingoid-derived bioactive lipids are preferred. Together the arachidonic acid-derived and glycerol-derived bioactive lipids may be referred to in the context of this invention as "non-sphingoid bioactive lipids."

Specifically excluded from the class of bioactive lipids according to the invention are phosphatidylcholine and phosphatidylserine, as well as their metabolites and derivatives that function primarily as structural members of the inner and/or outer leaflet of cellular membranes.

The term "biologically active," in the context of an antibody or antibody fragment or variant, refers to an antibody or antibody fragment or antibody variant that is capable of binding the desired epitope and in some ways exerting a biologic effect. Biological effects include, but are not limited to, the modulation of a growth signal, the modulation of an anti-apoptotic signal, the modulation of an apoptotic signal, the modulation of the effector function cascade, and modulation of other ligand interactions.

A "biomarker" is a specific biochemical in the body which has a particular molecular feature that makes it useful for measuring the progress of disease or the effects of treatment. For example, S1P is a biomarker for certain hyperproliferative and/or cardiovascular conditions.

The term "cardiotherapeutic agent" refers to an agent that is therapeutic to diseases and diseases caused by or associated with cardiac and myocardial diseases and disorders.

"Cardiovascular therapy" encompasses cardiac therapy (treatment of myocardial ischemia and/or heart failure) as well as the prevention and/or treatment of other diseases associated with the cardiovascular system, such as heart disease. The term "heart disease" encompasses any type of disease, disorder, trauma or surgical treatment that involves the heart or myocardial tissue. Of particular interest are conditions associated with tissue remodeling. The term "cardiotherapeutic agent" refers to an agent that is therapeutic to diseases and diseases caused by or associated with cardiac and myocardial diseases and disorders.

A "carrier" refers to a moiety adapted for conjugation to a hapten, thereby rendering the hapten immunogenic. A representative, non-limiting class of carriers is proteins, examples of which include albumin, keyhole limpet hemocyanin, hemaglutanin, tetanus, and diptheria toxoid. Other classes and examples of carriers suitable for use in accordance with the invention are known in the art. These, as well as later discovered or invented naturally occurring or synthetic carriers, can be adapted for application in accordance with the invention.

As used herein, the expressions "cell," "cell line," and "cell culture" are used interchangeably and all such designations include progeny. Thus, the words "transformants" and "transformed cells" include the primary subject cell and cultures derived there from without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

"Cerebrovascular therapy" refers to therapy directed to the prevention and/or treatment of diseases and disorders associated with cerebral ischemia and/or hypoxia. Of particular interest is cerebral ischemia and/or hypoxia resulting from global ischemia resulting from a heart disease, including without limitation heart failure.

The term "chemotherapeutic agent" means anti-cancer and other anti-hyperproliferative agents. Thus chemotherapeutic agents are a subset of therapeutic agents in general. Chemotherapeutic agents include, but are not limited to: DNA damaging agents and agents that inhibit DNA synthesis: anthracyclines (doxorubicin, donorubicin, epirubicin), alkylating agents (bendamustine, busulfan, carboplatin, carmustine, chlorambucil, cyclophosphamide, dacarbazine, hexamethylmelamine, ifosphamide, lomustine, mechlorethamine, melphalan, mitotane, mytomycin, pipobroman, procarbazine, streptozocin, thiotepa; and triethylenemelamine), platinum derivatives (cisplatin, carboplatin, cis diammine-dichloroplatinum), and topoisomerase inhibitors (Camptosar); antimetabolites such as capecitabine, chlorodeoxyadenosine, cytarabine (and its activated form, ara-CMP), cytosine arabinoside, dacabazine, floxuridine, fludarabine, 5-fluorouracil, 5-DFUR, gemcitabine, hydroxyurea, 6-mercaptopurine, methotrexate, pentostatin, trimetrexate, 6-thioguanine); antiangiogenics (bevacizumab, thalidomide, sunitinib, lenalidomide, TNP-470, 2-methoxyestradiol, ranibizumab, sorafenib, erlotinib, bortezomib, pegaptanib, endostatin); vascular disrupting agents (flavonoids/flavones, DMXAA, combretastatin derivatives such as CA4DP, ZD6126, AVE8062A, etc.); biologics such as antibodies (Herceptin, Avastin, Panorex, Rituxin, Zevalin, Mylotarg, Campath, Bexxar, Erbitux); endocrine therapy: aromatase inhibitors (4-hydroandrostendione, exemestane, aminoglutehimide, anastrazole, letozole), anti-estrogens (Tamoxifen, Toremifine, Raoxifene, Faslodex), steroids such as dexamethasone; immuno-modulators: cytokines such as IFN-beta and IL2), inhibitors to integrins, other adhesion proteins and matrix metalloproteinases); histone deacetylase inhibitors like suberoylanilide hydroxamic acid; inhibitors of signal transduction such as inhibitors of tyrosine kinases like imatinib (Gleevec); inhibitors of heat shock proteins like 17-N-allylamino-17-demethoxygeldanamycin; retinoids such as all trans retinoic acid; inhibitors of growth factor receptors or the growth factors themselves; anti-mitotic compounds and/or tubulin-depolymerizing agents such as the taxoids (paclitaxel, docetaxel, taxotere, BAY 59-8862), navelbine, vinblastine, vincristine, vindesine and vinorelbine; anti-inflammatories such as COX inhibitors and cell cycle regulators, e.g., check point regulators and telomerase inhibitors.

The term "chimeric" antibody (or immunoglobulin) refers to a molecule comprising a heavy and/or light chain which is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly, et al., infra; Morrison et al., Proc. Natl. Acad. Sci. U.S.A., vol. 81:6851 (1984)).

The term "combination therapy" refers to a therapeutic regimen that involves the provision of at least two distinct therapies to achieve an indicated therapeutic effect. For example, a combination therapy may involve the administration of two or more chemically distinct active ingredients, for example, a fast-acting chemotherapeutic agent and an anti-lipid antibody, or two different antibodies. Alternatively, a combination therapy may involve the administration of an anti-lipid antibody together with the delivery of another treatment, such as radiation therapy and/or surgery. Further, a combination therapy may involve administration of an anti-lipid antibody together with one or more other biological agents (e.g., anti-VEGF, TGFβ, PDGF, or bFGF agent), chemotherapeutic agents and another treatment such as radiation and/or surgery. In the context of the administration of two or more chemically distinct active ingredients, it is understood that the active ingredients may be administered as part of the same composition or as different compositions. When administered as separate compositions, the compositions comprising the different active ingredients may be administered at the same or different times, by the same or different routes, using the same of different dosing regimens, all as the particular context requires and as determined by the attending physician. Similarly, when one or more anti-lipid antibody species, for example, an anti-LPA antibody, alone or in conjunction with one or more chemotherapeutic agents are combined with, for example, radiation and/or surgery, the drug(s) may be delivered before or after surgery or radiation treatment.

The term "constant domain" refers to the C-terminal region of an antibody heavy or light chain. Generally, the constant domains are not directly involved in the binding properties of an antibody molecule to an antigen, but exhibit various effector functions, such as participation of the antibody in antibody-dependent cellular toxicity. Here, "effector functions" refer to the different physiological effects of antibodies (e.g., opsonization, cell lysis, mast cell, basophil and eosinophil degranulation, and other processes) mediated by the recruitment of immune cells by the molecular interaction between the Fc domain and proteins of the immune system. The isotype of the heavy chain determines the functional properties of the antibody. Their distinctive functional properties are conferred by the carboxy-terminal portions of the heavy chains, where they are not associated with light chains.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A "derivatized bioactive lipid" is a bioactive lipid, e.g., LPA, which has a polar head group and at least one hydrocarbon chain, wherein a carbon atom within the hydrocarbon chain is derivatized with a reactive group [e.g., a sulfhydryl (thiol) group, a carboxylic acid group, a cyano group, an ester, a hydroxy group, an alkene, an alkyne, an acid chloride group or a halogen atom] that may or may not be protected. This derivatization serves to activate the bioactive lipid for reaction with a molecule, e.g., for conjugation to a carrier.

A "derivatized bioactive lipid conjugate" refers to a derivatized bioactive lipid that is covalently conjugated to a carrier. The carrier may be a protein molecule or may be a moiety such as polyethylene glycol, colloidal gold, adjuvants or silicone beads. A derivatized bioactive lipid conjugate may be used as an immunogen for generating an antibody response according to the instant invention, and the same or a different bioactive lipid conjugate may be used as a detection reagent for detecting the antibody thus produced. In some embodiments the derivatized bioactive lipid conjugate is attached to a solid support when used for detection.

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA 90:6444-6448 (1993).

"Effective concentration" refers to the absolute, relative, and/or available concentration and/or activity, for example of certain undesired bioactive lipids. In other words, the effective concentration of a bioactive lipid is the amount of lipid available, and able, to perform its biological function. In the present invention, an immune-derived moiety such as, for example, a monoclonal antibody directed to a bioactive lipid (such as, for example, C1P) is able to reduce the effective concentration of the lipid in at least one fluid or milieu, possibly a physiological fluid or milieu, by binding to the lipid and rendering it unable to perform its biological function. In this example, the lipid itself is still present (it is not degraded by the antibody, in other words) but can no longer bind its receptor or other targets to cause a downstream effect, so "effective concentration" rather than absolute concentration is the appropriate measurement. Methods and assays exist for directly and/or indirectly measuring the effective concentration of bioactive lipids.

An "epitope" or "antigenic determinant" refers to that portion of an antigen that reacts with an antibody antigen-binding portion derived from an antibody.

The term "expression cassette" refers to a nucleotide molecule capable of affecting expression of a structural gene (i.e., a protein coding sequence, such as an antibody of the invention) in a host compatible with such sequences. Expression cassettes include at least a promoter operably linked with the polypeptide-coding sequence, and, optionally, with other sequences, e.g., transcription termination signals. Additional regulatory elements necessary or helpful in effecting expression may also be used, e.g., enhancers. Thus, expression cassettes include plasmids, expression vectors, recombinant viruses, any form of recombinant "naked DNA" vector, and the like.

A "fully human antibody" can refer to an antibody produced in a genetically engineered (i.e., transgenic) mouse (e.g. from Medarex) that, when presented with an immunogen, can produce a human antibody that does not necessarily require CDR grafting. These antibodies are fully human (100% human protein sequences) from animals such as mice in which the non-human antibody genes are suppressed and replaced with human antibody gene expression. The applicants believe that antibodies could be generated against bioactive lipids when presented to these genetically engineered mice or other animals who might be able to produce human frameworks for the relevant CDRs.

A "hapten" is a substance that is non-immunogenic but can react with an antibody or antigen-binding portion derived from an antibody. In other words, haptens have the property of antigenicity but not immunogenicity. A hapten is generally a small molecule that can, under most circumstances, elicit an immune response (i.e., act as an antigen) only when attached to a carrier, for example, a protein, polyethylene glycol (PEG), colloidal gold, silicone beads, or the like. The carrier may be one that also does not elicit an immune response by itself. A representative, non-limiting class of hapten molecules is proteins, examples of which include albumin, keyhole limpet hemocyanin, hemaglutanin, tetanus, and diphtheria toxoid. Other classes and examples of hapten molecules are known in the art. These, as well as later discovered or invented naturally occurring or synthetic haptens, can be adapted for application in accordance with the invention.

The term "heteroconjugate antibody" can refer to two covalently joined antibodies. Such antibodies can be prepared using known methods in synthetic protein chemistry, including using crosslinking agents. As used herein, the term "conjugate" refers to molecules formed by the covalent attachment of one or more antibody fragment(s) or binding moieties to one or more polymer molecule(s).

"Humanized" forms of non-human (e.g., murine) antibodies are chimeric antibodies that contain minimal sequence derived from non-human immunoglobulin. Or, looked at another way, a humanized antibody is a human antibody that also contains selected sequences from non-human (e.g., murine) antibodies in place of the human sequences. A humanized antibody can include conservative amino acid substitutions or non-natural residues from the same or different species that do not significantly alter its binding and/or biologic activity. Such antibodies are chimeric antibodies that contain minimal sequence derived from non-human immunoglobulins. For the most part, humanized antibodies are human immunoglobulins (recipient antibody) in which residues from a complementary-determining region (CDR) of the recipient are replaced by residues from a CDR of a non-human species (donor antibody) such as mouse, rat, camel, bovine, goat, or rabbit having the desired properties. In some instances, framework region (FR) residues of the human immunoglobulin are replaced by corresponding non-human residues.

Furthermore, humanized antibodies can comprise residues that are found neither in the recipient antibody nor in the imported CDR or framework sequences. These modifications are made to further refine and maximize antibody performance. Thus, in general, a humanized antibody will comprise all of at least one, and in one aspect two, variable domains, in which all or all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), or that of a human immunoglobulin. See, e.g., Cabilly, et al., U.S. Pat. No. 4,816,567; Cabilly, et al., European Patent No. 0,125,023 B1; Boss, et al., U.S. Pat. No. 4,816,397; Boss, et al., European Patent No. 0,120,694 B1; Neuberger, et al., WO 86/01533; Neuberger, et al., European Patent No. 0,194,276 B1; Winter, U.S. Pat. No. 5,225,539; Winter, European Patent No. 0,239,400 B1; Padlan, et al., European Patent Application No. 0,519,596 A1; Queen, et al. (1989), Proc. Nat'l Acad. Sci. USA, vol. 86:10029-10033). For further details, see Jones et al., Nature 321:522-525 (1986); Reichmann et al., Nature 332:323-329 (1988); and Presta, Curr. Op. Struct. Biol. 2:593-596 (1992) and Hansen, WO2006105062.

The term "hyperproliferative disorder" refers to diseases and disorders associated with, the uncontrolled proliferation of cells, including but not limited to uncontrolled growth of organ and tissue cells resulting in cancers and benign tumors. Hyperproliferative disorders associated with endothelial cells can result in diseases of angiogenesis such as angiomas, endometriosis, obesity, age-related macular degeneration and various retinopathies, as well as the proliferation of endothelial cells and smooth muscle cells that cause restenosis as a consequence of stenting in the treatment of atherosclerosis. Hyperproliferative disorders involving fibroblasts (i.e., fibrogenesis) include but are not limited to disorders of excessive scarring (i.e., fibrosis) such as age-related macular degeneration, cardiac remodeling and failure associated with myocardial infarction, excessive wound healing such as commonly occurs as a consequence of surgery or injury, keloids, and fibroid tumors and stenting.

An "immune-derived moiety" includes any antibody (Ab) or immunoglobulin (Ig), and refers to any form of a peptide, polypeptide derived from, modeled after or encoded by, an immunoglobulin gene, or a fragment of such peptide or polypeptide that is capable of binding an antigen or epitope (see, e.g., Immunobiology, 5th Edition, Janeway, Travers, Walport, Shlomchiked. (editors), Garland Publishing (2001)). In the present invention, the antigen is a lipid molecule, such as a bioactive lipid molecule.

An "immunogen" is a molecule capable of inducing a specific immune response, particularly an antibody response in an animal to whom the immunogen has been administered. In the instant invention, the immunogen is a derivatized bioactive lipid conjugated to a carrier, i.e., a "derivatized bioactive lipid conjugate". The derivatized bioactive lipid conjugate used as the immunogen may be used as capture material for detection of the antibody generated in response to the immunogen. Thus the immunogen may also be used as a detection reagent. Alternatively, the derivatized bioactive lipid conjugate used as capture material may have a different linker and/or carrier moiety from that in the immunogen.

The phrase "in silico" refers to computer simulations that model natural or laboratory processes To "inhibit," particularly in the context of a biological phenomenon, means to decrease, suppress or delay. For example, a treatment yielding "inhibition of tumorigenesis" may mean that tumors do not form at all, or that they form more slowly, or are fewer in number than in the untreated control.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition, such as one that is conjugated directly or indirectly to the antibody. The label may itself be detectable by itself (e.g., radioisotope labels or fluorescent labels) or, in the case of an enzymatic label, may catalyze chemical alteration of a substrate compound or composition that is detectable.

A "ligand" is a substance that is able to bind to and form a complex with a biomolecule to serve a biological purpose. Thus an antigen may be described as a ligand of the antibody to which it binds.

A "liposome" is a small vesicle composed of various types of lipids, phospholipids and/or surfactant that is useful for delivery of a drug (such as the anti-sphingolipid antibodies disclosed herein and, optionally, a chemotherapeutic agent) to a mammal. The components of the liposome are commonly arranged in a bilayer formation, similar to the lipid arrangement of biological membranes. An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

In the context of this invention, a "liquid composition" refers to one that, in its filled and finished form as provided from a manufacturer to an end user (e.g., a doctor or nurse), is a liquid or solution, as opposed to a solid. Here, "solid" refers to compositions that are not liquids or solutions. For example, solids include dried compositions prepared by lyophilization, freeze-drying, precipitation, and similar procedures.

The expression "linear antibodies" when used throughout this application refers to the antibodies described in Zapata et al. Protein Eng. 8(10):1057-1062 (1995). Briefly, these antibodies comprise a pair of tandem Fd segments ($V_H$-$C_H1$-$V_H$-$C_H1$) that form a pair of antigen binding regions. Linear antibodies can be bispecific or monospecific.

The term "metabolites" refers to compounds from which a given bioactive lipid is made, as well as those that result from the degradation of the bioactive lipid; that is, compounds that are involved in the respective metabolic pathways of each bioactive lipid. The term "metabolic precursors" may be used to refer to compounds from which each bioactive lipid is made.

The term "monoclonal antibody" (mAb) as used herein refers to an antibody obtained from a population of substantially homogeneous antibodies, or to said population of antibodies. The individual antibodies comprising the population are essentially identical, except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352:624-628 (1991) and Marks et al., J. Mol. Biol. 222:581-597 (1991), for example, or by other methods known in the art. The monoclonal antibodies herein specifically include chimeric antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"Monotherapy" refers to a treatment regimen based on the delivery of one therapeutically effective compound, whether administered as a single dose or several doses over time.

The term "multispecific antibody" can refer to an antibody, or a monoclonal antibody, having binding properties for at least two different epitopes. In one embodiment, the epitopes are from the same antigen. In another embodiment, the epitopes are from two or more different antigens. Methods for making multispecific antibodies are known in the art. Multispecific antibodies include bispecific antibodies (having binding properties for two epitopes), bispecific antibodies (three epitopes) and so on. For example, multispecific antibodies can be produced recombinantly using the co-expression of two or more immunoglobulin heavy chain/light chain pairs. Alternatively, multispecific antibodies can be prepared using chemical linkage. One of skill can produce multispecific antibodies using these or other methods as may be known in the art. Multispecific antibodies include multispecific antibody fragments. One example of a multispecific (in this case, bispecific) antibody comprehended by this invention is an antibody having binding properties for an S1P epitope and a C1P epitope, which thus is able to recognize and bind to both S1P and C1P. Another example of a bispecific antibody comprehended by this invention is an antibody having binding properties for an epitope from a bioactive lipid and an epitope from a cell surface antigen. Thus the antibody is able to recognize and bind the bioactive lipid and is able to recognize and bind to cells, e.g., for targeting purposes.

"Neoplasia" or "cancer" refers to abnormal and uncontrolled cell growth. A "neoplasm", or tumor or cancer, is an abnormal, unregulated, and disorganized proliferation of cell growth, and is generally referred to as cancer. A neoplasm may be benign or malignant. A neoplasm is malignant, or cancerous, if it has properties of destructive growth, invasiveness, and metastasis. Invasiveness refers to the local spread of a neoplasm by infiltration or destruction of surrounding tissue, typically breaking through the basal laminas that define the boundaries of the tissues, thereby often entering the body's circulatory system. Metastasis typically refers to the dissemination of tumor cells by lymphatics or blood vessels. Metastasis also refers to the migration of tumor cells by direct extension through serous cavities, or subarachnoid or other spaces. Through the process of metastasis, tumor cell migration to other areas of the body establishes neoplasms in areas away from the site of initial appearance.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The "parent" antibody herein is one that is encoded by an amino acid sequence used for the preparation of the variant. The parent antibody may be a native antibody or may already be a variant, e.g., a chimeric antibody. For example, the parent antibody may be a humanized or human antibody.

A "patentable" composition, process, machine, or article of manufacture according to the invention means that the subject matter satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically exclude the non-patentable embodiment(s). Also, the claims appended hereto are to be interpreted both to provide the broadest reasonable scope, as well as to preserve their validity. Furthermore, the claims are to be interpreted in a way that (1) preserves their validity and (2) provides the broadest reasonable interpretation under the circumstances, if one or more of the statutory requirements for patentability are amended or if the standards change for assessing whether a particular statutory requirement for patentability is satisfied from the time this application is filed or issues as a patent to a time the validity of one or more of the appended claims is questioned.

The term "pharmaceutically acceptable salt" refers to a salt, such as used in formulation, which retains the biological effectiveness and properties of the agents and compounds of this invention and which are is biologically or otherwise undesirable. In many cases, the agents and compounds of this invention are capable of forming acid and/or base salts by virtue of the presence of charged groups, for example, charged amino and/or carboxyl groups or groups similar thereto. Pharmaceutically acceptable acid addition salts may be prepared from inorganic and organic acids, while pharmaceutically acceptable base addition salts can be prepared from inorganic and organic bases. For a review of pharmaceutically acceptable salts (see Berge, et al. (1977) J. Pharm. Sci., vol. 66, 1-19).

A "plurality" means more than one.

The term "promoter" includes all sequences capable of driving transcription of a coding sequence in a cell. Thus, promoters used in the constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. Transcriptional regulatory regions suitable for use in the present invention include but are not limited to the human cytomegalovirus (CMV) immediate-early enhancer/promoter, the SV40 early enhancer/promoter, the *E. coli* lac or trp promoters, and other promoters known to control expression of genes in prokaryotic or eukaryotic cells or their viruses.

The term "recombinant DNA" refers to nucleic acids and gene products expressed therefrom that have been engineered, created, or modified by man. "Recombinant" polypeptides or proteins are polypeptides or proteins produced by recombinant DNA techniques, for example, from cells transformed by an exogenous DNA construct encoding the desired polypeptide or protein. "Synthetic" polypeptides or proteins are those prepared by chemical synthesis.

The terms "separated", "purified", "isolated", and the like mean that one or more components of a sample contained in a sample-holding vessel are or have been physically removed from, or diluted in the presence of, one or more other sample components present in the vessel. Sample components that may be removed or diluted during a separating or purifying step include, chemical reaction products, non-reacted chemicals, proteins, carbohydrates, lipids, and unbound molecules.

By "solid phase" is meant a non-aqueous matrix such as one to which the antibody of the present invention can adhere. Examples of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g. an affinity chromatography column). This term also includes a discontinuous solid phase of discrete particles, such as those described in U.S. Pat. No. 4,275,149.

The term "species" is used herein in various contexts, e.g., a particular species of chemotherapeutic agent. In each context, the term refers to a population of chemically indistinct molecules of the sort referred in the particular context.

The term "specific" or "specificity" in the context of antibody-antigen interactions refers to the selective, non-random interaction between an antibody and its target epitope. Here, the term "antigen" refers to a molecule that is recognized and bound by an antibody molecule or other immune-derived moiety. The specific portion of an antigen that is bound by an antibody is termed the "epitope". This interaction depends on the presence of structural, hydrophobic/hydrophilic, and/or electrostatic features that allow appropriate chemical or molecular interactions between the molecules. Thus an antibody is commonly said to "bind" (or "specifically bind") or be "reactive with" (or "specifically reactive with), or, equivalently, "reactive against" (or "specifically reactive against") the epitope of its target antigen. Antibodies are commonly described in the art as being "against" or "to" their antigens as shorthand for antibody binding to the antigen. Thus an "antibody that binds C1P," an "antibody reactive against C1P," an "antibody reactive with C1P," an "antibody to C1P" and an "anti-C1P antibody" all have the same meaning in the art. Antibody molecules can be tested for specificity of binding by comparing binding to the desired antigen to binding to unrelated antigen or analogue antigen or antigen mixture under a given set of conditions. Preferably, an antibody according to the invention will lack significant binding to unrelated antigens, or even analogs of the target antigen. "Specifically associate" and "specific association" and the like refer to a specific, non-random interaction between two molecules, which interaction depends on the presence of structural, hydrophobic/hydrophilic, and/or electrostatic features that allow appropriate chemical or molecular interactions between the molecules.

The term "sphingolipid" as used herein refers to the class of compounds in the art known as sphingolipids, including, but not limited to the following compounds (see http//www.lipidmaps.org for chemical formulas, structural information, etc. for the corresponding compounds):

Sphingoid bases [SP01]
Sphing-4-enines (Sphingosines) [SP0101]
Sphinganines [SP0102]
4-Hydroxysphinganines (Phytosphingosines) [SP0103]
Sphingoid base homologs and variants [SP0104]
Sphingoid base 1-phosphates [SP0105]
Lysosphingomyelins and lysoglycosphingolipids [SP0106]
N-methylated sphingoid bases [SP0107]
Sphingoid base analogs [SP0108]
Ceramides [SP02]
N-acylsphingosines (ceramides) [SP0201]
N-acylsphinganines (dihydroceramides) [SP0202]
N-acyl-4-hydroxysphinganines (phytoceramides) [SP0203]
Acylceramides [SP0204]
Ceramide 1-phosphates [SP0205]
Phosphosphingolipids [SP03]
Ceramide phosphocholines (sphingomyelins) [SP0301]
Ceramide phosphoethanolamines [SP0302]
Ceramide phosphoinositols [SP0303]
Phosphonosphingolipids [SP04]
Neutral glycosphingolipids [SP05]
Simple Glc series (GlcCer, LacCer, etc) [SP0501]
GalNAcb1-3Gala1-4Galb1-4Glc-(Globo series) [SP0502]
GalNAcb1-4Galb1-4Glc-(Ganglio series) [SP0503]
Galb1-3GlcNAcb1-3Galb1-4Glc-(Lacto series) [SP0504]
Galb1-4GlcNAcb1-3Galb1-4Glc-(Neolacto series) [SP0505]
GalNAcb1-3Gala1-3Galb1-4Glc-(Isoglobo series) [SP0506]
GlcNAcb1-2Mana1-3Manb1-4Glc-(Mollu series) [SP0507]
GalNAcb1-4GlcNAcb1-3Manb1-4Glc-(Arthro series) [SP0508]
Gal-(Gala series) [SP0509]
Other [SP0510]
Acidic glycosphingolipids [SP06]
Gangliosides [SP0601]
Sulfoglycosphingolipids (sulfatides) [SP0602]
Glucuronosphingolipids [SP0603]
Phosphoglycosphingolipids [SP0604]
Other [SP0600]
Basic glycosphingolipids [SP07]
Amphoteric glycosphingolipids [SP08]
Arsenosphingolipids [SP09]

The term "sphingolipid metabolite" refers to a compound from which a sphingolipid is made, as well as a that results from the degradation of a particular sphingolipid. In other words, a "sphingolipid metabolite" is a compound that is involved in the sphingolipid metabolic pathways. Metabolites include metabolic precursors and metabolic products. The term "metabolic precursors" of sphingolipids refers to compounds from which sphingolipids are made. Metabolic precursors of particular interest include but are not limited to SPC, sphingomyelin, dihydrosphingosine, dihydroceramide, and 3-ketosphinganine. The term "metabolic products" refers to compounds that result from the degradation of sphingolipids, such as phosphorylcholine (e.g., phosphocholine, choline phosphate), fatty acids, including free fatty acids, and hexadecanal (e.g., palmitaldehyde).

Herein, "stable" refers to an interaction between two molecules (e.g., a peptide and a TLR molecule) that is sufficiently stable such that the molecules can be maintained for the desired purpose or manipulation. For example, a "stable" interaction between a peptide and a TLR molecule refers to one wherein the peptide becomes and remains associated with a TLR molecule for a period sufficient to achieve the desired effect.

A "subject" or "patient" refers to an animal in need of treatment that can be effected by molecules of the invention. Animals that can be treated in accordance with the invention include vertebrates, with mammals such as bovine, canine, equine, feline, ovine, porcine, and primate (including humans and non-human primates) animals being particularly preferred examples.

A "surrogate marker" refers to laboratory measurement of biological activity within the body that indirectly indicates the effect of treatment on disease state. Examples of surrogate markers for hyperproliferative and/or cardiovascular conditions include SPHK and/or S1PRs.

A "therapeutic agent" refers to a drug or compound that is intended to provide a therapeutic effect including, but not limited to: anti-inflammatory drugs including COX inhibitors and other NSAIDS, anti-angiogenic drugs, chemotherapeutic drugs as defined above, cardiovascular agents, immunomodulatory agents, agents that are used to treat neurodegenerative disorders, opthalmic drugs, anti-fibrotics, etc.

A "therapeutically effective amount" (or "effective amount") refers to an amount of an active ingredient, e.g., an agent according to the invention, sufficient to effect treatment when administered to a subject in need of such treatment. Accordingly, what constitutes a therapeutically effective amount of a composition according to the invention may be readily determined by one of ordinary skill in the art. In the context of cancer therapy, a "therapeutically effective amount" is one that produces an objectively measured change in one or more parameters associated with cancer cell survival or metabolism, including an increase or decrease in the expression of one or more genes correlated with the particular cancer, reduction in tumor burden, cancer cell lysis, the detection of one or more cancer cell death markers in a biological sample (e.g., a biopsy and an aliquot of a bodily fluid such as whole blood, plasma, serum, urine, etc.), induction of induction apoptosis or other cell death pathways, etc. Of course, the therapeutically effective amount will vary depending upon the particular subject and condition being treated, the weight and age of the subject, the severity of the disease condition, the particular compound chosen, the dosing regimen to be followed, timing of administration, the manner of administration and the like, all of which can readily be determined by one of ordinary skill in the art. It will be appreciated that in the context of combination therapy, what constitutes a therapeutically effective amount of a particular active ingredient may differ from what constitutes a therapeutically effective amount of the active ingredient when administered as a monotherapy (i.e., a therapeutic regimen that employs only one chemical entity as the active ingredient).

The compositions of the invention are used in methods of bioactive lipid-based therapy. As used herein, the terms "therapy" and "therapeutic" encompasses the full spectrum of prevention and/or treatments for a disease, disorder or physical trauma. A "therapeutic" agent of the invention may act in a manner that is prophylactic or preventive, including those that incorporate procedures designed to target individuals that can be identified as being at risk (pharmacogenetics); or in a manner that is ameliorative or curative in nature; or may act to slow the rate or extent of the progression of at least one symptom of a disease or disorder being treated; or may act to minimize the time required, the occurrence or extent of any discomfort or pain, or physical limitations associated with recuperation from a disease, disorder or physical trauma; or may be used as an adjuvant to other therapies and treatments.

The term "treatment" or "treating" means any treatment of a disease or disorder, including preventing or protecting against the disease or disorder (that is, causing the clinical symptoms not to develop); inhibiting the disease or disorder (i.e., arresting, delaying or suppressing the development of clinical symptoms; and/or relieving the disease or disorder (i.e., causing the regression of clinical symptoms). As will be appreciated, it is not always possible to distinguish between "preventing" and "suppressing" a disease or disorder because the ultimate inductive event or events may be unknown or latent. Those "in need of treatment" include those already with the disorder as well as those in which the disorder is to be prevented. Accordingly, the term "prophylaxis" will be understood to constitute a type of "treatment" that encompasses both "preventing" and "suppressing". The term "protection" thus includes "prophylaxis".

The term "therapeutic regimen" means any treatment of a disease or disorder using chemotherapeutic and cytotoxic agents, radiation therapy, surgery, gene therapy, DNA vaccines and therapy, siRNA therapy, anti-angiogenic therapy, immunotherapy, bone marrow transplants, aptamers and other biologics such as antibodies and antibody variants, receptor decoys and other protein-based therapeutics.

The "variable" region of an antibody comprises framework and complementarity determining regions (CDRs, otherwise known as hypervariable regions). The variability is not evenly distributed throughout the variable domains of antibodies. It is concentrated in six CDR segments, three in each of the light chain and the heavy chain variable domains. The more highly conserved portions of variable domains are called the framework region (FR). The variable domains of native heavy and light chains each comprise four FRs (FR1, FR2, FR3 and FR4, respectively), largely adopting a β-sheet configuration, connected by three hypervariable regions, which form loops connecting, and in some cases forming part of, the beta-sheet structure. The term "hypervariable region" when used herein refers to the amino acid residues of an antibody which are responsible for antigen binding. The hypervariable region comprises amino acid residues from a "complementarity determining region" or "CDR" (for example residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (for example residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). "Framework" or "FR" residues are those variable domain residues other than the hypervariable region residues as herein defined.

The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

A "vector" or "plasmid" or "expression vector" refers to a nucleic acid that can be maintained transiently or stably in a cell to effect expression of one or more recombinant genes. A vector can comprise nucleic acid, alone or complexed with other compounds. A vector optionally comprises viral or bacterial nucleic acids and/or proteins, and/or membranes. Vectors include, but are not limited, to replicons (e.g., RNA replicons, bacteriophages) to which fragments of DNA may be attached and become replicated. Thus, vectors include, but are not limited to, RNA, autonomous self-replicating circular or linear DNA or RNA and include both the expression and non-expression plasmids. Plasmids can be commercially available, publicly available on an unrestricted basis, or can be constructed from available plasmids as reported with published protocols. In addition, the expression vectors may also contain a gene to provide a phenotypic trait for selection of transformed host cells such as dihydrofolate reductase or neomycin resistance for eukaryotic cell culture, or such as tetracycline or ampicillin resistance in *E. coli.*

SUMMARY OF THE INVENTION

The instant application provides compositions and methods relating to anti-LPA agents, particularly anti-LPA antibodies, including humanized anti-LPA antibodies. Anti-LPA agents comprising a variable domain having an amino acid sequence selected from a set of selected sequences are provided, as are anti-LPA agents comprising a heavy chain and a light chain, wherein each immunoglobulin heavy chain comprises a variable domain having an amino acid sequence selected from a set of selected heavy chain variable domain sequences, and each immunoglobulin light chain comprises a variable domain having an amino acid sequence selected from a group of selected light chain sequences. In some embodiments the anti-LPA agent comprises two immunoglobulin heavy chains and two immunoglobulin light chains, wherein one or both of the heavy chains comprise an amino acid sequence from a set of selected heavy chain variable domain sequences, and wherein one or both of the light chains comprise an amino acid sequence from a set of selected light chain variable domain sequences. The two light chain variable domain sequences may be the same or different, as may the two heavy chain variable domain sequences.

The anti-LPA agent may be an antibody, an antibody derivative, or a non-antibody-derived moiety, and may be a full-length antibody or an antibody fragment. The anti-LPA agent may be conjugated to a polymer, a radionuclide, a chemotherapeutic agent, or a detection agent. Pharmaceutical compositions comprising a pharmaceutically acceptable carrier and an anti-LPA agent are also provided.

Further provided are isolated nucleic acid molecules that encode an immunoglobulin heavy chain variable domain or an immunoglobulin light chain variable domain that comprises an amino acid sequence according specific sequences provided. Vectors and host cells are also provided.

In addition, isolated polypeptides reactive with LPA in a physiological context are provided; these comprise an amino acid sequence that has a sequence identity of at least 65 percent with a peptide amino acid sequence selected from a specified group. In some embodiments these polypeptides are fragments of a variable domain of an animal immunoglobulin heavy or light chain, a full length variable domain of an immunoglobulin heavy or light chain or a full length immunoglobulin heavy or light chain.

Methods of administering an anti-LPA agent, isolated polypeptide which specifically binds LPA or an isolated antibody molecule are provided. Methods of treating or preventing a disease or disorder correlated with elevated levels of LPA are also provided, wherein a composition such as the antibodies, peptides or anti-LPA agents of the invention are administered to a subject in an amount effective to reduce in vivo the effective concentration of LPA, thereby effecting treatment or prevention of the disease or disorder. In some embodiments the disease or disorder may be cancer, an inflammatory disorder, a cerebrovascular disease, a cardiovascular disease, an ocular disorder, a disease and disorder associated with excessive fibrogenesis, a disease or disorder associated with metastasis, a disease or disorder associated with tumor growth, and a disease or disorder associated with pathologic angiogenesis, and the anti-LPA agent, isolated polypeptide, isolated antibody or multivalent binding molecule may be administered in combination with another therapeutic agent to effect treatment or prevention of the disease or disorder. Also provided are methods of decreasing the effective concentration of LPA in a bodily fluid or tissue of a subject, including a human subject.

Methods for detecting LPA or an LPA metabolite are also provided, utilizing the compositions of the invention; these may be attached to a solid support and the method may be an ELISA assay.

BRIEF DESCRIPTION OF THE DRAWINGS

A brief summary of each of the figures and tables described in this specification are provided below, as is a list of various nucleotide and amino acid sequences described herein.

DETAILED DESCRIPTION OF THE INVENTION

A. Derivatized and/or Conjugated LPA

1. Compositions

Figure 1A:
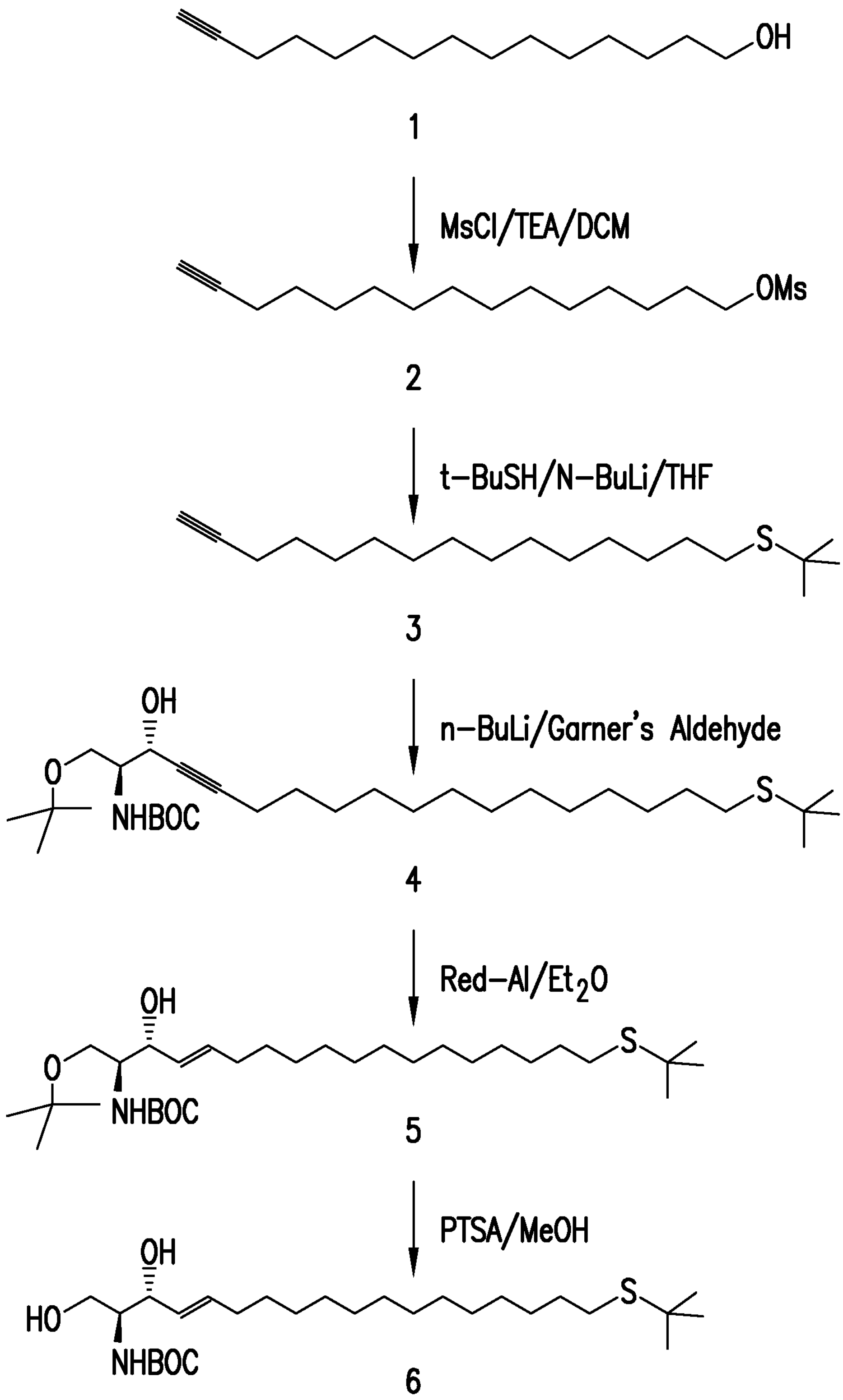
FIG. 1. Organic synthesis scheme for making of a typical thiolated-S1P analog that was used as a key component of an immunogen, as well as a key component of the laydown material for the ELISA and BiaCore assays.

LPA can be derivatized in such a way as to facilitate the immunogenic response (i.e., antibody production). In one embodiment, the LPA may be derivatized in order to allow conjugation of the LPA molecule to a carrier molecule. In one embodiment, a carbon atom within the hydrocarbon chain of the LPA is derivatized with a pendant reactive group [e.g., a sulfhydryl(thiol) group, a carboxylic acid group, a cyano group, an ester, a hydroxy group, an alkene, an alkyne, an acid chloride group or a halogen atom] that may or may not be protected. This derivatization serves to activate the bioactive lipid for reaction with a molecule, e.g., for conjugation to a carrier. In one embodiment, the derivatized LPA is thiolated LPA. In one embodiment, the derivatized LPA is derivatized C12 or C18 LPA. In one embodiment, the thiolated LPA is conjugated via a crosslinker, e.g., a bifunctional crosslinker such as IOA or SMCC, to a carrier, which may be a protein. It may be useful to conjugate the LPA in this way to a protein or other carrier that is immunogenic in the species to be immunized, e.g., keyhole limpet hemocyanin (KLH), serum albumin (including bovine serum albumin or BSA), bovine thyroglobulin, or soybean trypsin inhibitor, using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups. Non-protein carriers (e.g., colloidal gold) are also known in the art for use in antibody production.

The derivatized or derivatized and conjugated LPA may be used to generate anti-LPA antibodies (polyclonal and/or monoclonal). The derivatized or derivatized and conjugated LPA may also be used in the methods of the invention, particularly in diagnostic methods.

2. Research and Diagnostic Uses for Derivatized LPA

The derivatized LPAs may be used to detect and/or purify anti-LPA antibodies and may be conjugated to a carrier as described above. The derivatives and conjugates are preferably conjugated to a solid support for use in diagnostic methods, including clinical diagnostic methods. For example, detection and/or quantitation of LPA antibodies may be used in diagnosing various medical conditions in LPA plays a role. Quantitation of LPA antibodies is also useful in a clinical setting to evaluate dosing, halflife and drug levels after treatment with, e.g., an anti-LPA antibody such as LT3000 described herein.

In one embodiment, the derivatized LPA conjugate (e.g., thiolated LPA conjugated to BSA or KLH) is used as laydown material in ELISAs which are used to detect anti-LPA antibodies. In one embodiment the LPA is thiolated C12 LPA or thiolated C18 LPA conjugated to BSA. This embodiment is useful, for example, as laydown material (to coat the plate) in ELISA assays for detection of LPA. For example, in an LPA competitive ELISA, the plate is coated with derivatized and/or derivatized and conjugated LPA. A set of one or more LPA standards and one or more samples (e.g., serum or cell culture supernatant) is mixed with the mouse anti-LPA antibody of the invention and added to the derivitized-LPA-coated plate. The antibody competes for binding to either plate-bound LPA or LPA in the sample or standard. Following incubation and several ELISA steps, the absorbance at 450 nm is measured and the LPA concentration in the samples is determined by comparison to the standard curve.

The derivatized or derivatized and conjugated LPA may also be coupled to a solid support (e.g., resin or other column matrix, beads, membrane, plate) and used to isolate and/or purify anti-LPA antibodies, e.g., from blood or serum. Such anti-LPA antibodies may be newly generated antibodies such as those of the invention (e.g., mammalian monoclonal or polyclonal antibodies to LPA) or may be native human anti-LPA antibodies.

Thus the derivatized LPA and derivatized and conjugated LPA of the invention are useful both for research and in clinical diagnostics.

3. Diagnostic Kits Incorporating Derivatized LPA

As a matter of convenience, the derivatized LPAs of the present invention can be provided in a kit, for example, a packaged combination of reagents in predetermined amounts with instructions for performing the diagnostic assay.

As described above, In one embodiment, the derivatized LPA conjugate (e.g., thiolated LPA conjugated to BSA or KLH) is used as laydown material (to coat the plate) in ELISA kits which are used to detect anti-LPA antibodies. Such kits are useful for detection of LPA. For example, in an LPA competitive ELISA kit, the plate (provided) is coated with derivatized and/or derivatized and conjugated LPA. A set of one or more LPA standards (generally provided in the kit) and one or more samples (e.g., serum or cell culture supernatant) is mixed with the mouse anti-LPA antibody of the invention and added to the derivitized-LPA-coated plate. The antibody competes for binding to either plate-bound LPA or LPA in the sample or standard. Following incubation and several ELISA steps (instructions and reagents for which are provided in the kit), the absorbance at 450 nm is measured and the LPA concentration in the samples is determined by comparison to the standard curve. In one embodiment the LPA used for laydown material in the ELISA kit is thiolated C12 LPA or thiolated C18 LPA conjugated to BSA. The antibody used in the kit may be polyclonal or monoclonal antibody, preferably a monoclonal antibody.

A kit incorporating an Lpath derivatized and conjugated LPA of the invention and an Lpath anti-LPA antibody of the invention, is commercially available from Echelon Biosciences, Inc., Salt Lake City, Utah (Lysophosphatidic Assay Kit, Cat. No. K-2800).

B. Anti-LPA Agents, Including Anti-LPA Antibodies

1. Introduction

The use of monoclonal antibodies (mAbs) as a therapeutic treatment for a variety of diseases and disorders is rapidly increasing because they have been shown to be safe and efficacious therapeutic agents. Approved therapeutic monoclonal antibodies include Avastin™, Erbitux™, and Rituxan™. Additional monoclonal antibodies are in various phases of clinical development for a variety of diseases with the majority targeting various forms of cancer. In general, monoclonal antibodies are generated in non-human mammals. The therapeutic utility of murine monoclonal antibodies may be improved with chimerization or humanization of non-human mammalian antibodies. Humanization greatly lessens the development of an immune response against the administered therapeutic monoclonal antibodies and thereby avoids the reduction of half-life and therapeutic efficacy consequent on such a response. For the most part, the humanization process consists of grafting the murine complementary determining regions (CDRs) into the framework region (FR) of a human immunoglobulin. Backmutation to murine amino acid residues of selected residues in the FR is often required to improve or regain affinity that is lost in the initial grafted construct.

The manufacture of monoclonal antibodies is a complex process that stems from the variability of the immunoglobulin protein itself. The heterogeneity can be attributed to the formation of alternative disulfide pairings, deamidation and the formation of isoaspartyl residues, methionine and cysteine oxidation, cyclization of N-terminal glutamine residues to pyroglutamate and partial enzymatic cleavage of C-terminal lysines by mammalian carboxypeptidases. Engineering is commonly applied to antibody molecules to improve their properties, such as enhanced stability, resistance to proteases, aggregation behavior and enhance the expression level in heterologous systems.

2. Disease Associations of LPA and Therapeutic Uses for Anti-LPA Agents

LPA has been associated with a number of diseases and disorders. For review, see Gardell et al., (2006) Trends Mol Med. 12(2):65-75 and Chun J. and Rosen, H., (2006) Curr. Pharma. Design 12:161-171. These include autoimmune disorders such as diabetes, multiple sclerosis and scleroderma; hyperproliferative disorders including cancer; disorders associated with angiogenesis and neovascularization; obesity; neurodegenerative diseases including Alzheimer's disease; schizophrenia, immune-related disorders such as transplant rejection and graft-vs.-host disease, and others.

a. Hyperproliferative Disorders

One aspect of the invention concerns methods for treating hyperproliferative disorders. These methods comprise administering to a mammal (e.g., a bovine, canine, equine, ovine, or porcine animal, particularly a human) known or suspected to suffer from an LPA-associated hyperproliferative disorder a therapeutically effective amount of a composition comprising an agent that interferes with LPA concentration and/or activity, preferably in a pharmaceutically or veterinarily acceptable carrier, as the intended application may require. LPA-associated hyperproliferative disorders include neoplasias, disorders associated with endothelial cell proliferation, and disorders associated with fibrogenesis. Most often, the neoplasia will be a cancer. Typical disorders associated with endothelial cell proliferation are angiogenesis-dependent disorders, for example, cancers caused by a solid tumors, hematological tumors, and age-related macular degeneration. Disorders associated with fibrogenesis include those than involve aberrant cardiac remodeling, such as cardiac failure.

There are many known hyperproliferative disorders, in which cells of various tissues and organs exhibit aberrant patterns of growth, proliferation, migration, signaling, senescence, and death. While a number of treatments have been developed to address some of these diseases, many still remain largely untreatable with existing technologies, while in other cases, while treatments are available, they are frequently less than optimal and are seldom curative.

Cancer represents perhaps the most widely recognized class of hyperproliferative disorders. Cancers are a devastating class of diseases, and together, they have a mortality rate second only to cardiovascular disease. Many cancers are not fully understood on a molecular level. As a result, cancer is a major focus of research and development programs for both the United States government and pharmaceutical companies. The result has been an unprecedented R&D effort and the production of many valuable therapeutic agents to help in the fight against cancer.

Unfortunately the enormous amount of cancer research has not been enough to overcome the significant damage caused by cancer. There are still over one million new cases of cancer diagnosed annually and over five hundred thousand deaths in the United States alone. This is a dramatic demonstration that even though an enormous effort has been put forth to discover new therapeutics for cancer, effective therapeutic agents to combat the disease remain elusive.

Cancer is now primarily treated with one or a combination of three types of therapies, surgery, radiation, and chemotherapy. Surgery involves the bulk removal of diseased tissue. While surgery is sometimes effective in removing tumors located at certain sites, for example, in the breast, colon, and skin, it cannot be used in the treatment of tumors located in other areas, such as the backbone, nor in the treatment of disseminated neoplastic conditions such as leukemia. Radiation therapy involves the exposure of living tissue to ionizing radiation causing death or damage to the exposed cells. Side effects from radiation therapy may be acute and temporary, while others may be irreversible. Chemotherapy involves the disruption of cell replication or cell metabolism.

Further insult is that current therapeutic agents usually involve significant drawbacks for the patient in the form of toxicity and severe side effects. Therefore, many groups have recently begun to look for new approaches to fighting the war against cancer. These new so-called "innovative therapies" include gene therapy and therapeutic proteins such as monoclonal antibodies.

The first monoclonal antibody used in the clinic for the treatment of cancer was Rituxan (rituximab) which was launched in 1997, and has demonstrated the utility of monoclonal antibodies as therapeutic agents. Thus, not surprisingly, twenty monoclonal antibodies have since been approved for use in the clinic, including nine that are prescribed for cancer. The success of these products, as well as the reduced cost and time to develop monoclonal antibodies as compared with small molecules has made monoclonal antibody therapeutics the second largest category of drug candidates behind small molecules. Further, the exquisite specificity of antibodies as compared to small molecule therapeutics has proven to be a major advantage both in terms of efficacy and toxicity. For cancer alone there are currently more than 270 industry antibody R&D projects with more than 50 companies involved in developing new cancer antibody therapeutics. Consequently, monoclonal antibodies are poised to become a major player in the treatment of cancer and they are estimated to capture an increasing share of the cancer therapeutic market. Generally therapeutic mAbs are targeted to proteins; only recently has it been feasible to raise mAbs to bioactive lipids (for example, antibodies to S1P, see Applicants' US Application Serial No. 20070148168).

The identification of extracellular mediators that promote tumor growth and survival is a critical step in discovering therapeutic interventions that will reduce the morbidity and mortality of cancer. As described below, LPA is considered to be a pleiotropic, tumorigenic growth factor. LPA promotes tumor growth by stimulating cell proliferation, cell survival, and metastasis. LPA also promotes tumor angiogenesis by supporting the migration and survival of endothelial cells as they form new vessels within tumors. Taken together, LPA initiates a proliferative, pro-angiogenic, and anti-apoptotic sequence of events contributing to cancer progression. Thus, therapies that modulate, and, in particular, reduce LPA levels in vivo will be effective in the treatment of cancer.

Typically, the methods of the invention for treating or preventing a hyperproliferative disorder such as cancer involve administering to a subject suffering from a hyperproliferative disorder an effective amount of each of an agent (or a plurality of different agent species) according to the invention and a cytotoxic agent. Cytotoxic agents include chemotherapeutic drugs.

A related aspect concerns methods of reducing toxicity of a therapeutic regimen for treatment or prevention of a hyperproliferative disorder. Such methods comprise administering to a subject suffering from a hyperproliferative disorder an effective amount of an agent (or a plurality of different agent species) according to the invention before, during, or after administration of a therapeutic regimen intended to treat or prevent the hyperproliferative disorder. It is believed that by sensitizing cells, e.g., cancer cells, to chemotherapeutic drugs, efficacy can be achieved at lower doses and hence lower toxicity due to chemotherapeutic drugs.

Yet another aspect of the invention concerns methods of enhancing a survival probability of a subject treated for a hyperproliferative disorder by administering to a subject suffering from a hyperproliferative disorder an agent (or a plurality of different agent species) according to the invention before, during, or after administration of a therapeutic regimen intended to treat or prevent the hyperproliferative disorder to enhance the subject's survival probability.

3. Fibrosis, Wound Healing and Scar Formation

Fibroblasts, particularly myofibroblasts, are key cellular elements in scar formation in response to cellular injury and inflammation (Tomasek et al. (2002), Nat Rev Mol Cell Biol, vol 3: 349-63, and Virag and Murry (2003), Am J Pathol, vol 163: 2433-40). Collagen gene expression by myofibroblasts is a hallmark of remodeling and necessary for scar formation (Sun and Weber (2000), Cardiovasc Res, vol 46: 250-6, and Sun and Weber (1996), J Mol Cell Cardiol, vol 28: 851-8).

Fibrosis can be described as the formation or development of excess or aberrant fibrous connective tissue in an organ or tissue as part of a pathological reparative or reactive process, in contrast to normal wound healing or development. The most common forms of fibrosis are: liver, lung, kidney, skin, uterine and ovarian fibroses. Some conditions, such as scleroderma, sarcoidosis and others, are characterized by fibrosis in multiple organs and tissues.

Recently, the bioactive lysophospholipid lysophosphatidic acid (LPA) has been recognized for its role in tissue repair and wound healing. Watterson et al., Wound Repair Regen. (2007) 15:607-16. As a biological mediator, LPA has been recognized for its role in tissue repair and wound healing (Watterson, 2007). In particular, LPA is linked to pulmonary and renal inflammation and fibrosis. LPA is detectable in human bronchioalveolar lavage (BAL) fluids at baseline and its expression increases during allergic inflammation Georas, S, N. et al. (2007) Clin Exp Allergy. (2007) 37: 311-22. Furthermore, LPA promotes inflammation in airway epithelial cells. Barekzi, E. et al (2006) Prostaglandins Leukot Essent Fatty Acids. 74:357-63. Recently, pulmonary and renal fibrosis have been linked to increased LPA release and signaling though the LPA type 1 receptor ($LPA_1$). LPA levels were elevated in bronchialveolar lavage (BAL) samples from IPF patients and bleomycin-induced lung fibrosis in mice was dependent on activation of $LPA_1$. Tager et al., (2008) Proc Am Thorac Soc. 5: 363. (2008) Following unilateral ureteral obstruction in mice, tubulointerstitial fibrosis was reduced in $LPA_1$ knock-out mice and pro-fibrotic cytokine expression was attenuated in wild-type mice treated with an $LPA_1$ antagonist. J. P. Pradere et al., (2007) J. Am. Soc. Nephrol. 18:3110-3118. LPA has been shown to have direct fibrogenic effects in cardiac fibroblasts by stimulating collagen gene expression and proliferation. Chen, et al. (2006) FEBS Lett. 580:4737-45. Combined, these studies demonstrate a role for LPA in tissue repair and fibrosis, and identify bioactive lipids as a previously unrecognized class of targets in the treatment of fibrotic disorders.

a. Scleroderma

The compositions and methods of the invention will be useful in treating disorders and diseases characterized, at least in part, by aberrant neovascularization, angiogenesis, fibrogenesis, fibrosis, scarring, inflammation, and immune response. One such disease is scleroderma, which is also referred to as systemic sclerosis.

Scleroderma is an autoimmune disease that causes scarring or thickening of the skin, and sometimes involves other areas of the body, including the lungs, heart, and/or kidneys. Scleroderma is characterized by the formation of scar tissue (fibrosis) in the skin and organs of the body, which can lead to thickening and firmness of involved areas, with consequent reduction in function. Today, about 300,000 Americans have scleroderma, according to the Scleroderma Foundation. One-third or less of those affected have widespread disease, while the remaining two-thirds primarily have skin symptoms. When the disease affects the lungs and causing scarring, breathing can become restricted because the lungs can no longer expand as they should. To measure breathing capability, doctors use a device that assesses forced vital capacity (FVC). In people with an FVC of less than 50 percent of the expected reading, the 10-year mortality rate from scleroderma-related lung disease is about 42 percent. One reason the mortality rate is so high is that no effective treatment is currently available.

Without wishing to be bound by any particular theory, it is believed that inappropriate concentrations of lipids such as S1P and for LPA, and/or their metabolites, cause or contribute to the development of scleroderma. As such, the compositions and methods of the invention can be used to treat scleroderma, particularly by decreasing the effective in vivo concentration of a particular target lipid, for example, LPA.

Evidence indicates that LPA is a pro-fibrotic growth factor that can contribute to fibroblast activation, proliferation, and the resulting increased fibroblast activity associated with maladaptive scarring and remodeling. Moreover, potential roles for LPA in skin fibroblast activity have been demonstrated. For example, it has been shown that LPA stimulates the migration of murine skin fibroblasts (Hama et al., J Biol. Chem. 2004 Apr. 23; 279(17):17634-9).

b. Pulmonary Fibrosis

Pulmonary fibrosis, sometimes referred to as interstitial lung disease or ILD, affects more than 5 million people worldwide. Within the USA the prevalence of the disease seems to be under-estimated and vary from 3 to 6 cases for 100,000 inhabitants to 28 per 100,000. Within Europe; the numbers vary depending on the countries, and is reported around 1 to 24 cases per 100,000 without a clear gender effect. The disease is usually diagnosed between 40 and 70 years of age. The median survival is 3 to 5 years. Despite its prevalence, there are no therapies available to halt or reverse the progression of IPF and there are no FDA-approved courses of treatment. Thus, there is an unmet need for new therapeutic strategies to treat IPF as well as other diseases that involve pathological tissue fibrosis.

Interstitial lung disease, or ILD, includes more than 180 chronic lung disorders, which are chronic, nonmalignant and noninfectious. Interstitial lung diseases are named for the tissue between the air sacs of the lungs called the interstitium—the tissue affected by fibrosis (scarring). Interstitial lung diseases may also be called interstitial pulmonary fibrosis or pulmonary fibrosis. The symptoms and course of these diseases may vary from person to person, but the common link between the many forms of ILD is that they all begin with an inflammation, e.g.: bronchiolitis—inflammation that involves the bronchioles (small airways); alveolitis—inflammation that involves the alveoli (air sacs); vasculitis—inflammation that involves the small blood vessels (capillaries)

More than 80% of interstitial lung diseases are diagnosed as pneumoconiosis, drug-induced disease, or hypersensitivity pneumonitis. The other types are:

Occupational and environmental exposures: Many jobs, particularly those that involve working with asbestos, ground stone, or metal dust, can cause pulmonary fibrosis. The small particles are inhaled, damage the alveoli, and cause fibrosis. Some organic substances, such as moldy hay can also initiate pulmonary fibrosis; this is known as farmer's lung.

Asbestosis is usually caused when small needle-like particles of asbestos are inhaled into the lungs. This can cause lung scarring (pulmonary fibrosis) and in addition can lead to lung cancer. The key to asbestosis is prevention. In manufacturing asbestos products, both employer and employee must be aware of government standards and should take all precautions against inhaling the particles. The paramount danger in working with asbestos comes when old, friable (crumbly) asbestos-containing products are replaced or destroyed. In those circumstances, particles can be released into the air and breathed into the lungs. Today however, the asbestos fibres usually are "locked in" by binders such as cement, rubber or plastics, thus preventing the particles from floating free in the air. Cigarette smoking has an interactive relationship with asbestos—the asbestos worker who smokes has a much higher chance of developing lung cancer than does the non-smoker.

Silicosis is another disease producing pulmonary fibrosis in which the cause is known. It is a disease that results from breathing in free crystalline silica dust. All types of mining in which the ore is extracted from quartz rock can produce silicosis if precautions are not taken. This includes the mining of gold, lead, zinc, copper, iron, anthracite (hard) coal, and some bituminous (soft) coal. Workers in foundries, sandstone grinding, tunneling, sandblasting, concrete breaking, granite carving, and china manufacturing also encounter silica.

Large silica particles are stopped in the upper airways. But the tiniest specks of silica can be carried down to the alveoli where they lead to pulmonary fibrosis. Silicosis can be either mild or severe, in direct proportion to the percentage and concentration of silica in the air and the duration of exposure. Silicosis can be prevented by measures specifically designed for each industry and each job. Dust control is essential. Sometimes this is accomplished by the wetting down of mines, improved ventilation, or the wearing of masks.

Idiopathic pulmonary fibrosis: Although a number of separate diseases can initiate pulmonary fibrosis, many times the cause is unknown. When this is so, the condition is called "idiopathic (of unknown origin) pulmonary fibrosis". In idiopathic pulmonary fibrosis, careful examination of the patient's environmental and occupational history gives no clues to the cause. Some physicians and scientists believe that the disease is an infectious or allergic condition, however bacteria and other microorganisms are not routinely found in the lungs of such patients. On the other hand, the condition does sometimes appear to follow a viral-like illness. Thus, although the cause of pulmonary fibrosis is known in many cases, the idiopathic variety still remains a mystery.

Sarcoidosis is disease characterized by the formation of granulomas (areas of inflammatory cells), which can attack any area of the body but most frequently affects the lungs.

Certain medicines may have the undesirable side effect of causing pulmonary fibrosis; for example, Nitrofurantoin (sometimes used for urinary tract infections); Amiodarone (sometimes prescribed for an irregular heart rate); Bleomycin, cyclophosphamide, and methotrexate (sometimes prescribed to fight cancer).

Radiation, such as given as treatment for breast cancer, may also cause pulmonary fibrosis. Other diseases characterized, at least in part, by pulmonary fibrosis include tuberculosis, rheumatoid arthritis, systemic lupus erythematosis, systemic sclerosis, grain handler's lung, mushroom worker's lung, bagassosis, detergent worker's lung, maple bark stripper's lung, malt worker's lung, paprika splitter lung, bird breeder's lung and Hermansky Pudlak syndrome. Pulmonary fibrosis can also be genetically inherited.

Clinical Features:

Breathlessness is the hallmark of pulmonary fibrosis. Many lung diseases show breathlessness as the main symptom—a fact that can complicate and confuse diagnosis. Usually the breathlessness idiopathic pulmonary fibrosis first appears during exercise. The condition may progress to the point where any exertion is impossible. A dry cough is a common symptom. The fingertips may enlarge at the ends and take on a bulbous appearance. This is often referred to as "clubbing".

Additional symptoms may include: shortness of breath, especially with exertion, fatigue and weakness, loss of appetite, loss of weight, dry cough that does not produce phlegm, discomfort in chest, labored breathing and hemorrhage in lungs.

Diagnosis

In addition to a complete medical history and physical examination, the following tests maybe required to refine and/or confirm the diagnosis of pulmonary fibrosis: pulmonary function tests—to determine characteristics and capabilities of the lungs; spirometry—to measure the amount of air that can be forced out; peak flow meter—to evaluate changes in breathing and response to medications; blood tests—to analyze the amount of carbon dioxide and oxygen in the blood; X-ray; computerized axial tomography (CAT) scan; bronchoscopy—to examine the lung using a long, narrow tube called a bronchoscope; bronchoalveolar lavage—to remove cells from lower respiratory tract to help identify inflammation and exclude certain causes; and lung biopsy—to remove tissue from the lung for examination in the pathology laboratory.

Treatment

If one of the known causes of pulmonary fibrosis exists, then treatment of that underlying disease or removal of the patient from the environment causing the disease can be effective. This may include treatment with: oral medications, including corticosteroids; influenza vaccine; pneumococcal pneumonia vaccine, oxygen therapy from portable tanks and/or lung transplantation.

Many times treatment is limited only to treating the inflammatory response that occurs in the lungs. This is done in the hope that stopping the inflammation will prevent the laying down of scar tissue or fibrosis in the lungs and thus stop the progression of the disease.

Corticosteroids are the drugs which are usually administered in an attempt to stop the inflammation. The advantage of this treatment has not been proven in every case, although it does appear that if the drugs are given early on in the course of the disease, there is a better chance of improvement. Corticosteroid medications can have various side effects and so patients taking these medications must be frequently reassessed by their physicians in order to judge the safety and benefit of this therapy.

Other drugs have been tried but convincing evidence of their efficacy is lacking. Drug therapy of pulmonary fibrosis may not always be successful, and so supportive (non-medication) therapy may be used to ease the breathlessness that accompanies this condition.

LPA and Pulmonary Fibrosis

Although the exact etiology is not known, IPF is believed to result from an aberrant wound healing response following pulmonary injury. Scotton, C. J. and Chambers, R. C. (2007) Chest, 132:1311-21. In particular, increased proliferation and migration of lung fibroblasts as well as the formation of scar tissue-producing myofibroblasts are key events in the pathogenesis of IPF. Myofibroblasts are smooth muscle-like fibroblasts that express alpha-smooth muscle actin ($\alpha$-SMA) and contain a contractile apparatus composed of actin filaments and associated proteins that are organized into prominent stress fibers. In addition to their normal role in tissue homeostasis and repair, myofibroblasts are pathological mediators in numerous fibrotic disorders. Hinz, B. (2007) J Invest Dermatol. 127:526-37. Increased number and density of myofibroblasts has been demonstrated in the fibrotic foci of animal models of lung fibrosis. Myofibroblasts are formed following tissue injury whereby increased levels of growth factors, cytokines and mechanical stimuli promote transformation of resident tissue fibroblasts into contractile, scar tissue-producing myofibroblasts. In the lung and other tissues, persistent, elevated levels of biochemical mediators including TGF$\beta$, CTGF, PDGF and various inflammatory cytokines, promotes myofibroblast formation and exaggerated scar tissue production which leads to tissue fibrosis (Scotton, 2007). Thus, current clinical strategies for treating IPF and other fibrotic disorders have targeted biochemical factors that promote myofibroblast formation and subsequent fibrous tissue production.

Recently, the bioactive lysophospholipid lysophosphatidic acid (LPA) has been recognized for its role in tissue repair and wound healing (Watterson, 2007). LPA is a bioactive lysophospholipid (<500 Dalton) with a single hydrocarbon backbone and a polar head group containing a phosphate group. LPA elicits numerous cellular effects through the interaction with specific G protein-coupled receptors (GPCR), designated EGD2/$LPA_1$, EDG4/$LPA_2$, EDG7/$LPA_3$, and $LPA_4$: Anliker B. and J. Chun, (2004) Seminars in Cell & Developmental Biology, 15: 457-465. As a biological mediator, LPA has been recognized for its role in tissue repair and wound healing (Watterson, 2007). In particular, LPA is linked to pulmonary and renal inflammation and fibrosis. LPA is detectable in human bronchioalveolar lavage (BAL) fluids at baseline and its expression increases during allergic inflammation (Georas, 2007). Furthermore, LPA promotes inflammation in airway epithelial cells (Barekzi, 2006). Recently, pulmonary and renal fibrosis have been linked to increased LPA release and signaling though the LPA type 1 receptor ($LPA_1$). LPA levels were elevated in bronchialveolar lavage (BAL) samples from IPF patients and bleomycin-induced lung fibrosis in mice was dependent on activation of $LPA_1$ (Tager, 2008). Following unilateral ureteral obstruction in mice, tubulointerstitial fibrosis was reduced in $LPA_1$ knockout mice and pro-fibrotic cytokine expression was attenuated in wild-type mice treated with an $LPA_1$ antagonist (Pradere, 2007). Combined, these studies demonstrate a role for LPA in tissue repair and fibrosis, and identify bioactive lipids as a previously unrecognized class of targets in the treatment of IPF and other fibrotic disorders.

c. Hepatic (Liver) Fibrosis

The liver possesses a remarkable regenerative capacity, therefore the process of repair by regeneration proceeds to complete restitutio ad integrum (full restoration). If however the damage has affected the reticular framework, the repair will occur by scar formation (fibrosis) which may lead to rearrangement of the blood circulation and to cirrhosis.

The reaction to injury proceeds as is follows: Damage (necrosis), accompanied by cellular changes and tissue changes; inflammatory reaction; and repair (either by regeneration (restitutio ad integrum) or by scarring (fibrosis).

Chronic liver diseases lead to fibrosis which leads to disturbance of the architecture, portal hypertension and may produce such an irreversible rearrangement of the circulation as to cause cirrhosis. There is a fine line between fibrosis and cirrhosis. Fibrosis is not only the result of necrosis, collapse and scar formation but also the result of disturbances in the synthesis and degradation of matrix by injured mesenchymal cells that synthesize the various components of the matrix which in the liver are the following categories: collagens, glycoproteins and proteoglycans.

Evaluation of Liver Fibrosis

Evaluation of liver fibrosis can be histological, e.g., with Masson trichrome stain, silver reticulin stain, specific antibodies for collagen types, desmin and vimentin for lipocytes, or vimentin for myofibroblasts, or may be biochemical, e.g, by: determination of various enzymes in matrix or of serum laminin in benign fibrosis.

Classifications of Liver Fibrosis

There are 2 main types, congenital and acquired liver fibrosis. The former is a genetic disorder, which causes polycystic liver diseases. The latter has many different categories and is mainly caused by liver cell injuries. Pathologically, fibrosis can be classified as:

Portal area fibrosis: There is fibroblasts proliferation and fibers expansion from the portal areas to the lobule. Finally, these fibers connected to form bridging septa. This kind of fibrosis is mainly seen in viral hepatitis and malnutritional liver fibrosis.

Intra-lobular fibrosis: There is almost no fibroblast found in normal lobule. When large numbers of liver cells degenerate and undergo necrosis, the reticular fiber frame collapses and becomes thick collagen fibers. At the same time, intra lobule fibrotic tissue proliferates and surrounds the liver cells.

Central fibrosis: Proliferated fibrotic tissue mainly surrounds the center vein and causes the thickening of the wall of the center vein.

Peri-micro-bile-duct fibrosis: Type fibrosis mainly caused by long-term bile retention and mainly happens around the bile ducts. Microscopically, there are connective tissues surrounding the newly formed bile canaliulus and bile-plugs. The base-membrane of the bile canaliulus becomes fibrotic.

Immunologically, liver fibrosis can be classified as:

Passive fibrosis: There is extensive necrosis of the liver cells and secondary liver structure collapse and scar formation, which causes connective tissue proliferation.

Active fibrosis: Lymph cells and other inflammatory cells infiltration and recurrent and consistent inflammation promote the connective tissue to invade the lobule.

Causally, liver fibrosis can be classified as:

Viral hepatitis fibrosis: Usually caused by chronic hepatitis B, C, and D. Worldwide, there are three hundred fifty million of hepatitis B virus carriers, and one hundred seventy million of hepatitis C infected people. About 15% of HBV and 85% of HCV infected persons will develop chronic hepatitis and lead to fibrosis. In which, the liver shows peri-portal area inflammation and piece-meal necrosis and fibrosis. With such large population being affected, this is the most important category of the liver fibrosis.

Parasitic infection fibrosis: This kind of liver fibrosis is mainly happening in developing countries and is caused by schistosomiasis. There are two hundred and twenty million people in Asia, Africa, South and Center America suffering from this infection. The recurrent infection and the eggs of schistosome accumulated in the liver can cause liver fibrosis and cirrhosis.

Alcoholic fibrosis: It is mainly caused by the oxidized metabolite of alcohol, acetaldehyde. In western countries, the incidence of this disorder is positively related to the amount of alcohol consumption. The total cases of alcoholic fibrosis in the USA is about three times higher than the number of hepatitis C. Alcoholic fibrosis causes two morphological changes in the liver: fatty liver and cellular organelles deterioration. The fibrosis first appears around the center veins and at the same time, the liver parenchymal inflammation. Gradually the fibrosis expends to the whole liver.

Biliary fibrosis: There is primary and secondary biliary fibrosis. Primary biliary hepatic fibrosis (PBHF) is an autoimmune disorder in which chronic intra-liver bile retention caused the liver fibrosis. It is more often affect female around the age 40 to 60. In serum tests, elevated gamma globulin and positive for the anti-mitochondria antibody. Pathological studies found that the fibrosis mainly around the micro-bile ducts and peri-portal area fibrosis and inflammation. Secondary biliary fibrosis happens following the obstruction of the bile ducts, which causes peri-portal inflammation and progressive fibrosis.

Metabolic fibrosis: This category is not common and has fewer cases. Wilson's disease or liver lenticular degeneration and hemochromatosis are the main disorders that cause metabolic fibrosis. The former is a genetic disorder and causes cooper metabolism disorder and deposits in the liver. The latter is an iron metabolic disorder and causes hemoglobin deposits in the liver. Both of these metabolic disorders can cause liver fibrosis and cirrhosis.

Intoxication fibrosis: When long-term contact with liver-toxic substances, such as carbon-tetrachloride, organophosphorus, dimethyl nitrosamine, thioacetamide, or taking liver toxic medications, such as isoniazid, thio-oxidizing pyrimidine, wintermin, tetracycline, acetaminophen etc. can all cause various degrees of liver cell injuries, necrosis, bile retention, or allergic inflammation and cause liver fibrosis.

Malnutritional fibrosis: This type is mainly caused by insufficient or imbalanced nutritional intake. A long-term low protein or high fat diet can cause fatty liver and lead to fibrosis.

Cardiogenic fibrosis: Chronic congestive heart failure can cause long lasting liver vein stagnancy causing ischemic degeneration of the liver cells. In this type of liver fibrosis, the connective tissue hypertrophy starts at the center of the liver lobule and gradually expands to rest of the lobule.

Diagnosis and Staging of Liver Fibrosis

The gold standard for assessing the health of the liver is the liver biopsy. However since the procedure requires that a needle be inserted through the skin there is a potential for complications even though the incidence of complications is extremely low. The complications of a liver biopsy can include internal bleeding, and puncturing another organ such as the lungs, stomach, intestines, or any other organs that are close to the liver. In regards to accuracy of the biopsy the sample liver tissue size is important for correctly staging and grading a liver biopsy. Another problem is that the tissue taken from one part of the liver may not be 100% representative of the entire liver. Once the liver tissue sample is collected it is graded and staged by a specialist (pathologist), which could lead to possible human error in interpreting the results. In addition there is no standardized interpretation protocol so it is difficult to compare the results of different biopsies read by different pathologists. Price is also an issue since a typical liver biopsy can cost between $1,500 and $2,000.

Given these potential problems it is not surprising that there is a lot of research that is being conducted on the development of non-invasive tests. The tests that have been developed so far have had mixed results in accuracy when compared to the results of a liver biopsy. There have been few prospective clinical trials that have compared the results from various non-invasive markers to the results from a liver biopsy.

In order to objectively evaluate the stage of fibrosis, liver biopsy, especially a series of biopsies, is the main method used today. From the biopsy, it is possible to diagnose the liver inflammation grade and also the stage of the fibrosis. The most commonly used scoring system is Kanel scoring system, which stages the fibrosis from 0 to 5. (At the same time the biopsy diagnosis also give a ranking of inflammation grade, which is from 0 to 4) Stage 0: normal; Stage 1: portal expansion with fibrosis (<⅓ tracts with wisps of bridging); Stage 2: bridging fibrosis; Stage 3: marked bridging fibrosis or early cirrhosis (with thin septa fibrosis); Stage 4: definite cirrhosis with <50% of biopsy fibrosis; Stage 5: definite cirrhosis with >50% of biopsy fibrosis.

Blood tests to diagnose liver fibrosis: Because biopsy is an invasive procedure, many patients are wary of the procedure. Blood tests are being studied as a method to evaluate the fibrosis progression. The most commonly used serum chemical analysis method is by measuring the amount of HA (hyaluronic acid), LN (Laminin), CIV (collagen IV), PCIII (procollagen type III) in the serum. They can be used as a reference index of fibrosis activities. From the blood tests, the ratio of AST/ALT is found and when it is greater than 1, it often shows that the degree of fibrosis is relatively advanced. Combined with whether is there an enlarged spleen and depletion of platelets count and albumin level, we can also estimate the stage of the fibrosis. In advanced fibrosis, the spleen is usually enlarged with platelets counts lower than 100 and albumin lower than 3.5. With blood test results, the evaluation of the severity of fibrosis is only useful to access the stage 0, 1 and 3, 4, and 5. It is not able to distinguish the stages between 2 and 3.

Medical imagery diagnosis B-ultrasonic, CT, and MRI can also be used to evaluate the liver fibrosis. The B-ultrasonic image is often used to check the size of the spleen, measure the diameter of the main stern of the portal vein, the diameters of right and left portal vein branches, the diameter of vein at the portal of the spleen, and the blood flow speed of the portal vein. GI endoscopies can be used to see whether varices exists in the stomach and esophagus. These can be used as a reference for the hepatologist to evaluate the stage of fibrosis.

In general, the term fibrosis refers to the abnormal formation of fibrous (scar) tissue. For hepatitis patients, fibrosis means that the liver has been under assault by the hepatitis for some time. Early stages of fibrosis are identified by discrete, localized areas of scarring in one portal (zone) of the liver. Later stages of fibrosis are identified by "bridging" fibrosis, which is scar tissue that crosses across zones of the liver. The rate at which people progress from inflammation to fibrosis, and eventually to cirrhosis seems to vary tremendously, but in most people the progression is very slow. There is a growing body of evidence that people who respond to interferon therapy for HCV infection may experience a decrease in the amount of tissue scarring. This speaks to the liver's ability to regenerate itself. If fibrosis advances far enough, it is described as Cirrhosis. Liver biopsy is conducted to assess the degree of inflammation (grade) and degree of scarring (stage). Diagnosis: One of the major clinical problems facing the hepatology and gastroenterology community is how best to evaluate and manage the increasing numbers of patients identified with hepatitis C virus (HCV). In the last decade, advances in serologic and virologic testing for HCV and improvements in therapy have led more patients to be identified and to seek treatment. However, little progress has been made in improving either our ability to determine the degree of hepatic injury, particularly fibrosis, or to predict the risk of disease progression for the individual patient.

The clinician relies on the biopsy results for both prognostic and therapeutic decision making, which can have a major impact on the patient's life. A single-pass liver biopsy is able to correctly diagnose the stage of fibrosis or presence of cirrhosis in 80% of patients. Factors that improve the diagnostic accuracy of liver biopsy include the presence of a uniform disease throughout the liver such as HCV, multiple passes, type of needle used, and an unfragmented biopsy core of 2 cm or greater in length. Even with experienced physicians performing the liver biopsy and expert pathologists interpreting the biopsy, this gold standard has up to a 20% error rate in staging disease.

d. Renal (Kidney) Fibrosis

LPA is linked to renal inflammation and fibrosis. Recently, renal fibrosis has been linked to increased LPA release and signaling though the LPA type 1 receptor ($LPA_1$). Following unilateral ureteral obstruction in mice, tubulointerstitial fibrosis was reduced in $LPA_1$ knock-out mice and pro-fibrotic cytokine expression was attenuated in wild-type mice treated with an $LPA_1$ antagonist (Pradere, 2007).

e. Other fibroses

Uterine fibroses are non-malignant tumors known as uterine leiomyomata (commonly called fibroids). They can be isolated or grow in clusters, with sizes varying from the size of an apple seed to the size of a grapefruit or larger. Diagnosis of uterine fibroids is generally achieved by ultrasound, X-rays, CAT scan, laparoscopy and/or hysteroscopy. Treatment of uterine fibroids can be either medical (drug treatment, e.g., non-steroid anti-inflammatory drugs or gonadotropin release hormone agonists) or surgical (e.g., myomectomy, hysterectomy, endometrial ablation or myolysis, with recent development of less invasive methods such as uterine fibroid embolization and thermal ultrasound ablation.

Fibrosis of the skin can be described as a thickening or hardening of the skin, and occurs in scleroderma and other fibrotic skin diseases. When severe, fibrosis can limit movement and normal function. A keloid is an excessive scar that forms in response to trauma, sometimes minor trauma such as ear piercing or acne. Unlike normal scar formation, keloids have disproportionate proliferation of fibroblasts resulting in masses of collagenous tissue. The scar therefore protrudes above the surface of the surrounding skin and infiltrates skin which was not originally traumatized. Roles for LPA in skin fibroblast activity have been demonstrated. For example, it has been shown that LPA stimulates the migration of murine skin fibroblasts (Hama et al., J Biol. Chem. 2004 Apr. 23; 279(17):17634-9). Thus it is believed that anti-LPA agents such as antibodies are useful for treatment of aberrant skin fibrosis such as keloids or skin fibrosis.

Cardiac Fibrosis

LPA has also been shown to have direct fibrogenic effects in cardiac fibroblasts by stimulating collagen gene expression and fibroblast proliferation. Chen, et al. (2006) FEBS Lett. 580:4737-45. Thus anti-LPA agents such as antibodies are expected to have anti-fibrotic effects in cardiac cells as well, and thus to be effective in treatment of cardiac fibrosis.

Agents that reduce the effective concentration of LPA, such as Lpath's anti-LPA mAb, are believed to be useful in methods for treating diseases and conditions characterized by aberrant fibrosis.

4. Cardiovascular and Cerebrovascular Disorders

Because LPA is involved in fibrogenesis and wound healing of liver tissue (Davaille et al., J. Biol. Chem. 275:34268-34633, 2000; Ikeda et al., Am J. Physiol. Gastrointest. Liver Physiol 279:G304-G310, 2000), healing of wounded vasculatures (Lee et al., Am. J. Physiol. Cell Physiol. 278:C612-C618, 2000), and other disease states, or events associated with such diseases, such as cancer, angiogenesis and inflammation (Pyne et al., Biochem. J. 349:385-402, 2000), the compositions and methods of the disclosure may be applied to treat not only these diseases but cardiac diseases as well, particularly those associated with tissue remodeling. LPA have some direct fibrogenic effects by stimulating collagen gene expression and proliferation of cardiac fibroblasts. Chen, et al. (2006) FEBS Lett. 580:4737-45.

5. Obesity and Diabetes

Autotaxin, a phospholipase D responsible for LPA synthesis, has been found to be secreted by adipocytes and its expression is up-regulated in adipocytes from obese-diabetic db/db mice as well as in massively obese women subjects and human patients with type 2 diabetes, independently of obesity (Ferry et al. (2003) JBC 278:18162-18169; Boucher et al. (2005) Diabetologia 48:569-577, cited in Pradere et al. (2007) BBA 1771:93-102. LPA itself has been shown to influence proliferation and differentiation of preadipocytes. Pradere et al., 2007. Together this suggests a role for anti-LPA agents in treatment of obesity and diabetes.

3. Antibody Generation and Characterization

The examples hereinbelow describe the production of anti-LPA agents, particularly anti-LPA antibodies, with desirable properties from a therapeutic perspective including: (a) binding affinity for LPA and/or its variants, including 18:2, 18:1, 18:0, 16:0, 12:0 and 20:4 LPA. Antibody affinities may be determined as described in the examples herein below. Preferably antibodies bind LPA with a high affinity, e.g., a $K_d$ value of no more than about $1\times10^{-7}$ M; possibly no more than about $1\times10^{-8}$ M; and possibly no more than about $5\times10^{-9}$ M. In a physiological context, it is preferable for an antibody to bind LPA with an affinity that is higher than the LPA's affinity for an LPA receptor. It will be understood that this need not necessarily be the case in a nonphysiological context such as a diagnostic assay.

Aside from antibodies with strong binding affinity for LPA, it is also desirable to select chimeric, humanized or variant antibodies which have other beneficial properties from a therapeutic perspective. For example, the antibody may be one that reduces scar formation or alters tumor progression. One assay for determining the activity of the anti-LPA antibodies of the invention is ELISA. Preferably the humanized or variant antibody fails to elicit an immunogenic response upon administration of a therapeutically effective amount of the antibody to a human patient. If an immunogenic response is elicited, preferably the response will be such that the antibody still provides a therapeutic benefit to the patient treated therewith.

According to one embodiment of the invention, humanized anti-LPA antibodies bind the epitope as herein defined. To screen for antibodies that bind to the epitope on an LPA bound by an antibody of interest (e.g., those that block binding of the antibody to LPA), a routine cross-blocking assay such as that described in Antibodies, A Laboratory Manual, Cold Spring Harbor Laboratory, Ed Harlow and David Lane (1988), can be performed. Alternatively, epitope mapping, e.g. as described in Champe et al., J. Biol. Chem. 270:1388-1394 (1995), can be performed to determine whether the antibody binds an epitope of interest.

The antibodies of the invention have a heavy chain variable domain comprising an amino acid sequence represented by the formula: FR1-CDRH1-FR2-CDRH2-FR3-CDRH3-FR4, wherein "FR1-4" represents the four framework regions and "CDRH1-3" represents the three hypervariable regions of an anti-LPA antibody variable heavy domain. FR1-4 may be derived from a consensus sequence (for example the most common amino acids of a class, subclass or subgroup of heavy or light chains of human immunoglobulins) or may be derived from an individual human antibody framework region or from a combination of different framework region sequences. Many human antibody framework region sequences are compiled in Kabat et al., supra, for example. In one embodiment, the variable heavy FR is provided by a consensus sequence of a human immunoglobulin subgroup as compiled by Kabat et al., supra.

The human variable heavy FR sequence may have substitutions therein, e.g. wherein the human FR residue is replaced by a corresponding nonhuman residue (by "corresponding nonhuman residue" is meant the nonhuman residue with the same Kabat positional numbering as the human residue of interest when the human and nonhuman sequences are aligned), but replacement with the nonhuman residue is not necessary. For example, a replacement FR residue other than the corresponding nonhuman residue may be selected by phage display.

The antibodies of the preferred embodiment herein have a light chain variable domain comprising an amino acid sequence represented by the formula: FR1-CDRL1-FR2-CDRL2-FR3-CDRL3-FR4, wherein "FR1-4" represents the four framework regions and "CDRL1-3" represents the three hypervariable regions of an anti-LPA antibody variable light domain. FR1-4 may be derived from a consensus sequence (for example the most common amino acids of a class, subclass or subgroup of heavy or light chains of human immunoglobulins) or may be derived from an individual human antibody framework region or from a combination of different framework region sequences. In one preferred embodiment, the variable light FR is provided by a consensus sequence of a human immunoglobulin subgroup as compiled by Kabat et al., supra.

The human variable light FR sequence may have substitutions therein, e.g. wherein the human FR residue is replaced by a corresponding mouse residue, but replacement with the nonhuman residue is not necessary. For example, a replacement residue other than the corresponding nonhuman residue may be selected by phage display. Methods for generating humanized anti-LPA antibodies of interest herein are elaborated in more detail below.

a. Antibody Preparation

Methods for generating anti-LPA antibodies and variants of anti-LPA antibodies are described in the Examples below. Humanized anti-LPA antibodies may be prepared, based on a nonhuman anti-LPA antibody. Fully human antibodies may also be prepared, e.g, in a genetically engineered (i.e., transgenic) mouse (e.g. from Medarex) that, when presented with an immunogen, can produce a human antibody that does not necessarily require CDR grafting. These antibodies are fully human (100% human protein sequences) from animals such as mice in which the non-human antibody genes are suppressed and replaced with human antibody gene expression. The applicants believe that antibodies could be generated against bioactive lipids when presented to these genetically engineered mice or other animals that might be able to produce human frameworks for the relevant CDRs.

Where a variant is to be generated, the parent antibody is prepared. Exemplary techniques for generating such nonhuman antibody and parent antibodies will be described in the following sections.

(i) Antigen Preparation.

The antigen to be used for production of antibodies may be, e.g., intact LPA or a portion of an LPA (e.g. an LPA fragment comprising the epitope). Other forms of antigens useful for generating antibodies will be apparent to those skilled in the art. It has been found that derivatized LPA conjugated to a carrier is particularly useful as an immunogen for generation of anti-LPA antibodies.

(ii) Polyclonal Antibodies.

Polyclonal antibodies are preferably raised in animals (vertebrate or invertebrates, including mammals, birds and fish, including cartilaginous fish) by multiple subcutaneous (sc) or intraperitoneal (ip) injections of the relevant antigen and an adjuvant. It may be useful to conjugate the relevant antigen to a protein or other carrier that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups. Non-protein carriers (e.g., colloidal gold) are also known in the art for antibody production.

Animals are immunized against the antigen, immunogenic conjugates, or derivatives by combining, e.g., 100 ug or 5 ug of the protein or conjugate (for rabbits or mice, respectively) with three volumes of Freund's complete adjuvant and injecting the solution intradermally at multiple sites. One month later the animals are boosted with one-fifth to one-tenth of the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(iii) Monoclonal Antibodies.

Monoclonal antibodies may be made using the hybridoma method first described by Kohler et al., Nature, 256:495 (1975), or may be made by other methods such as recombinant DNA methods (U.S. Pat. No. 4,816,567). In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbant assay (ELISA).

The binding affinity of the monoclonal antibody can, for example, be determined by the Scatchard analysis of Munson et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are well known in the art, and which are then transfected into host cells such as *E coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

(iv) Humanization and Amino Acid Sequence Variants:

General methods for humanization of antibodies are described in update U.S. Pat. No. 5,861,155, US19960652558 19960606, U.S. Pat. No. 6,479,284, US20000660169 20000912, U.S. Pat. No. 6,407,213, US19930146206 19931117, U.S. Pat. No. 6,639,055, US20000705686 20001102, U.S. Pat. No. 6,500,931, US19950435516 19950504, U.S. Pat. No. 5,530,101, U.S. Pat. No. 5,585,089, US19950477728 19950607, U.S. Pat. No. 5,693,761, US19950474040 19950607, U.S. Pat. No. 5,693,762, US19950487200 19950607, U.S. Pat. No. 6,180, 370, US19950484537 19950607, US2003229208, US20030389155 20030313, U.S. Pat. No. 5,714,350, US19950372262 19950113, U.S. Pat. No. 6,350,861, US19970862871 19970523, U.S. Pat. No. 5,777,085, US19950458516 19950517, U.S. Pat. No. 5,834,597, US19960656586 19960531, U.S. Pat. No. 5,882,644, US19960621751 19960322, U.S. Pat. No. 5,932,448, US19910801798 19911129, U.S. Pat. No. 6,013,256, US19970934841 19970922, U.S. Pat. No. 6,129,914, US19950397411 19950301, U.S. Pat. No. 6,210,671, v, U.S. Pat. No. 6,329,511, US19990450520 19991129, US2003166871, US20020078757 20020219, U.S. Pat. No. 5,225,539, US19910782717 19911025, U.S. Pat. No. 6,548, 640, US19950452462 19950526, U.S. Pat. No. 5,624,821, and US19950479752 19950607. In certain embodiments, it may be desirable to generate amino acid sequence variants of these humanized antibodies, particularly where these improve the binding affinity or other biological properties of the antibody.

Amino acid sequence variants of the anti-LPA antibody are prepared by introducing appropriate nucleotide changes into the anti-LPA antibody DNA, or by peptide synthesis. Such variants include, for example, deletions from, and/or insertions into and/or substitutions of, residues within the amino acid sequences of the anti-LPA antibodies of the examples herein. Any combination of deletion, insertion, and substitution is made to arrive at the final construct, provided that the final construct possesses the desired characteristics. The amino acid changes also may alter post-translational processes of the humanized or variant anti-LPA antibody, such as changing the number or position of glycosylation sites.

A useful method for identification of certain residues or regions of the anti-LPA antibody that are preferred locations for mutagenesis is called "alanine scanning mutagenesis," as described by Cunningham and Wells Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with LPA antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed anti-LPA antibody variants are screened for the desired activity. Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an N-terminal methionyl residue or the antibody fused to an epitope tag. Other insertional variants include the fusion of an enzyme or a polypeptide which increases the serum half-life of the antibody to the N- or C-terminus of the antibody.

Another type of variant is an amino acid substitution variant. These variants have at least one amino acid residue removed from the antibody molecule and a different residue inserted in its place. The sites of greatest interest for substitutional mutagenesis include the hypervariable regions, but FR alterations are also contemplated. Conservative substitutions are preferred, but more substantial changes may be introduced and the products may be screened. Examples of substitutions are listed below:

Exemplary Amino Acid Residue Substitutions
Ala (A) val; leu; ile val
Arg (R) lys; gln; asn lys
Asn (N) gln; his; asp, lys; gln arg
Asp (D) glu; asn glu
Cys (C) ser; ala ser
Gln (Q) asn; glu asn
Glu (E) asp; gln asp
Gly (G) ala ala
His (H) asn; gln; lys; arg arg
Ile (I) leu; val; met; ala; leu phe; norleucine
Leu (L) norleucine; ile; val; ile met; ala; phe
Lys (K) arg; gin; asn arg
Met (M) leu; phe; ile leu
Phe (F) leu; val; ile; ala; tyr tyr
Pro (P) ala ala
Ser (S) thr thr
Thr (T) ser ser
Trp (W) tyr; phe tyr
Tyr (Y) trp; phe; thr; ser phe
Val (V) ile; leu; met; phe; leu ala; norleucine Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the antibody also may be substituted, to improve the oxidative stability of the molecule and prevent aberrant crosslinking. Conversely, cysteine bond(s) may be added to the antibody to improve its stability (particularly where the antibody is an antibody fragment such as an Fv fragment).

One type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked and/or or O-linked. N-linked refers to the attachment of the carbohydrate moiety to the side chain of an asparagine residue. The tripeptide sequences asparagine-X-serine and asparagine-X-threonine, where X is any amino acid except proline, are the most common recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-sphingolipid antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-sphingolipid antibody.

(v) Human Antibodies.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); and U.S. Pat. Nos. 5,591,669, 5,589,369 and 5,545,807. Human antibodies can also be derived from phage-display libraries (Hoogenboom et al., J. Mol. Biol., 227:381 (1991); Marks et al., J. Mol. Biol., 222:581-597 (1991); and U.S. Pat. Nos. 5,565,332 and 5,573,905). Human antibodies may also be generated by in vitro activated B cells (see U.S. Pat. Nos. 5,567,610 and 5,229,275).

(vi) Antibody Fragments.

In certain embodiments, the anti-LPA agent is an antibody fragment which retains at least one desired activity, including antigen binding. Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992) and Brennan et al., Science 229:81 (1985)). However, these fragments can now be produced directly by recombinant host cells. For example, Fab'-SH fragments can be directly recovered from *E. coli* and chemically coupled to form $F(ab')_2$ fragments (Carter et al., Bio/Technology 10:163-167 (1992)). In another embodiment, the $F(ab')_2$ is formed using the leucine zipper GCN4 to promote assembly of the $F(ab')_2$ molecule. According to another approach, Fv, Fab or $F(ab')_2$ fragments can be isolated directly from recombinant host cell culture. Other techniques for the production of antibody fragments will be apparent to the skilled practitioner.

(vii) Multispecific Antibodies and Other Agents.

In some embodiments, the anti-LPA agent will comprise a first binding moiety and a second binding moiety, wherein the first binding moiety is specifically reactive with a first molecule that is an LPA or LPA metabolite and the second binding moiety is specifically reactive with a second molecule that is a molecular species different from the first molecule. Such agents may comprise a plurality of first binding moieties, a plurality of second binding moieties, or a plurality of first binding moieties and a plurality of second binding moieties. Preferably, the ratio of first binding moieties to second binding moieties is about 1:1, although it may range from about 1000:1 to about 1:1000, wherein the ratio is preferably measured in terms of valency.

In those embodiments wherein the first moiety is an antibody, the binding moiety may also be an antibody. In preferred embodiments, the first and second moieties are linked via a linker moiety, which may have two to many 100's or even thousand of valencies for attachment of first and second binding moieties by one or different chemistries. Examples of bispecific antibodies include those which are reactive against two different epitopes; in some embodiment one epitope is an LPA epitope and the second epitope is another bioactive lipid, e.g., S1P. In other embodiments the bispecific antibody is reactive against an epitope on LPA and against an epitope found on the cell surface. This serves to target the LPA-specific antibody moiety to the cell.

The compositions of the invention may also comprise a first agent and a second agent, wherein the first agent comprises a first binding moiety specifically reactive with a first molecule selected from the group consisting of an LPA and an LPA metabolite and the second agent comprises a second binding moiety specifically reactive with a second molecule that is a molecular species different than the first molecule. The first and/or second agent may be an antibody. The ratio of first agent to second agent may range from about 1,000:1 to 1:1,000, although the preferred ratio is about 1:1. In preferred embodiments, the agent that interferes with LPA activity is an antibody specifically reactive with LPA. In some embodiments, it may be desirable to generate multispecific (e.g. bispecific) anti-LPA antibodies having binding specificities for at least two different epitopes. Exemplary bispecific antibodies may bind to two different epitopes of the LPA. Alternatively, an anti-LPA arm (of the antibody) may be combined with an arm which binds to a different molecule; for example, S1P or a cell-surface specific antigen for localization of the antibody to the cell surface. Bispecific antibodies can be prepared as full length antibodies or antibody fragments (e.g., $F(ab')_2$ bispecific antibodies).

According to another approach for making bispecific antibodies, the interface between a pair of antibody molecules can be engineered to maximize the percentage of heterodimers that are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See WO96/27011 published Sep. 6, 1996.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science 229:81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes. In yet a further embodiment, Fab'-SH fragments directly recovered from *E. coli* can be chemically coupled in vitro to form bispecific antibodies. Shalaby et al., J. Exp. Med. 175:217-225 (1992).

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol. 152:5368 (1994). Alternatively, the bispecific antibody may be a "linear antibody" produced as described in Zapata et al. Protein Eng. 8(10):1057-1062 (1995).

Antibodies with more than two valencies are contemplated. For example, trispecific antibodies can be prepared. Tutt et al., J. Immunol. 147:60 (1991).

The antibody (or polymer or polypeptide) of the invention comprising one or more binding sites per arm or fragment thereof will be referred to herein as "multivalent" antibody. For example a "bivalent" antibody of the invention comprises two binding sites per Fab or fragment thereof whereas a "trivalent" polypeptide of the invention comprises three binding sites per Fab or fragment thereof. In a multivalent polymer of the invention, the two or more binding sites per Fab may be binding to the same or different antigens. For example, the two or more binding sites in a multivalent polypeptide of the invention may be directed against the same antigen, for example against the same parts or epitopes of said antigen or against two or more same or different parts or epitopes of said antigen; and/or may be directed against different antigens; or a combination thereof. Thus, a bivalent polypeptide of the invention for example may comprise two identical binding sites, may comprise a first binding sites directed against a first part or epitope of an antigen and a second binding site directed against the same part or epitope of said antigen or against another part or epitope of said antigen; or may comprise a first binding sites directed against a first part or epitope of an antigen and a second binding site directed against the a different antigen. However, as will be clear from the description hereinabove, the invention is not limited thereto, in the sense that a multivalent polypeptide of the invention may comprise any number of binding sites directed against the same or different antigens. In one embodiment the multivalent polypeptide comprises at least two ligand binding elements, one of which contains one or more CDR peptide sequences shown herein. In another embodiment there multivalent polypeptide comprises three ligand binding sites, each independently selected from the CDR sequences disclosed herein.

At least one of the ligand binding elements binds LPA. In one embodiment at least one of the ligand binding elements binds another target; in another embodiment, all of the ligand binding elements bind LPA. In one embodiment there are up to to 10,000 binding elements in a multivalent binding molecule, and the ligand binding elements may be linked to a scaffold.

The antibody (or polymer or polypeptide) of the invention that contains at least two binding sites per Fab or fragment thereof, in which at least one binding site is directed against a first antigen and a second binding site directed against a second antigen different from the first antigen, will also be referred to as "multispecific." Thus, a "bispecific" polymer comprises at least one site directed against a first antigen and at least one a second site directed against a second antigen, whereas a "trispecific" is a polymer that comprises at least one binding site directed against a first antigen, at least one further binding site directed against a second antigen, and at least one further binding site directed against a third antigen; etc. Accordingly, in their simplest form, a bispecific polypeptide of the invention is a bivalent polypeptide (per Fab) of the invention. However, as will be clear from the description hereinabove, the invention is not limited thereto, in the sense that a multispecific polypeptide of the invention may comprise any number of binding sites directed against two or more different antigens.

(viii) Other Modifications.

Other modifications of the anti-LPA antibody are contemplated. For example, the invention also pertains to immunoconjugates comprising the antibody described herein conjugated to a cytotoxic agent such as a toxin (e.g., an enzymatically active toxin of bacterial, fungal, plant or animal origin, or fragments thereof), or a radioactive isotope (for example, a radioconjugate). Conjugates are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

The anti-LPA antibodies disclosed herein may also be formulated as immunoliposomes. Liposomes containing the antibody are prepared by methods known in the art, such as described in Epstein et al., Proc. Natl. Acad. Sci. USA 82:3688 (1985); Hwang et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. For example, liposomes can be generated by the reverse phase evaporation method with a lipid composition comprising phosphatidyl choline, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257: 286-288 (1982) via a disulfide interchange reaction. Another active ingredient is optionally contained within the liposome.

Enzymes or other polypeptides can be covalently bound to the anti-LPA antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature 312:604-608 (1984)).

In certain embodiments of the invention, it may be desirable to use an antibody fragment, rather than an intact antibody, to increase penetration of target tissues and cells, for example. In this case, it may be desirable to modify the antibody fragment in order to increase its serum half life. This may be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis). See WO96/32478 published Oct. 17, 1996.

Covalent modifications of the anti-LPA antibody are also included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues. Exemplary covalent modifications of polypeptides are described in U.S. Pat. No. 5,534,615, specifically incorporated herein by reference. A preferred type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. No. 4,640,835; 4,496,689; 4,301,144; 4,670,417; 4,791,192 or 4,179,337.

b. Vectors, Host Cells and Recombinant Methods

The invention also provides isolated nucleic acid encoding the anti-LPA antibody, vectors and host cells comprising the nucleic acid, and recombinant techniques for the production of the antibody.

For recombinant production of the antibody, the nucleic acid encoding it may be isolated and inserted into a replicable vector for further cloning (amplification of the DNA) or for expression. In another embodiment, the antibody may be produced by homologous recombination, e.g. as described in U.S. Pat. No. 5,204,244, specifically incorporated herein by reference. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence, e.g., as described in U.S. Pat. No. 5,534,615 issued Jul. 9, 1996 and specifically incorporated herein by reference.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-sphingolipid antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244, 234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of glycosylated anti-sphingolipid antibodies are derived from multicellularorganisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/−DHFR (CHO, Urlaub et al., Proc. Natl. Acad. Sci. USA 77:4216 (1980)); mouse Sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

The host cells used to produce the antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. No. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology 10:163-167 (1992) describe a procedure for isolating antibodies that are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the Bakerbond ABX™ resin (J. T. Baker, Phillipsburg, N.J.) is useful for purification. Other techniques for protein purification, such as fractionation on an ion-exchange column, ethanol precipitation, Reverse Phase HPLC, chromatography on silica, chromatography on heparin SEPHAROSE™, chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

c. Pharmaceutical Formulations, Dosing and Routes of Administration

The present invention provides anti-LPA antibodies and related compositions and methods to reduce blood and tissue levels of the bioactive lipid, LPA.

The therapeutic methods and compositions of the invention are said to be "LPA-based" in order to indicate that these therapies can change the relative, absolute or effective concentration(s) of undesirable or toxic lipids "Undesirable lipids" include toxic bioactive lipids, as well as metabolites, particularly metabolic precursors, of toxic lipids. One example of an undesirable bioactive lipid of particular interest is LPA.

One way to control the amount of undesirable LPA in a patient is by providing a composition that comprises one or more anti-LPA antibodies to bind one or more LPAs, thereby acting as therapeutic "sponges" that reduce the level of free undesirable LPA. When a compound is stated to be "free," the compound is not in any way restricted from reaching the site or sites where it exerts its undesirable effects. Typically, a free compound is present in blood and tissue, which either is or contains the site(s) of action of the free compound, or from which a compound can freely migrate to its site(s) of action. A free compound may also be available to be acted upon by any enzyme that converts the compound into an undesirable compound.

Anti-LPA antibodies may be formulated in a pharmaceutical composition that is useful for a variety of purposes, including the treatment of diseases, disorders or physical trauma. Pharmaceutical compositions comprising one or more anti-LPA antibodies of the invention may be incorporated into kits and medical devices for such treatment. Medical devices may be used to administer the pharmaceutical compositions of the invention to a patient in need thereof, and according to one embodiment of the invention, kits are provided that include such devices. Such devices and kits may be designed for routine administration, including self-administration, of the pharmaceutical compositions of the invention. Such devices and kits may also be designed for emergency use, for example, in ambulances or emergency rooms, or during surgery, or in activities where injury is possible but where full medical attention may not be immediately forthcoming (for example, hiking and camping, or combat situations).

Therapeutic formulations of the antibody are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization; for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished for instance by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and .gamma. ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

For therapeutic applications, the anti-LPA agents, e.g., antibodies, of the invention are administered to a mammal, preferably a human, in a pharmaceutically acceptable dosage form such as those discussed above, including those that may be administered to a human intravenously as a bolus or by continuous infusion over a period of time, or by intramuscular, intraperitoneal, intra-cerebrospinal, subcutaneous, intra-articular, intrasynovial, intrathecal, oral, topical, or inhalation routes.

For the prevention or treatment of disease, the appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 .mu.g/kg to about 50 mg/kg (e.g., 0.1-20 mg/kg) of antibody is an initial candidate dosage for administration to the patient, whether, for example, by one or more separate administrations, or by continuous infusion. A typical daily or weekly dosage might range from about 1 μg/kg to about 20 mg/kg or more, depending on the factors mentioned above. For repeated administrations over several days or longer, depending on the condition, the treatment is repeated until a desired suppression of disease symptoms occurs. However, other dosage regimens may be useful. The progress of this therapy is easily monitored by conventional techniques and assays, including, for example, radiographic imaging. Detection methods using the antibody to determine LPA levels in bodily fluids or tissues may be used in order to optimize patient exposure to the therapeutic antibody.

According to another embodiment of the invention, the composition comprising an agent, e.g, a mAb, that interferes with LPA activity is administered as a monotherapy, while in other preferred embodiments, the composition comprising the agent that interferes with LPA activity is administered as part of a combination therapy. In some cases the effectiveness of the antibody in preventing or treating disease may be improved by administering the antibody serially or in combination with another agent that is effective for those purposes, such as a chemotherapeutic drug for treatment of cancer. In other cases, the anti-LPA agent may serve to enhance or sensitize cells to chemotherapeutic treatment, thus permitting efficacy at lower doses and with lower toxicity. Preferred combination therapies include, in addition to administration of the composition comprising an agent that interferes with LPA activity, delivering a second therapeutic regimen selected from the group consisting of administration of a chemotherapeutic agent, radiation therapy, surgery, and a combination of any of the foregoing.

Such other agents may be present in the composition being administered or may be administered separately. Also, the antibody is suitably administered serially or in combination with the other agent or modality, e.g., chemotherapeutic drug or radiation for treatment of cancer.

Exemplary routes of administration of an immune-derived moiety, preferably as part of a therapeutic composition, include systemic administration, parenteral administration (e.g., via injection via an intravenous, intramuscular, intrathecal, epidural or subcutaneous route), transdermal, intradermal or transmucosal delivery, intraocular or periocular injection, mucosal or topical administration or by inhalation.

d. Research and Diagnostic, Including Clinical Diagnostic Uses for the Anti-LPA Agents of the Invention The anti-LPA agents, e.g., antibodies, of the invention may be used to detect and/or purify LPA, e.g., from bodily fluid(s).

For use of anti-LPA antibodies as affinity purification agents, the antibodies are immobilized on a solid support such as beads, a Sephadex resin or filter paper, using methods well known in the art. The immobilized antibody is contacted with a sample containing the LPA to be purified, and thereafter the support is washed with a suitable solvent that will remove substantially all the material in the sample except the LPA, which is bound to the immobilized antibody. Finally, the support is washed with another suitable solvent, such as glycine buffer, for instance between pH 3 to pH 5.0, that will release the LPA from the antibody.

Anti-LPA antibodies may also be useful in diagnostic assays for LPA, e.g., detecting its presence in specific cells, tissues, or bodily fluids. Such diagnostic methods may be useful in diagnosis, e.g., of a hyperproliferative disease or disorder. Thus clinical diagnostic uses as well as research uses are comprehended by the invention. In these methods, the anti-LPA antibody is preferably attached to a solid support, e.g., bead, column, plate, gel, filter, membrane, etc.

For diagnostic applications, the antibody may be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in Current Protocols in Immunology, Volumes 1 and 2, Coligen et al., Ed. Wiley-Interscience, New York, N.Y., Pubs. (1991), for example, and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in Current Protocols in Immunology, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, beta-galactosidase, glucoamylase, lysozyme, saccharide oxidases (e.g., glucose oxidase, galactose oxidase, and glucose-6-phosphate dehydrogenase), heterocyclicoxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzym. (ed J. Langone & H. Van Vunakis), Academic press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) .beta.-D-galactosidase (.beta.-D-Gal) with a chromogenic substrate (e.g., p-nitrophenyl-β-D-galactosidase) or fluorogenic substrate 4-methylumbelliferyl-.beta.-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment of the invention, the anti-LPA antibody need not be labeled, and the presence thereof can be detected, e.g., using a labeled antibody which binds to the anti-LPA antibody.

The antibodies of the present invention may be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987).

Competitive binding assays rely on the ability of a labeled standard to compete with the test sample analyte for binding with a limited amount of antibody. The amount of LPA in the test sample is inversely proportional to the amount of standard that becomes bound to the antibodies. To facilitate determining the amount of standard that becomes bound, the antibodies generally are insoluble before or after the competition, so that the standard and analyte that are bound to the antibodies may conveniently be separated from the standard and analyte that remain unbound.

Sandwich assays involve the use of two antibodies, each capable of binding to a different immunogenic portion, or epitope, of the protein to be detected. In a sandwich assay, the test sample analyte is bound by a first antibody that is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the blood or tissue sample may be fresh or frozen or may be embedded in paraffin and fixed with a preservative such as formalin, for example.

The antibodies may also be used for in vivo diagnostic assays. Generally, the antibody is labeled with a radionuclide (such as $^{111}In$, $^{99}Tc$, $^{14}C$, $^{131}I$, $^{3}H$, $^{32}P$, or $^{35}S$) so that the bound target molecule can be localized using immunoscintillography.

e. Diagnostic Kits Incorporating the Anti-LPA Agents of the Invention

As a matter of convenience, the antibody of the present invention can be provided in a kit, for example, a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

f. Articles of Manufacture

In another aspect of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the anti-sphingolipid antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The invention will be better understood by reference to the following Examples, which are intended to merely illustrate the best mode now known for practicing the invention. The scope of the invention is not to be considered limited thereto.

EXAMPLES

The invention will be further described by reference to the following detailed examples. These Examples are in no way to be considered to limit the scope of the invention in any manner.

Example 1

Synthetic Scheme for Making a Representative Thiolated Analog of S1P

Figure 1B:
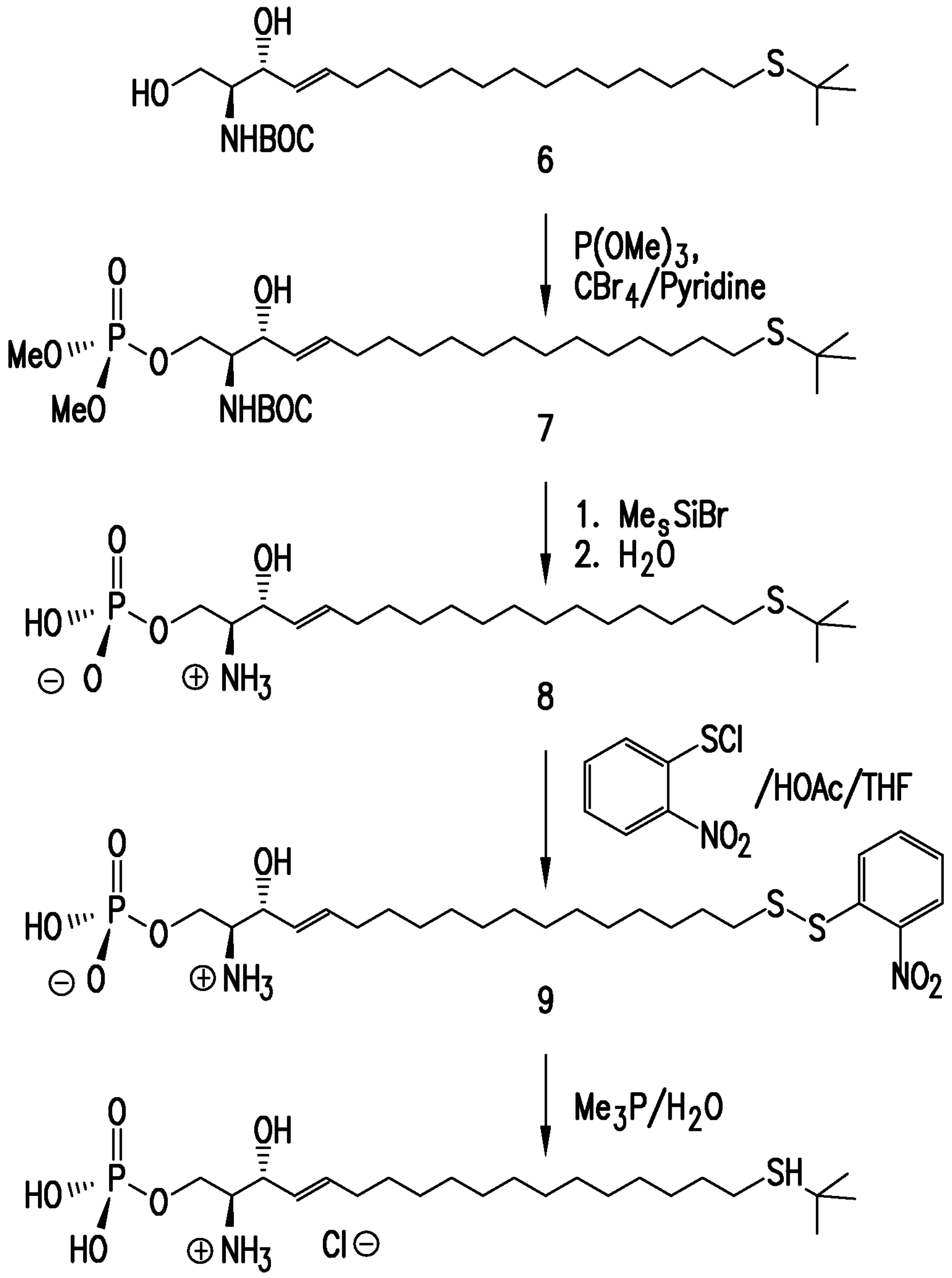
Figure 1C:
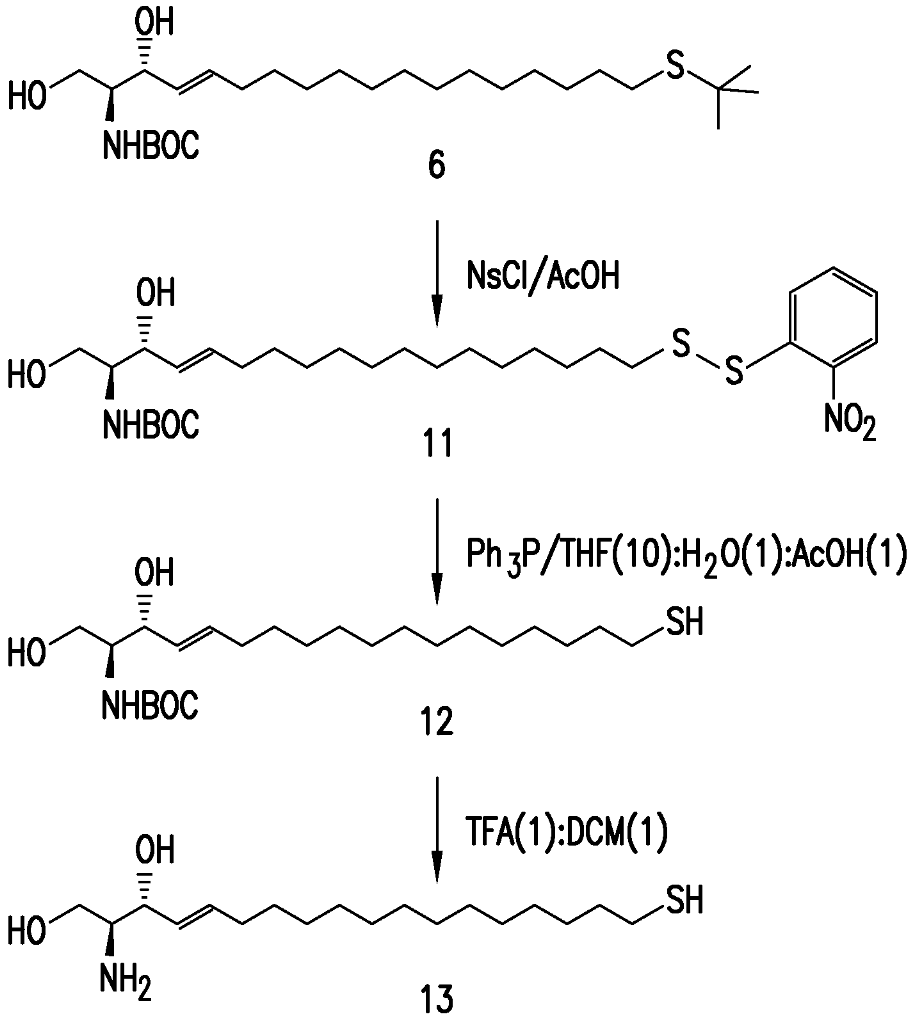

The synthetic approach described in this example results in the preparation of an antigen by serial addition of structural elements using primarily conventional organic chemistry. A scheme for the approach described in this example is provided in FIG. 1, and the compound numbers in the synthetic description below refer to the numbered structures in FIG. 1.

This synthetic approach began with the commercially available 15-hydroxyl pentadecyne, 1, and activation by methyl sulphonyl chloride of the 15-hydroxy group to facilitate hydroxyl substitution to produce the sulphonate, 2. Substitution of the sulphonate with t-butyl thiol yielded the protected thioether, 3, which was condensed with Garner's aldehyde to produce 4. Gentle reduction of the alkyne moiety to an alkene (5), followed by acid catalyzed opening of the oxazolidene ring yielded S-protected and N-protected thiol substituted sphingosine, 6. During this last step, re-derivatization with di-t-butyl dicarbonate was employed to mitigate loss of the N—BOC group during the acid-catalyzed ring opening.

As will be appreciated, compound 6 can itself be used as an antigen for preparing haptens to raise antibodies to sphingosine, or, alternatively, as starting material for two different synthetic approaches to prepare a thiolated S1P analog. In one approach, compound 6 phosphorylation with trimethyl phosphate produced compound 7. Treatment of compound 7 with trimethylsilyl bromide removed both methyl groups from the phosphate and the t-butyloxycarbonyl group from the primary amine, leaving compound 8 with the t-butyl group on the sulfur as the only protecting group. To remove this group, the t-butyl group was displaced by NBS to form the disulfide, 9, which was then reduced to form the thiolated S1P analog, 10.

Another approach involved treating compound 6 directly with NBSCl to form the disulfide, 11, which was then reduced to form the N-protected thiolated S1P analog, 12. Treatment of this compound with mild acid yielded the thiolated sphingosine analog, 13, which can be phosphorylated enzymatically with, e.g., sphingosine kinase, to yield the thiolated S1P analog, 10.

Modifications of the presented synthetic approach are possible, particularly with regard to the selection of protecting and de-protecting reagents, e.g., the use of trimethyl disulfide triflate described in Example 3 to de-protect the thiol.

Compound 2.

DCM (400 mL) was added to a 500 mL RB flask charged with 1 (10.3 g, 45.89 mmol), and the resulting solution cooled to 0° C. Next, TEA (8.34 g, 82.60 mmol, 9.5 mL) was added all at once followed by MsCl (7.88 g, 68.84 mmol, 5.3 mL) added drop wise over 10 min. The reaction was allowed to stir at RT for 0.5 h or until the disappearance of starting material ($R_f$=0.65, 5:1 hexanes:EtOAc). The reaction was quenched with $NH_4Cl$ (300 mL) and extracted (2×200 mL) DCM. The organic layers were dried over $MgSO_4$, filtered and the filtrate evaporated to a solid (13.86 g, 99.8% yield). $^1H$ NMR ($CDCl_3$) δ 4.20 (t, J=6.5 Hz, 2H), 2.98 (s, 3H), 2.59 (td, J=7 Hz, 3 Hz, 2H), 1.917 (t, J=3 Hz, 1H), 1.72 (quintet, J=7.5 Hz, 2H), 1.505 (quintet, J=7.5 Hz, 2H), 1.37 (br s, 4H), 1.27 (br s, 14H). $^{13}C\{^1H\}$ NMR ($CDCl_3$) δ 85.45, 70.90, 68.72, 46.69, 38.04, 30.22, 30.15, 30.14, 30.07, 29.81, 29.76, 29.69, 29.42, 29.17, 26.09, 19.06, 9.31. The principal ion observed in a HRMS analysis (ES-TOF) of compound 2 was m/z=325.1804 (calculated for $C_{16}H_{30}O_3S$: M+$Na^+$ 325.1808).

Compound 3.

A three-neck 1 L RB flask was charged with t-butylthiol (4.54 g, 50.40 mmol) and THF (200 mL) and then placed into an ice bath. n-BuLi (31.5 mL of 1.6 M in hexanes) was added over 30 min. Next, compound 2 (13.86 g, 45.82 mmol), dissolved in THF (100 mL), was added over 2 min. The reaction is allowed to stir for 1 hour or until starting material disappeared ($R_f$=0.7, 1:1 hexanes/EtOAc). The reaction was quenched with saturated $NH_4Cl$ (500 mL) and extracted with $EtO_2$ (2×250 mL), dried over $MgSO_4$, filtered, and the filtrate evaporated to yield a yellow oil (11.67 g, 86% yield). $^1H$ NMR ($CDCl_3$) δ 2.52 (t, J=7.5 Hz, 2H), 2.18 (td, J=7 Hz, 2.5 Hz, 2H), 1.93 (t, J=2.5 Hz, 1H), 1.55 (quintet, J=7.5 Hz, 2H), 1.51 (quintet, J=7 Hz, 2H), 1.38 (br s, 4H), 1.33 (s, 9H), 1.26 (s, 14H). $^{13}C\{^1H\}$ NMR ($CDCl_3$) δ 85.42, 68.71, 68.67, 54.07, 42.37, 31.68, 30.58, 30.28, 30.26, 30.19, 30.17, 29.98, 29.78, 29.44, 29.19, 29.02, 19.08.

Compound 4.

A 250 mL Schlenk flask charged with compound 3 (5.0 g, 16.85 mmol) was evacuated and filled with nitrogen three times before dry THF (150 mL) was added. The resulting solution cooled to −78° C. Next, n-BuLi (10.5 mL of 1.6M in hexanes) was added over 2 min. and the reaction mixture was stirred for 18 min. at −78° C. before the cooling bath was removed for 20 min. The dry ice bath was returned. After 15 min., Garner's aldeyde (3.36 g, 14.65 mmol) in dry THF (10 mL) was then added over 5 min. After 20 min., the cooling bath was removed. Thin layer chromatography (TLC) after 2.7 hr. showed that the Garner's aldehyde was gone. The reaction was quenched with saturated aqueous $NH_4Cl$ (300 mL) and extracted with $Et_2O$ (2×250 mL). The combined $Et_2O$ phases were dried over $Na_2SO_4$, filtered, and the filtrate evaporated to give crude compound 4 and its syn diastereomer (not shown in FIG. 1) as a yellow oil (9.06 g). This material was then used in the next step without further purification.

Compound 5.

To reduce the triple bond in compound 4, the oil was dissolved in dry $Et_2O$ (100 mL) under nitrogen. RED-Al (20 mL, 65% in toluene) was slowly added to the resulting solution at RT to control the evolution of hydrogen gas ($H_2$). The reaction was allowed to stir at RT overnight or when TLC showed the disappearance of the starting material ($R_f$=0.6 in 1:1 EtOAc: hexanes) and quenched slowly with cold MeOH or aqueous $NH_4Cl$ to control the evolution of $H_2$. The resulting white suspension was filtered through a Celite pad and the filtrate was extracted with EtOAc (2×400 mL). Combined EtOAc extracts were dried over $MgSO_4$, filtered, and the filtrate evaporated to leave crude compound 5 and its syn diastereomer (not shown in FIG. 1) as a yellow oil (7.59 g).

Compound 6.

The oil containing compound 5 was dissolved in MeOH (200 mL), PTSA hydrate (0.63 g) was added, and the solution stirred at RT for 1 day and then at 50° C. for 2 days, at which point TLC suggested that all starting material (5) was gone. However, some polar material was present, suggesting that the acid had partially cleaved the BOC group. The reaction was worked up by adding saturated aqueous $NH_4Cl$ (400 mL), and extracted with ether (3×300 mL). The combined ether phases were dried over $Na_2SO_4$, filtered, and the filtrate evaporated to dryness, leaving 5.14 g of oil. In order to reprotect whatever amine had formed, the crude product was dissolved in $CH_2Cl_2$ (150 mL), to which was added $BOC_2O$ (2.44 g) and TEA (1.7 g). When TLC (1:1 hexanes/EtOAc) showed no more material remaining on the baseline, saturated aqueous $NH_4Cl$ (200 mL) was added, and, after separating the organic phase, the mixture was extracted with $CH_2Cl_2$ (3×200 mL). Combined extracts were dried over $Na_2SO_4$, filtered, and the filtrated concentrated to dryness to yield a yellow oil (7.7 g) which was chromatographed on a silica column using a gradient of hexanes/EtOAc (up to 1:1) to separate the diastereomers. By TLC using 1:1 PE/EtOAc, the $R_f$ for the anti isomer, compound 6, was 0.45. For the syn isomer (not shown in FIG. 1) the $R_f$ was 0.40. The yield of compound 6 was 2.45 g (39% overall based on Garner's aldehyde). $^1H$ NMR of anti isomer ($CDCl_3$) δ 1.26 (br s, 20H), 1.32 (s, 9H), 1.45 (s, 9H), 1.56 (quintet, 2H, J=8 Hz), 2.06 (q, 2H, J=7 Hz), 2.52 (t, 2H, J=7 Hz), 2.55 (br s, 2H), 3.60 (br s, 1H), 3.72 (ddd, 1H, J=11.5 Hz, 7.0 Hz, 3.5 Hz), 3.94 (dt, 1H, J=11.5 Hz, 3.5 Hz), 4.32 (d, 1H, J=4.5 Hz), 5.28 (br s, 1H), 5.54 (dd, 1H, J=15.5 Hz, 6.5 Hz), 5.78 (dt, 1H, J=15.5 Hz, 6.5 Hz). $^{13}C\ \{^1H\}$ NMR ($CDCl_3$) δ 156.95, 134.80, 129.66, 80.47, 75.46, 63.33, 56.17, 42.44, 32.98, 31.70, 30.58, 30.32, 30.31, 30.28, 30.20, 30.16, 30.00, 29.89, 29.80, 29.08, 29.03.

Anal. Calculated for $C_{27}H_{53}NO_4S$: C, 66.48; H, 10.95; N, 2.87. Found: C, 65.98; H, 10.46; N, 2.48.

Compound 7.

To a solution of the alcohol compound 6 (609.5 mg, 1.25 mmol) dissolved in dry pyridine (2 mL) was added $CBr_4$ (647.2 mg, 1.95 mmol, 1.56 equiv). The flask was cooled in an ice bath and $P(OMe)_3$ (284.7 mg, 2.29 mmol, 1.84 equiv) was added drop wise over 2 min. After 4 min. the ice bath was removed and after 12 hr. the mixture was diluted with ether (20 mL). The resulting mixture washed with aqueous HCl (10 mL, 2 N) to form an emulsion which separated on dilution with water (20 mL). The aqueous phase was extracted with ether (2×10 mL), then EtOAc (2×10 mL). The ether extracts and first EtOAc extract were combined and washed with aqueous HCl (10 mL, 2 N), water (10 mL), and saturated aqueous $NaHCO_3$ (10 mL). The last EtOAc extract was used to back-extract the aqueous washes. Combined organic phases were dried over $MgSO_4$, filtered, and the filtrate concentrated to leave crude product (1.16 g), which was purified by flash chromatography over silica (3×22 cm column) using $CH_2Cl_2$, then $CH_2Cl_2$-EtOAc (1:20, 1:6, 1:3, and 1:1—product started to elute, 6:4, 7:3). Early fractions contained 56.9 mg of oil. Later fractions provided product (compound 7, 476.6 mg, 64%) as clear, colorless oil.

Anal. Calculated for $C_{29}H_{58}NO_7PS$ (595.82): C, 58.46; H, 9.81; N, 2.35. Found: C, 58.09; H, 9.69; N, 2.41.

Compound 8.

A flask containing compound 7 (333.0 mg, 0.559 mmol) and a stir bar was evacuated and filled with nitrogen. Acetonitrile (4 mL, distilled from $CaH_2$) was injected by syringe and the flask now containing a solution was cooled in an ice bath. Using a syringe, $(CH_3)_3SiBr$ (438.7 mg, 2.87 mmol, 5.13 equiv.) was added over the course of 1 min. After 35 min., the upper part of the flask was rinsed with an additional portion of acetonitrile (1 mL) and the ice bath was removed. After another 80 min., an aliquot was removed, the solution dried by blowing nitrogen gas over it, and the residue analyzed by $^1H$ NMR in $CDCl_3$, which showed only traces of peaks ascribed to P—$OCH_3$ moieties. After 20 min., water (0.2 mL) was added to the reaction mixture, followed by the $CDCl_3$ solution used to analyze the aliquot, and the mixture was concentrated to ca. 0.5 mL volume on a rotary evaporator. Using acetone (3 mL) in portions the residue was transferred to a tared test tube, forming a pale brown solution. Water (3 mL) was added in portions. After addition of 0.3 mL, cloudiness was seen. After a total of 1 mL, a gummy precipitate had formed. As an additional 0.6 mL of water was added, more cloudiness and gum separated, but the final portion of water seemed not to change the appearance of the mixture. Overall, this process was accomplished over a period of several hours. The tube was centrifuged and the supernatant removed by pipet. The solid, no longer gummy, was dried over $P_4O_{10}$ in vacuo, leaving compound 8 (258.2 mg, 95%) as a monohydrate.

Anal. Calculated for $C_{22}H_{46}NO_5PS+H_2O$ (485.66): C, 54.40; H, 9.96; N, 2.88. Found: C, 54.59; H, 9.84; N, 2.95.

Compound 9.

Compound 8 (202.6 mg, 0.417 mmol) was added in a glove box to a test tube containing a stir bar, dry THF (3 mL) and glacial HOAc (3 mL). NBSCl (90 mg, 0.475 mmol, 1.14 equiv) were added, and after 0.5 hr., a clear solution was obtained. After a total of 9 hr., an aliquot was evaporated to dryness and the residue analyzed by $^1$H NMR in $CDCl_3$. The peaks corresponding to $CH_2StBu$ and $CH_2SSAr$ suggested that reaction was about 75% complete, and comparison of the spectrum with that of pure NBSCl in $CDCl_3$ suggested that none of the reagent remained in the reaction. Therefore, an additional portion (24.7 mg, 0.130 mmol, 0.31 equiv) was added, followed 3 hr. later by an additional portion (19.5 mg, 0.103 mmol, 0.25 equiv). After another 1 hr., the mixture was transferred to a new test tube using THF (2 mL) to rinse and water (1 mL) was added.

Compound 10.

$PMe_3$ (82.4 mg, 1.08 mmol, 1.52 times the total amount of 2-nitrobenzenesulfenyl chloride added) was added to the clear solution compound 9 described above. The mixture grew warm and cloudy, with precipitate forming over time. After 4.5 hr., methanol was added, and the tube centrifuged. The precipitate settled with difficulty, occupying the bottom 1 cm of the tube. The clear yellow supernatant was removed using a pipet. Methanol (5 mL, deoxygenated with nitrogen) was added, the tube was centrifuged, and the supernatant removed by pipet. This cycle was repeated three times. When concentrated, the final methanol wash left only 4.4 mg of residue. The bulk solid residue was dried over $P_4O_{10}$ in vacuo, leaving compound 10 (118.2 mg, 68%) as a monohydrochloride.

Anal. Calculated for $C_{18}H_{38}NO_5S+HCl$ (417.03): C, 51.84; H, 9.43; N, 3.36. Found: C, 52.11; H, 9.12; N, 3.30.

Compound 11.

Compound 6 (1.45 g, 2.97 mmol) was dissolved in AcOH (20 mL), and NBSCl (0.56 g, 2.97 mmol) was added all at once. The reaction was allowed to stir for 3 hr. or until the disappearance of the starting material and appearance of the product was observed by TLC [product $R_f$=0.65, starting material $R_f$=0.45, 1:1 EtOAc/hexanes]. The reaction was concentrated to dryness on a high vacuum line and the residue dissolved in THF/$H_2O$ (100 mL of 10:1).

Compound 12.

$Ph_3P$ (0.2.33 g, 8.91 mmol) was added all at once to the solution above that contained compound 11 and the reaction was allowed to stir for 3 hr. or until the starting material disappeared. The crude reaction mixture was concentrated to dryness on a high vacuum line, leaving a residue that contained compound 12.

Compound 13.

The residue above containing compound 12 was dissolved in DCM (50 mL) and TFA (10 mL). The mixture was stirred at RT for 5 hr. and concentrated to dryness. The residue was the loaded onto a column with silica gel and chromatographed with pure DCM, followed by DCM containing 5% MeOH, then 10% MeOH, to yield the final product, compound 13, as a sticky white solid (0.45 g, 46% yield from 5). $^1$H NMR ($CDCl_3$) δ 1.27 (s), 1.33 (br m), 1.61 (p, 2H, J=7.5 Hz), 2.03 (br d, 2H, J=7 Hz), 2.53 (q, 2H, J=7.5 Hz), 3.34 (br s, 1H), 3.87 (br d, 2H, J=12 Hz), 4.48 (br s, 2H), 4.58 (br s, 2H), 5.42 (dd, 1H, J=15 Hz, 5.5 Hz), 5.82 (dt, 1H, J=15 Hz, 5.5 Hz), 7.91 (br s, 4H). $^{13}C\{^1H\}$ NMR ($CDCl_3$) δ 136.85, 126.26, 57.08, 34.76, 32.95, 30.40, 30.36, 30.34, 30.25, 30.19, 30.05, 29.80, 29.62, 29.09, 25.34.

Example 2

Synthetic Schemes for Making Thiolated Fatty Acids

Figure 2A:
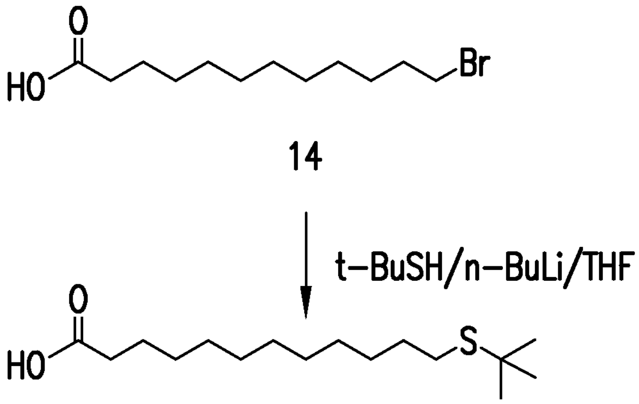
FIG. 2. Organic synthesis scheme for making the thiolated-related fatty acid used in the synthesis of the thiolated-LPA analog of FIG. 3.
Figure 2B:
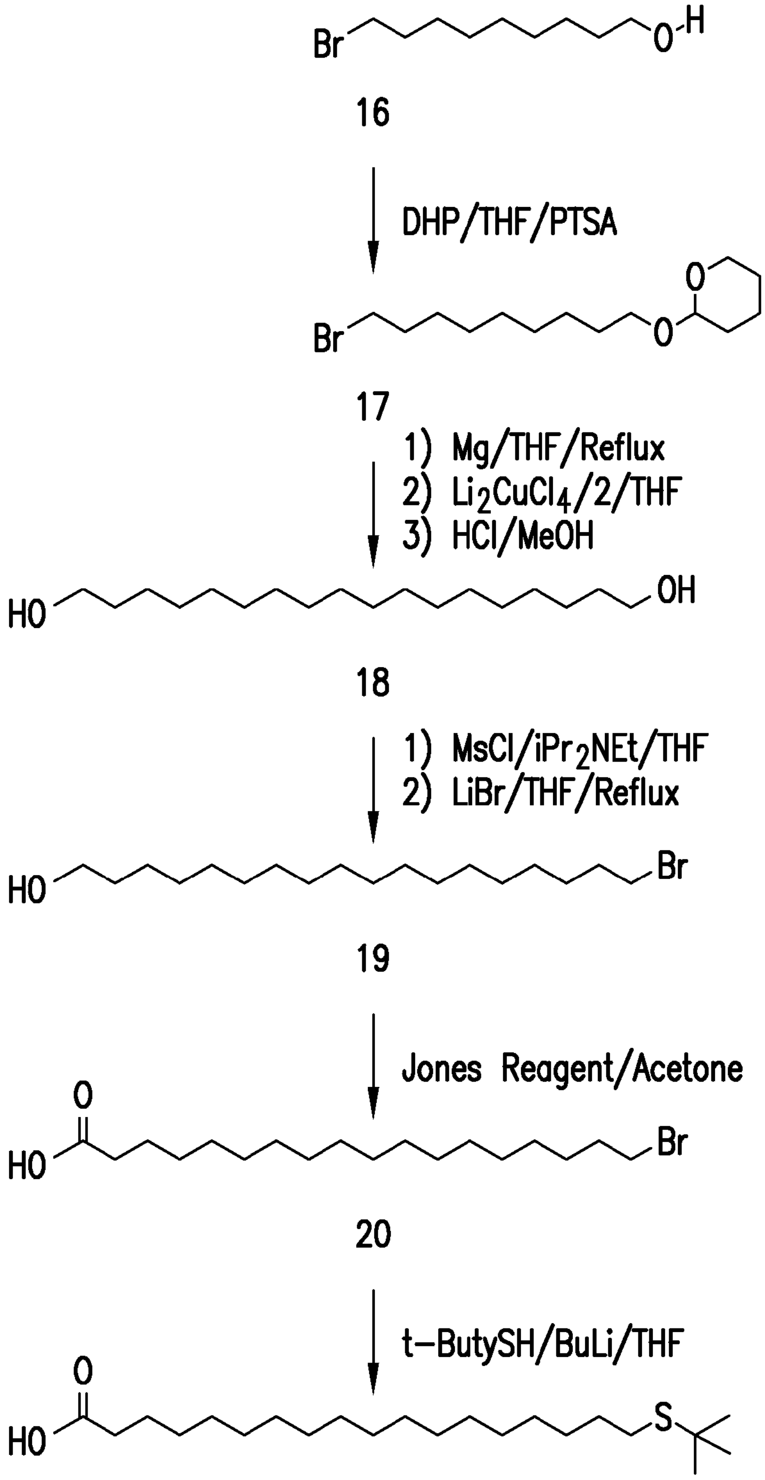

The synthetic approach described in this example details the preparation of a thiolated fatty acid to be incorporated into a more complex lipid structure that could be further complexed to a protein or other carrier and administered to an animal to elicit an immune response. The approach uses using conventional organic chemistry. A scheme showing the approach taken in this example is provided in FIG. 2, and the compound numbers in the synthetic description below refer to the numbered structures in FIG. 2.

Two syntheses are described. The first synthesis, for a C-12 thiolated fatty acid, starts with the commercially available 12-dodecanoic acid, compound 14. The bromine is then displaced with t-butyl thiol to yield the protected C-12 thiolated fatty acid, compound 15. The second synthesis, for a C-18 thiolated fatty acid, starts with the commercially available 9-bromo-nonanol (compound 16). The hydroxyl group in compound 16 is protected by addition of a dihydroyran group and the resulting compound, 17, is dimerized through activation of half of the brominated material via a Grignard reaction, followed by addition of the other half. The 18-hydroxy octadecanol (compound 18) produced following acid-catalyzed removal of the dihydropyran protecting group is selectively mono-brominated to form compound 19. During this reaction approximately half of the alcohol groups are activated for nucleophilic substitution by formation of a methane sulfonic acid ester. The alcohol is then oxidized to form the 18-bromocarboxylic acid, compound 20, which is then treated with t-butyl thiol to displace the bromine and form the protected, thiolated C-18 fatty acid, compound 21.

The protected thiolated fatty acids, each a t-butyl thioether, can be incorporated into a complex lipid and the protecting group removed using, e.g., one of the de-protecting approaches described in Examples 1 and 3. The resulting free thiol then can be used to complex with a protein or other carrier prior to inoculating animal with the hapten.

A. Synthesis of a C-12 Thiolated Fatty Acid

Compound 15.

t-Butyl thiol (12.93 g, 143 mmol) was added to a dry Schlenk flask, and Schlenk methods were used to put the system under nitrogen. Dry, degassed THF (250 mL) was added and the flask cooled in an ice bath. n-BuLi (55 mL of 2.5 M in hexanes, 137.5 mmol) was slowly added over 10 min by syringe. The mixture was allowed to stir at 0° C. for an hour. The bromoacid, compound 14 (10 g, 36 mmol), was added as a solid and the reaction heated and stirred at 60° C. for 24 hr. The reaction was quenched with 2 M HCl (250 mL), and extracted with ether (2×300 mL). The combined ethereal layers were dried with magnesium sulfate, filtered, and the filtrate concentrated by rotary evaporation to yield the thioether acid, compound 15 (10 g, 99% yield) as a beige powder. $^1$H NMR ($CDCl_3$, 500 MHz) δ 1.25-1.35 (br s, 12H), 1.32 (s, 9H), 1.35-1.40 (m, 2H), 1.50-1.60 (m, 2H), 1.60-1.65 (m, 2H), 2.35 (t, 2H, J=7.5 Hz), 2.52 (t, 2H, J=7.5 Hz). Principal ion in HRMS (ES-TOF) was observed at m/z 311.2020, calculated for $M+Na^+$311.2015.

B. Synthesis of a C-12 Thiolated Fatty Acid

Compound 17.

A dry Schlenk flask was charged with compound 16 (50 g, 224.2 mmol) and dissolved in dry degassed THF (250 mL) distilled from sodium/benzophenone. The flask was cooled in an ice bath and then PTSA (0.5 g, 2.6 mmol) was added. Dry, degassed DHP (36 g, 42.8 mmol) was then added slowly over 5 min. The mixture was allowed to warm up to RT and left to stir overnight and monitored by TLC (10:1 PE:EtOAc) until the reaction was deemed done by the complete disappearance of the spot for the bromoalcohol. TEA (1 g, 10 mmol) was then added to quench the PTSA. The mixture was then washed with cold sodium bicarbonate solution and extracted with EtOAc (3×250 mL). The organic layers were then dried with magnesium sulfate and concentrated to yield 68.2 g of crude product which was purified by column chromatography (10:1 PE:EtOAc) to yield 60 g (99% yield) of a colorless oil. $^1H$ NMR ($CDCl_3$, 500 MHz) δ 1.31 (br s, 6H), 1.41-1.44 (m, 2H), 1.51-1.62 (obscured multiplets, 6H), 1.69-1.74 (m, 1H), 1.855 (quintet, J=7.6 Hz, 2H), 3.41 (t, J=7 Hz, 2H), 3.48-3.52 (m, 2H), 3.73 (dt, 2H, J=6.5 Hz), 3.85-3.90 (m, 2H), 4.57 (t, 2H, J=3 Hz).

Compound 18.

Magnesium shavings (2.98 g, 125 mmol) were added to a flame-dried Schlenk flask along with a crystal of iodine. Dry THF (200 mL) distilled from sodium was then added and the system was degassed using Schlenk techniques. Compound 17 (30 g, 97 mmol) was then slowly added to the magnesium over 10 min. and the solution was placed in an oil bath at 65° C. and allowed to stir overnight. The reaction was deemed complete by TLC by quenching an aliquot with acetone and observing the change in RF in a 10:1 PE:EtOAc mixture. The Grignard solution was then transferred by cannula to a three-necked flask under nitrogen containing additional compound 17 (30 g, 97 mmol). The flask containing the resulting mixture was then cooled to 0° C. in an ice bath and a solution of $Li_2CuCl_4$ (3 mL of 1 M) was then added via syringe. The reaction mixture turned a very dark blue within a few minutes. This mixture was left to stir overnight. The next morning the reaction was deemed complete by TLC (10:1 PE:EtOAc), quenched with a saturated $NH_4Cl$ solution, and then extracted into ether (3×250 mL). The ether layers were dried with magnesium sulfate and concentrated to yield crude product (40 g), which was dissolved in MeOH. Concentrated HCl (0.5 mL) was then added, which resulted in the formation of a white emulsion, which was left to stir for 3 hr. The white emulsion was then filtered to yield 16 g (58% yield) of the pure diol, compound 18. $^1H$ NMR ($CDCl_3$, 200 MHz) δ 1.26 (br s, 24H), 1.41-1.42 (m, 4H), 1.51-1.68 (m, 4H), 3.65 (t, 4H, J=6.5 Hz).

Compound 19.

The symmetrical diol, compound 18 (11 g, 38.5 mmol), was added to a dry Schlenk flask under nitrogen, then dry THF (700 mL) distilled from sodium was added. The system was degassed and the flask put in an ice bath. Diisopropylethylamine (6.82 mL, 42.3 mmol) was added via syringe, followed by MsCl (3.96 g, 34.4 mmol) added slowly, and the mixture was left to stir for 1 hr. The reaction was quenched with saturated $NaH_2PO_4$ solution (300 mL), and then extracted with EtOAc (3×300 mL). The organic layers were then combined, dried with $MgSO_4$, and concentrated to yield 14 g of a mixture of the diol, monomesylate, and dimesylate. NMR showed a 1:0.8 mixture of $CH_2OH$:$CH_2OMs$ protons. The mixture was then dissolved in dry THF (500 mL), deoxygenated, and to it was added LiBr (3.5 g, 40.23 mmol). This mixture was allowed reflux overnight, upon which the reaction was quenched with water (150 mL), and extracted with EtOAc (3×250 mL). The organic layer was then dried with $MgSO_4$, and concentrated to yield a mixture of brominated products that were then purified by flash chromatography (DCM) to yield compound 19 (3.1 g, 25% yield) as a white powder. $^1H$ NMR ($CDCl_3$, 500 MHz) δ 1.26 (br s, 26H), 1.38-1.46 (m, 2H), 1.55 (quintet, 2H, J=7.5 Hz), 1.85 (quintet, 2H, J=7.5 Hz), 3.403 (t, 2H, J=6.8 Hz), 3.66 (t. 2H, J=6.8 Hz).

Compound 20.

A round bottom flask was charged with compound 19 (2.01 g, 5.73 mmol) and the solid dissolved in reagent grade acetone (150 mL). Simultaneously, Jones reagent was prepared by dissolving $CrO_3$ (2.25 g, 22 mmol) in $H_2SO_4$ (4 mL) and then slowly adding 10 mL of cold water and letting the solution stir for 10 min. The cold Jones reagent was then added to the round bottom flask slowly over 5 min., after which the solution stirred for 1 hr. The resulting orange solution turned green within several minutes. The mixture was then quenched with water (150 mL) extracted twice in ether (3×150 mL). The ether layers were then dried with magnesium sulfate, and concentrated to yield compound 20 (2.08 g, 98% yield) as a white powder. $^1H$ NMR ($CDCl_3$, 200 MHz) δ 1.27 (br s, 26H), 1.58-1.71 (m, 2H), 1.77-1.97 (m, 2H), 2.36 (t, 2H, J=7.4 Hz), 3.42 (t, 2H, J=7 Hz).

Compound 21.

t-Butylthiol (11.32 g, 125 mmol) was added to a dry Schlenk flask and dissolved in dry THF (450 mL) distilled from sodium. The solution was deoxygenated by bubbling nitrogen through it before the flask was placed in an ice bath. n-BuLi solution in hexanes (70 mL of 1.6 M) was then added slowly via syringe over 10 min. This mixture was allowed to stir for 1 hr., then compound 20 (5.5 g, 16.2 mmol) was added and the solution was left to reflux at 60° C. overnight. The next morning an aliquot was worked up, analyzed by NMR, and the reaction deemed complete. The reaction was quenched with HCl (200 mL of 2 M) and extracted with ether (3×250 mL). The ethereal layers were then dried with magnesium sulfate, filtered, and the filtrate concentrated to yield the product, compound 21, as a white solid (5 g, 90% yield). $^1H$ NMR ($CDCl_3$, 200 MHz) δ 1.26 (br s, 26H), 1.32 (br s, 9H), 1.48-1.70 (m, 4H), 2.35 (t, 2H, J=7.3 Hz), 2.52 (t, 2H, J=7.3 Hz). $^{13}C$ NMR ($CDCl_3$, 200 MHz) δ 24.69, 28.35, 29.05, 29.21, 29.28, 29.39, 29.55, 29.89, 31.02 (3C), 33.98, 41.75, 179.60.

Example 3

Synthetic Scheme for Making a Thiolated Analog of LPA

Figure 3A:
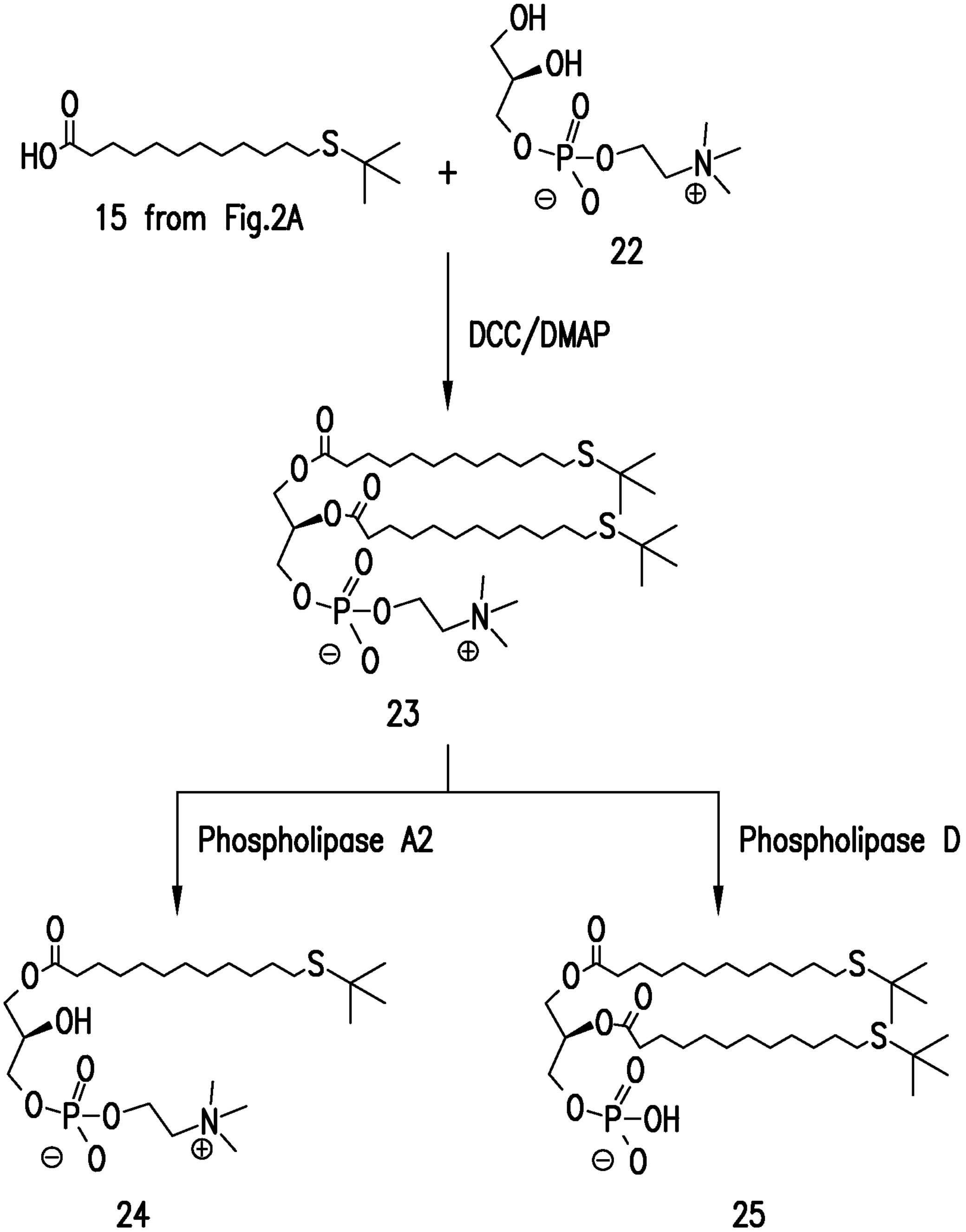
FIG. 3. Organic synthesis scheme for making the thiolated-LPA analog that is a key component of an immunogen, as well as a key component of the laydown material for the ELISA and other assays.
Figure 3B:
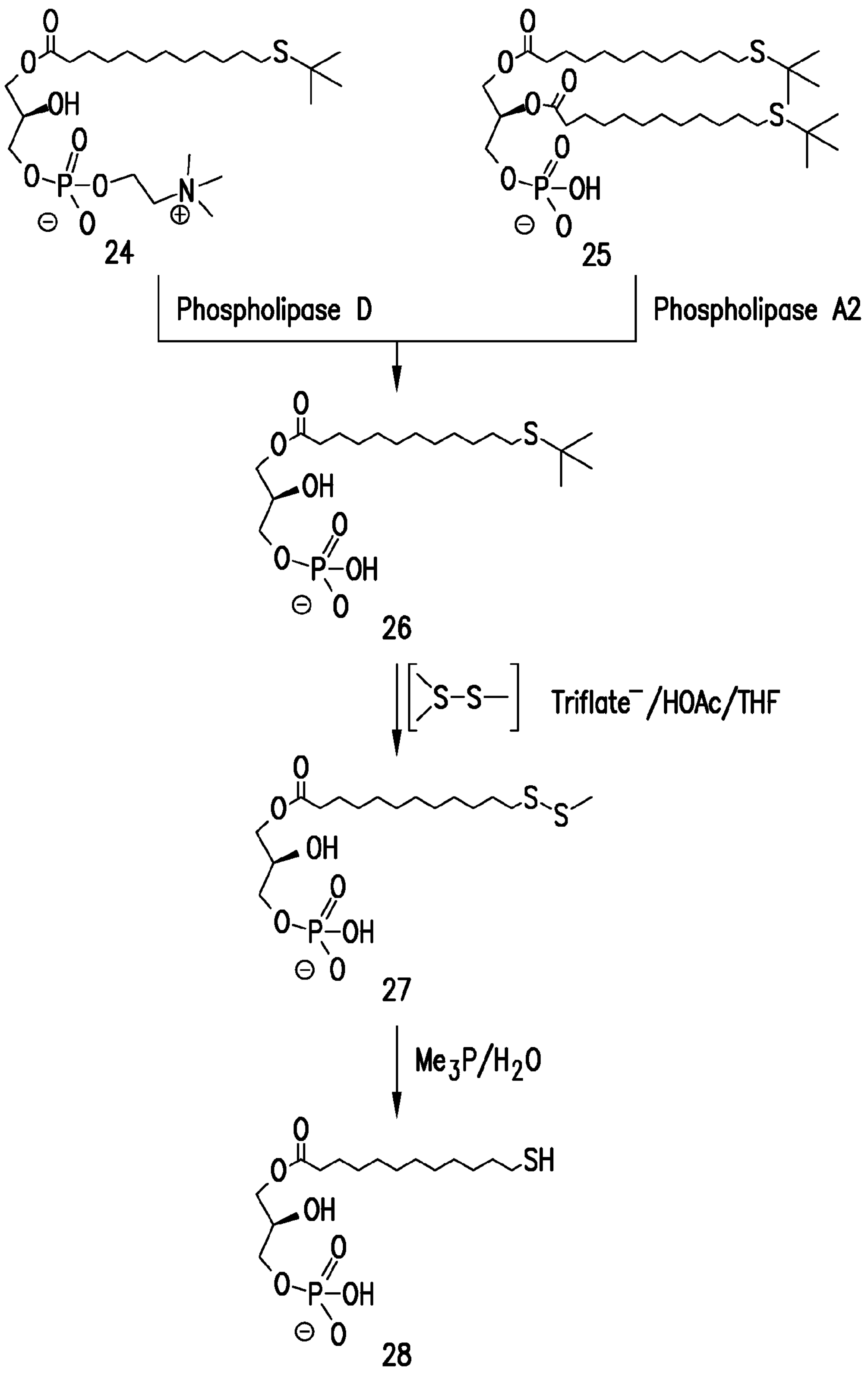

The synthetic approach described in this example results in the preparation of thiolated LPA. The LPA analog can then be further complexed to a carrier, for example, a protein carrier, which can then be administered to an animal to elicit an immugenic response to LPA. This approach uses both organic chemistry and enzymatic reactions, the synthetic scheme for which is provided in FIG. 3. The compound numbers in the synthetic description below refer to the numbered structures in FIG. 3.

The starting materials were compound 15 in Example 2 and enantiomerically pure glycerophoshocholine (compound 22). These two chemicals combined to yield the di-acetylated product, compound 23, using DCC to facilitate the esterification. In one synthetic process variant, the resulting diacylated glycerophosphocholine was treated first with phospholipase-A2 to remove the fatty acid at the sn-2 position of the glycerol backbone to produce compound 24. This substance was further treated with another enzyme, phospholipase-D, to remove the choline and form compound 26. In another synthetic process variant, the phospholipase-D treatment preceded the phospholipase-A2 treatment to yield compound 25, and treatment of compound 25 with phospholipase-D then yields compound 26. Both variants lead to the same product, the phosphatidic acid derivative, compound 26. The t-butyl protecting group in compound 26 is then removed, first using trimethyl disulfide triflate to produce compound 27, followed by a disulfide reduction to produce the desired LPA derivative, compound 28. As those in the art will appreciate, the nitrobenzyl sulfenyl reaction sequence described in Example 1 can also be used to produce compound 28.

Compound 23.

To a flame-dried Schlenk flask were added the thioether acid, compound 15 (10 g, 35.8 mmol), compound 22 (glycerophosphocholine-$CdCl_2$ complex, 4.25 g, 8.9 mmol), DCC (7.32 g, 35.8 mmol), and DMAP (2.18 g, 17.8 mmol), after which the flask was evacuated and filled with nitrogen. A minimal amount of dry, degassed DCM was added (100 mL), resulting in a cloudy mixture. The flask was covered with foil and then left to stir until completed, as by TLC (silica, 10:5:1 DCM:MeOH:concentrated $NH_4OH$). The insolubility of compound 16 precluded monitoring its disappearance by TLC, but the reaction was stopped when the product spot of $R_f$0.1 was judged not to be increasing in intensity. This typically required 3 to 4 days, and in some cases, addition of more DCC and DMAP. Upon completion, the reaction mixture was filtered, and the filtrate concentrated to yield a yellow oil, which was purified using flash chromatography using the solvent system described above to yield 3.6 g (50% yield) of a clear wax containing a mixture of compound 23 and monoacylated products in a ratio of 5 to 1, as estimated from comparing the integrals for the peaks for the $(CH_3)_3N$—, —$CH_2$StBu and —$CH_2$COO-moieties. Analysis of the oil by HRMS (ESI-TOF) produced a prominent ion at m/z 820.4972, calculated for $M+Na^+ = C_{40}H_{80}NNaO_8PS_2^+$ 820.4960.

A. Synthesis Variant 1—Phospholipase-A2 Treatment

Compound 24.

A mixture of compound 23 and monoacetylated products as described above (3.1 g, 3.9 mmol) was dissolved in $Et_2O$ (400 mL) and methanol (30 mL). Borate buffer (100 mL, pH 7.4 0.1M, 0.072 mM in $CaCl_2$) was added, followed by phospholipase-A2 (from bee venom, 130 units, Sigma). The resulting mixture was left to stir for 10 hr., at which point TLC (silica, MeOH:water 4:1—the previous solvent system 10:5:1 DCM:MeOH:concentrated $NH_4OH$ proved ineffective) showed the absence of the starting material ($R_f$=0.7) and the appearance of a new spot ($R_f$=0.2). The organic and aqueous layers were separated and the aqueous layer was washed with ether (2×250 mL). The product was extracted from the aqueous layer with a mixture of DCM:MeOH (2:1, 2×50 mL). The organic layers were then concentrated by rotary evaporation to yield product as a white wax (1.9 g, 86% yield) that NMR showed to be a pure product (compound 24). $^1H$ NMR ($CDCl_3$, 500 MHz) δ 1.25-1.27 (br s, 12H), 1.31 (s, 9H), 1.35-1.45 (m, 2H), 1.52-1.60 (m, 4H), 2.31 (t, 2H, J=7.5 Hz), 2.51 (t, 2H, J=7.5 Hz), 3.28 (br s, 9H) 3.25-3.33 (br s, 2H), 3.78-3.86 (m, 1H), 3.88-3.96 (m, 2H), 4.04-4.10 (m, 2H), 4.26-4.34 (m, 2H). Analysis of the wax by HRMS (ESI-TOF) produced a prominent ion at m/z 550.2936, calculated for $M+Na^+$550.2943 ($C_{24}H_{50}NNaO_7PS_2^+$), and an m/z at 528.3115, calculated for $MH^+$528.3124 ($C_{24}H_{51}NO_7PS_2^+$).

Anal. Calculated for $C_{24}H_{50}NO_7PS+2H_2O$ (563.73): C, 51.13; H, 9.66; N, 2.48. Found: C, 50.90; H, 9.37; N, 2.76.

Compound 26.

The lyso compound 24 (1.5 g, 2.7 mmol) was dissolved in a mixture of sec-butanol (5 mL) and $Et_2O$ (200 mL), and the resulting cloudy mixture was sonicated until the cloudiness dissipated. Buffer (200 mL, pH 5.8, 0.2 M NaOAc, 0.08 M $CaCl_2$) was added, followed by cabbage extract (80 mL of extract from savoy cabbage (which contains phospholipase-D), containing 9 mg of protein/mL). The reaction was stirred for 1 day and monitored by TLC ($C_{18}$RP $SiO_2$, 5:1 ACN: water), $R_f$ of starting material and product=0.3 and 0.05, respectively. In order to push the reaction to completion, as needed an additional portion of cabbage extract (50 mL) was added and the reaction stirred a further day. This process was repeated twice more, as needed to complete the conversion. When the reaction was complete, the mixture was concentrated on the rotary evaporator to remove the ether, and then EDTA solution (0.5 M, 25 mL) was added and the product extracted into a 5:4 mixture of MeOH:DCM (300 mL). Concentration of the organic layer followed by recrystallization of the residue from DCM and acetone afforded pure product (0.9 g, 75% yield). $^1H$ NMR ($CDCl_3$, 200 MHz) δ 1.25-1.27 (br s, 12H), 1.33 (s, 9H), 1.52-1.60 (m, 4H), 2.34 (t, 2H, J=7.5 Hz), 2.52 (t, 2H, J=7.5 Hz), 3.6-3.8 (br s, 1H), 3.85-3.97 (br s, 2H), 4.02-4.18 (m, 2H).

Compound 27.

The protected sample LPA, compound 26 (, 0.150 g, 0.34 mmol), was methanol washed and added to a vial in the glove box. This was then suspended in a mixture of AcOH:THF (1:1, 10 mL), which never fully dissolved even after 1 hr. of sonication. Solid $[Me_2SSMe]$OTf (0.114 g, 0.44 mmol) was then added. This was left to stir for 18 hr. The reaction was monitored by removing an aliquot, concentrating it to dryness under vacuum, and re-dissolving or suspending the residue in $CD_3OD$ for observing the $^1H$ NMR shift of the $CH_2$ peak closest to the sulfur. The starting material had a peak at 2.52 ppm, whereas the unsymmetrical disulfide formed at this juncture had a peak at around 2.7 ppm. This material (compound 27) was not further isolated or characterized.

Compound 28.

The mixture containing compound 27 was treated with water (100 μL) immediately followed by $PMe_3$ (0.11 g, 1.4 mmol). After stirring for 3 hr. the solvent was removed by vacuum to yield an insoluble white solid. Methanol (5 mL) was added, the mixture centrifuged, and the mother liquor decanted. Vacuum concentration yielded 120 mg (91% yield) of compound 28, a beige solid. Compound 28 is a thiolated LPA hapten that can be conjugated to a carrier, for example, albumin or KLH, via disulfide bond formation. Characterization of compound 28: $^1H$ NMR (1:1 $CD_3OD:CD_3CO_2D$, 500 MHz) δ 1.25-1.35 (br s, 12H), 1.32-1.4 (m, 2H), 1.55-1.6 (m, 4H), 2.34 (t, 2H, J=7), 2.47 (t, 2H, J=8.5), 3.89-3.97 (br s, 2H), 3.98-4.15 (m, 2H), 4.21 (m, 1H). Negative ion ES of the sample dissolved in methanol produced a predominant ion at m/z=385.1.

Example 4

Antibodies to S1P

One type of therapeutic antibody specifically binds undesirable sphingolipids to achieve beneficial effects such as, e.g., (1) lowering the effective concentration of undesirable, toxic sphingolipids (and/or the concentration of their metabolic precursors) that would promote an undesirable effect such as a cardiotoxic, tumorigenic, or angiogenic effect; (2) to inhibit the binding of an undesirable, toxic, tumorigenic, or angiogenic sphingolipids to a cellular receptor therefore, and/ or to lower the concentration of a sphingolipid that is available for binding to such a receptor. Examples of such therapeutic effects include, but are not limited to, the use of anti-S1P antibodies to lower the in vivo serum concentration of available S1P, thereby blocking or at least limiting S1P's tumorigenic and angiogenic effects and its role in post-MI heart failure, cancer, or fibrogenic diseases.

Thiolated S1P (compound 10 of FIG. 1) was synthesized to contain a reactive group capable of cross-linking the essential structural features of S1P to a carrier moiety such as KLH. Prior to immunization, the thio-S1P analog was conjugated via IOA or SMCC cross-linking to protein carriers (e.g., KLH) using standard protocols. SMCC is a heterobifunctional crosslinker that reacts with primary amines and sulfhydryl groups, and represents a preferred crosslinker.

Swiss Webster or BALB-C mice were immunized four times over a two month period with 50 μg of immunogen (SMCC facilitated conjugate of thiolated-S1P and KLH) per injection. Serum samples were collected two weeks after the second, third, and fourth immunizations and screened by direct ELISA for the presence of anti-S1P antibodies. Spleens from animals that displayed high titers of the antibody were subsequently used to generate hybridomas per standard fusion procedures. The resulting hybridomas were grown to confluency, after which the cell supernatant was collected for ELISA analysis. Of the 55 mice that were immunized, 8 were good responders, showing significant serum titers of antibodies reactive to S1P. Fusions were subsequently carried out using the spleens of these mice and myeloma cells according to established procedures. The resulting 1,500 hybridomas were then screened by direct ELISA, yielding 287 positive hybridomas. Of these 287 hybridomas screened by direct ELISA, 159 showed significant titers. Each of the 159 hybridomas was then expanded into 24-well plates. The cell-conditioned media of the expanded hybridomas were then re-screened to identify stable hybridomas capable of secreting antibodies of interest. Competitive ELISAs were performed on the 60 highest titer stable hybridomas.

Of the 55 mice and almost 1,500 hybridomas screened, one hybridoma was discovered that displayed performance characteristics that justified limited dilution cloning, as is required to ultimately generate a true monoclonal antibody. This process yielded 47 clones, the majority of which were deemed positive for producing S1P antibodies. Of these 47 clones, 6 were expanded into 24-well plates and subsequently screened by competitive ELISA. From the 4 clones that remained positive, one was chosen to initiate large-scale production of the S1P monoclonal antibody. SCID mice were injected with these cells and the resulting ascites was protein A-purified (50% yield) and analyzed for endotoxin levels (<3 EU/mg). For one round of ascites production, 50 mice were injected, producing a total of 125 mL of ascites. The antibodies were isotyped as IgG1 kappa, and were deemed >95% pure by HPLC. The antibody was prepared in 20 mM sodium phosphate with 150 mM sodium chloride (pH 7.2) and stored at −70° C.

The positive hybridoma clone (designated as clone 306D326.26) was deposited with the ATCC (safety deposit storage number SD-5362), and represents the first murine mAb (Sphingomab™) directed against S1P. The clone also contains the variable regions of the antibody heavy and light chains that could be used for the generation of a "humanized" antibody variant, as well as the sequence information needed to construct a chimeric antibody.

Screening of serum and cell supernatant for S1P-specific antibodies was by direct ELISA using the thiolated S1P analog described in Example 1 (i.e., compound 10) as the antigen. A standard ELISA was performed, as described below, except that 50 ul of sample (serum or cell supernatant) was diluted with an equal volume of PBS/0.1% Tween-20 (PBST) during the primary incubation. ELISAs were performed in 96-well high binding ELISA plates (Costar) coated with 0.1 μg of chemically-synthesized compound 10 conjugated to BSA in binding buffer (33.6 mM Na2CO3, 100 mM NaHCO3; pH 9.5). The thiolated-S1P-BSA was incubated at 37° C. for 1 hr. at 4° C. overnight in the ELISA plate wells. The plates were then washed four times with PBS (137 mM NaCl, 2.68 mM KCl, 10.14 mM Na2HPO4, 1.76 mM KH2PO4; pH 7.4) and blocked with PBST for 1 hr. at room temperature. For the primary incubation step, 75 uL of the sample (containing the S1P to be measured), was incubated with 25 uL of 0.1 ug/mL anti-S1P mAb diluted in PBST and added to a well of the ELISA plate. Each sample was performed in triplicate wells. Following a 1 hr. incubation at room temperature, the ELISA plates were washed four times with PBS and incubated with 100 ul per well of 0.1 ug/mL HRP goat anti-mouse secondary (Jackson Immunoresearch) for 1 hr. at room temperature. Plates were then washed four times with PBS and exposed to tetramethylbenzidine (Sigma) for 1-10 minutes. The detection reaction was stopped by the addition of an equal volume of 1M H2SO4. Optical density of the samples was determined by measurement at 450 nm using an EL-X-800 ELISA plate reader (Bio-Tech).

For cross reactivity, a competitive ELISA was performed as described above, except for the following alterations. The primary incubation consisted of the competitor (S1P, SPH, LPA, etc.) and a biotin-conjugated anti-S1P mAb. Biotinylation of the purified monoclonal antibody was performed using the EZ-Link Sulfo-NHS-Biotinylation kit (Pierce). Biotin incorporation was determined as per kit protocol and ranged from 7 to 11 biotin molecules per antibody. The competitor was prepared as follows: lipid stocks were sonicated and dried under argon before reconstitution in DPBS/BSA [1 mg/ml fatty acid-free BSA (Calbiochem) in DPBS (Invitrogen 14040-133)]. Purified anti-S1P mAb was diluted as necessary in PBS/0.5% Triton X-100. Competitor and antibody solutions were mixed together so to generate 3 parts competitor to 1 part antibody. A HRP-conjugated streptavidin secondary antibody (Jackson Immunoresearch) was used to generate signal.

Another aspect of the competitive ELISA data is that it shows that the anti-S1P mAb was unable to distinguish the thiolated-S1P analog (compound 10) from the natural S1P that was added in the competition experiment. It also demonstrates that the antibody does not recognize any oxidation products because the analog was constructed without any double bonds (as is also also true for the LPA analog described in Example 3). The anti-S1P mAb was also tested against natural product containing the double bond that was allowed to sit at room temperature for 48 hours. Reverse phase HPLC of the natural S1P was performed according to methods reported previously (Deutschman, et al. (July 2003), Am Heart J., vol. 146(1):62-8), and the results showed no difference in retention time. Further, a comparison of the binding characteristics of the monoclonal antibody to the various lipids tested indicates that the epitope recognized by the antibody do not involve the hydrocarbon chain in the region of the double bond of natural S1P. On the other hand, the epitope recognized by the monoclonal antibody is the region containing the amino alcohol on the sphingosine base backbone plus the free phosphate. If the free phosphate is linked with a choline (as is the case with SPC), then the binding was somewhat reduced. If the amino group is esterified to a fatty acid (as is the case with C1P), no antibody binding was observed. If the sphingosine amino alcohol backbone was replaced by a glycerol backbone (as is the case with LPA), there the S1P-specific monoclonal exhibited no binding. These epitope mapping data indicate that there is only one epitope on S1P recognized by the monoclonal antibody, and that this epitope is defined by the unique polar headgroup of S1P.

In a similar experiment using ELISA measurements, suitable control materials were evaluated to ensure that this anti-S1P monoclonal antibody did not recognize either the protein carrier or the crosslinking agent. For example, the normal crosslinker SMCC was exchanged for IOA in conjugating the thiolated-S1P to BSA as the laydown material in the ELISA. When IOA was used, the antibody's binding characteristics were nearly identical to when BSA-SMCC-thiolated-S1P was used. Similarly, KLH was exchanged for BSA as the protein that was complexed with thiolated-S1P as the laydown material. In this experiment, there was also no significant difference in the binding characteristics of the antibody.

Binding kinetics: The binding kinetics of S1P to its receptor or other moieties has, traditionally, been problematic because of the nature of lipids. Many problems have been associated with the insolubility of lipids. For BIAcore measurements, these problems were overcome by directly immobilizing S1P to a BIAcore chip. Antibody was then flowed over the surface of the chip and alterations in optical density were measured to determine the binding characteristics of the antibody to S1P. To circumvent the bivalent binding nature of antibodies, S1P was coated on the chip at low densities. Additionally, the chip was coated with various densities of S1P (7, 20, and 1000 RU) and antibody binding data was globally fit to a 1:1 interaction model. Changes in optical density resulted due to the binding of the monoclonal antibody to S1P at three different densities of S1P. Overall, the affinity of the monoclonal antibody to S1P was determined to be very high, in the range of approximately 88 picomolar (pM) to 99 nM, depending on whether a monovalent or bivalent binding model was used to analyze the binding data.

Example 5

Chimeric mAb to S1P

A chimeric antibody to S1P was generated using the variable regions (Fv) containing the active S1P binding regions of the murine antibody from a particular hybridoma (ATCC safety deposit storage number SD-5362) with the Fc region of a human IgG1 immunoglobulin. The Fc regions contained the CL, ChL, and Ch3 domains of the human antibody. Without being limited to a particular method, chimeric antibodies could also have been generated from Fc regions of human IgG1, IgG2, IgG3, IgG4, IgA, or IgM. As those in the art will appreciate, "humanized" antibodies can be generated by grafting the complementarity determining regions (CDRs, e.g. CDR1-4) of the murine anti-S1P mAb with a human antibody framework regions (e.g., Fr1, Fr4, etc.) such as the framework regions of an IgG1.

For the direct ELISA experiments, the chimeric antibody to S1P had similar binding characteristics to the fully murine monoclonal antibody. ELISAs were performed in 96-well high-binding ELISA plates (Costar) coated with 0.1 ug of chemically-synthesized, thiolated S1P conjugated to BSA in binding buffer (33.6 mM $Na_2CO_3$, 100 mM $NaHCO_3$; pH 9.5). The thiolated S1P-BSA was incubated at 37° C. for 1 hr. or at 4° C. overnight in the ELISA plate. Plates were then washed four times with PBS (137 mM NaCl, 2.68 mM KCl, 10.14 mM $Na_2HPO_4$, 1.76 mM $KH_2PO_4$; pH 7.4) and blocked with PBST for 1 hr. at room temperature. For the primary incubation step, 75 uL of the sample (containing the S1P to be measured), was incubated with 25 μL of 0.1 μg/mL anti-S1P monoclonal antibody diluted in PBST and added to a well of the ELISA plate. Each sample was performed in triplicate wells. Following a 1 hr incubation at room temperature, the ELISA plates were washed four times with PBS and incubated with 100 ul per well of 0.1 ug/mL HRP goat anti-mouse secondary (Jackson Immunoresearch) for 1 hr. at room temperature. Plates were then washed four times with PBS and exposed to tetramethylbenzidine (Sigma) for 1-10 minutes. The detection reaction was stopped by the addition of an equal volume of 1M $H_2SO_4$. Optical density of the samples was determined by measurement at 450 nm using an EL-X-800 ELISA plate reader (Bio-Tech).

The preferred method of measuring either antibody titer in the serum of an immunized animal or in cell-conditioned media (i.e., supernatant) of an antibody-producing cell such as a hybridoma, involves coating the ELISA plate with a target ligand (e.g., a thiolated analog of S1P, LPA, etc.) that has been covalently linked to a protein carrier such as BSA.

Example 6

Monoclonal Antibodies to LPA

Antibody Production

Although polyclonal antibodies against naturally-occurring LPA have been reported in the literature (Chen J H, et al., Bioorg Med Chem. Lett. 2000 Aug. 7; 10(15):1691-3), monoclonal antibodies have not been described. Using an approach similar to that described in Example 4, a C-12 thio-LPA analog (compound 28 in Example 3) as the key component of a hapten formed by the cross-linking of the analog via the reactive SH group to a protein carrier (KLH) via standard chemical cross-linking using either IOA or SMCC as the cross-linking agent, monoclonal antibodies against LPA were generated. To do this, mice were immunized with the thio-LPA-KLH hapten (in this case, thiolated-LPA:SMCC:KLH) using methods described in Example 4 for the generation of anti-S1P monoclonal antibodies. Of the 80 mice immunized against the LPA analog, the five animals that showed the highest titers against LPA (determined using an ELISA in which the same LPA analog (compound 28) as used in the hapten was conjugated to BSA using SMCC and laid down on the ELISA plates) were chosen for moving to the hybridoma phase of development.

The spleens from these five mice were harvested and hybridomas were generated by standard techniques. Briefly, one mouse yielded hybridoma cell lines (designated 504A). Of all the plated hybridomas of the 504A series, 66 showed positive antibody production as measured by the previously-described screening ELISA.

Table 1, below, shows the antibody titers in cell supernatants of hybridomas created from the spleens of two of mice that responded to an LPA analog hapten in which the thiolated LPA analog was cross-linked to KLH using heterobifunctional cross-linking agents. These data demonstrate that the anti-LPA antibodies do not react either to the crosslinker or to the protein carrier. Importantly, the data show that the hybridomas produce antibodies against LPA, and not against S1P.

TABLE 1

| LPA hybridomas | | | | | |
|---|---|---|---|---|---|
| mouse # | 3rd bleed titer OD at 1:312,500 | Superna-tants from 24 well | LPA binding OD at 1:20 | S1P binding OD at 1:20 | Cross reactivity w/S1P* |
| 1 | 1.242 | 1.A.63 | 1.197 | 0.231 | low |
| | | 1.A.65 | 1.545 | 0.176 | none |
| 2 | 0.709 | 2.B.7 | 2.357 | 0.302 | low |
| | | 2.B.63 | 2.302 | 0.229 | low |
| | | 2.B.83 | 2.712 | 0.175 | none |
| | | 2.B.104 | 2.57 | 0.164 | none |
| | | 2.B.IB7 | 2.387 | 0.163 | none |
| | | 2.B.3A6 | 2.227 | 0.134 | none |

*Cross reactivity with S1P from 24 well supernatants: high = OD >1.0-2.0 at [1:20]; mid = OD 0.4-1.0 at [1:20]; low = OD 0.4-0.2 at [1:20]; none = OD <0.2 OD at [1:20].

The development of anti-LPA mAbs in mice was monitored by ELISA (direct binding to 12:0 and 18:1 LPA and competition ELISA). A significant immunological response was observed in at least half of the immunized mice and five mice with the highest antibody titer were selected to initiate hybridoma cell line development following spleen fusion.

After the initial screening of over 2000 hybridoma cell lines generated from these 5 fusions, a total of 29 anti-LPA secreting hybridoma cell lines exhibited high binding to 18:1 LPA. Of these hybridoma cell lines, 24 were further subcloned and characterized in a panel of ELISA assays. From the 24 clones that remained positive, six hybridoma clones were selected for further characterization. Their selection was based on their superior biochemical and biological properties. Mouse hybridoma cell lines 504B3-6C2, 504B7.1, 504B58/3F8, 504A63.1 and 504B3A6 (corresponding to clones referred to herein as B3, B7, B58, A63, and B3A6, respectively) were received on May 8, 2007 by the American Type Culture Collection (ATCC Patent Depository, 10801 University Blvd., Manassas, Va. 20110) for patent deposit purposes on behalf of LPath Inc. and were granted deposit numbers PTA-8417, PTA-8420, PTA-8418, PTA-8419 and PTA-8416, respectively.

All anti-LPA antibodies and portions thereof referred to herein were derived from these cell lines.

Direct Binding Kinetics

The binding of 6 anti-LPA mAbs (B3, B7, B58, A63, B3A6, D22) to 12:0 and 18:1 LPA (0.1 uM) was measured by ELISA. $EC_{50}$ values were calculated from titration curves using 6 increasing concentrations of purified mAbs (0 to 0.4 ug/ml). $EC_{50}$ represents the effective antibody concentration with 50% of the maximum binding. Max denotes the maximal binding (expressed as OD450). Results are shown in Table 2.

TABLE 2

| Direct Binding Kinetics of Anti-LPA mAbs | | | | | | | |
|---|---|---|---|---|---|---|---|
| | | B3 | B7 | B58 | D22 | A63 | B3A6 |
| 12:0 LPA | $EC_{50}$ (nM) | 1.420 | 0.413 | 0.554 | 1.307 | 0.280 | 0.344 |
| | Max (OD450) | 1.809 | 1.395 | 1.352 | 0.449 | 1.269 | 1.316 |
| 18:1 LPA | $EC_{50}$ (nM) | 1.067 | 0.274 | 0.245 | 0.176 | 0.298 | 0.469 |
| | Max (OD450) | 1.264 | 0.973 | 0.847 | 0.353 | 1.302 | 1.027 |

The kinetics parameters $k_a$ (association rate constant), $k_d$ (disassociation rate constant) and $K_D$ (association equilibrium constant) were determined for the 6 lead candidates using the BIAcore 3000 Biosensor machine. In this study, LPA was immobilized on the sensor surface and the anti-LPA mAbs were flowed in solution across the surface. As shown, all six mAbs bound LPA with similar $K_D$ values ranging from 0.34 to 3.8 pM and similar kinetic parameters.

The Anti-LPA Murine Mabs Exhibit High Affinity to LPA

LPA was immobilized to the sensor chip at densities ranging 150 resonance units. Dilutions of each mAb were passed over the immobilized LPA and kinetic constants were obtained by nonlinear regression of association/dissociation phases. Errors are given as the standard deviation using at least three determinations in duplicate runs. Results are shown in Table 3. Apparent affinities were determined by $K_D=k_d/k_a$.

$k_a$=Association rate constant in $M^{-1}s^{-1}$$k_d$=Dissociation rate constant in $s^{-1}$

TABLE 3

| Affinity of anti-LPA mAb for LPA | | | |
|---|---|---|---|
| mAbs | $k_a$ ($M^{-1}$ $s^{-1}$) | $k_d$ ($s^{-1}$) | $K_D$ (pM) |
| A63 | $4.4 \pm 1.0 \times 10^5$ | $1 \times 10^{-6}$ | $2.3 \pm 0.5$ |
| B3 | $7.0 \pm 1.5 \times 10^5$ | $1 \times 10^{-6}$ | $1.4 \pm 0.3$ |
| B7 | $6.2 \pm 0.1 \times 10^5$ | $1 \times 10^{-6}$ | $1.6 \pm 0.1$ |
| D22 | $3.0 \pm 0.9 \times 10^4$ | $1 \times 10^{-6}$ | $33 \pm 10$ |
| B3A6 | $1.2 \pm 0.9 \times 10^6$ | $1.9 \pm 0.4 \times 10^{-5}$ | $16 \pm 1.2$ |

Specificity Profile of Six Anti-LPA Mabs.

Many isoforms of LPA have been identified to be biologically active and it is preferable that the mAb recognize all of them to some extent to be of therapeutic relevance. The specificity of the anti-LPA mAbs was evaluated utilizing a competition assay in which the competitor lipid was added to the antibody-immobilized lipid mixture.

Competition ELISA assays were performed with the anti-LPA mAbs to assess their specificity. 18:1 LPA was captured on ELISA plates. Each competitor lipid (up to 10 uM) was serially diluted in BSA (1 mg/ml)-PBS and then incubated with the mAbs (3 nM). Mixtures were then transferred to LPA coated wells and the amount of bound antibody was measured with a secondary antibody. Data are normalized to maximum signal ($A_{450}$) and are expressed as percent inhibition. Assays were performed in triplicate. $IC_{50}$: Half maximum inhibition concentration; MI: Maximum inhibition (% of binding in the absence of inhibitor); - - -: not estimated because of weak inhibition. A high inhibition result indicates recognition of the competitor lipid by the antibody. As shown in Table 4, all the anti-LPA mAbs recognized the different LPA isoforms.

TABLE 4

Specificity profile of anti-LPA mAbs.

| | 14:0 LPA | | 16:0 LPA | | 18:1 LPA | | 18:2 LPA | | 20:4 LPA | |
|---|---|---|---|---|---|---|---|---|---|---|
| | $IC_{50}$ uM | MI % | $IC_{50}$ uM | MI % | $IC_{50}$ uM | MI % | $IC_{50}$ uM | MI % | $IC_{50}$ uM | MI % |
| B3 | 0.02 | 72.3 | 0.05 | 70.3 | 0.287 | 83 | 0.064 | 72.5 | 0.02 | 67.1 |
| B7 | 0.105 | 61.3 | 0.483 | 62.9 | >2.0 | 100 | 1.487 | 100 | 0.161 | 67 |
| B58 | 0.26 | 63.9 | 5.698 | >100 | 1.5 | 79.3 | 1.240 | 92.6 | 0.304 | 79.8 |
| B104 | 0.32 | 23.1 | 1.557 | 26.5 | 28.648 | >100 | 1.591 | 36 | 0.32 | 20.1 |
| D22 | 0.164 | 34.9 | 0.543 | 31 | 1.489 | 47.7 | 0.331 | 31.4 | 0.164 | 29.5 |
| A63 | 1.147 | 31.9 | 5.994 | 45.7 | — | — | — | — | 0.119 | 14.5 |
| B3A6 | 0.108 | 59.9 | 1.151 | 81.1 | 1.897 | 87.6 | — | — | 0.131 | 44.9 |

Interestingly, the anti-LPA mAbs were able to discriminate between 12:0 (lauroyl), 14:0 (myristoyl), 16:0 (palmitoyl), 18:1 (oleoyl), 18:2 (linoleoyl) and 20:4 (arachidonoyl) LPAs. A desirable $EC_{50}$ rank order for ultimate drug development is 18:2>18:1>20:4 for unsaturated lipids and 14:0>16:0>18:0 for the saturated lipids, along with high specificity. The specificity of the anti-LPA mAbs was assessed for their binding to LPA related biolipids such as distearoyl-phosphatidic acid, lysophosphatidylcholine, S1P, ceramide and ceramide-1-phosphate. None of the antibodies demonstrated cross-reactivity to distearoyl PA and LPC, the immediate metabolic precursor of LPA.

Example 7

Anti-Cancer Activities of Anti-LPA Monoclonal Antibodies

Cancer Cell Proliferation

LPA is a potent growth factor supporting cell survival and proliferation by stimulation of $G_i$, $G_q$ and $G_{12/13}$ via GPCR-receptors and activation of downstream signaling events. Cell lines were tested for their proliferative response to LPA (0.01 mM to 10 mM). Cell proliferation was assayed by using the cell proliferation assay kit from Chemicon (Temecula Calif.) (Panc-1) and the Cell-Blue titer from Pierce (Caki-1). Each data point is the mean of three independent experiments. LPA increased proliferation of 7 human-derived tumor cell lines in a dose dependent manner including SKOV3 and OVCAR3 (ovarian cancer), Panc-1 (pancreatic cancer), Caki-1 (renal carcinoma cell), DU-145 (prostate cancer), A549 (lung carcinoma), and HCT-116 (colorectal adenocarcinoma) cells and one rat-derived tumor cell line, RBL-2H3 (rat leukemia cells). Even though tumor-derived cells normally have high basal levels of proliferation, LPA appears to further augment proliferation in most tumor cell lines. Anti-LPA mAbs (B7 and B58) were assessed for the ability to inhibit LPA-induced proliferation in selected human cancer cell lines. The increase in proliferation induced by LPA was shown to be mitigated by the addition of anti-LPA mAb.

Anti-LPA mAb Sensitizes Tumor Cells to Chemotherapeutic Agents

The ability of LPA to protect ovarian tumor cells against apoptosis when exposed to clinically-relevant levels of the chemotherapeutic agent, paclitaxel (Taxol) was investigated. SKVO3 cells were treated with 1% FBS (S), Taxol (0.5 mM), +1-anti-LPA mAbs for 24 h. LPA protected SKOV3 cells from Taxol-induced apoptosis. Apoptosis was assayed by measurement of the caspase activity as recommended by the manufacturer (Promega). As anticipated, LPA protected most of the cancer cell lines tested from taxol-induced cell death. When the anti-LPA antibody B7 was added to a selection of the LPA responsive cells, it blocked the ability of LPA to protect cells from death induced by the cytotoxic chemotherapeutic agent. Moreover, the anti-LPA antibody was able to remove the protection provided by serum. Serum is estimated to contain about 5-20 uM LPA. Taxol induced caspase-3,7 activation in SKOV3 cells and the addition of serum to cells protected cells from apoptosis. Taxol-induced caspase activation was enhanced by the addition of LT3000 to the culture medium. This suggests that the protective and anti-apoptotic effects of LPA were removed by the selective antibody mediated neutralization of the LPA present in serum.

Anti-LPA mAb Inhibits LPA-Mediated Migration of Tumor Cells

An important characteristic of metastatic cancers is that the tumor cells escape contact inhibition and migrate away from their tissue of origin. LPA has been shown to promote metastatic potential in several cancer cell types. Accordingly, we tested the ability of anti-LPA mAb to block LPA-dependent cell migration in several human cancer cell lines by using the cell monolayer scratch assay. Cells were seeded in 96 well plates and grown to confluence. After 24 h of starvation, the center of the wells was scratched with a pipette tip. In this art-accepted “scratch assay,” the cells respond to the scratch wound in the cell monolayer in a stereotypical fashion by migrating toward the scratch and close the wound. Progression of migration and wound closure are monitored by digital photography at 10× magnification at desired timepoints. Cells were not treated (NT), treated with LPA (2.5 mM) with or w/o mAb B7 (10 μg/ml) or an isotype matching non-specific antibody (NS) (10 μg/ml). In untreated cells, a large gap remains between the monolayer margins following the scratch. LPA-treated cells in contrast, have only a small gap remaining at the same timepoint, and a few cells are making contact across the gap. In cells treated with both LPA and the anti-LPA antibody B7, the gap at this timepoint was several fold larger than the LPA-only treatment although not as large as the untreated control cells. This shows that the anti-LPA antibody had an inhibitory effect on the LPA-stimulated migration of renal cell carcinoma (Caki-1) cells. Similar data were obtained with mAbs B3 and B58. This indicates that the anti-LPA mAb can reduce LPA-mediated migration of cell lines originally derived from metastatic carcinoma.

Anti-LPA Mabs Inhibit Release of Pro-Tumorigenic Cytokines from Tumor Cells

LPA is involved in the establishment and progression of cancer by providing a pro-growth tumor microenvironment and promoting angiogenesis. In particular, increases of the pro-growth factors such as IL-8 and VEGF have been observed in cancer cells. IL-8 is strongly implicated in cancer progression and prognosis. IL-8 may exert its effect in cancer through promoting neovascularization and inducing chemotaxis of neutrophils and endothelial cells. In addition, overexpression of IL-8 has been correlated to the development of a drug resistant phenotype in many human cancer types.

Three anti-LPA mAbs (B3, B7 and B58) were tested for their abilities to reduce in vitro IL-8 production compared to a non-specific antibody (NS). Caki-1 cells were seeded in 96 well plates and grown to confluency. After overnight serum starvation, cells were treated with 18:1 LPA (0.2 mM) with or without anti-LPA mAb B3, B7, B58 or NS (Non-Specific). After 24 h, cultured supernatants of renal cancer cells (Caki-1), treated with or without LPA and in presence of increasing concentrations of the anti-LPA mAbs B3, B7 and B58, were collected and analyzed for IL-8 levels using a commercially available ELISA kit (Human Quantikine Kit, R&D Systems, Minneapolis, Minn.). In cells pre-treated with the anti-LPA mAbs, IL-8 expression was significantly reduced in a dose-dependent manner (from 0.1-30 μg/mL mAb) whereas LPA increased the expression of IL-8 by an average of 100% in non-treated cells. The inhibition of IL-8 release by the anti-LPA mAbs was also observed in other cancerous cell lines such as the pancreatic cell line Panc-1. These data suggest that the blockade of the pro-angiogenic factor release is an additional and potentially important effect of these anti-LPA mAbs.

Anti-LPA Mabs Inhibit Angiogenesis In Vivo

One of the anti-LPA mAbs (B7) was tested for its ability to mitigate angiogenesis in vivo using the Matrigel Plug assay. This assay utilizes Matrigel, a proprietary mixture of tumor remnants including basement membranes derived from murine tumors. When Matrigel, or its derivate growth factor-reduced (GFR) Matrigel, is injected sc into an animal, it solidifies and forms a 'plug.' If pro-angiogenic factors are mixed with the matrix prior to placement, the plug will be invaded by vascular endothelial cells which eventually form blood vessels. Matrigel can be prepared either alone or mixed with recombinant growth factors (bFGF, VEGF), or tumor cells and then injected sc in the flanks of 6-week old nude (NCr Nu/Nu) female mice. In this example, Caki-1 (renal carcinoma) cells were introduced inside the Matrigel and are producing sufficient levels of VEGF and/or IL8 and LPA. Matrigel plugs were prepared containing $5\times10^5$ Caki-1 cells from mice treated with saline or with 10 mg/kg of anti-LPA mAb-B7, every 3 days starting 1 day prior to Matrigel implantation. Plugs were stained for endothelial CD31, followed by quantitation of the micro-vasculature formed in the plugs. Quantitation data were means+/−SEM of at least 16 fields/section from 3 plugs. The plugs from mice treated with the anti-LPA mAb B7 demonstrated a prominent reduction in blood vessel formation, as assayed by endothelial staining for CD31, compared to the plugs from saline-treated mice. Quantification of stained vessels demonstrates a greater than 50% reduction in angiogenesis in Caki-1-containing plugs from animals treated with mAb B7 compared to saline-treated animals. This was a statistically significant reduction ($p<0.05$ for mAb B7 vs. Saline as determined by Student's T-test) in tumor cell angiogenesis as a result of anti-LPA mAb treatment.

Anti-LPA Mabs Reduces Tumor Progression in a Murine Model of Metastasis

One important characteristic of tumor progression is the ability of a tumor to metastasize and form secondary tumor nodules at remote sites. In vitro studies described hereinabove have demonstrated the ability of LPA to induce tumor cells to escape contact inhibition and promote migration in a scratch assay for cell motility. In these studies, the anti-LPA mAbs also inhibited LPA's tumor growth promoting effectors. The efficacy of the anti-LPA mAb to inhibit tumor metastasis in vivo was also evaluated. The phenomenon of tumor metastasis has been difficult to mimic in animal models. Many investigators utilize an "experimental" metastasis model in which tumor cells are directly injected into the blood stream.

Blood vessel formation is an integral process of metastasis because an increase in the number of blood vessels means cells have to travel a shorter distance to reach circulation. It is believed that anti-LPA mAb will inhibit in vivo tumor cell metastasis, based on the finding that the anti-LPA mAb can block several integral steps in the metastatic process.

Study: The highly metastatic murine melanoma (B16-F10) was used to examine the therapeutic effect of anti-LPA mAbs on metastasis in vivo. This model has demonstrated to be highly sensitive to cPA inhibitors of autotaxin. 4 week old female (C57BL/6) mice received an injection of B16-F10 murine melanoma tumor cells (100 uL of $5\times10^4$ cells/animal) via the tail vein. Mice (10 per group) were administered 25 mg/kg of the anti-LPA mAb (either B3 or B7) or saline every three days by i.p. injection. After 18 days, lungs were harvested and analyzed. The pulmonary organs are the preferred metastatic site of the melanoma cells, and were therefore closely evaluated for metastatic nodules. The lungs were inflated with 10% buffered formalin via the trachea, in order to inflate and fix simultaneously, so that even small foci could be detectable on histological examination. Lungs were separated into five lobes and tumors were categorized by dimension (large >5 mm; medium 1-4 mm; small <1 mm) and counted under a dissecting microscope. Upon examination of the lungs, the number of tumors was clearly reduced in antibody-treated animals. For animals treated with mAb B3, large tumors were reduced by 21%, medium tumors by 17% and small tumors by 22%. Statistical analysis by student's T-test gave a $p<0.05$ for number of small tumors in animals treated with mAb B3 vs saline.

As shown in the above examples, it has now been shown that the tumorigenic effects of LPA are extended to renal carcinoma (e.g., Caki-1) and pancreatic carcinoma (Panc-1) cell lines. LPA induces tumor cell proliferation, migration and release of pro-angiogenic and/or pro-metastatic agents, such as VEGF and IL-8, in both cell lines. It has now been shown that three high-affinity and specific monoclonal anti-LPA antibodies demonstrate efficacy in a panel of in vitro cell assays and in vivo tumor models of angiogenesis and metastasis.

Example 8

Cloning of the Murine Anti-LPA Antibodies—Overview

Chimeric antibodies to LPA were generated using the variable domains (Fv) containing the active LPA binding regions of one of three murine antibodies from hybridomas with the Fc region of a human IgG1 immunoglobulin. The Fc regions contained the CH1, CH2, and CH3 domains of the human antibody. Without being limited to a particular method, chimeric antibodies could also have been generated from Fc regions of human IgG1, IgG2, IgG3, IgG4, IgA, or IgM. As those in the art will appreciate, "humanized" antibodies can be generated by grafting the complementarity determining regions (CDRs, e.g. CDR1-4) of the murine anti-LPA mAbs with a human antibody framework regions (e.g., Fr1, Fr4, etc.) such as the framework regions of an IgG1.

The overall strategy for cloning of the murine mAb against LPA consisted of cloning the murine variable domains of both the light chain (VL) and the heavy chain (VH) from each antibody. The consensus sequences of the genes show that the constant region fragment is consistent with a gamma isotype and that the light chain is consistent with a kappa isotype. The murine variable domains were cloned together with the constant domain of the human antibody light chain (CL) and with the constant domain of the human heavy chain (CH1, CH2, and CH3), resulting in a chimeric antibody construct.

The variable domains of the light chain and the heavy chain were amplified by PCR. The amplified fragments were cloned into an intermediate vector (pTOPO). After verification of the sequences, the variable domains were then assembled together with their respective constant domains. The variable domain of the light chain was cloned into pCONkappa2 and the variable domain of the heavy chain was cloned into pCONgamma1f. The cloning procedure included the design of an upstream primer to include a signal peptide sequence, a consensus Kozak sequence preceding the ATG start codon to enhance translation initiation, and the 5' cut site, HindIII. The downstream primer was designed to include the 3' cut site ApaI for the heavy chain and BsiWI for the light chain.

The vectors containing the variable domains together with their respective constant domains were transfected into mammalian cells. Three days after transfections, supernatants were collected and analyzed by ELISA for binding to LPA. Detailed methods for cloning, expression and characterization of the anti-LPA antibody variable domains are shown on the following pages.

Binding characteristics for the chimeric antibodies are shown in Table 5. "HC" and "LC" indicate the identities of the heavy chain and light chain, respectively.

TABLE 5

Binding characteristics of the chimeric anti-LPA antibodies B3, B7, and B58.

| | HC | x | LC | Titer (ug/ml) | EC50 (ng/ml) | Max OD |
|---|---|---|---|---|---|---|
| 1 | B7 | | B7 | 3.54 | 43.24 | 2.237 |
| 2 | B7 | | B58 | 1.84 | 25.79 | 1.998 |
| 3 | B7 | | B3 | 2.58 | 24.44 | 2.234 |
| 4 | B58 | | B7 | 3.80 | 38.99 | 2.099 |
| 5 | B58 | | B58 | 3.42 | 41.3 | 2.531 |
| 6 | B58 | | B3 | 2.87 | 29.7 | 2.399 |
| 7 | B3 | | B7 | 4.18 | 49.84 | 2.339 |
| 8 | B3 | | B58 | 0.80 | 20.27 | 2.282 |
| 9 | B3 | | B3 | 4.65 | 42.53 | 2.402 |

It can be seen from Table 5 that it is possible to optimize antibody binding to LPA by recombining light chains and heavy chains from different hybridomas (i.e., different clones) into chimeric molecules.

Materials and Methods for the Cloning, Expression and Characterization of the Anti-LPA Antibody Variable Domains Cloning of the Variable Domains from Hybridoma Cell Lines Clones from the anti-LPA hybridoma cell lines were grown in DMEM (Dulbecco's Dulbecco's Modified Eagle Medium with GlutaMAX™ I, 4500 mg/L D-Glucose, Sodium Puruvate; Gibco/Invitrogen, Carlsbad, Calif., 111-035-003), 10% FBS (Sterile Fetal Clone I, Perbio Science), and 1× glutamine/Penicillin/Streptomycin (Gibco/Invitrogen). Total RNA was isolated from $10^7$ hybridoma cells using a procedure based on the RNeasy Mini kit (Qiagen, Hilden Germany). The RNA was used to generate first strand cDNA following the manufacturer's protocol for SMART RACE cDNA Amplification Kit (Clonetech).

The immunoglobulin heavy chain variable domain (VH) cDNA was amplified by PCR using primers listed in Table 6. Heavy Chain variable domain PCR set-up was as follows: MHCG1 (known IgG1 constant region primer) combined with Group 1 and Group 2 V region primers for all five antibodies. The product of each reaction was ligated into the pCR2.1®-TOPO® vector (Invitrogen, Carlsbad Calif.) using the TOPO-TA Cloning® kit and sequence.

Similarly, the immunoglobulin light chain variable domains (VK) were amplified using the primers listed in Table 7. The light chain variable domain PCR set-up was as follows: Two constant region primers were each combined with Group 1, Group 2 and Group 3 V region primers for all five antibodies. The product of each reaction was ligated into the pCR2.1®-TOPO® vector using the TOPO-TA Cloning® kit and sequence.

The list of oligonucleotides was designed according to the literature (Dattamajumdar, A. K., Jacobson, D. P., Hood, L. E. and Osman, G. E. (1991) Rapid cloning of any rearranged mouse immunoglobulin variable genes. Immunogenetics. 43(3):141-51; Coloma, M. J., Hastings, A., Wims, L. A. and Morrison, S. L. (1992) Novel vectors for the expression of antibody molecules using variable domains generated by polymerase chain reaction. J Immunol Methods, 152(1):89-104; Coronella, J. A., Telleman, P., Truong, T. D., Ylera, F. and Junghans, R. P. (2000) Amplification of IgG VH and VL (Fab) from single human plasma cells and B cells. Nucleic Acids Res., 28(20):E85).

TABLE 6

List of oligonucleotides for the cloning of the heavy chain variable domains from the anti-LPA monoclonal antibodies.

| | | Heavy Chain | SEQ ID NO: |
|---|---|---|---|
| | Variable | | |
| Group 1 | MHV1 | ATGAAATGCAGCTGGGGCATSTTCTTC | 1 |
| | MHV2 | ATGGGATGGAGCTRTATCATSYTCTT | 2 |
| | MHV3 | ATGAAGWTGTGGTTAAACTGGGTTTTT | 3 |
| | MHV4 | ATGRACTTTGGGYTCAGCTTGRTTT | 4 |
| | MHV5 | ATGGACTCCAGGCTCAATTTAGTTTTCCTT | 5 |
| | MHV6 | ATGGCTGTCYTRGSGCTRCTCTTCTGC | 6 |
| Group 2 | MHV7 | ATGGRATGGAGCKGGRTCTTTMTCTT | 7 |
| | MHV8 | ATGAGAGTGCTGATTCTTTTGTG | 8 |
| | MHV9 | ATGGMTTGGGTGTGGAMCTTGCTATTCCTG | 9 |
| | MHV10 | ATGGGCAGACTTACATTCTCATTCCTG | 10 |
| | MHV11 | ATGGATTTTGGGCTGATTTTTTTTATTG | 11 |
| | MHV12 | ATGATGGTGTTAAGTCTTCTGTACCTG | 12 |
| | MH1: | ATATCCACCA TGGRATGSAG CTGKGTMATS CTCTT | 13 |
| | Constant | | |
| | MHCG1 | CAGTGGATAGACAGATGGGGG | 14 |
| | MHCG2a | CAGTGGATAGACCGATGGGGC | 15 |
| | MHCG2b | CAGTGGATAGACTGATGGGGG | 16 |
| | MHCG3 | CAAGGGATAGACAGATGGGGC | 17 |
| | MVG1R | 5'-GGCAGCACTAGTAGGGGCCAGTGGATA-3' | 18 |

TABLE 7

List of oligonucleotides used for the cloning of the light chain variable domains from the anti-LPA monoclonal antibodies.

| | | Light chain | SEQ ID NO: |
|---|---|---|---|
| | Variable | | |
| Group 1 | MLALT1 | GGGCACCATGGAGACAGACACACTCCTGCTAT | 19 |
| | MLALT2 | GGGCACCATGGATTTTCAAGTGCAGATTTTCAG | 20 |
| | MLALT3 | GGGCACCATGGAGWCACAKWCTCAGGTCTTTR TA | 21 |
| | MLALT4 | GGGCACCATGKCCCCWRCTCAGYTYCTKGT | 22 |
| | MLALT5 | 5'-CACCATGAAGTTGCCTGTTAGGCTGTT G-3' | 23 |
| Group 2 | MKV1a | ATGAAGTTGVVTGTTAGGCTGTTGGTGCTG | 24 |
| | MKV2 | ATGGAGWCAGACACACTCCTGYTATGGGTG | 25 |
| | MKV3 | ATGAGTGTGCTCACTCAGGTCCTGGSGTTG | 26 |
| | MKV4 | ATGAGGRCCCCTGCTCAGWTTYTTGGMWTCTTG | 27 |
| | MKV5 | ATGGATTTWAGGTGCAGATTWTCAGCTTC | 28 |
| | MKV6 | ATGAGGTKCKKTGKTSAGSTSCTGRGG | 29 |
| | MKV7 | ATGGGCWTCAAGATGGAGTCACAKWYYCWGG | 30 |
| | MKV8 | ATGTGGGGAYCTKTTTYCMMTTTTTCAATTG | 31 |
| | MKV9 | ATGGTRTCCWCASCTCAGTTCCTTG | 32 |
| | MKV10 | ATGTATATATGTTTGTTGTCTATTTCT | 33 |
| | MKV11 | ATGGAAGCCCCAGCTCAGCTTCTCTTCC | 34 |
| | VK8 | TGGGTATCTGGTRCSTGTG | 35 |
| | MKV20 | ATGGAGWCAGACACACTSCTG | 36 |
| Group 3 | CL12A | ATGRAGTYWCAGACCCAGGTCTTYRT | 37 |
| | CL12B | ATGGAGACACATTCTCAGGTCTTTGT | 38 |
| | CL13 | ATGGATTCACAGGCCCAGGTTCTTAT | 39 |
| | CL14 | ATGATGAGTCCTGCCCAGTTCCTCTT | 40 |
| | CL15 | ATGAATTTGCCTGTTCATCTCTTGGTGCT | 41 |
| | CL16 | ATGGATTTTCAATTGGTCCTCATCTCCTT | 42 |
| | CL17A | ATGAGGTGCCTARCTSAGTTCCTGRG | 43 |
| | CL17B | ATGAAGTACTCTGCTCAGTTTCTAGG | 44 |
| | CLI7C | ATGAGGCATTCTCTTCAATTCTTGGG | 45 |
| | Constant | | |
| | MKC | ACTGGATGGTGGGAAGATGG | 46 |
| | 33615: | 5'GAAGATCTAGACTTACTA TGCAGCATCA GC-3' | 47 |

TOPO2.1 clones containing the heavy and light chain variable domains were sequenced and CDR regions were determined. The variable domain of the light chain was then amplified by PCR adding a leader sequence and cut sites suggested by the manufacturer for cloning into the Lonza light chain expression vector, pCONkappa2 (5' HindIII, 3' BsiWI, LC leader sequence: ATG TCT GTG CCT ACC CAG GTG CTG GGA CTG CTG CTG CTG TGG CTG ACA GAC GCC CGC TGT, SEQ ID NO: 48). The variable domain of the heavy chain was then amplified by PCR adding a leader sequence and cut sites suggested by Lonza for cloning into the Lonza heavy chain expression vector, pCONgamma1f (5' HindIII, 3' ApaI, HC leader sequence: ATG GAA TGG AGC TGG GTG TTC CTG TTC TTT CTG TCC GTG ACC ACA GGC GTG CAT TCT, SEQ ID NO: 49). Final products were then inserted into light or heavy chain expression vectors, containing the constant regions, with digestion and ligation the Rapid Ligation Kit (Roche).

The heavy and light chain plasmids were transformed into One Shot® TOP10 chemically competent bacterial cells (Invitrogen) and stocked in glycerol. Large-scale plasmid DNA was prepared as described by the manufacturer (Qiagen, endotoxin-free MAXIPREP™ kit). DNA samples, purified using Qiagen's QIAprep Spin Miniprep Kit or EndoFree Plasmid Mega/Maxi Kit, were sequenced using an ABI 3730×1 automated sequencer, which also translates the fluorescent signals into their corresponding nucleobase sequence. Primers were designed at the 5' and 3' ends so that the sequence obtained would overlap.

PCR Amplification of the Variable Domains

The Polymerase Chain Reactions (PCR) were performed using Invitrogen's Pfx DNA polymerase kit with 10× buffer and 50 mM MgSO4 (cat#11708-013) and 10 mM dNTPs (Invitrogen, cat#18427-013). The reaction mixture consisted of 5 ul 10× pfx amplification buffer, 1.5 ul 10 mM dNTPs, 1 ul 50 mM MgSO4, 1.5 ul oligonucleotide 1, 1.5 ul oligonucleotide 2, 0.5 ul template (~50 ng), 0.5 ul Pfx DNA polymerase, 38.5 ul sterile water. All reagents were added minus Pfx and then Pfx was added immediately before starting the thermocycler. After denaturation of the templates at 95° C. for 3 minutes, 35 cycles of 95° C. for 30 seconds, annealing at 58° C. with a 5° C.+/−gradient and extension at 68° C. for 30 seconds were performed. After a final extension at 68° C. for 5 minutes, the samples were kept at 4° C.

Restriction Digest and Ligation Reactions to Clone the Variable Domains

The restriction digests were performed on DNA to prepare fragment for ligation or for cloning verification prior to checking the molecular sequence. All restriction enzymes were purchased from Invitrogen or New England Biolabs which come with the corresponding buffers required for each enzyme. The DNA (usually 5-10 ul to check for positive clones and 20-26 ul for DNA to be ligated) were mixed with the enzyme buffer, 0.5 to 1.0 ul of the restriction enzyme, and sterile water (to a total of 30 ul reaction). The reactions were incubated at appropriate temperature for the enzyme for 1 hr. Most enzymes were active at 37° C. however the incubation temperature could vary from room temperature to 55° C. depending on the enzymes. After adequate restriction enzyme digest, the GeneClean kit was used to clean the insert fragment and vector from agarose gel and any enzymes and buffers. Ligations were performed using Roche Rapid Ligation Kit (catalog #11635379001) that included T4 DNA 2× Ligation buffer, 5×DNA dilution buffer, and T4 DNA ligase. Inserts and vectors were ligated in a final 3:1 molar ratio for best results. Insert fragments were diluted appropriately for efficient ligations. 5 to 7 ul of the reaction was used to transformed *E. coli* TOP10 chemically competent cells.

Quantitative ELISA

Microtiter ELISA plates (Costar, Cat No. 3361) were coated with rabbit anti-mouse IgG, F(ab')$_2$ fragment specific antibody (Jackson, 315-005-047) diluted in 1M Carbonate Buffer (pH 9.5) at 37° C. for 1 h. Plates were washed with PBS and blocked with PBS/BSA/Tween-20 for 1 hr at 37° C. For the primary incubation, dilutions of non-specific mouse IgG or human IgG, whole molecule (used for calibration curve) and samples to be measured were added to the wells. Plates were washed and incubated with 100 ul per well of HRP conjugated anti-human diluted 1:50,000 (Jackson 109-035-003) for 1 hr at 37° C. After washing, the enzymatic reaction was detected with tetramethylbenzidine (Sigma, cat No T0440) and stopped by adding 1 M $H_2SO_4$. The optical density (OD) was measured at 450 nm using a Thermo Multiskan EX. Raw data were transferred to GraphPad software for analysis.

Direct ELISA

Microtiter ELISA plates (Costar, Cat No. 3361) were coated with LPA-BSA diluted in 1M Carbonate Buffer (pH 9.5) at 37° C. for 1 h. Plates were washed with PBS (137 mM NaCl, 2.68 mM KCl, 10.1 mM $Na_2HPO_4$, 1.76 mM $KH_2PO_4$; pH 7.4) and blocked with PBS/BSA/Tween-20 for 1 h at room temperature or overnight at 4° C. The samples to be tested were diluted at 0.4 ug/mL, 0.2 ug/mL, 0.1 ug/mL, 0.05 ug/mL, 0.0125 ug/mL, and 0 ug/mL and 100 ul added to each well. Plates were washed and incubated with 100 ul per well of HRP anti-human diluted 1:50,000 (Jackson 109-035-003) for 1 hr at 37° C. After washing, the enzymatic reaction was detected with tetramethylbenzidine (Sigma, Cat No T0440) and stopped by adding 1 M $H_2SO_4$. The optical density (OD) was measured at 450 nm using a Thermo Multiskan EX. Raw data were transferred to GraphPad software for analysis.

Transient Expression

The vectors were transfected into the human embryonic kidney cell line 293F using 293 fectin and using 293F-FreeStyle Media for culture. Transfections were performed at a cell density of $10^6$ cells/mL with 0.5 µg/mL. Supernatants were collected by centrifugation at 1100 rpm for 5 minutes at 25° C. 3 days after transfection. The expression level was quantified by quantitative ELISA and the binding was measured in a binding ELISA as described above.

The mouse $V_H$ and $V_L$ domains were sequenced using standard methods. Tables 8-17 show nucleic acid and amino acid sequences for the complementarity-determining regions (CDRs) of the variable ($V_H$ and $V_L$) domains for five mouse anti-LPA monoclonal antibody clones. For each CDRH1 amino acid sequence, the CDR defined according to Kabat is the 10-amino acid sequence shown. The five-amino acid portion of the Kabat sequence that is shown in bold is the canonical CDRH1 sequence.

TABLE 8

Mouse LPA CDR nucleic acid sequences of the mouse $V_H$ and $V_L$ domains for clone B3 of mouse anti-LPA monoclonal antibody

| CLONE | CDR | | SEQ ID NO: |
|---|---|---|---|
| | $V_H$ CDR | | |
| B3 | GGAGACGCCTTCACAAATTACTTA ATAGAG | CDRH1 | 50 |
| B3 | CTGATTTATCCTGATAGTGGTTAC ATTAACTACAATGAGAACTTCAA GGGC | CDRH2 | 51 |
| B3 | AGATTTGCTTACTACGGTAGTGGC TACTACTTTGACTAC | CDRH3 | 52 |
| | $V_L$ CDR | | |
| B3 | AGATCTAGTCAGAGCCTTCTAAA AACTAATGGAAACACCTATTTAC AT | CDRL1 | 53 |
| B3 | AAAGTTTCCAACCGATTTTCT | CDRL2 | 54 |
| B3 | TCTCAAAGTACACATTTTCCATTC ACG | CDRL3 | 55 |

TABLE 9

Mouse LPA CDR amino acid sequences of the mouse $V_H$ and $V_L$ domains for clone B3 of mouse anti-LPA monoclonal antibody

| CLONE | CDR | | SEQ ID NO: |
|---|---|---|---|
| | $V_H$ CDR | | |
| B3 | GDAFT**NYLIE*** | CDRH1 | 56 |
| B3 | LIYPDSGYINYNENFKG | CDRH2 | 57 |
| B3 | RFAYYGSGYYFDY | CDRH3 | 58 |

TABLE 9-continued

Mouse LPA CDR amino acid sequences of the mouse $V_H$ and $V_L$ domains for clone B3 of mouse anti-LPA monoclonal antibody

| CLONE | CDR | | SEQ ID NO: |
|---|---|---|---|
| | $V_L$ CDR | | |
| B3 | RSSQSLLKTNGNTYLH | CDRL1 | 59 |
| B3 | KVSNRFS | CDRL2 | 60 |
| B3 | SQSTHFPFT | CDRL3 | 61 |

*The CDRH1 sequence defined according to Chothia/AbM is the 10-amino acid sequence shown. The five-amino acid portion of this sequence shown in bold (NYLIE; SEQ ID NO: 62) is the CDRH1 sequence defined according to Kabat.

TABLE 10

Mouse LPA CDR nucleic acid sequences of the mouse $V_H$ and $V_L$ domains for clone B7 of mouse anti-LPA monoclonal antibody

| CLONE | CDR | | SEQ ID NO: |
|---|---|---|---|
| | $V_H$ CDR | | |
| B7 | GGATACGGCTTCATTAATTACT TAATAGAG | CDRH1 | 63 |
| B7 | CTGATTAATCCTGGAAGTGATT ATACTAACTACAATGAGAACT TCAAGGGC | CDRH2 | 64 |
| B7 | AGATTTGGTTACTACGGTAGC GGCAACTACTTTGACTAC | CDRH3 | 65 |
| | $V_L$ CDR | | |
| B7 | ACATCTGGTCAGAGCCTTGTCC ACATTAATGGAAACACCTATT TACAT | CDRL1 | 66 |
| B7 | AAAGTTTCCAACCTATTTTCT | CDRL2 | 67 |
| B7 | TCTCAAAGTACACATTTTCCAT TCACG | CDRL3 | 68 |

TABLE 11

Mouse LPA CDR amino acid sequences of the mouse $V_H$ and $V_L$ domains for clone B7 of mouse anti-LPA monoclonal antibody

| CLONE | CDR | | SEQ ID NO: |
|---|---|---|---|
| | $V_H$ CDR | | |
| B7 | GYGFI**NYLIE*** | CDRH1 | 69 |
| B7 | LINPGSDYTNYNENFKG | CDRH2 | 70 |
| B7 | RFGYYGSGNYFDY | CDRH3 | 71 |
| | $V_L$ CDR | | |
| B7 | TSGQSLVHINGNTYLH | CDRL1 | 72 |
| B7 | KVSNLFS | CDRL2 | 73 |
| B7 | SQSTHFPFT | CDRL3 | 74 |

*The CDRH1 sequence defined according to Chothia/AbM is the 10-amino acid sequence shown. The five-amino acid portion of this sequence shown in bold (NYLIE; SEQ ID NO: 62) is the CDRH1 sequence defined according to Kabat.

TABLE 12

Mouse LPA CDR nucleic acid sequences of the mouse $V_H$ and $V_L$ domains for clone B58 of mouse anti-LPA monoclonal antibody

| CLONE | | CDR | SEQ ID NO: |
|---|---|---|---|
| | $V_H$ CDR | | |
| B58 | GGAGACGCCTTCACTAATTACTTGATCGAG | CDRH1 | 75 |
| B58 | CTGATTATTCCTGGAACTGGTTATACTAACTACAATGAGAACTTCAAGGGC | CDRH2 | 76 |
| B58 | AGATTTGGTTACTACGGTAGTAGCAACTACTTTGACTAC | CDRH3 | 77 |
| | $V_L$ CDR | | |
| B58 | AGATCTAGTCAGAGCCTTGTACACAGTAATGGAAACACCTATTTACAT | CDRL1 | 78 |
| B58 | AAAGTTTCCAACCGATTTTCT | CDRL2 | 79 |
| B58 | TCTCAAAGTACACATTTTCCATTCACT | CDRL3 | 80 |

TABLE 13

Mouse LPA CDR amino acid sequences of the mouse $V_H$ and $V_L$ domains for clone B58 of mouse anti-LPA monoclonal antibody

| CLONE | | CDR | SEQ ID NO: |
|---|---|---|---|
| | $V_H$ CDR | | |
| B58 | GDAFT**NYLIE*** | CDRH1 | 81 |
| B58 | LIIPGTGYTNYNENFKG | CDRH2 | 82 |
| B58 | RFGYYGSSNYFDY | CDRH3 | 83 |
| | $V_L$ CDR | | |
| B58 | RSSQSLVHSNGNTYLH | CDRL1 | 84 |
| B58 | KVSNRFS | CDRL2 | 85 |
| B58 | SQSTHFPFT | CDRL3 | 86 |

*The CDRH 1 sequence defined according to Chothia/AbM is the 10-amino acid sequence shown. The five-amino acid portion of this sequence shown in bold (NYLIE; SEQ ID NO: 62) is the CDRH1 sequence defined according to Kabat.

TABLE 14

Mouse LPA CDR nucleic acid sequences of the mouse $V_H$ and $V_L$ domains for clone 3A6 of mouse anti-LPA monoclonal antibody

| CLONE | | CDR | SEQ ID NO: |
|---|---|---|---|
| | $V_H$ CDR | | |
| 3A6 | GGAGACGCCTTCACTAATTACTTGATCGAG | CDRH1 | 87 |
| 3A6 | CTGATTATTCCTGGAACTGGTTATACTAACTACAATGAGAACTTCAAGGGC | CDRH2 | 88 |
| 3A6 | AGATTTGGTTACTACGGTAGTGGCTACTACTTTGACTAC | CDRH3 | 89 |
| | $V_L$ CDR | | |
| 3A6 | AGATCTAGTCAGAGCCTTGTACACAGTAATGGAAACACCTATTTACAT | CDRL1 | 90 |

TABLE 14-continued

Mouse LPA CDR nucleic acid sequences of the mouse $V_H$ and $V_L$ domains for clone 3A6 of mouse anti-LPA monoclonal antibody

| CLONE | | CDR | SEQ ID NO: |
|---|---|---|---|
| 3A6 | AAAGTTTCCAACCGATTTTCT | CDRL2 | 91 |
| 3A6 | TCTCAAAGTACACATTTTCCATTCACG | CDRL3 | 92 |

TABLE 15

Mouse LPA CDR amino acid sequences of the mouse $V_H$ and $V_L$ domains for clone 3A6 of mouse anti-LPA monoclonal antibody

| CLONE | | CDR | SEQ ID NO: |
|---|---|---|---|
| | $V_H$ CDR | | |
| 3A6 | GDAFT**NYLIE*** | CDRH1 | 93 |
| 3A6 | LIIPGTGYTNYNENFKG | CDRH2 | 94 |
| 3A6 | RFGYYGSGYYFDY | CDRH3 | 95 |
| | $V_L$ CDR | | |
| 3A6 | RSSQSLVHSNGNTYLH | CDRL1 | 96 |
| 3A6 | KVSNRFS | CDRL2 | 97 |
| 3A6 | SQSTHFPFT | CDRL3 | 98 |

*The CDRH 1 sequence defined according to Chothia/AbM is the 10-amino acid sequence shown. The five-amino acid portion of this sequence shown in bold (NYLIE; SEQ ID NO: 62) is the CDRH1 sequence defined according to Kabat.

TABLE 16

Mouse LPA CDR nucleic acid sequences of the mouse $V_H$ and $V_L$ domains for clone A63 of mouse anti-LPA monoclonal antibody

| CLONE | | CDR | SEQ ID NO: |
|---|---|---|---|
| | $V_H$ CDR | | |
| A63 | GGCTTCTCCATCACCAGTGGTTATTACTGGACC | CDRH1 | 99 |
| A63 | TACATAGGCTACGATGGTAGCAATGACTCCAACCCATCTCTCAAAAAT | CDRH2 | 100 |
| A63 | GCGATGTTGCGGCGAGGATTTGACTAC | CDRH3 | 101 |
| | $V_L$ CDR | | |
| A63 | AGTGCCAGCTCAAGTTTAAGTTACATGCAC | CDRL1 | 102 |
| A63 | GACACATCCAAACTGGCTTCT | CDRL2 | 103 |
| A63 | CATCGGCGGAGTAGTTACACG | CDRL3 | 104 |

TABLE 17

Mouse LPA CDR amino acid sequences of the mouse $V_H$ and $V_L$ domains for clone A63 of mouse anti-LPA monoclonal antibody

| CLONE | | CDR | SEQ ID NO: |
|---|---|---|---|
| | $V_H$ CDR | | |
| A63 | GFSIT**SGYYWT*** | CDRH1 | 105 |
| A63 | YIGYDGSNDSNPSLKN | CDRH2 | 106 |
| A63 | AMLRRGFDY | CDRH3 | 107 |
| | $V_L$ CDR | | |
| A63 | SASSSLSYMH | CDRL1 | 108 |
| A63 | DTSKLAS | CDRL2 | 109 |
| A63 | HRRSSYT | CDRL3 | 110 |

*The CDRH1 sequence defined according to Chothia/AbM is the 11-amino acid sequence shown. The six-amino acid portion of this sequence shown in bold (SGYYWT; SEQ ID NO: 111) is the CDRH1 sequence defined according to Kabat.

Tables 18-27 show nucleotide and amino acid sequences (nucleotides in Tables 18, 20, 22, 24 and 26, amino acids in Tables 19, 21, 23, 25 and 27) of the variable domains ($V_H$ and $V_L$) of the anti-LPA antibodies. In each heavy chain amino acid sequence in Tables 18-27, amino acids 1-2 (KL) represent enzymatic cut sites recommended for use with the pCON expression vectors and amino acids 2-5 (AAT) are Kozak sequences in the corresponding nucleotide sequence. Amino acids 6-24 (SEQ ID NO: 49) are leader sequences recommended for use with the pCON heavy chain expression vector. The last five amino acids of the heavy chain sequences shown (ASTKG) are the beginning of the constant region sequence contained within the pCON heavy chain vector.

In each light chain amino acid sequence in Tables 18-27, amino acids 1-2 (KL) are enzymatic cut sites recommended for use with the pCON expression vectors and amino acids 2-5 (AAT) are Kozak sequences in the corresponding nucleotide sequence. Amino acids 6-25 (SEQ ID NO: 48) are leader sequences recommended for use with the pCON light chain expression vector. The last two amino acids (RT) of the light chain sequences shown are the cut site recommended for use with the pCON light chain vector.

Thus the actual heavy chain sequence (minus Kozak sequences, leaders and cut sites can be seen to be amino acids 25-146 of each amino acid sequence in Tables 18-27 and the actual light chain sequence (minus Kozak sequences, leaders and cut sites) can be seen to be amino acids 26-137 of each amino acid sequence in Tables 18-27. One of ordinary skill can readily determine which of the nucleic acid sequences in Tables 18-27 (even numbered tables) correspond to these amino acid sequences.

TABLE 18

Clone B3 nucleic acid sequences with leader sequence and cut sites added

| Sequence | SEQ ID NO: |
|---|---|
| B3 Heavy Chain | |
| AAGCTTGCCGCCACCATGGAATGGAGCTGGGTGTTCCTGT<br>TCTTTCTGTCCGTGACCACAGGCGTGCATTCTCAGGTCAA<br>GCTGCAGCAGTCTGGACCTGAGCTGGTAAGGCCTGGGACT<br>TCAGTGAAGGTGTCCTGCACGGCTTCTGGAGACGCCTTCA<br>CAAATTACTTAATAGAGTGGGTAAAACAGAGGCCTGGACA<br>GGGCCTTGAGTGGATTGGACTGATTTATCCTGATAGTGGT<br>TACATTAACTACAATGAGAACTTCAAGGGCAAGGCAACAC<br>TGACTGCAGACAGATCCTCCAGCACTGCCTACATGCAGCT<br>CAGCAGCCTGACATCTGAGGACTCTGCGGTCTATTTCTGT<br>GCAAGAAGATTTGCTTACTACGGTAGTGGCTACTACTTTG<br>ACTACTGGGGCCAAGGCACCACTCTCACAGTCTCCTCAGC<br>CTCCACCAAGGGCCC | 112 |
| B3 Light Chain | |
| AAGCTTGCCGCCACCATGTCTGTGCCTACCCAGGTGCTGG<br>GACTGCTGCTGCTGTGGCTGACAGACGCCCGCTGTGATGT<br>TGTGATGACCCAAACTCCACTCTCCCTGCCTGTCAGTCTT<br>GGAGATCAAGCCTCCATCTCTTGCAGATCTAGTCAGAGCC<br>TTCTAAAAACTAATGGAAACACCTATTTACATTGGTACCT<br>GCAGAAGCCAGGCCAGTCTCCAAAACTCCTAATCTTCAAA<br>GTTTCCAACCGATTTTCTGGGGTCCCGGACAGGTTCAGTG<br>GCAGTGGATCAGGGACAGACTTCACACTCAAGATCAGCAG<br>AGTGGAGGCTGAGGATCTGGGAGTTTATTTCTGCTCTCAA<br>AGTACACATTTTCCATTCACGTTCGGCACGGGGACAAAAT<br>TGGAAATAAAACGTACG | 113 |

TABLE 19

Clone B3 amino acid sequences with leader sequence and cut sites added

| Sequence | SEQ ID NO: |
|---|---|
| B3 Heavy Chain | |
| KLAATMEWSWVFLFFLSVTTGVHSQVKLQQSGPELVRPGT<br>SVKVSCTASGDAFTNYLIEWVKQRPGQGLEWIGLIYPDSG<br>YINYNENFKGKATLTADRSSSTAYMQLSSLTSEDSAVYFC<br>ARRFAYYGSGYYFDYWGQGTTLTVSSASTKG | 114 |
| B3 Light Chain | |
| KLAATMSVPTQVLGLLLLWLTDARCDVVMTQTPLSLPVSL<br>GDQASISCRSSQSLLKTNGNTYLHWYLQKPGQSPKLLIFK<br>VSNRFSGVPDRFSGSGSGTDFTLKISRVEAEDLGVYFCSQ<br>STHFPFTFGTGTKLEIKRT | 115 |

TABLE 20

Clone B7 nucleic acid sequences with leader sequence and cut sites added

| Sequence | SEQ ID NO: |
|---|---|
| B7 Heavy Chain | |
| AAGCTTGCCGCCACCATGGAATGGAGCTGGGTGTTCCTGT<br>TCTTTCTGTCCGTGACCACAGGCGTGCATTCTCAGGTCCA<br>ACTGCAGCAGTCTGGAGCTGAGCTGGTAAGGCCTGGGACT<br>TCAGTGAAGGTGTCCTGCAAGGCTTCTGGATACGGCTTCA<br>TTAATTACTTAATAGAGTGGATAAAACAGAGGCCTGGACA<br>GGGCCTTGAGTGGATTGGACTGATTAATCCTGGAAGTGAT<br>TATACTAACTACAATGAGAACTTCAAGGGCAAGGCAACAC<br>TGACTGCAGACAAGTCCTCCAGCACTGCCTACATGCACCT<br>CAGCAGCCTGACATCTGAGGACTCTGCGGTCTATTTCTGT<br>GCAAGAAGATTTGGTTACTACGGTAGCGGCAACTACTTTG<br>ACTACTGGGGCCAAGGCACCACTCTCACAGTCTCCTCAGC<br>CTCCACCAAGGGCCC | 116 |

TABLE 20 -continued

| Clone B7 nucleic acid sequences with leader sequence and cut sites added | |
|---|---|
| Sequence | SEQ ID NO: |
| B7 Light Chain | |
| AAGCTTGCCGCCACCATGTCTGTGCCTACCCAGGTGCTGG<br>GACTGCTGCTGCTGTGGCTGACAGACGCCCGCTGTGATGT<br>TGTGATGACCCAAACTCCACTCTCCCTGCCTGTCAGTCTT<br>GGAGATCAAGCCTCCATCTCTTGCACATCTGGTCAGAGCC<br>TTGTCCACATTAATGGAAACACCTATTTACATTGGTACCT<br>GCAGAAGCCAGGCCAGTCTCCAAAGCTCCTCATCTACAAA<br>GTTTCCAACCTATTTTCTGGGGTCCCAGACAGGTTCAGTG<br>GCAGTGGATCAGGGACAGATTTCACACTCAAGATCAGCAG<br>AGTGGAGGCTGAGGATCTGGGAGTTTATTTCTGCTCTCAA<br>AGTACACATTTTCCATTCACGTTCGGCACGGGGACAAAAT<br>TGGAAATAAAACGTACG | 117 |

TABLE 21

| Clone B7 amino acid sequences with leader sequence and cut sites added | |
|---|---|
| Sequence | SEQ ID NO: |
| B7 Heavy Chain | |
| KLAATMEWSWVFLFFLSVTTGVHSQVQLQQSGAELVRPGT<br>SVKVSCKASGYGFINYLIEWIKQRPGQGLEWIGLINPGSD<br>YTNYNENFKGKATLTADKSSSTAYMHLSSLTSEDSAVYFC<br>ARRFGYYGSGNYFDYWGQGTTLTVSSASTKG | 118 |
| B7 Light Chain | |
| KLAATMSVPTQVLGLLLLWLTDARCDVVMTQTPLSLPVSL<br>GDQASISCTSGQSLVHINGNTYLHWYLQKPGQSPKLLIYK<br>VSNLFSGVPDRFSGSGSGTDFTLKISRVEAEDLGVYFCSQ<br>STHFPFTFGTGTKLEIKRT | 119 |

TABLE 22

| Clone B58 nucleic acid sequences with leader sequence and cut sites added | |
|---|---|
| Sequence | SEQ ID NO: |
| B58 Heavy Chain | |
| AAGCTTGCCGCCACCATGGAATGGAGCTGGGTGTTCCTGT<br>TCTTTCTGTCCGTGACCACAGGCGTGCATTCTCAGGTCCA<br>GCTGCAGCAGTCTGGAGCTGAGCTGGTCAGGCCTGGGACT<br>TCAGTGAAGGTGTCCTGCAAGGCTTCTGGAGACGCCTTCA<br>CTAATTACTTGATCGAGTGGGTAAAGCAGAGGCCTGGACA<br>GGGCCTTGAGTGGATTGGACTGATTATTCCTGGAACTGGT<br>TATACTAACTACAATGAGAACTTCAAGGGCAAGGCAACAC<br>TGACTGCAGACAAATCCTCCAGCACTGCCTACATGCAGCT<br>CAGCAGCCTGACATCTGAGGACTCTGCGGTCTATTTCTGT<br>GCAAGAAGATTTGGTTACTACGGTAGTAGCAACTACTTTG<br>ACTACTGGGGCCAAGGCACCACTCTCACAGTCTCCTCAGC<br>CTCCACCAAGGGCCC | 120 |
| B58 Light Chain | |
| AAGCTTGCCGCCACCATGTCTGTGCCTACCCAGGTGCTGG<br>GACTGCTGCTGCTGTGGCTGACAGACGCCCGCTGTGATGT<br>TGTGATGACCCAAACTCCACTCTCCCTGCCTGTCAGTCTT<br>GGAGATCAAGCCTCCATCTCTTGCAGATCTAGTCAGAGCC<br>TTGTACACAGTAATGGAAACACCTATTTACATTGGTACCT<br>GCAGAAGCCAGGCCAGTCTCCAAAGCTCCTGATCTACAAA<br>GTTTCCAACCGATTTTCTGGGGTCCCAGACAGGTTCAGTG | 121 |

TABLE 22-continued

| Clone B58 nucleic acid sequences with leader sequence and cut sites added | |
|---|---|
| Sequence | SEQ ID NO: |
| GCAGTGGACCAGGGACAGATTTCACACTCAAGATCAGCAG<br>AGTGGAGGCTGAGGATCTGGGAATTTATTTCTGCTCTCAA<br>AGTACACATTTTCCATTCACTTTCGGCACGGGGACAAAAT<br>TGGAAATAAAACGTACG | |

TABLE 23

| Clone B58 amino acid sequences with leader sequence and cut sites added | |
|---|---|
| Sequence | SEQ ID NO: |
| B58 Heavy Chain | |
| KLAATMEWSWVFLFFLSVTTGVHSQVQLQQSGAELVRPGT<br>SVKVSCKASGDAFTNYLIEWVKQRPGQGLEWIGLIIPGTG<br>YTNYNENFKGKATLTADKSSSTAYMQLSSLTSEDSAVYFC<br>ARRFGYYGSSNYFDYWGQGTTLTVSSASTKG | 122 |
| B58 Light Chain | |
| KLAATMSVPTQVLGLLLLWLTDARCDVVMTQTPLSLPVSL<br>GDQASISCRSSQSLVHSNGNTYLHWYLQKPGQSPKLLIYK<br>VSNRFSGVPDRFSGSGPGTDFTLKISRVEAEDLGIYFCSQ<br>STHFPFTFGTGTKLEIKRT | 123 |

TABLE 24

| Clone 3A6 nucleic acid sequences with leader sequence and cut sites added | |
|---|---|
| Sequence | SEQ ID NO: |
| 3A6 Heavy Chain | |
| AAGCTTGCCGCCACCATGGAATGGAGCTGGGTGTTCCTGT<br>TCTTTCTGTCCGTGACCACAGGCGTGCATTCTCAGGTCCA<br>GCTGCAGCAGTCTGGAGCTGAGCTGGTCAGGCCTGGGACT<br>TCAGTGAAGTTGTCCTGCAAGGCTTCTGGAGACGCCTTCA<br>CTAATTACTTGATCGAGTGGGTAAAGCAGAGGCCTGGACA<br>GGGCCTTGAGTGGATTGGACTGATTATTCCTGGAACTGGT<br>TATACTAACTACAATGAGAACTTCAAGGGCAAGGCAACAC<br>TGACTGCAGACAAGTCCTCCAGCACTGCCTACATGCAGCT<br>CAGCAGCCTGACATCTGAGGACTCTGCGGTCTATTTCTGT<br>GCAAGAAGATTTGGTTACTACGGTAGTGGCTACTACTTTG<br>ACTACTGGGGCCAAGGCACCACTCTCACAGTCTCCTCAGC<br>CTCCACCAAGGGCCC | 124 |
| 3A6 Light Chain | |
| AAGCTTGCCGCCACCATGTCTGTGCCTACCCAGGTGCTGG<br>GACTGCTGCTGCTGTGGCTGACAGACGCCCGCTGTGATGT<br>TGTGATGACCCAAACTCCACTCTCCCTGCCTGTCAGTCTT<br>GGAGATCAAGCCTCCATCTCTTGCAGATCTAGTCAGAGCC<br>TTGTACACAGTAATGGAAACACCTATTTACATTGGTACCT<br>GCAGAAGCCAGGCCAGTCTCCAAAGCTCCTGATCTACAAA<br>GTTTCCAACCGATTTTCTGGGGTCCCAGACAGGTTCAGTG<br>GCAGTGGACCAGGGACAGATTTCACACTCAAGATCAGCAG<br>AGTGGAGGCTGAGGATCTGGGAGTTTATTTCTGCTCTCAA<br>AGTACACATTTTCCATTCACGTTCGGCACGGGCACAAAAT<br>TGGAAATAAAACGTACG | 125 |

TABLE 25

Clone 3A6 amino acid sequences with leader sequence and cut sites added

| Sequence | SEQ ID NO: |
|---|---|
| 3A6 Heavy Chain | |
| KLAATMEWSWVFLFFLSVTTGVHSQVQLQQSGAELVRPGT<br>SVKLSCKASGDAFTNYLIEWVKQRPGQGLEWIGLIIPGTG<br>YTNYNENFKGKATLTADKSSSTAYMQLSSLTSEDSAVYFC<br>ARRFGYYGSGYYFDYWGQGTTLTVSSASTKG | 126 |
| 3A6 Light Chain | |
| KLAATMSVPTQVLGLLLLWLTDARCDVVMTQTPLSLPVSL<br>GDQASISCRSSQSLVHSNGNTYLHWYLQKPGQSPKLLIYK<br>VSNRFSGVPDRFSGSGPGTDFTLKISRVEAEDLGVYFCSQ<br>STHFPFTFGTGTKLEIKRT | 127 |

TABLE 26

Clone A63 nucleic acid sequences with leader sequence and cut sites added

| Sequence | SEQ ID NO: |
|---|---|
| A63 Heavy Chain | |
| AAGCTTGCCGCCACCATGGAATGGAGCTGGGTGTTCCTGT<br>TCTTTCTGTCCGTGACCACAGGCGTGCATTCTGATATACA<br>GCTTCAGGAGTCAGGACCTGGCCTCGTGAAACCTTCTCAG<br>TCTCTGTCTCTCACCTGCTCTGTCACTGGCTTCTCCATCA<br>CCAGTGGTTATTACTGGACCTGGATCCGGCAGTTTCCAGG<br>AAACAAACTGGAGTGGGTGGCCTACATAGGCTACGATGGT<br>AGCAATGACTCCAACCCATCTCTCAAAAATCGAATCTCCA<br>TCACCCGTGACACATCTAAGAACCAGTTTTTCCTGAAGTT<br>GAATTCTGTGACTACTGAGGACACAGCCACATATTACTGT<br>GCAAGAGCGATGTTGCGGCGAGGATTTGACTACTGGGGCC<br>AAGGCACCACTCTCACAGTCTCCTCAGCCTCCACCAAGGG<br>CCC | 128 |
| A63 Light Chain | |
| AAGCTTGCCGCCACCATGTCTGTGCCTACCCAGGTGCTGG<br>GACTGCTGCTGCTGTGGCTGACAGACGCCCGCTGTCAAAT<br>TGTTCTCACCCAGTCTCCAGCAATCATGTCTGCATCTCCA<br>GGGGAGAAGGTCACCATGACCTGCAGTGCCAGCTCAAGTT<br>TAAGTTACATGCACTGGTACCAGCAGAAGCCAGGCACCTC<br>CCCCAAAAGATGGATTTATGACACATCCAAACTGGCTTCT<br>GGAGTCCCTGCTCGCTTCAGTGGCAGTGGGTCTGGGACCT<br>CTTATTCTCTCACAATCAGCAGCATGGAGGCTGAAGATGC<br>TGCCACTTATTACTGCCATCGGCGGAGTAGTTACACGTTC<br>GGAGGGGGGACCAAGCTGGAAATAAAACGTACG | 129 |

TABLE 27

Clone A63 amino acid sequences with leader sequence and cut sites added

| Sequence | SEQ ID NO: |
|---|---|
| A63 Heavy Chain | |
| KLAATMEWSWVFLFFLSVTTGVHSDIQLQESGPGLVKPSQ<br>SLSLTCSVTGFSITSGYYWTWIRQFPGNKLEWVAYIGYDG<br>SNDSNPSLKNRISITRDTSKNQFFLKLNSVTTEDTATYYC<br>ARAMLRRGFDYWGQGTTLTVSSASTKG | 130 |
| A63 Light Chain | |
| KLAATMSVPTQVLGLLLLWLTDARCQIVLTQSPAIMSASP<br>GEKVTMTCSASSSLSYMHWYQQKPGTSPKRWIYDTSKLAS | 131 |

TABLE 27-continued

Clone A63 amino acid sequences with leader sequence and cut sites added

| Sequence | SEQ ID NO: |
|---|---|
| GVPARFSGSGSGTSYSLTISSMEAEDAATYYCHRRSSYTF<br>GGGTKLEIKRT | |

For purposes of convenience, Tables 28-32 below are provided to show the amino acid sequences of the anti-LPA antibody variable domains shown in Tables 19-27 (odd numbered tables), without the leader and cut sites.

TABLE 28

Clone B3 variable domain amino acid sequences without leader sequence and cut sites

| Sequence | SEQ ID NO: |
|---|---|
| B3 Heavy Chain | |
| QVKLQQSGPELVRPGTSVKVSCTASGDAFTNYLIEWVKQR<br>PGQGLEWIGLIYPDSGYINYNENFKGKATLTADRSSSTAY<br>MQLSSLTSEDSAVYFCARRFAYYGSGYYFDYWGQGTTLTV<br>SS | 132 |
| B3 Light Chain | |
| DVVMTQTPLSLPVSLGDQASISCRSSQSLLKTNGNTYLHW<br>YLQKPGQSPKLLIFKVSNRFSGVPDRFSGSGSGTDFTLKI<br>SRVEAEDLGVYFCSQSTHFPFTFGTGTKLEIK | 133 |

TABLE 29

Clone B7 variable domain amino acid sequences without leader sequence and cut sites

| Sequence | SEQ ID NO: |
|---|---|
| B7 Heavy Chain | |
| QVQLQQSGAELVRPGTSVKVSCKASGYGFINYLIEWIKQR<br>PGQGLEWIGLINPGSDYTNYNENFKGKATLTADKSSSTAY<br>MHLSSLTSEDSAVYFCARRFGYYGSGNYFDYWGQGTTLTV<br>SS | 134 |
| B7 Light Chain | |
| DVVMTQTPLSLPVSLGDQASISCTSGQSLVHINGNTYLHW<br>LYQKPGQSPICLLIYKVSNLFSGVPDRFSGSGSGTDFTLK<br>ISRVEAEDLGVYFCSQSTHFPFTFGTGTKLEIK | 135 |

TABLE 30

Clone B58 variable domain amino acid sequences without leader sequence and cut sites

| Sequence | SEQ ID NO: |
|---|---|
| B58 Heavy Chain | |
| QVQLQQSGAELVRPGTSVKVSCKASGDAFTNYLIEWVKQR<br>PGQGLEWIGLIIPGTGYTNYNENFKGKATLTADKSSSTAY<br>MQLSSLTSEDSAVYFCARRFGYYGSSNYFDYWGQGTTLTV<br>SS | 136 |

TABLE 30-continued

| Clone B58 variable domain amino acid sequences without leader sequence and cut sites | |
|---|---|
| Sequence | SEQ ID NO: |
| B58 Light Chain | |
| DVVMTQTPLSLPVSLGDQASISCRSSQSLVHSNGNTYLHW LYQKPGQSPKLLIYKVSNRFSGVPDRFSGSGPGTDFTLKI SRVEAEDLGIYFCSQSTHFPFTFGTGTKLEIK | 137 |

TABLE 31

| Clone 3A6 variable domain amino acid sequences without leader sequence and cut sites | |
|---|---|
| Sequence | SEQ ID NO: |
| 3A6 Heavy Chain | |
| QVQLQQSGAELVRPGTSVKLSCKASGDAFTNYLIEWVKQR PGQGLEWIGLIIPGTGYTNYNENFKGKATLTADKSSSTAY MQLSSLTSEDSAVYFCARRFGYYGSGYYFDYWGQGTTLTV SS | 138 |
| 3A6 Light Chain | |
| DVVMTQTPLSLPVSLGDQASISCRSSQSLVHSNGNTYLHW YLQKPGQSPKLLIYKVSNRFSGVPDRFSGSGPGTDFTLKI SRVEAEDLGVYFCSQSTHFPFTFGTGTKLEIK | 139 |

TABLE 32

| Clone A63 variable domain amino acid sequences without leader sequence and cut sites | |
|---|---|
| Sequence | SEQ ID NO: |
| A63 Heavy Chain | |
| DIQLQESGPGLVKPSQSLSLTCSVTGFSITSGYYWTWIRQ FPGNKLEWVAYIGYDGSNDSNPSLICNRISITRDTSKNQF FLICLNSVITEDTATYYCARAMLRRGFDYWGQGTTLTVSS | 140 |
| A63 Light Chain | |
| QIVLTQSPAIMSASPGEKVTMTCSASSSLSYMHWYQQKPG TSSPKRWIYDTSKLASGVPARFSGSGSGTSYSLTISSMEA TYYEDAACHRRSSYTFGGGTKLEIK | 141 |

Example 9

Lpath's Murine Antibody, Lpathomab™ (LT3000)—Overview

Murine antibody clone B7 was chosen for further study and renamed Lpathomab™, also known as LT3000. As described above, this murine anti-LPA mAb, was derived from a hybridoma cell line following immunization of mice with a protein-derivatized LPA immunogen. A hybridoma cell line with favorable properties was identified and used to produce a monoclonal antibody using standard hybridoma culture techniques.

A comprehensive series of pre-clinical efficacy studies were performed to confirm the potential therapeutic utility of an anti-LPA-antibody-based approach. It is believed that antibody neutralization (e.g., reduction in effective concentration) of extracellular LPA could result in a marked decrease in disease progression in humans. For cancer, LPA neutralization could result in inhibition of tumor proliferation and the growing vasculature needed to support tumor growth. Furthermore, recent research suggests that many angiogenesis inhibitors may also act as anti-invasive and anti-metastatic compounds that could also mitigate the spread of cancer to sites distant from the initial tumor. For fibrosis, LPA neutralization could result in a reduction of the inflammation and fibrosis associated with the aberrant wound-healing response following tissue injury. Thus, Lpathomab™ could have several mechanisms of action, including:

- A direct effect on tumor cell growth, migration and susceptibility to chemotherapeutic agents
- An indirect effect on tumors through anti-angiogenic effects
- An additional indirect effect on tumors by preventing the release and neutralization of synergistic pro-angiogenic growth factors
- A direct effect on proliferation, migration, and transformation of fibroblasts to the myofibroblast phenotype and collagen production by myofibroblasts
- An indirect effect on tissue fibrosis by preventing the expression and release of synergistic pro-angiogenic, pro-inflammatory and pro-fibrotic growth factors

Example 10

Biophysical Properties of Lpathomab/LT3000

Lpathomab/LT3000 has high affinity for the signaling lipid LPA ($K_D$ of 1-50 pM as demonstrated by surface plasmon resonance in the BiaCore assay, and in a direct binding ELISA assay); in addition, LT3000 demonstrates high specificity for LPA, having shown no binding affinity for over 100 different bioactive lipids and proteins, including over 20 bioactive lipids, some of which are structurally similar to LPA. The murine antibody is a full-length IgG1k isotype antibody composed of two identical light chains and two identical heavy chains with a total molecular weight of 155.5 kDa. The biophysical properties are summarized in Table 33.

TABLE 33

| General Properties of Lpathomab (LT3000) | |
|---|---|
| Identity | LT3000 |
| Antibody isotype | Murine IgG1k |
| Specificity | Lysophosphatidic acid (LPA) |
| Molecular weight | 155.5 kDa |
| OD of 1 mg/mL | 1.35 (solution at 280 nm) |
| $K_D$ | 1-50 pM |
| Apparent Tm | 67° C. at pH 7.4 |
| Appearance | Clear if dissolved in 1x PBS buffer (6.6 mM phosphate, 154 mM sodium chloride, pH 7.4) |
| Solubility | >40 mg/mL in 6.6 mM phosphate, 154 mM sodium chloride, pH 7.4 |

Lpathomab has also shown biological activity in preliminary cell based assays such as cytokine release, migration and invasion; these are summarized in Table 34 along with data showing specificity of LT3000 for LPA isoforms and other bioactive lipids, and in vitro biological effects of LT3000.

TABLE 34

| LT3000 (Lpathomab, B7 antibody) | | | | | |
|---|---|---|---|---|---|
| A. Competitor Lipid | 14:0 LPA | 16:0 LPA | 18:1 LPA | 18:2 LPA | 20:4 LPA |
| $IC_{50}$ (μM) | 0.105 | 0.483 | >2.0 | 1.487 | 0.161 |
| MI (%) | 61.3 | 62.9 | 100 | 100 | 67 |
| B. Competitor Lipid | LPC | S1P | C1P | Cer | DSPA |
| MI (%) | 0 | 2.7 | 1.0 | 1 | 0 |
| C. Cell based assay | LPA isoform | % Inhibition (over LPA taken as 100) | | | |
| Migration | 18:1 | 35* | | | |
| Invasion | 14:0 | 95* | | | |
| IL-8 Release | 18:1 | 20 | | | |
| IL-6 Release | 18:1 | 23* | | | |
| | | % Induction (over LPA + TAXOL taken as 100) | | | |
| Apoptosis | 18:1 | 79 | | | |

A. Competition ELISA assay was performed with Lpathomab and 5 LPA isoforms. 18:1 LPA was captured on ELISA plates. Each competitor lipid (up to 10 μM) was serially diluted in BSA/PBS and incubated with 3 nM Lpathomab. Mixtures were then transferred to LPA coated wells and the amount of bound antibody was measured. B. Competition ELISA was performed to assess specificity of Lpathomab. Data were normalized to maximum signal ($A_{450}$) and were expressed as percent inhibition (n = 3). $IC_{50}$: half maximum inhibition concentration; MI %: maximum inhibition (% of binding in the absence of inhibitor). C. Migration assay: Lpathomab (150 μg/mL) reduced SKOV3 cell migration triggered by 1 μM LPA (n = 3); Invasion assay: Lpathomab (15 mg/mL) blocked SKOV3 cell invasion triggered by 2 μM LPA (n = 2); Cytokine release of human IL-8 and IL-6: Lpathomab (300-600 μg/mL, respectively) reduced 1 μM LPA-induced release of pro-angiogenic and metastatic IL-8 and IL-6 in SKOV3 conditioned media (n = 3). Apoptosis: SKOV3 cells were treated with 1 μM Taxol; 1 μM LPA blocked Taxol induced apoptosis. The addition to Lpathomab (150 μg/mL) blocked LPA-induced protection from apoptosis (n = 1). Data Analysis: Student-t test,

*denotes $p < 0.05$.

The potent and specific binding of Lpathomab/LT3000 to LPA results in reduced availability of extracellular LPA with potentially therapeutic effects against cancer-, angiogenic- and fibrotic-related disorders.

A second murine anti-LPA antibody, B3, was also subjected to binding analysis as shown in Table 35.

TABLE 35

| Biochemical characteristics of B3 antibody | | |
|---|---|---|
| | High density surface | Low density surface |
| A. BIACORE | | |
| Lipid Chip | 12:0 LPA | 18:0 LPA |
| $K_D$ (pM), site 1 (site2) | 61 (32) | 1.6 (0.3) |
| B. Competition Lipid Cocktail ($C_{16}$:$C_{18}$:$C_{18:1}$:$C_{18:2}$:$C_{20:4}$, ratio 3:2:5:11:2) | | |
| $IC_{50}$ | (μM) 0.263 | |
| C. Neutralization Assay | | |
| B3 antibody (nmol) | LPA (nmol) | |
| 0 | 0.16 | |
| 0.5 | 0.0428 | |
| 1 | 0.0148 | |
| 2 | under limit of detection | |

A. Biacore analysis for B3 antibody. 12:0 and 18:0 isoforms of LPA were immobilized onto GLC sensor chips; solutions of B3 were passed over the chips and sensograms were obtained for both 12:0 and 18:0 LPA chips. Resulted sensograms showed complex binding kinetics of the antibody due to monovalent and bivalent antibody binding capacities. $K_D$ values were calculated approximately for both LPA 12 and LPA 18.
B. Competition ELISA assay was performed with B3 and a cocktail of LPA isoforms ($C_{16}$:$C_{18}$:$C_{18:1}$:$C_{18:2}$:$C_{20:4}$ in ratio 3:2:5:11:2). Competitor/Cocktail lipid (up to 10 μM) was serially diluted in BSA/PBS and incubated with 0.5 μg/mL B3. Mixtures were then transferred to a LPA coated well plate and the amount of bound antibody was measured. Data were normalized to maximum signal ($A_{450}$) and were expressed as $IC_{50}$ (half maximum inhibition concentration).
C. Neutralization assay: Increasing concentrations of B3 were conjugated to a gel. Mouse plasma was then activated to increase endogenous levels of LPA. Activated plasma samples were then incubated with the increasing concentrations of the antibody-gel complex. LPA leftover which did not complex to the antibody was then determined by ELISA. LPA was sponged up by B3 in an antibody concentration dependent way.

Selected studies conducted with Lpathomab/LT3000/B7 and B3 are described in the following examples.

Example 11

Lpathomab™ in Cancer and Angiogenesis Models

The pleiotropic effects of LPA suggest that reduced availability (effective concentration) of extracellular LPA will (i) reduce growth, metastasis and angiogenesis of primary tumors and (ii) counter-act LPA's protective anti-apoptotic effect on tumor. Because of Lpathomab™/LT3000's potent and specific binding to LPA, we hypothesized that in vivo treatment of LT3000 in preclinical models of cancer would result in various therapeutic benefits.

Preclinical studies were conducted using a variety of in vitro and in vivo systems, demonstrating that Lpathomab™/LT3000 (administered every 3 days at doses of 10-50 mg/kg) exhibits a profile of activity that is consistent with various mechanisms of action, including:

Inhibition of tumor growth in human tumor xenograft models in vivo;

Reduction in LPA-dependent cell proliferation and invasion of human tumor in vitro;

Reduction in angiogenesis, together with reductions in circulating levels of tumorigenic/angiogenic growth factors including IL6, IL8, GM-CSF, MMP2 in vivo;

Reduced metastatic potential; and

Neutralization of LPA-induced protection against tumor-cell death.

In in vitro models:

Reduced proliferation of OVCAR3 ovarian cancer cells;

Neutralization of LPA-induced release of IL-8 from Caki-1, IL-8 and IL-6 from SKOV3 (ovarian) tumor cells in vitro;

Mitigation of LPA's effects in protecting SKOV3 tumor cells from apoptosis (which suggests enhanced efficacy when used in combination with standard chemotherapeutic agents);

Inhibition of LPA-induced tumor cell migration and invasion from chemotherapeutic agents.

In in vivo models:

Inhibition of metastasis and progression of orthotopic and subcutaneous human tumors implanted in nude mice;

Reduction of tumor-associated angiogenesis in subcutaneous SKOV3 xenograft models and in prostate DU145 cancer cells;

Neutralization of bFGF- and VEGF-induced angiogenesis in the murine Matrigel plug assay; and Reduced choroidal neovascularization in a model of laser-induced injury of Bruch's membrane in the eye.

Reduced inflammation and fibrosis with modulation of cytokines and growth factors following bleomycin lung injury;

Further details on efficacy of LT3000 in disease models can be found in, e.g., WO 2008/150841 and corresponding US application US-2009-0136483-A1, both of which are commonly assigned with the instant application and incorporated herein by reference in their entirety.

Example 12

Humanization of Lpathomab (LT3000)

The present example describes the generation of humanized variants of LT3000 and their biochemical properties. A summary of these variants and properties is in Table 41.

Suitable acceptor human FR sequences were selected from the IMGT and Kabat databases based on a homology to LT3000 using a sequence alignment and analysis program (SR v7.6). Lefranc, M. P. (2003) Nucl. Acids Res. 31:307-310; Kabat, E. A. et al. (1991) Sequences of Proteins of Immunological Interest, NIH National Techn. Inform. Service, pp. 1-3242. Sequences with high identity at FR, vernier, canonical and VH-VL interface residues (VCI) were initially selected. From this subset, sequences with the most non-conservative VCI substitutions, unusual proline or cysteine residues and somatic mutations were excluded. AJ002773 was thus selected as the human framework on which to base the humanized version of LT3000 heavy chain variable domain and DQ187679 was thus selected as the human framework on which to base the humanized version of LT3000 light chain variable domain.

TABLE 41

Summary of humanization data

| Anti-LPA mAb variants | | | BackMut# | | Yield | $EC_{50}$ | Tm | $K_D$ (C12) | $K_D$ (C18) |
|---|---|---|---|---|---|---|---|---|---|
| Variant | LC | HC | LC | HC | ug IgG1 | ng/ml | ° C. | pM | pM |
| LT 3000 | Murine | Murine | n/a | n/a | — | 268 | 67 | 27 (7) | 11 (5) |
| LT3010 | 510 | 610 | n/a | n/a | — | 448 | 71.5 | 58 (66) | 159 (151) |
| LT3011 | 502 | 603 | 3 | 3 | 172 | 675 | 71 | nd | nd |
| LT3012 | 502 | 604 | 3 | 4 | 128 | 326 | 67.5 | 132 (102) | 201 (170) |
| LT3013 | 506 | 603 | 1 | 3 | 242 | 1302 | 71.5 | nd | nd |
| LT3014 | 506 | 604 | 1 | 4 | 451 | 560 | 66 | 218 (76) | 370 (340) |
| LT3015 | 502 | 602 | 3 | 6 | 416 | 293 | 71.5 | 80 (94) | 58 (60) |
| LT3016 | 506 | 602 | 1 | 6 | 318 | 506 | 71.5 | 126 (87) | 126 (108) |

Materials 3,3',5,5'-tetramethylbenzidine liquid substrate (TMB) was from Sigma-Aldrich (St. Louis, Mo.). Fatty acid-free bovine serum albumin (BSA) was from Calbiochem (La Jolla, Calif.). Immobilized Protein A, Immobilized Papain and protein desalting spin column were from Pierce (Rockford, Ill.). Anti-human IgG (Fc specific) antibody was purchased from Bethyl (Montgomery, Tex.). Reference IgGs (non-specific human IgG and mouse IgG), anti-human IgG (H+L)-horseradish peroxidase conjugate and anti-mouse IgG (H+L)-horseradish peroxidase conjugate were from Jackson ImmunoResearch Laboratories (West Grove, Pa.). Lysophosphatidic acid (LPA) and other lipids used in the competition ELISA were purchased from Avanti Polar Lipids (Alabaster, Ala.). Biotinylated LPA was purchased from Echelon Biosciences (Salt Lake City, Utah).

Humanization

The variable domains $V_H$ and $V_L$ of the murine anti-LPA monoclonal antibody, LT3000 (Lpathomab) were humanized by grafting the murine CDRs into human framework regions (FR), with the goal of producing an antibody that retains high affinity, specificity and binding capacity for LPA. Lefranc, M. P, (2003). Nucleic Acids Res, 31: 307-10; Martin, A. C. and J. M. Thornton, (1996) J Mol Biol, 1996. 263: 800-15; Morea, V., A. M. Lesk, and A. Tramontano (2000) Methods, 20: 267-79; Foote, J. and G. Winter, (1992) J Mol Biol, 224: 487-99; Chothia, C., et al., (1985). J Mol Biol, 186:651-63.

A three-dimensional (3D) model containing the humanized VL and VH sequences was constructed to identify FR residues juxtaposed to residues that form the CDRs. These FR residues potentially influence the CDR loop structure and the ability of the antibody to retain high affinity and specificity for the antigen. Based on this analysis, 6 residues in AJ002773 and 3 residues in DQ187679 were identified, deemed significantly different from LT3000, and considered for mutation back to the murine sequence. Framework selection and backmutation identification was conducted by DataMabs, LLP, Radlett, Hertfordshire, UK. A list of the humanized variants is summarized in Table 42. The 12V mutation, which is present within the light chain of every variant studied, supports the presentation of residues in the CDRL3. Other light chain back mutations include Q45K, which is solvent exposed, and the conservative Y87F mutation, located on the side of the variable domain opposite the CDRs. Based on their position, the heavy chain back mutations appear more likely to influence the stability and LPA-binding properties of the mAb. I24A and V28G support residues that form the CDRH1 and the cluster of back mutations (I37V, M481, V67A and I69L) form an elaborate network of hydrophobic interactions that likely effect the stability of the folded variable domain and the position of the CDRH2. The role of these back mutations on LPA binding, thermostability and cytokine released were investigated to identify the lead candidate for development of a fully humanized, anti-LPA monoclonal antibody.

TABLE 42

Vector designation and expression level of the chimeric and the humanized variants in HEK293 cells.

| | Light Chain | | Heavy Chain | | Culture V | Expression |
|---|---|---|---|---|---|---|
| mAb | pATH | Back mutations | pATH | Back mutations | ml | (ug/ml) |
| LT3010 | 510 | none | 610 | None | 30 | 8.44 |
| LT3011 | 502 | I2V, Q45K, Y87F | 603 | S24A, I28G, M48I | 60 | 2.88 |
| LT3012 | 502 | I2V, Q45K, Y87F | 604 | 128G, M48I, V67A, I69L | 30 | 11.2 |
| LT3013 | 506 | I2V | 603 | S24A, I28G, M48I | 60 | 5.33 |
| LT3014 | 506 | I2V | 604 | I28G, M48I, V67A, I69L | 60 | 5.83 |
| LT3015 | 502 | I2V, Q45K, Y87F | 602 | S24A, I28G, V37I, M48I, V67A, I69L | 60 | 5.99 |
| LT3016 | 506 | I2V | 602 | S24A, I28G, V37I, M48I, V67A, I69L | 60 | 3.74 |

Expression of the Humanized Variants

The humanized variants shown in the table above were transiently expressed in HEK 293 cells in serum-free conditions, purified and then characterized in a panel of assays. Plasmids containing sequences of each light chain (pATH500 series) and heavy chain (pATH600 series) were transfected into mammalian cells for production. After 5 days of culture, the mAb titer was determined using quantitative ELISA. All combinations of the heavy and light chains yielded between 2-12 ug of antibody per ml of cell culture. SDS-PAGE under reducing conditions revealed two bands at 25 kDa and 50 kDa with high purity (>98%), consistent with the expected masses of the light and heavy chains. A single band was observed under non-reducing conditions with the expected mass of ~150 KDa.

Characterization of the Humanized Variants

The biophysical properties of the humanized variants were characterized for their binding affinity, binding capacity, yield, potency and stability. Table 41 presents the binding affinities of the variants as determined by BiaCore analysis. All the humanized anti-LPA mAb variants exhibited binding affinity in the low picomolar range similar to the chimeric anti-LPA antibody (also known as LT3010) and the murine antibody (LT3000). All of the humanized variants exhibited a $T_M$ similar to or higher than that of LT3000, and most had a Tm of approximately 71° C. With regard to specificity, the humanized variants demonstrated similar specificity profiles to that of LT3000. For example, LT3000 demonstrated no cross-reactivity to lysophosphatidyl choline (LPC), phosphatidic acid (PA), various isoforms of lysophosphatidic acid (14:0 and 18:1 LPA, cyclic phosphatidic acid (cPA), and phosphatidylcholine (PC).

Activity of the Humanized Variants

Five humanized variants (LT3011, LT3013, LT3014, LT3015 and LT3016) were further assessed in in vitro cell assays. LPA is known to play an important role in eliciting the release of interleukin-8 (IL-8) from cancer cells. LT3000 reduced IL-8 release from ovarian cancer cells in a concentration-dependent manner. The humanized variants exhibited a similar reduction of IL-8 release compared to LT3000.

Some humanized variants were also tested for their effect on microvessel density (MVD) in a Matrigel tube formation assay for neovascularization. Both were shown to decrease MVD formation.

TABLE 43

Quantitation of microblood vessel density using CD31 immunostain with H&E counterstaining in matrigel plugs.

| | Control | LT3000 murine (8 mg/kg) | LT3000 murine (2 mg/kg) | Humanized variant #1 (LT3015) (8 mg/kg) | Humanized variant #1 (LT3015) (2 mg/kg) | Humanized variant #2 (LT3016) (2 mg/kg) |
|---|---|---|---|---|---|---|
| Average | 64.2 | 41.5 | 34 | 34.4 | 49 | 50.8 |
| S.E. | 8.0 | 14.2 | 13.7 | 4.2 | 31.5 | 18.8 |
| N = | 5 | 4 | 5 | 5 | 5 | 6 |
| Percent Inhibition | | 35.4 | 47.0 | 46.4 | 23.7 | 20.8 |

Humanized anti-LPA antibody LT3015 was chosen for further characterization.

Antibody Expression and Production in Mammalian Cells

The murine antibody genes were cloned from hybridomas. Synthetic genes containing the human framework sequences and the murine CDRs were assembled from synthetic oligonucleotides and cloned into pCR4Blunt-TOPO using blunt restriction sites. After sequencing and observing 100% sequence congruence, the heavy and light chains were cloned and expressed as a full length IgG1 chimeric antibody using the pConGamma vector for the heavy chain gene and pConKappa vector for the light chain gene (Lonza Biologics, Portsmouth N.H.). The expression cassette for each of these genes contained a promoter, a kozak sequence, and a terminator. These plasmids were transformed into *E. coli* (One Shot Top 10 chemically competent *E. coli* cells, Invitrogen, Cat No. C4040-10), grown in LB media and stocked in glycerol. Large scale plasmid DNA was prepared as described by the manufacturer (Qiagen, endotoxin-free MAXIPREP™ kit, Cat. No 12362). Plasmids were transfected into the human embryonic kidney cell line 293F using 293 fectin and using 293F-FreeStyle Media for culture. The transfected cultures expressed approximately 2-12 mg/L of humanized antibody.

Antibody Purification

Monoclonal antibodies were purified from culture supernatants using protein A affinity chromatography. Aliquots containing 0.5 ml of ProSep-vA-Ultra resin (Millipore, Cat. No 115115827) were added to gravity-flow disposable columns (Pierce, Cat. No 29924) and equilibrated with 10-15 ml of binding buffer (Pierce, Cat. No 21001). Culture supernatants containing transiently expressed humanized antibody were diluted 1:1 with binding buffer and passed over the resin. The antibody retained on the column was washed with 15 ml of binding buffer, eluted with low pH elution buffer (Pierce, Cat. No 21004) and collected in 1 ml fractions containing 100 ul of binding buffer to neutralize the pH. Fractions with absorbance (280 nm)>0.1 were dialyzed overnight (Slide-A-Lyzer Cassettes, 3500 MWCO, Pierce, Cat. No 66382) against 1 liter of PBS buffer (Cellgro, Cat. No 021-030). The dialyzed samples were concentrated using centricon-YM50 (Amicon, Cat. No 4225) concentrators and filtered through 0.22 uM cellulose acetate membranes (Costar, Cat. No 8160). The purity of each preparation was accessed using SDS-PAGE.

SDS-PAGE Electrophoresis

Each antibody sample was diluted to 0.5 ug/ul using gel loading buffer with (reduced) or without (non-reduced) 2-mercaptoethanol (Sigma, Cat. No M-3148). The reduced samples were heated at 95° C. for 5 min while the non-reduced samples were incubated at room temperature. A 4-12% gradient gel (Invitrogen, Cat. No NP0322) was loaded with 2 ug of antibody per lane and ran at 170 volts for 1 hour at room temperature in 1× NuPAGE MOPS SDS running buffer (Invitrogen, Cat. No NP0001). After electrophoresis, the antibodies were fixed by soaking the gel in 50% methanol, 10% acetic acid for ~10 min. The gel was then washed with 3×200 ml distilled water. Finally, the bands were visualized by staining the gel overnight in GelCode® Blue Stain (Pierce, Cat. No 2490) and destaining with water.

Quantitative ELISA

The antibody titer was determined using a quantitative ELISA. Goat-anti human IgG-Fc antibody (Bethyl A80-104A, 1 mg/ml) was diluted 1:100 in carbonate buffer (100 mM $NaHCO_3$, 33.6 mM $Na_2CO_3$, pH 9.5). Plates were coated by incubating 100 ul/well of coating solution at 37° C. for 1 hour. The plates were washed 4× with TBS-T (50 mM Tris, 0.14 M NaCl, 0.05% tween-20, pH 8.0) and blocked with 200 ul/well TBS/BSA (50 mM Tris, 0.14 M NaCl, 1% BSA, pH 8.0) for 1 hour at 37° C. Samples and standard were prepared on non-binding plates with enough volume to run in duplicate. The standard was prepared by diluting human reference serum (Bethyl RS10-110; 4 mg/ml) in TBS-T/BSA (50 mM Tris, 0.14 NaCl, 1% BSA, 0.05% Tween-20, pH 8.0) to the following concentrations: 500 ng/ml, 250 ng/ml, 125 ng/ml, 62.5 ng/ml, 31.25 ng/ml, 15.625 ng/ml, 7.8125 ng/ml, and 0.0 ng/ml. Samples were prepared by making appropriate dilutions in TBS-T/BSA, such that the optical density (OD) of the samples fell within the range of the standard; the most linear range being from 125 ng/ml 15.625 ng/ml. After washing the plates 4× with TBS-T, 100 ul of the standard/samples preparation was added to each well and incubated at 37° C. for 1 hour. Next the plates were washed 4× with TBS-T and incubated for 1 hour at 37° C. with 100 ul/well of HRP-goat anti-human IgG antibody (Bethyl A80-104P, 1 mg/ml) diluted 1:150,000 in TBS-T/BSA. The plates were washed 4× with TBS-T and developed using 100 ul/well of TMB substrate chilled to 4° C. After 7 minutes, the reaction was stopped with 1M $H_2SO_4$ (100 ul/well). The OD was measured at 450 nm, and the data was analyzed using Graphpad Prizm software. The standard curve was fit using a four parameter equation and used to calculate the human IgG content in the samples.

Direct Binding ELISA

The LPA-binding affinities of the humanized antibodies were determined using a direct binding ELISA assay. Microtiter ELISA plates (Costar) were coated overnight with 1.0 ug/ml C12:0 LPA conjugated to Imject malieimide activated bovine serum albumin (BSA) (Pierce Co.) diluted in 0.1 M carbonate buffer (pH 9.5) at 37° C. for 1 h. Plates were washed with PBS (137 mM NaCl, 2.68 mM KCl, 10.1 mM $Na_2HPO_4$, 1.76 mM $KH_2PO_4$; pH 7.4) and blocked with PBS/BSA/tween-20 for 1 hr at room temp or overnight at 4° C. For the primary incubation (1 hr at room temperature), a dilution series of the anti-LPA antibodies (0.4 ug/mL, 0.2 ug/mL, 0.1 ug/mL, 0.05 ug/mL, 0.0125 ug/mL, and 0 ug/mL) was added to the microplate (100 ml per well). Plates were washed and incubated with 100 ul per well of HRP conjugated goat anti-human (H+L) diluted 1:20,000 (Jackson, cat#109-035-003) for 1 hr at room temperature. After washing, the peroxidase was developed with tetramethylbenzidine substrate (Sigma, cat No T0440) and stopped by adding 1 M $H_2SO_4$. The optical density (OD) was measured at 450 nm using a Thermo Multiskan EX. The $EC_{50}$ (half-maximal binding concentration) was determined by a least-squares fit of the dose-response curves with a four parameter equation using the Graphpad Prism software.

The $EC_{50}$ of the humanized antibody, LT3015, was determined to be 75.6 ng/mL, as compared to the murine antibody, LT3000, which had an $EC_{50}$ of 65.3 ng/mL.

LPA Competition ELISA

The specificity of the humanized antibody was determined by competition ELISA. C18:0 LPA coating material was diluted to 0.33 ug/ml with carbonate buffer (100 mM NaHCO3, 33.6 mM Na2CO3, pH 9.5). Plates were coated with 100 ul/well of coating solution and incubated at 37° C. for 1 hour. The plates were washed 4 times with PBS (100 mM Na2HPO4, 20 mM KH2PO4, 27 mM KCl, 1.37 mM NaCl, pH 7.4) and blocked with 150 ul/well of PBS, 1% BSA, 0.1% tween-20 for 1 h at room temperature. The humanized, anti-LPA antibodies were tested against lipid competitors (14:0 LPA (Avanti, Cat. No 857120), 18:1 LPA (Avanti, Cat. No 857130), 18:1 LPC (Avanti, Cat. No 845875), cLPA (Avanti, Cat. No 857328), 18:1 PA (Avanti, Cat. No 840875), PC (Avanti, Cat. No 850454) at 5 uM, 2.5 uM, 1.25 uM, 0.625 uM, and 0.0 uM. The antibody was diluted to 0.5 ug/ml in PBS, 0.1% tween-20 and combined with the lipid samples at a 1:3 ratio of antibody to sample on a non-binding plate. The plates were washed 4 times with PBS and incubated for 1 hour at room temperature with 100 ul/well of the primary antibody/lipid complex. Next the plates were washed 4 times with PBS and incubated for 1 h at room temperature with 100 Owen of HRP-conjugated goat anti-human antibody diluted 1:20,000 in PBS, 1% BSA, 0.1% tween-20. Again the plates were washed 4 times with PBS and developed using TMB substrate (100 ul/well) at 4° C. After 8 minutes, the reaction was stopped with 100 ul/well of 1M H2SO4. The optical density (OD) was measured at 450 nm using a Thermo Multiskan EX. Raw data were transferred to GraphPad software for analysis.

The $IC_{50}$ for the humanized mAb LT3015 was determined to be 0.08 uM, whereas the $IC_{50}$ for the corresponding murine antibody, LT3000, was 0.28 uM.

Thermostability

The thermostability of the humanized antibodies were studied by measuring their LPA-binding affinity (EC50) after heating using the direct binding ELISA. Antibodies dissolved in PBS (Cellgo, Cat. No 021-040) were diluted to 25 ug/ml and incubated at 60° C., 65° C., 70° C., 75° C. and 80° C. for 10 min. Prior to increasing the temperature, 10 ul of each sample was removed and diluted with 90 ul of PBS and stored on ice. The samples were then vortexed briefly and the insoluble material was removed by centrifugation for 1 min at 13,000 rpm. The binding activity of the supernatant was determined using the direct LPA-binding ELISA and compared to a control, which consisted of the same sample without heat treatment.

The Tm for the humanized antibody, LT3015, was determined to be 71.5° C., higher than that of the murine parent antibody, LT3000, which had a Tm of 67° C.

Surface Plasmon Resonance

All binding data were collected on a ProteOn optical biosensor (BioRad, Hercules Calif.). 12:0 LPA-thiol and 18:0 LPA-thiol were coupled to a maleimide modified GLC sensor chip (Cat. No 176-5011). First, the GLC chip was activated with an equal mixture of sulfo-NHS/EDC for seven minutes followed by a 7 minute blocking step with ethyldiamine. Next sulfo-MBS (Pierce Co., cat #22312) was passed over the surfaces at a concentration of 0.5 mM in HBS running buffer (10 mM HEPES, 150 mM NaCl, 0.005% tween-20, pH 7.4). LPA-thiol was diluted into the HBS running buffer to a concentration of 10, 1 and 0.1 uM and injected for 7 minutes producing 3 different density LPA surfaces (~100, ~300 and ~1400 RU). Next, binding data for the humanized antibodies was collected using a 3-fold dilution series starting with 25 nM as the highest concentration (original stocks were each diluted 1 to 100). Surfaces were regenerated with a 10 second pulse of 100 mM HCl. All data were collected at 25° C. Controls were processed using a reference surface as well as blank injections. The response data from each surface showed complex binding behavior which a likely caused by various degrees of multivalent binding. In order to extract estimates of the binding constants, data from the varying antibody concentrations were globally fit using 1-site and 2-site models. This produced estimates of the affinity for the bivalent (site 1) and monovalent site (site 2).

LPA Molar Binding Capacity

The molar ratio of LPA:mAb was determined using a displacement assay. Borosilicate tubes (Fisherbrand, Cat. No 14-961-26) were coated with 5 nanomoles of biotinylated LPA (50 ug of lipid (Echelon Biosciences, Cat. No L-012B, Lot No F-66-136 were suspended in 705 ul of 1:1 chloroform: methanol yielding a 100 uM solution) using a dry nitrogen stream. The coated tubes were incubated with 75 ul (125 pmoles) of antibody dissolved in PBS (Cellgro, Cat. No 021-030) at room temperature. After 3 hours of incubation, the LPA:mAb complexes were separated from free lipid using protein desalting columns (Pierce, Cat, No 89849), and the molar concentration of bound biotinylated LPA was determined using the HABA/Avidin displacement assay (Pierce, Cat. No 28010) according to the manufacturer's instructions.

Measurement of LPA-Induced IL-6 and IL-8 Release in SKOV3 Cells

Anti-LPA antibodies inhibit the LPA-dependant release of human CXCL8/IL-8 in conditioned media of SKOV3 ovarian cells. SKOV3 cells (Lot No 4255558, passage 14) were harvested with 2 ml of 1× Trypsin EDTA (Mediatech Inc, Cat. No 25-053-CV) and resuspended in 8 ml of complete medium (10% FBS, Mediatech Inc. Cat. no 35-011-CV). The cells were centrifuged for 5 min (11,000 rpm) and re-suspended in 5 ml of complete medium. Cells were counted in duplicate with 0.4% Trypan blue (10 ul cells plus 90 ul Trypan blue, Invitrogen, Cat. No 15250-061) using a hemocytometer. In a 96-well plate, $1\times10^5$ cells per well were seeded (final volume 100 ul/well). The cells were allowed to attach and form a confluent monolayer by incubating overnight at 37° C. On the following day, cells were gently washed two times with minimum media (1 mg/ml BSA in McCoy's medium with L-glutamine, Mediatech, Cat. No 10-050-CV). The media was adjusted to 1% penicillin/streptomycin (Mediatech, Cat. No 30-002 CI) and 2.2 g/L sodium-bicarbonate (Mediatech, Cat. No 25-035-CI). Next, the cells were serum-starved at 37° C. for exactly 24 h, followed by cytokine stimulation with 1 uM C18:1 LPA (Avanti, Cat. No 857130) dissolved in 1 mg/ml BSA/PBS (Calbiochem, Cat. No 126575) which was pre-incubated in presence or absence of humanized LPA antibody LT3015 (150, 300 or 600 ug/mL) for one hour. Treatments were then added to the cells. After 22 h of cytokine stimulation, the cells were centrifuged for 5 min (13,500 rpm) at 4° C. and the supernatants (cell-conditioned media) were collected. The CXCL8/IL-8 levels in each supernatant were measured using the Quantikine human CXCL8/IL-8 ELISA kit according to vendor instructions (R&D Systems, Minneapolis Minn., Cat. No D8000C). The IL-6 levels were measured by ELISA using the Quantikine human IL-6 immunoassay kit (R&D systems, Cat. No. D6050). Data were analyzed by one-way ANOVA followed by Bonferroni's post test and expressed as human IL-8 or human IL-6 fold increase. Data are shown in Table 44 and Table 45 below.

TABLE 44

Inhibition of human IL-8 release by humanized anti-LPA antibody LT3015

| Stimulus condition | Human IL-8 Fold Increase (approx). |
|---|---|
| NT (no treatment) | 1 |
| 1 uM LPA | 7.1## |
| LPA + LT3015, 150 ug/mL | 5.7 |
| LPA + LT3015, 300 ug/mL | 4.5** |
| LPA + LT3015, 600 ug/mL | 2.7** |
| LT3015, 300 ug/mL | 1.1 |
| FBS (10%) | 20.1 |

(*p < 0.05, **p < 0.001 and ##p < 0.001, n = 3)

TABLE 45

Inhibition of human IL-6 release by humanized anti-LPA antibody LT3015

| Stimulus condition | Human IL-6 Fold Increase (approx). |
|---|---|
| NT (no treatment) | 1 |
| 1 uM LPA | 29## |
| LPA + LT3015, 150 ug/mL | 22.1 |
| LPA + LT3015, 300 ug/mL | 15.7* |
| LPA + LT3015, 600 ug/mL | 10.8** |
| LT3015, 300 ug/mL | 1.1 |
| FBS (10%) | 69.2 |

(*p < 0.05, **p < 0.001 and ##p < 0.001, n = 3)

Measurement of Tumor Cell Migration in the Scratch Assay

SKOV3 cells were plated at 15,000 cells per well in a 96-well plate. The following day the cells were serum starved in minimal media (McCoy's Media 5a, adjusted to contain L-Glutamine, 2.2 g/L Sodium Bicarbonate, 1% penicillin/streptomycin and 1 mg/ml BSA) for 24 hrs. At time 0 cells were scratched with a p200 pipet tip down the center of each well, washed with minimal media and pictures were taken prior to treatment. Cells were then treated with LPA (C18:1) at 0.2 uM, 1.0 uM and 10 uM concentrations which were pre-incubated at 37° C. with 1.0 uM LPA in the presence or absence of antibody at 150 ug/ml. Positive control (10% FBS treated cells) and antibody alone added to 1 uM LPA, were also tested. Cells were stimulated for 17 hrs at 37° C. in a 5%

$CO_2$ incubator. Pictures were taken again 17 hr post-treatment and % wound closure was measured by adjusting pictures to the same size and measuring the width of the scratch at time 0 and time 17 hr with a ruler. Data were analyzed by Student's t-test. Results are shown in Table 46:

TABLE 46

LT3015 prevents migration of ovarian cancer cells

| Treatment | Percent wound closure (approx.) |
|---|---|
| NT (no treatment) | 30 |
| 10% FBS | 98 |
| 0.2 uM LPA | 65 |
| 1.0 uM LPA | 81 |
| 10 uM LPA | 89 |
| LPA + LT3015 (150 ug/mL) | 59 |
| LT3015 (150 ug/mL) | 30 |

Intracellular Localization of LPA in Ovarian Cancer Cells

The intracellular localization of LPA in SKOV3 cells was determined by immunohistochemistry. SKOV3 cells were seeded on coverslips overnight and then processed for LPA staining. Cells were fixed in formalin, blocked in 1% fatty acid-free BSA and then stained using the murine anti-LPA mAb (LT3000, 0.1 mg/mL), incubated overnight at 4° C., as primary antibody. LPA presence was observed as punctuate staining evenly distributed across the cytoplasm. Controls labeled with secondary antibody only showed no fluorescent signal. LPA presence in cells has been confirmed by biochemical measurements (by ELISA).

Matrigel Assays

Female C57BL/6 mice around 8 to 10-weeks old and Matrigel Matrix High Concentration purchased from BD BioSciences (Franklin Lakes, N.J. (from BD) mixed with 50 ng/ml VEGF and 50 ng/ml bFGF, heparin 3 ng/ml as angiogenic stimuli were used for this study. There were five groups of mice, 10 Matrigel plugs were inoculated into five mice for each group on Day 0. One mouse group served as a control; four others receive drug treatment in four different doses by ip injection every other day. All treatments start at Day-1 and finish at Day 8.

Thirty C57bl/6 mice were implanted with Matrigel plugs in order to obtain 25 healthy mice with two well-shaped Matrigel plugs per mouse. On Day 0, 500 ul Matrigel at 40° C. was subcutaneously injected to each side of the mouse, injection area was shaved. To increase the contact area of injected Matrigel into subcutaneous tissues and form a round shape plug, a wide subcutaneous pocket was formed by swaying the needlepoint right and left after a routine subcutaneous insertion. The injection was done rapidly with an appropriate size needle (21G-25G) to ensure the entire content was delivered in one plug. The injected Matrigel rapidly formed a single solid gel plug.

Animals were treated with 8 or 2 mg/kg of antibody or saline beginning 1 day prior to the implantation of Matrigel plugs or with the vehicle. Treatments were administered ip, on a q2d schedule.

Plugs from each group were collected at Day 12. The mice were euthanized and mouse skin was pulled back to expose the plug. The plugs was dissected out and fixed for histological analysis. Sections of 5 μm from paraffin-embedded plugs were stained with anti-CD-31 antibodies. Blood vessel density in a cross sectional area of each Matrigel plugs were analyzed. For each treatment group, at least six or more Matrigel plugs were quantitatively analyzed to assess any statistical significant difference of microvessel density between groups.

Reduction of Tumor Progression

Human mAb LT3015 reduced ovarian tumor SKOV3 progression and circulating cytokines in biological fluids. Nude mice were engrafted with either 10 mg/kg LT3015, vehicle, or 2 mg/kg paclitaxel (Taxol). After 56 days, mice were sacrificed and the peritoneal cavities were analyzed for tumor burden and ascites fluid accumulation. Tumors were harvested and final tumor weights were determined along with ascites volumes. Data were analyzed by ANOVA and student's t-test analysis. A 32% reduction in tumor burden was observed in LT3015-treated mice. Serum and ascites levels of IL-6, IL-8, GM-CSF and VEGF were measured using ELISA kits from R&D systems, Minneapolis Minn. (Cat. No. D6050, D8000C, HSGM0 and DVE00, respectively) and a reduction in all was observed in LT3015-treated animals compared to vehicle controls, as shown in Table 47. *=p<0.05.

TABLE 47

LT3015 reduces SKOV3 tumor progression and circulating cytokines in vivo

| Analysis# | Vehicle | LT3015 10 mg/kg | Taxol 2 mg/kg |
|---|---|---|---|
| Tumor Burden (mg) | 1274 ± 209 | 861 ± 135 | 381 ± 73 |
| % Reduction | 100 | 32.4 | 70.1 |
| Ascites presence | 6/11 | 4/12 | 1/7 |
| Ascites volume (mL) | 3.563 ± 1.144 | 1.619 ± 0.6113 | 0.2 ± 0.0 |
| IL-8-serum (pg/mL) | 687.6 ± 114.1 | 324.3 ± 55.23* | 234.7 ± 83.04* |
| IL-6-serum (pg/mL) | 84.56 ± 16.62 | 28.02 ± 6.212* | 29.19 ± 9.568* |
| GM-CSF-serum (pg/mL) | 320.5 ± 43.18 | 225.9 ± 54.15 | 340.2 ± 62.98 |
| IL-8-ascites (pg/mL) | 2097 ± 132.1 | 1292 ± 363.1 | 2187 ± 0## |
| IL-6-ascites (pg/mL) | 1018 ± 103.6 | 400.0 ± 218.9* | ND |
| GM-CSF-ascites (pg/mL) | 1200 ± 248.2 | 1289 ± 482.5* | 2054 ± 0## |
| VEGF-ascites (pg/mL) | 3341 ± 202.5 | 2697 ± 255.6 | 3344 ± 0## |

#Mean ± S.E.
1 way ANOVA;
Bonferroni's post test *p < 0.05 (Ascites IL-8 and IL-6, Student t test *p < 0.05)
Sample numbers for ascites measurements;
N = 6 (Vehicle),
N = 4 (hu-Ab), and
N = 1(Taxol).

Thus from the foregoing examples it can be seen that antibody inhibitors of LPA, particularly the humanized monoclonal antibody LT3015, are well positioned for use in the treatment of ovarian cancer, or to augment the efficacy of current ovarian cancer therapy, by blocking the growth-promoting, angiogenic and/or metastatic effects of LPA. For example:

The half life of the murine antibody in mice is ~4 days when given by IV administration, and the antibody is fully distributed to the blood within 6-12 hours when given i.p.

Anti-LPA antibody (murine) significantly reduced SKOV3 tumor progression along with lowering serum and ascites levels of human IL-8, IL-6 and GM-CSF.

Anti-LPA antibody (murine) inhibited neovascularization in two classical angiogenesis models.

Anti-LPA antibody (murine) significantly reduced tumor size in a xenograft CAM assay using a human colon cancer cell line (COLO-205).

Anti-LPA antibody (murine) reduced the metastatic spread of B16-F10 cells to lungs.

The murine anti-LPA mAb, LT3000, was successfully humanized and the humanized mAb retains the binding, specificity and thermostability of the murine parent antibody.

Example 13

Preliminary Animal Pharmacokinetics of Lpathomab

Preliminary PK studies were conducted with Lpathomab. For IV dosed groups, mice were injected with a single 30 mg/kg dose and sacrificed at time points up to 15 days. Antibody was also given via i.p. administration and animals were sacrificed during the first 24 hrs to compare levels of mAb in the blood over this period of time for different routes of delivery. Pharmacokinetic parameters were assessed by WinNonlin. Three mice were sacrificed at each time point and plasma samples were collected and analyzed for mAb levels by ELISA. The half-life of Lpathomab in mice was determined to be 102 hrs (4.25 days) by i.v. administration. Moreover, the antibody is fully distributed to the blood within 6-12 hrs when given i.p., suggesting that the i.p. administration is suitable for xenografts and other studies.

TABLE 48

Pharmacokinetic profile of Lpathomab in mice

| Group | Treatment (mg/kg) | Pharmacokinetic Route | | Estimate | SD | CV % |
|---|---|---|---|---|---|---|
| 1 | 30 | I | AUC | 88.35 | 60.23 | 68.18 |
| | | | K10-HL | 102.7 | 77.48 | 75.91 |
| | | | Cmax | 0.6 | 0.13 | 21.71 |
| | | | Cl | 0.34 | 0.23 | 68.24 |
| | | | AUMC | 13009.8 | 18549.2 | 142.58 |
| | | | MRT | 147.25 | 111.78 | 75.91 |
| | | | Vss | 50 | 10.86 | 21.73 |

Software used to calculate the parameters: WinNonlin v1.1
AUC Area under the curve
K10-HL Elimination half-life
Cmax Dose related peak value
Cl Clearance
AUMC Area under the first moment curve
MRT Mean residence time
Vss Apparent volume of distribution, steady state

Example 14

Safety of Lpathomab Given by Intravenous Injection

Objective. This study assessed the safety of Lpathomab following intravenous injection of the antibody. C57BL/6N mice received Lpathomab (LT3000) for 7 consecutive days followed by a 7 day recovery period for selected animals of each treatment (recovery groups). Blood samples were collected and processed for multiple study parameters including classical hematology, coagulation time and clinical chemistry. Selected organs were weighed and compared with vehicle only controls.

Study design. Once a day, single iv bolus injections of Lpathomab or vehicle control were given at the following doses: 0, 30, 60, 120, and 240 mg/kg. After 7 days of treatment, animals were euthanized with the only exception of the recovery groups which were observed for an additional 7 days (recovery period). For each animal, necropsy consisted of an external examination, including identification of all clinically recorded lesions, as well as a detailed internal examination.

Results. There were no significant differences in the hematology parameters of antibody-treated groups compared to the control group. Almost all of the clinical chemistry parameters tested showed no significant changes when compared to control animals. There was, however a statistically significant reduction in triglycerides in both female and male mice (female, mean±SD: vehicle 89±17, mAb 120 mg/kg, 36±8 p<0.003*; mAb 240 mg/kg 46±18 p*<0.001; male, mean±SD: vehicle 133±24, mAb 240 mg/kg 50±8 p<0.01*; Student t-test). However, there were no statistically significant reductions in glucose, cholesterol, and ALT (alanine aminotransferase) or other CBC parameters. No changes were observed in the weights of mouse brains, hearts, lungs, pituitary glands, ovaries, spleens, testes, thymus glands, thyroid or uterus after Lpathomab treatment. There were, however, significant reductions in liver weights for both genders at certain doses. The highest treatment group of female mice showed significant reduction in liver weights compared to controls (mean±SD: vehicle 1.2±0.27, mAb 240 mg/kg 0.89±0.26 p<0.014*), and the three highest treatment groups in male mice (60, 120, and 240 mg/kg mAb) showed significant reductions when compared to controls (mean±SD: vehicle 1.28±0.06, mAb 1.03±0.07, p<0.0001; 1.08±0.11 p<0.002, 1.11±0.11 p<0.004 respectively; Student t-test).

Example 15

Humanized Anti-LPA Variable Region Sequences

Additional humanized anti-LPA variants of murine antibody B7 and murine antibody B3 heavy chains and of the B3 heavy chain were generated, as described above. The nucleotide and amino acid sequences of the variable regions of these variants are shown in Tables 49-57 below.

TABLE 49 pATH608 humanized B7 heavy chain variant (without leader sequence or cut sites)

| | SEQ ID NO: |
|---|---|
| DNA coding sequence | |
| GAGGTGCAGCTGGTGCAGAGCGGAGCCGAGGTGAAGAAGC<br>CCGGCGAGAGCCTGAAGATCAGCTGCCAGGCCTTCGGCTA | 142 |

TABLE 49-continued pATH608 humanized B7 heavy chain variant (without leader sequence or cut sites)

| | SEQ ID NO: |
|---|---|
| CGGCTTCATCAACTACCTGATCGAGTGGATCCGGCAGATG<br>CCCGGCCAGGGCCTGGAATGGATCGGCGCAATCAACCCCG<br>GCAGCGACTACACCAACTACAACGAGAACTTCAAGGGCCA<br>GGCCACCCTGAGCGCCGACAAGAGCAGCAGCACCGCCTAC<br>CTGCAGTGGAGCAGCCTGAAGGCCAGCGACACCGCCATGT<br>ACTTTTGCGCCAGGCGGTTCGGCTACTACGGCAGCGGCAA<br>CTACTTCGACTACTGGGGCCAGGGCACCATGGTGACCGTG<br>AGCAGC | |
| Translated amino acid sequence | |
| EVQLVQSGAEVKKPGESLKISCQAFGYGFINYLIEWIRQM<br>PGQGLEWIGAINPGSDYTNYNENFKGQATLSADKSSSTAY<br>LQWSSLKASDTAMYFCARRFGYYGSGNYFDYWGQGTMVTV<br>SS | 143 |

TABLE 50 pATH700 humanized B3 light chain variant (without leader sequence or cut sites)

| | SEQ ID NO: |
|---|---|
| DNA coding sequence | |
| GACGTGGTGATGACCCAGACCCCCCTGAGCCTGCCCGTGA<br>CCCCAGGCGAACCCGCCAGCATCAGCTGTAGAAGCTCCCA<br>GTCCCTGCTGAAAACCAACGGCAACACCTATCTGCACTGG<br>TATCTGCAGAAGCCCGGCCAGAGCCCCAAGCTGCTGATCT<br>ACAAGGTGTCCAACCGGTTCAGCGGCGTGCCCGACAGATT<br>CAGCGGCAGCGGCTCCGGCACCGACTTCACCCTGAAGATC<br>AGCCGGGTGGAGGCCGAGGACGTGGGCGTGTACTTCTGCA<br>GCCAGTCCACCCACTTCCCTTTCACCTTCGGCCAGGGCAC<br>AAAGCTGGAAATCAAG | 144 |
| Translated amino acid sequence | |
| DVVMTQTPLSLPVTPGEPASISCRSSQSLLKTNGNTYLHW<br>YLQKPGQSPKLLIYKVSNRFSGVPDRFSGSGSGTDFTLKI<br>SRVEAEDVGVYFCSQSTHFPFTFGQGTKLEIK | 145 |

TABLE 51 pATH701 humanized B3 light chain variant (without leader sequence or cut sites)

| | SEQ ID NO: |
|---|---|
| DNA coding sequence | |
| GACGTGGTGATGACCCAGACCCCCCTGAGCCTGCCCGTGA<br>CCCCAGGCGAACCCGCCAGCATCAGCTGTAGAAGCTCCCA<br>GTCCCTGCTGAAAACCAACGGCAACACCTATCTGCACTGG<br>TATCTGCAGAAGCCCGGCCAGAGCCCCCAGCTGCTGATCT<br>ACAAGGTGTCCAACCGGTTCAGCGGCGTGCCCGACAGATT<br>CAGCGGCAGCGGCTCCGGCACCGACTTCACCCTGAAGATC<br>AGCCGGGTGGAGGCCGAGGACGTGGGCGTGTACTACTGCA<br>GCCAGTCCACCCACTTCCCTTTCACCTTCGGCCAGGGCAC<br>CAAGCTGGAAATCAAG | 146 |
| Translated amino acid sequence | |
| DVVMTQTPLSLPVTPGEPASISCRSSQSLLKTNGNTYLHW<br>YLQKPGQSPQLLIYKVSNRFSGVPDRFSGSGSGTDFTLKI<br>SRVEAEDVGVYYCSQSTHFPFTFGQGTKLEIK | 147 |

TABLE 52 pATH702 humanized B3 light chain variant (without leader sequence or cut sites)

| | SEQ ID NO: |
|---|---|
| DNA coding sequence | |
| GACGTGGTGATGACCCAGACCCCCCTGAGCCTGCCCGTGA<br>CCCCAGGCGAACCCGCCAGCATCAGCTGTAGAAGCTCCCA<br>GAGCCTGCTGAAAACCAACGGCAACACCTATCTGCACTGG<br>TATCTGCAGAAGCCCGGCCAGAGCCCCAAGCTGCTGATTT<br>TCAAGGTGTCCAACCGGTTCAGCGGCGTGCCCGACAGATT<br>CAGCGGCAGCGGCTCCGGCACCGACTTCACCCTGAAGATC<br>AGCCGGGTGGAGGCCGAGGACGTGGGCGTGTACTTCTGCA<br>GCCAGTCCACCCACTTCCCTTTCACCTTCGGCCAGGGCAC<br>AAAGCTGGAAATCAAG | 148 |
| Translated amino acid sequence | |
| DVVMTQTPLSLPVTPGEPASISCRSSQSLLKTNGNTYLHW<br>YLQKPGQSPKLLIFKVSNRFSGVPDRFSGSGSGTDFTLKI<br>SRVEAEDVGVYFCSQSTHFPFTFGQGTKLEIK | 149 |

TABLE 53 pATH800 humanized B3 heavy chain variant (without leader sequence or cut sites)

| | SEQ ID NO: |
|---|---|
| DNA coding sequence | |
| GAGGTGCAGCTGGTGCAGAGCGGAGC-<br>CGAAGTGAAGAAG<br>CCCGGCGAGAGCCTGAAGATCAGCTGC-<br>CAGGCCTTCGGC<br>TACGGCTTCATCAACTACCTGATC-<br>GAGTGGATCCGGCAG<br>ATGCCCGGACAGGGCCTGGAATGGATCG-<br>GCCTGATCTAC<br>CCCGACAGCGGCTACATCAATTACAAC-<br>GAGAACTTCAAG<br>GGCCAGGCCACCCTGAGCGCCGACAA-<br>GAGCAGCAGCACC<br>GCCTATCTGCAGTGGAGCAGCCTGAAG-<br>GCCAGCGACACC<br>GCCATGTACTTTTGCGCCAGGCGGT-<br>TCGCCTACTACGGC<br>AGCGGCTACTACTTCGACTACTGGGGC-<br>CAGGGCACAATG<br>GTGACCGTGTCTAGC | 150 |
| Translated amino acid sequence | |
| EVQLVQSGAEVICKPGESLKISCQAF-<br>GYGFINYLIEWIR<br>QMPGQGLEWIGLIYPDSGYINYNEN-<br>FKGQATLSADKSSS<br>TAYLQWSSLKASDTAMYFCARRFAYYGS-<br>GYYFDYWGQGT<br>MVTVSS | 151 |

TABLE 54 pATH801 humanized B3 heavy chain variant (without leader sequence or cut sites)

| | SEQ ID NO: |
|---|---|
| DNA coding sequence | |
| GAGGTGCAGCTGGTGCAGAGCGGCGCT-<br>GAAGTGAAGAAG | 152 |

TABLE 54-continued

| pATH801 humanized B3 heavy chain variant (without leader sequence or cut sites) | SEQ ID NO: |
|---|---|
| CCCGGCGAGAGCCTGAAGATCAGCTGC-<br>CAGGCCTTCGGC<br>TACGCCTTCACCAACTACCTGATC-<br>GAGTGGGTGCGCCAG<br>ATGCCCGGACAGGGCCTGGAATG-<br>GATGGGCCTGATCTAC<br>CCCGACAGCGGCTACATCAACTACAAC-<br>GAGAACTTCAAG<br>GGCCAGGTGACCATCAGCGCCGACAA-<br>GAGCAGCAGCACC<br>GCCTATCTGCAGTGGAGCAGCCTGAAG-<br>GCCAGCGACACC<br>GCCATGTACTTTTGCGCCAGGCGGT-<br>TCGCCTACTACGGC<br>AGCGGCTACTACTTCGACTACTGGGGC-<br>CAGGGCACAATG<br>GTGACCGTGTCCAGC | |
| Translated amino acid sequence | |
| EVQLVQSGAEVKKPGESLKISCQAF-<br>GYAFTNYLIEWVRQ<br>MPGQGLEWMGLIYPDSGYINYNEN-<br>FKGQVTISADKSSST<br>AYLQWSSLKASDTAMYFCARRFAYYGS-<br>GYYFDYWGQGTM<br>VTVSS | 153 |

TABLE 55

| pATH802 humanized B3 heavy chain variant (without leader sequence or cut sites) | SEQ ID NO: |
|---|---|
| DNA coding sequence | |
| GAGGTGCAGCTGGTGCAGAGCGGCGCT-<br>GAAGTGAAGAAG<br>CCCGGCGAGAGCCTGAAGATCAGCTGC-<br>CAGGCCTTCGGC<br>TACGCCTTCACCAACTACCTGATC-<br>GAGTGGGTGCGCCAG<br>ATGCCCGGACAGGGCCTGGAATGGATCG-<br>GCCTGATCTAC<br>CCCGACAGCGGCTACATCAACTACAAC-<br>GAGAACTTCAAG<br>GGCCAGGCCACCCTGAGCGCCGACAA-<br>GAGCAGCAGCACC<br>GCCTATCTGCAGTGGAGCAGCCTGAAG-<br>GCCAGCGACACC<br>GCCATGTACTTTTGCGCCAGGCGGT-<br>TCGCCTACTACGGC<br>AGCGGCTACTACTTCGACTACTGGGGC-<br>CAGGGCACAATG<br>GTGACCGTGTCCAGC | 154 |
| Translated amino acid sequence | |
| EVQLVQSGAEVICKPGESLKISCQAF-<br>GYAFTNYLIEWVR<br>QMPGQGLEWIGLIYPDSGYINYNEN-<br>FKGQATLSADKSSS<br>TAYLQWSSLKASDTAMYFCARRFAYYGS-<br>GYYFDYWGQGT<br>MVTVSS | 155 |

TABLE 56

| pATH803 humanized B3 heavy chain variant (without leader sequence or cut sites) | SEQ ID NO: |
|---|---|
| DNA coding sequence | |
| GAGGTGCAGCTGGTGCAGAGCGGAGC-<br>CGAAGTGAAGAAG<br>CCCGGCGAGAGCCTGAAGATCAGCTGC-<br>CAGGCCTTCGGC<br>GACGCCTTCACCAACTACCTGATC-<br>GAGTGGGTGCGCCAG<br>ATGCCCGGACAGGGCCTGGAATG-<br>GATGGGCCTGATCTAC<br>CCCGACAGCGGCTACATCAACTACAAC-<br>GAGAACTTCAAG<br>GGCCAGGTGACCATCAGCGCCGACA-<br>GAAGCAGCAGCACC<br>GCCTATCTGCAGTGGAGCAGCCTGAAG-<br>GCCAGCGACACC<br>GCCATGTACTTTTGCGCCAGGCGGT-<br>TCGCCTACTACGGC<br>AGCGGCTACTACTTCGACTACTGGGGC-<br>CAGGGCACAATG<br>GTGACCGTGTCCAGC | 156 |
| Translated amino acid sequence | |
| EVQLVQSGAEVKKPGESLKISCQAF-<br>GDAFTNYLIEWVRQ<br>MPGQGLEWMGLIYPDSGYINYNEN-<br>FKGQVTISADRSSST<br>AYLQWSSLKASDTAMYFCARRFAYYGS-<br>GYYFDYWGQGTM<br>VTVSS | 157 |

TABLE 57

| pATH804 humanized B3 heavy chain variant (without leader sequence or cut sites) | SEQ ID NO: |
|---|---|
| DNA coding sequence | |
| GAGGTGCAGCTGGTGCAGAGCGGAGC-<br>CGAAGTGAAGAAG<br>CCCGGCGAGAGCCTGAAGATCAGCTGC-<br>CAGGCCTTCGGC<br>GACGCCTTCACCAACTACCTGATC-<br>GAGTGGGTGCGCCAG<br>ATGCCCGGACAGGGCCTGGAATGGATCG-<br>GCCTGATCTAC<br>CCCGACAGCGGCTACATCAACTACAAC-<br>GAGAACTTCAAG<br>GGCCAGGCCACCCTGAGCGCCGACA-<br>GAAGCAGCAGCACC<br>GCCTATCTGCAGTGGAGCAGCCTGAAG-<br>GCCAGCGACACC<br>GCCATGTACTTTTGCGCCAGGCGGT-<br>TCGCCTACTACGGC<br>AGCGGCTACTACTTCGACTACTGGGGC-<br>CAGGGCACAATG<br>GTGACCGTGTCCAGC | 158 |
| Translated amino acid sequence | |
| EVQLVQSGAEVKKPGESLKISCQAF-<br>GDAFTNYLIEWVRQ<br>MPGQGLEWIGLIYPDSGYINYNEN-<br>FKGQATLSADRSSST<br>AYLQWSSLKASDTAMYFCARRFAYYGS-<br>GYYFDYWGQGTM<br>VTVSS | 159 |

A comparison of the variant sequences is shown in Tables 58 and 60. Backmutations are shown in bold. CDR sequences are shown in gray. Canonical residues are numbered according to the CDR (1, 2 or 3) which which they are associated.

TABLE 58

Sequences of the variable domains of anti-LPA light chain humanized variants. CDRs are shaded, backmutations are in bold.

| | VK sequence |
|---|---|
| Canon-ical | 1 1 1 1 1 2 |
| Vernier | * * ** **** |
| Inter-face | F F F F F |
| Kabat number | 1 2 3 4 5 6<br>1234567890123456789012345 67abcde8901234567890123456789012345678901234567890 |
| B7 VK murine | DVVMTQTPLSLPVSLGDQASISCTSGQSLVHINGNTYLHWYLQKPGQSPKLLIYKVSNLFSGVPD |
| B7RKA | DIVMTQTPLSLPVTPGEPASISCTSGQSLVHINGNTYLHWYLQKPGQSPQLLIYKVSNLFSGVPD |
| B7RKB | DVVMTQTPLSLPVTPGEPASISCTSGQSLVHINGNTYLHWYLQKPGQSP**K**LLIYKVSNLFSGVPD |
| B7RKC | DIVMTQTPLSLPVTPGEPASISCTSGQSLVHINGNTYLHWYLQKPGQSP**K**LLIYKVSNLFSGVPD |
| B7RKD | DVVMTQTPLSLPVTPGEPASISCTSGQSLVHINGNTYLHWYLQKPGQSPQLLIYKVSNLFSGVPD |
| B7RKE | DVVMTQTPLSLPVTPGEPASISCTSGQSLVHINGNTYLHWYLQKPGQSP**K**LLIYKVSNLFSGVPD |
| B7RKF | DVVMTQTPLSLPVTPGEPASISCTSGQSLVHINGNTYLHWYLQKPGQSPQLLIYKVSNLFSGVPD |
| B3-700 | DVVMTQTPLSLPVTPGEPASISC**R**S**S**QSL**LKT**NGNTYLHWYLQKPGQSP**K**LLIYKVSN**R**FSGVPD |
| B3-701 | DVVMTQTPLSLPVTPGEPASISC**R**S**S**QSL**LKT**NGNTYLHWYLQKPGQSPQLLIYKVSN**R**FSGVPD |
| B3-702 | DVVMTQTPLSLPVTPGEPASISC**R**S**S**QSL**LKT**NGNTYLHWYLQKPGQSP**K**LLI**F**KVSN**R**FSGVPD |

| | VK sequence | SEQ ID NO: |
|---|---|---|
| Canon-ical | 2 1 3 3 3 | |
| Vernier | * * ** * * | |
| Inter-face | F F F F | |
| Kabat number | 7 8 9 10<br>12345678901234567890123456789012345678901234567 | |
| B7 VK murine | RFSGSGSGTDFTLKISRVEAEDLGVYFCSQSTHFPFTFGTGTKLEIK | 160 |
| B7RKA | RFSGSGSGTDFTLKISRVEAEDVGVYYCSQSTHFPFTFGQGTKLEIK | 161 |
| B7RKB | RFSGSGSGTDFTLKISRVEAEDVGVY**F**CSQSTHFPFTFGQGTKLEIK | 162 |
| B7RKC | RFSGSGSGTDFTLKISRVEAEDVGVY**F**CSQSTHFPFTFGQGTKLEIK | 163 |
| B7RKD | RFSGSGSGTDFTLKISRVEAEDVGVY**F**CSQSTHFPFTFGQGTKLEIK | 164 |
| B7RKE | RFSGSGSGTDFTLKISRVEAEDVGVYYCSQSTHFPFTFGQGTKLEIK | 165 |
| B7RKF | RFSGSGSGTDFTLKISRVEAEDVGVYYCSQSTHFPFTFGQGTKLEIK | 166 |
| B3-700 | RFSGSGSGTDFTLKISRVEAEDVGVY**F**CSQSTHFPFTFGQGTKLEIK | 167 |
| B3-701 | RFSGSGSGTDFTLKISRVEAEDVGVYYCSQSTHFPFTFGQGTKLEIK | 168 |
| B3-702 | RFSGSGSGTDFTLKISRVEAEDVGVY**F**CSQSTHFPFTFGQGTKLEIK | 169 |

TABLE 59

LPA humanized antibody light chain variant variable domain sequences and vectors containing them.

| Vector name | Description | Number of backmutations | Identity of backmutations |
|---|---|---|---|
| pATH500LC | pCONkappa (Lonza vector alone) | | |
| pATH501 | B7 humanized light chain RKA in vector pATH500LC | 0 | — |
| pATH502 | B7 humanized light chain RKB in vector pATH500 | 3 | I2V, Q45K, Y87F |
| pATH503 | B7 humanized light chain RKC in vector pATH500 | 2 | Q45K, Y87F |
| pATH504 | B7 humanized light chain RKD in vector pATH500 | 2 | I2V, Y87F |
| pATH505 | B7 humanized light chain RKE in vector pATH500 | 2 | I2V, Q45K |
| pATH506 | B7 humanized light chain RKF in vector pATH500 | 1 | I2V |
| pATH700 | B3 humanized light chain B3-700 in vector pATH500 | 9 | I2V, T24R, G26S, V27cL, H27dK, I27eT, Q45K, L54R, Y87F |

TABLE 59-continued

| LPA humanized antibody light chain variant variable domain sequences and vectors containing them. | | | |
|---|---|---|---|
| **Vector name** | **Description** | **Number of backmutations** | **Identity of backmutations** |
| pATH701 | B3 humanized light chain B3-701 in vector pATH500 | 7 | I2V, T24R, G26S, V27cL, H27dK, I27eT, L54R, |
| pATH702 | B3 humanized light chain B3-702 in vector pATH500 | 10 | I2V, T24R, G26S, V27cL, H27dK, I27eT, Q45K, Y49F, L54R, Y87F |

TABLE 60

Sequences of the variable domains of anti-LPA heavy chain humanized variants. CDRs are shaded, backmutations are in bold

| Kabat # | 1 2 3 4 5 6 7<br>1234567890123456789012345678901234567890123456789012a34567890123456789 0 |
|---|---|
| Canon-ical | 1 11 1 1 2 22 |
| Vernier | * **** *** * * |
| Inter-face | I I I I I |
| B7 VH murine | QVQLQQSGAELVRPGTSVKVSCKASGYGFINYLIEWIKQRPGQGLEWIGLINPGSDYTNYNENFKGKATLT |
| B7RH0 | EVQLVQSGAEVKKPGESLKISCQSFGYIFINYLIEWVRQMPGQGLEWMGLINPGSDYTNYNENFKGQVTIS |
| B7RH1 | EVQLVQSGAEVKKPGESLKISCQ**A**FGYGFINYLIEWIRQMPGQGLEWIGLINPGSDYTNYNENFKGQ**A**T**L**S |
| B7RH2 | EVQLVQSGAEVKKPGESLKISCQSFGYGFINYLIEWIRQMPGQGLEWIGLINPGSDYTNYNENFKGQ**A**T**L**S |
| B7RH3 | EVQLVQSGAEVKKPGESLKISCQ**A**FGYIFINYLIEWIRQMPGQGLEWIGLINPGSDYTNYNENFKGQ**A**T**L**S |
| B7RH4 | EVQLVQSGAEVKKPGESLKISCQ**A**FGYGFINYLIEWVRQMPGQGLEWIGLINPGSDYTNYNENFKGQ**A**T**L**S |
| B7RH5 | EVQLVQSGAEVKKPGESLKISCQ**A**FGYGFINYLIEWIRQMPGQGLEWMGLINPGSDYTNYNENFKGQ**A**T**L**S |
| B7RH6 | EVQLVQSGAEVKKPGESLKISCQ**A**FGYGFINYLIEWIRQMPGQGLEWIGLINPGSDYTNYNENFKGQVT**L**S |
| B7RH7 | EVQLVQSGAEVKKPGESLKISCQ**A**FGYGFINYLIEWIRQMPGQGLEWIGLINPGSDYTNYNENFKGQ**A**TIS |
| B7RH8 | EVQLVQSGAEVKKPGESLKISCQ**A**FGYGFINYLIEWVRQMPGQGLEWIGLINPGSDYTNYNENFKGQVTIS |
| B7RH9 | EVQLVQSGAEVKKPGESLKISCQSFGYGFINYLIEWVRQMPGQGLEWIGLINPGSDYTNYNENFKGQ**A**T**L**S |
| B7HX | EVQLVQSGAEVKKPGESLKISCQ**A**FGYGFINYLIEWIRQMPGQGLEWIGLINPGSDYTNYNENFKGQ**A**T**L**S |
| B7HY | EVQLVQSGAEVKKPGESLKISCQ**A**FGYGFINYLIEWIRQMPGQGLEWIGLINPGSDYTNYNENFKGQ**A**T**L**S |
| B7HZ | EVQLVQSGAEVKKPGESLKISCQ**A**FGYGFINYLIEWIRQMPGQGLEWIGLINPGSDYTNYNENFKGQ**A**T**L**S |
| B7-608 | EVQLVQSGAEVKKPGESLKISCQ**A**FGYGFINYLIEWIRQMPGQGLEWIG**A**INPGSDYTNYNENFKGQ**A**T**L**S |
| B7-800 | EVQLVQSGAEVKKPGESLKISCQ**A**FGYGFINYLIEWIRQMPGQGLEWIGLI**Y**PDSGYINYNENFKGQ**A**T**L**S |
| B7-801 | EVQLVQSGAEVKKPGESLKISCQ**A**FGY**A**F**T**NYLIEWVRQMPGQGLEWMGLI**Y**PDSGYINYNENFKGQVTIS |
| B7-802 | EVQLVQSGAEVKKPGESLKISCQ**A**FGY**A**F**T**NYLIEWVRQMPGQGLEWIGLI**Y**PDSGYINYNENFKGQ**A**T**L**S |
| B7-803 | EVQLVQSGAEVKKPGESLKISCQ**A**FG**DA**F**T**NYLIEWVRQMPGQGLEWMGLI**Y**PDSGYINYNENFKGQVTIS |
| B7-804 | EVQLVQSGAEVKKPGESLKISCQ**A**FG**DA**F**T**NYLIEWVRQMPGQGLEWIGLI**Y**PDSGYINYNENFKGQ**A**T**L**S |

| Kabat # | 8 9 10 11<br>123456789012abc34567890123456789 0abcde1234567890123 | SEQ ID NO: |
|---|---|---|
| Canon-ical | 2 1 | |
| Vernier | * * * ** * | |
| Inter-face | I I I I I | |
| B7 VH | ADKSSSTAYMHLSSLTSEDSAVYFCARRFGYYGSGNYFDYWGQGTTLTVSS | 170 |

TABLE 60-continued

Sequences of the variable domains of anti-LPA heavy chain humanized variants. CDRs are shaded, backmutations are in bold

| | | |
|---|---|---|
| murine | | |
| B7RH0 | ADKSSSTAYLQWSSLKASDTAMYFCARRFGYYGSGNYFDYWGQGTMVTVSS | 171 |
| B7RH1 | ADKSSSTAYLQWSSLKASDTAMYFCARRFGYYGSGNYFDYWGQGTMVTVSS | 172 |
| B7RH2 | ADKSSSTAYLQWSSLKASDTAMYFCARRFGYYGSGNYFDYWGQGTMVTVSS | 173 |
| B7RH3 | ADKSSSTAYLQWSSLKASDTAMYFCARRFGYYGSGNYFDYWGQGTMVTVSS | 174 |
| B7RH4 | ADKSSSTAYLQWSSLKASDTAMYFCARRFGYYGSGNYFDYWGQGTMVTVSS | 175 |
| B7RH5 | ADKSSSTAYLQWSSLKASDTAMYFCARRFGYYGSGNYFDYWGQGTMVTVSS | 176 |
| B7RH6 | ADKSSSTAYLQWSSLKASDTAMYFCARRFGYYGSGNYFDYWGQGTMVTVSS | 177 |
| B7RH7 | ADKSSSTAYLQWSSLKASDTAMYFCARRFGYYGSGNYFDYWGQGTMVTVSS | 178 |
| B7RH8 | ADKSSSTAYLQWSSLKASDTAMYFCARRFGYYGSGNYFDYWGQGTMVTVSS | 179 |
| B7RH9 | ADKSSSTAYLQWSSLKASDTAMYFCARRFGYYGSGNYFDYWGQGTMVTVSS | 180 |
| B7HX | ADKSSSTAYLQWSSLKASDTAMYFCARRFGYYGSGNYFDYWGQGTMVTVSS | 181 |
| B7HY | ADKSSSTAYLQWSSLKASDTAMYFCARRFGYYGSGNYFDYWGQGTMVTVSS | 182 |
| B7HZ | ADKSSSTAYLQWSSLKASDTAMYFCARRFGYYGSGNYFDYWGQGTMVTVSS | 183 |
| B7-608 | ADKSSSTAYLQWSSLKASDTAMYFCARRFGYYGSGNYFDYWGQGTMVTVSS | 184 |
| B7-800 | ADKSSSTAYLQWSSLKASDTAMYFCARRF**A**YYGSG**Y**YFDYWGQGTMVTVSS | 185 |
| B7-801 | ADKSSSTAYLQWSSLKASDTAMYFCARRF**A**YYGSG**Y**YFDYWGQGTMVTVSS | 186 |
| B7-802 | ADKSSSTAYLQWSSLKASDTAMYFCARRF**A**YYGSG**Y**YFDYWGQGTMVTVSS | 187 |
| B7-803 | AD**R**SSSTAYLQWSSLKASDTAMYFCARRF**A**YYGSG**Y**YFDYWGQGTMVTVSS | 188 |
| B7-804 | AD**R**SSSTAYLQWSSLKASDTAMYFCARRF**A**YYGSG**Y**YFDYWGQGTMVTVSS | 189 |

TABLE 61

LPA humanized antibody heavy chain variant variable domain sequences and vectors containing them.

| Vector name | Description | Number of backmutations | Identity of backmutations |
|---|---|---|---|
| pATH600HC | pCONgamma (Lonza vector alone) | | |
| pATH601 | B7 humanized heavy chain RH0 in vector pATH600 | 0 | — |
| pATH602 | B7 humanized heavy chain RH1 in vector pATH600 | 6 | S24A, I28G, V37I, M48I, V67A, I69L |
| pATH603 | B7 humanized heavy chain RH8 in vector pATH600 | 3 | S24A, I28G, M48I |
| pATH604 | B7 humanized heavy chain RH9 in vector pATH600 | 4 | I28G, M48I, V67A, I69L |
| pATH605 | B7 humanized heavy chain HX in vector pATH600 | 2 | I28G and M48I |
| pATH606 | B7 humanized heavy chain HY in vector pATH600 | 2 | S24A and M48I |
| pATH607 | B7 humanized heavy chain HZ in vector pATH600 | 4 | S24A, I28G, V37I, M48I |
| pATH608 | B7 humanized heavy chain B7-608 in vector pATH600 | 7 | S24A, I28G, V37I, M48I, L50A, V67A, I69L, |
| pATH800 | B3 humanized heavy chain B3-800 in vector pATH600 | 12 | S24A, I28G, V37I, M48I, N52Y, G53D, D55G, T57I, V67A, I69L, G97A, N100cY |
| pATH801 | B3 humanized heavy chain B3-801 in vector pATH600 | 9 | S24A, I28A, I30T, N52Y, G53D, D55G, T57I, G97A, N100cY |
| pATH802 | B3 humanized heavy chain B3-802 in vector pATH600 | 12 | S24A, I28A, I30T, M48I, N52Y, G53D, D55G, T57I, V67A, I69L, G97A, N100cY |
| pATH803 | B3 humanized heavy chain B3-803 in vector pATH600 | 11 | S24A, Y27D, I28A, I30T, N52Y, G53D, D55G, T57I, K73R, G97A, N100cY |
| pATH804 | B3 humanized heavy chain B3-804 in vector pATH600 | 14 | S24A, Y27D, I28A, I30T, M48I, N52Y, G53D, D55G, T57I, V67A, I69L, K73R, G97A, N100cY |

Example 16

Creation of the Vector pATH3015 for Cell Line Development

LT3015 is a recombinant, humanized, monoclonal antibody that binds with high affinity to the bioactive lipid lysophosphatidic acid (LPA). LT3015 is a full-length IgG1k isotype antibody composed of two identical light chains and two identical heavy chains with a total molecular weight of 150 kDa. The heavy chain contains an N-linked glycosylation site. The two heavy chains are covalently coupled to each other through two intermolecular disulfide bonds, consistent with the structure of a human IgG1.

LT3015 was originally derived from a murine monoclonal antibody which was produced using hybridomas generated from mice immunized with LPA. The humanization of the murine antibody involved the insertion of the six murine complementarity determining regions (CDRs) in place of those of a human antibody framework selected for its structure similarity to the murine parent antibody. A series of substitutions were made in the framework to engineer the humanized antibody. These substitutions are called back mutations and replace human with murine residues that are involved in the interaction with the antigen. The final humanized version contains six murine back mutation in the human framework of variable domain of the heavy chain (pATH602) and three murine back mutations in the human framework of the variable domain of the light chain (pATH502).

The variable domains of the humanized anti-LPA monoclonal antibody were cloned into the vector IgG1k of the Lonza Biologics' GS gene expression system to generate the vector pATH3015. This expression system consists of an expression vector carrying the constant domains of the antibody genes and the selectable marker glutamine synthetase (GS). GS is the enzyme responsible for the biosynthesis of glutamine from glutamate and ammonia. The vector carrying both the antibody genes and the selectable marker were transfected into the Chinese Hamster Ovary (CHOK1SV) cell line providing sufficient glutamine for the cells to survive without exogenous glutamine. In addition, the specific GS inhibitor, methionine sulphoximine (MSX) was supplemented in the medium to inhibit endogenous GS activity such that only the cell lines with GS activity provided by the vector could survive. The transfected cells were selected for their ability to grow in glutamine-free medium in the presence of MSX.

This example illustrates the cloning steps of the variable domains of the humanized anti-LPA monoclonal antibody into the double gene vector IgG1κ of the Lonza Biologic's GS gene expression system to generate pATH3015.

Vectors

The humanized genes were cloned into the Lonza Biologics GS gene expression system consisting of the GS expression pCON vector with human antibody constant regions. The constant region genes of the pCON vectors were isolated from genomic DNA of human peripheral blood cells.

pCONgamma1f: Heavy chain vector containing IgG1f constant region pCONkappa2: Light chain vector containing the constant region Construction of Single-Gene Vectors The humanized variable regions were assembled by synthetic oligonucleotides and/or PCR products. Assembled products contained the restriction sites for subcloning into pCONgammaf1 for the heavy chain or pCONkappa2 for the light chain and included a kozak and signal peptide sequences.

The heavy chain variable region was cloned into pCR4Blunt-TOPO using blunt and blunt restriction sites. The plasmid DNA was purified with Pure Yield Plasmid Midiprep (Promega) from transformed bacteria. The final construct was verified by sequencing which found 100% sequence match within the used restriction sites. The heavy chain fragment was then subcloned into pCONgamma1f using HindIII and ApaI restriction sites. The plasmid DNA was purified with Pure Yield Plasmid Midiprep (Promega) from transformed bacteria. The final construct was verified by sequencing which found 100% sequence match within the used restriction sites.

The light chain variable region was cloned into pCR4Blunt-TOPO using blunt and blunt restriction sites. The plasmid DNA was purified with Pure Yield Plasmid Midiprep (Promega) from transformed bacteria. The final construct was verified by sequencing which found 100% sequence match within the used restriction sites. The light chain fragment was then subcloned into pCONkappa2 using HindIII and BsiWI restriction sites. The plasmid DNA was purified with Pure Yield Plasmid Midiprep (Promega) from transformed bacteria. The final construct was verified by sequencing which found 100% sequence match within the used restriction sites.

Signal Peptide Design

To direct the protein towards the secretory pathway, a signal sequence was introduced immediately upstream and in frame with the variable region of both the light and heavy chains. The signal peptide sequences used were the ones recommended by Lonza Biologics and are from the murine monoclonal antibody B72.3:

```
Heavy Chain Leader - IgG
                                           (SEQ ID NO: 49)
ATG GAA TGG AGC TGG GTG TTC CTG TTC TTT CTG TCC

GTG ACC ACA GGC GTG CAT TCT

Light Chain Leader - kappa
                                           (SEQ ID NO: 48)
ATG TCT GTG CCT ACC CAG GTG CTG GGA CTG CTG CTG

CTG TGG CTG ACA GAC GCC CGC TGT
```

Construction of Double-Gene Vectors

The two single-gene vectors containing the full length heavy chain gene sequence and the full length light chain gene sequence were combined into one single vector carrying the GS selectable marker. Each antibody gene in the double-gene vector is under control of separate hCMV-MIE (human cytomegalovirus major immediate early) promoter and has its own polyadenylation signal.

Cloning

The single-gene vectors were digested with the restriction enzymes NotI and SalI releasing the heavy chain expression cassette from pCONgamma and opening the light chain vector, pCONkappa, which contains the light chain genes along with the GS selection marker. De-phosphorylation of the digested vector pCONkappa was performed to reduce background "vector-only" colonies. Digested products were run on an agarose gel and bands of interest were cut out of the gel and cleaned using Bio101 GeneClean kit. For ligation, high efficiency ligase was used (Roche Rapid DNA Ligation Kit). To obtain recombinant plasmid from ligation reactions, transformations were performed using high efficiency *E. coli* from Invitrogen (One Shot TOP10 Chemically Competent Cells).

Analysis of Double-Gene Vector Transformants

Bacterial colonies which contained successful ligations were identified by growth of the bacterial colonies, DNA extraction using Qiagen Miniprep Spin Kit, restriction enzyme digestion with appropriate enzymes, and run on an agarose gel to visually identify positive recombinants by the size of the insert and vector products. Restriction enzyme HindIII was used to screen for positive restriction digests to ensure both heavy and light chain regions were present in the final construct. Sequencing was performed on all positive clones.

Molecular Biology Protocols

Restriction Digest

Restriction digests were performed on DNA to prepare fragment for ligation or for cloning verification prior to checking the molecular sequence. All restriction enzymes were purchased from Invitrogen or New England Biolabs which come with the corresponding buffers required for each enzyme.

Procedure:

1 DNA (usually 5-10 μL to check for positive clones and 20-26 μL for DNA to be ligated).

2 3 μL 10× enzyme buffer 3 0.5 to 1.0 μL enzyme

4 Sterile water (to a total of 30 μL reaction volume)

5 Reactions were incubated at correct temperature for the enzyme for 1 hour. Most enzymes were active at 37° C.

however the incubation temperature could vary from room temperature to 55° C. depending on the enzymes. The restriction enzymes used for the cloning of pATH3015 were: NotI (Invitrogen 15441-025, using buffer React 3 at 37° incubation temperature); SalI (Invitrogen 15217-011, using buffer React 10 at 37° incubation temperature), PvuI ((Invitrogen 25420-118, using buffer React 7 at 37° incubation temperature) and a combination of NotI/SalI using buffer React 10 at 37° incubation temperature.

Ligation

Ligations were performed using Roche Rapid Ligation Kit (cat. no 11635379001) that included T4 DNA 2× Ligation buffer, 5×DNA dilution buffer, and T4 DNA ligase.

Procedure:

After adequate restriction enzyme digest, the GeneClean kit was used to clean the insert fragment and vector from agarose gel and any enzymes and buffers. Inserts and vectors were ligated in a final 3:1 molar ratio for best results. Insert fragments were diluted appropriately for efficient ligations.

Ligation Reaction:

Volume ratios of inset to vector varied depending on dilutions of DNA. Typically a final 3:1 insert to vector molar ratio was used.

Standard Ligation Reaction:

1 X μL insert (3:1 insert to vector molar ratio).
2 X μL vector (3:1 insert to vector molar ratio).
3 Volume was brought up to 10 μL with 1× dilution buffer.
4 10 μL 2× ligation buffer was added.
5 1 μL T4 DNA ligase was added.
6 The reaction was incubated at room temperature for 5 minutes.
7 Transform 5 to 7 μL into *E. coli* TOP10 chemically competent cells.

Purification of DNA

The plasmid DNA was prepared using Qiagen Miniprep Kit (Qiagen, cat. no 27106) according to the manufacturer's protocol.

Procedure for the Purification of Small Bacterial Cultures for Screening Recombinants (Plasmid Purification with Qiagen Miniprep Kit (Qiagen, cat. no 27106))

1 Harvest bacterial cells by centrifugation in epi tubes at 13.2 k rpm in microcentrifuge for 30 seconds.
2 Resuspend the bacterial pellet in 0.25 mL buffer P1 (resuspension buffer with RNase A at 100 μg/mL).
3 Add 0.25 mL buffer P2 (lysis buffer), mix by inverting tube 4-6 times.
4 Add 0.35 mL buffer N3 (neutralization buffer) to the lysate and mix immediately by inverting vigorously 4-6 times.
5 Centrifuge tubes at 13.2 k rpm in microcentrifuge for 10 minutes.
6 Pour supernatant into QIAprep spin column and centrifuge 13.2 k rpm 30 seconds to bind DNA to the column.
7 Discard flow-through.
8 Wash the QIAprep spin column with 0.5 mL buffer PB and centrifuge 30 seconds. Discard flow-through.
9 Wash QIAprep spin column with 0.75 mL buffer PE and centrifuge 30 seconds. Discard flow-through and centrifuge for an additional 1 minute.
10 Place the QIAprep spin column into a clean 1.5 mL microcentrifuge tube. Add 50 μL UltraPure DNase/RNase free water (Gibco, cat. no 10977-015) to each spin column and let stand 1 minute.
11 Centrifuge 1 minute to elute DNA.

Procedure for the Large Scale DNA Purification of Final Double-Gene Vector for Stable Cell Transfection (Plasmid Purification with EndoFree Plasmid Purification Kit from Qiagen, cat. no 12362)

1 Harvest bacterial cells by centrifugation at 6000×g for 15 minutes at 4° C.
2 Resuspend the bacterial pellet in 10 mL buffer P1 (resuspension buffer with RNase A at 100 μg/mL and LyseBlue added at 1/1000 dilution).
3 Add 10 mL buffer P2 (lysis buffer), mix by inverting tube 4-6 times and incubate at room temperature for 5 minutes.
4 Place the QIAfilter cartridge, with a cap on the outlet nozzle, into a 50 mL conical tube.
5 Add 10 mL chilled buffer P3 (neutralization buffer) to the lysate and mix immediately by inverting vigorously 4-6 times.
6 Pour the lysate into the barrel of the QIAfilter cartridge and incubate at room temperature for 10 minutes.
7 Remove the cap from the QIAfilter cartridge outlet nozzle. Gently insert the plunger into the QIAfilter cartridge and filter the cell lysate into a 50 mL conical tube.
8 Add 2.5 mL buffer ER (endotoxin removal buffer), mix by inverting the tube 10 times and incubate on ice for 30 minutes. Buffer ER prevents LPS molecules from binding to the resin in the QIAGEN-tips allowing purification of DNA containing less than 0.1 endotoxin units per ug DNA.
9 Equilibrate a QIAGEN-tip 500 by applying 10 mL buffer QBT (equilibration buffer) and allow the column to empty by gravity flow.
10 Apply the filtered lysate to the QIAGEN-tip and allow it to enter the resin by gravity flow.
11 Wash the QIAGEN-tip with 2×30 mL buffer QC (wash buffer).
12 Elute DNA with 15 mL buffer QN (elution buffer).
13 Precipitate DNA by adding 10.5 mL room temperature isopropanol to the eluted DNA. Mix and centrifuge immediately at 14000×g for 30 minutes at 4° C. Carefully decant the supernatant.
14 Wash DNA pellet with 5 mL endotoxin-free room-temperature 70% ethanol and centrifuge at 14000×g for 10 minutes. Carefully decant the supernatant without disturbing the pellet.
15 Air-dry the pellet for 10-20 minutes.
16 Resuspend the DNA pellet in 100 μL UltraPure DNase/RNase free water (Gibco, cat. no 10977-015).

Linearization of DNA

Prior to transfection by electroporation, the double-gene vector pATH3015 was linearized with Pvu I.

Procedure:

1 Digest should contain 0.5 mg of DNA in 750 μL final volume.
2 Add 75 μL 10× restriction enzyme buffer, 50 units of Pvu I and sterile water to a final volume of 750 μL.
3 Digest the DNA overnight at 37° C.

Clean Linearized DNA

Proteins were removed from the digest by standard phenol-chloroform extraction. The aqueous and non-aqueous phases were separated using Phase Lock Gel by Eppendorf (cat. no E0032005250).

Procedure:

1 Centrifuge Phase-Lock gel conicals at 1500 rpm for 1 minute to pellet gel.
2 Add sample to the Phase-Lock gel.
3 Add equal volume Phenol/Chloroform/Isoamyl alcohol (25:24:1), mix well, without vortexing.
4 Centrifuge Phase-Lock gels at 1500 rpm for 5 minutes to separate aqueous and non-aqueous phases.

5 Add equal aqueous phase volume of chloroform and mix well without vortexing.

6 Centrifuge Phase-Lock gels at 1500 rpm for 5 minutes to separate aqueous and non-aqueous phases.

7 Remove aqueous phase into an Eppendorf tubes for ethanol precipitation.

Evaluation of pATH3015 for Expression Linearized DNA

The plasmid pATH3015 linearized (a) or uncut (b) was transfected into the human embryonic kidney cell line 293F using 293 fectin and using 293F-FreeStyle Media for culture. Transfections were performed at a cell density of $10^6$ cells/mL with 0.5 μg/mL. Supernatants were collected by centrifugation at 1100 rpm for 5 minutes at 25° C. 3 days after transfection. The expression level was quantified by quantitative ELISA and the binding was measured in a binding ELISA. The linearized and the uncut pATH3015 vector demonstrated expression and binding to LPA in mammalian cells.

The variable domains of the humanized anti-LPA monoclonal antibody were cloned into the Lonza Biologics GS gene expression system to generate the vector pATH3015. The vector is of the isotype IgG1K and allotype f. This expression system consists of an expression vector carrying the constant domains of the light chain and the heavy chain antibody genes and the selectable marker Glutamine synthetase (GS). GS is the enzyme responsible for the biosynthesis of glutamine from glutamate and ammonia. The vector carrying both the antibody genes and the selectable marker is then transfected into the Chinese Hamster Ovary (CHOK1 SV) cell line providing sufficient glutamine for the cells to survive without exogenous glutamine. In addition, the cell line is adapted to grow in serum-free medium.

The variable regions of the humanized anti-LPA monoclonal antibody were amplified by PCR from the original vectors and include a consensus Kozak sequence at the 5' end. The PCR fragments were then ligated into the corresponding pCon vectors creating single gene vector clones. After sequence verification and testing of expression and binding to LPA by transient expression, the expression cassette containing the heavy chain variable domain and its corresponding constant domain was cloned as a Not I-Sal I fragment into the light chain single gene vector generating the doubling gene vector pATH3015. After sequencing the vector to ensure that the cloning did not alter the DNA sequence, pATH3015 was linearized with a unique cutter-Pvu I in the β-lactamase gene. This vector was then tested by transient transfection and it was observed that the cloning had not disrupted the expected binding of the antibody protein LT3015 to LPA.

pATH3015 was introduced by electroporation into the Lonza proprietary Chinese Hamster Ovary (CHOK1SV) host cell line adapted for growth in serum-free medium. The cell line derived from this transfection is designated LH2 and is used to produce drug substance. The expressed drug LT3015 has the following characteristics:

TABLE 62

| Characteristics of LT3015 | |
|---|---|
| Drug Substance | LT3015 |
| DNA | pATH3015 |
| Isotype | IgG1κ |
| Molecular | 6 murine back mutation in the heavy chain |
| Substitutions | 3 murine back mutations in the light chain |
| Specificity | LPA |
| Expression System | Lonza Biologics' GS gene expression system |
| Potency | in vitro and in vivo potency |

pATH3016 was produced similarly to pATH3015. As described above, the heavy chains of pATH3015 and 3016 are identical (derived from pATH602, having six backmutations), but pATH3016 light chain (derived from pATH506) contains only the single backmutation 12V. The humanized monoclonal antibody produced from pATH3016 is LT3016. Both pATH3015 and pATH3016 were deposited with the American Type Culture Collection (Manassas Va.) and have ATCC Patent Deposit Designations PTA-9219 and PTA-9220, respectively.

All of the compositions and methods described and claimed herein can be made and executed without undue experimentation in light of the present disclosure. While the compositions and methods of this invention have been described in terms of preferred embodiments, it will be apparent to those of skill in the art that variations may be applied to the compositions and methods. All such similar substitutes and modifications apparent to those skilled in the art are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications, including those to which priority or another benefit is claimed, are herein incorporated by reference to the same extent as if each individual publication was specifically and individually indicated to be incorporated by reference.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An antibody or antigen-binding antibody fragment that binds lysophosphatidic acid (LPA) under physiological conditions, wherein each immunoglobulin heavy chain variable domain comprises the amino acid sequence of SEQ ID NO: 189 and each immunoglobulin light chain variable domain comprises the amino acid sequence of SEQ ID NO: 169.

2. An antibody or antigen-binding antibody fragment according to claim 1 that is selected from the group consisting of a full-length antibody or an Fab fragment.

3. An antibody or antigen-binding antibody fragment according to claim 1 that is a monoclonal antibody or an antigen-binding antibody fragment of a humanized antibody.

4. An antibody or antigen-binding antibody fragment according to claim 1 that is a humanized antibody or an antigen-binding antibody fragment of a humanized antibody.

5. A composition comprising a pharmaceutically acceptable carrier and an antibody or antigen-binding antibody fragment according to claim 1.

* * * * *

SEQUENCE LISTING

```
<160> NUMBER OF SEQ ID NOS: 189

<210> SEQ ID NO 1
<211> LENGTH: 27
<212> TYPE: DNA
<213> ORGANISM: artificial
```

<220> FEATURE:
<223> OTHER INFORMATION: primer

<400> SEQUENCE: 1
atgaaatgca gctggggcat sttcttc 27

<210> SEQ ID NO 2
<211> LENGTH: 26
<212> TYPE: DNA
<213> ORGANISM: artificial
<220> FEATURE:
<223> OTHER INFORMATION: primer

<400> SEQUENCE: 2
atgggatgga gctrtatcat sytctt 26

<210> SEQ ID NO 3
<211> LENGTH: 27
<212> TYPE: DNA
<213> ORGANISM: artificial
<220> FEATURE:
<223> OTHER INFORMATION: primer

<400> SEQUENCE: 3
atgaagwtgt ggttaaactg ggttttt 27

<210> SEQ ID NO 4
<211> LENGTH: 25
<212> TYPE: DNA
<213> ORGANISM: artificial
<220> FEATURE:
<223> OTHER INFORMATION: primer

<400> SEQUENCE: 4
atgractttg ggytcagctt grttt 25

<210> SEQ ID NO 5
<211> LENGTH: 30
<212> TYPE: DNA
<213> ORGANISM: artificial
<220> FEATURE:
<223> OTHER INFORMATION: primer

<400> SEQUENCE: 5
atggactcca ggctcaattt agttttcctt 30

<210> SEQ ID NO 6
<211> LENGTH: 27
<212> TYPE: DNA
<213> ORGANISM: artificial
<220> FEATURE:
<223> OTHER INFORMATION: primer

<400> SEQUENCE: 6
atggctgtcy trgsgctrct cttctgc 27

<210> SEQ ID NO 7
<211> LENGTH: 26
<212> TYPE: DNA
<213> ORGANISM: artificial
<220> FEATURE:
<223> OTHER INFORMATION: primer

<400> SEQUENCE: 7
atggratgga gckggrtctt tmtctt 26

-continued

<210> SEQ ID NO 8
<211> LENGTH: 23
<212> TYPE: DNA
<213> ORGANISM: artificial
<220> FEATURE:
<223> OTHER INFORMATION: primer

<400> SEQUENCE: 8
atgagagtgc tgattctttt gtg 23

<210> SEQ ID NO 9
<211> LENGTH: 30
<212> TYPE: DNA
<213> ORGANISM: artificial
<220> FEATURE:
<223> OTHER INFORMATION: primer

<400> SEQUENCE: 9
atggmttggg tgtggamctt gctattcctg 30

<210> SEQ ID NO 10
<211> LENGTH: 27
<212> TYPE: DNA
<213> ORGANISM: artificial
<220> FEATURE:
<223> OTHER INFORMATION: primer

<400> SEQUENCE: 10
atgggcagac ttacattctc attcctg 27

<210> SEQ ID NO 11
<211> LENGTH: 28
<212> TYPE: DNA
<213> ORGANISM: artificial
<220> FEATURE:
<223> OTHER INFORMATION: primer

<400> SEQUENCE: 11
atggattttg ggctgatttt ttttattg 28

<210> SEQ ID NO 12
<211> LENGTH: 27
<212> TYPE: DNA
<213> ORGANISM: artificial
<220> FEATURE:
<223> OTHER INFORMATION: primer

<400> SEQUENCE: 12
atgatggtgt taagtcttct gtacctg 27

<210> SEQ ID NO 13
<211> LENGTH: 35
<212> TYPE: DNA
<213> ORGANISM: artificial
<220> FEATURE:
<223> OTHER INFORMATION: primer

<400> SEQUENCE: 13
atatccacca tggratgsag ctgkgtmats ctctt 35

<210> SEQ ID NO 14
<211> LENGTH: 21
<212> TYPE: DNA
<213> ORGANISM: artificial
<220> FEATURE:
<223> OTHER INFORMATION: primer

<400> SEQUENCE: 14
cagtggatag acagatgggg g 21

<210> SEQ ID NO 15
<211> LENGTH: 21
<212> TYPE: DNA
<213> ORGANISM: artificial
<220> FEATURE:
<223> OTHER INFORMATION: primer

<400> SEQUENCE: 15
cagtggatag accgatgggg c 21

<210> SEQ ID NO 16
<211> LENGTH: 21
<212> TYPE: DNA
<213> ORGANISM: artificial
<220> FEATURE:
<223> OTHER INFORMATION: primer

<400> SEQUENCE: 16
cagtggatag actgatgggg g 21

<210> SEQ ID NO 17
<211> LENGTH: 21
<212> TYPE: DNA
<213> ORGANISM: artificial
<220> FEATURE:
<223> OTHER INFORMATION: primer

<400> SEQUENCE: 17
caagggatag acagatgggg c 21

<210> SEQ ID NO 18
<211> LENGTH: 27
<212> TYPE: DNA
<213> ORGANISM: artificial
<220> FEATURE:
<223> OTHER INFORMATION: primer

<400> SEQUENCE: 18
ggcagcacta gtaggggcca gtggata 27

<210> SEQ ID NO 19
<211> LENGTH: 32
<212> TYPE: DNA
<213> ORGANISM: artificial
<220> FEATURE:
<223> OTHER INFORMATION: primer

<400> SEQUENCE: 19
gggcaccatg gagacagaca cactcctgct at 32

<210> SEQ ID NO 20
<211> LENGTH: 33
<212> TYPE: DNA
<213> ORGANISM: artificial
<220> FEATURE:
<223> OTHER INFORMATION: primer

<400> SEQUENCE: 20
gggcaccatg gattttcaag tgcagatttt cag 33

<210> SEQ ID NO 21
<211> LENGTH: 34
<212> TYPE: DNA
<213> ORGANISM: artificial

<220> FEATURE:
<223> OTHER INFORMATION: primer

<400> SEQUENCE: 21
gggcaccatg gagwcacakw ctcaggtctt trta 34

<210> SEQ ID NO 22
<211> LENGTH: 30
<212> TYPE: DNA
<213> ORGANISM: artificial
<220> FEATURE:
<223> OTHER INFORMATION: primer

<400> SEQUENCE: 22
gggcaccatg kccccwrctc agytyctkgt 30

<210> SEQ ID NO 23
<211> LENGTH: 28
<212> TYPE: DNA
<213> ORGANISM: artificial
<220> FEATURE:
<223> OTHER INFORMATION: primer

<400> SEQUENCE: 23
caccatgaag ttgcctgtta ggctgttg 28

<210> SEQ ID NO 24
<211> LENGTH: 30
<212> TYPE: DNA
<213> ORGANISM: artificial
<220> FEATURE:
<223> OTHER INFORMATION: primer

<400> SEQUENCE: 24
atgaagttgv vtgttaggct gttggtgctg 30

<210> SEQ ID NO 25
<211> LENGTH: 30
<212> TYPE: DNA
<213> ORGANISM: artificial
<220> FEATURE:
<223> OTHER INFORMATION: primer

<400> SEQUENCE: 25
atggagwcag acacactcct gytatgggtg 30

<210> SEQ ID NO 26
<211> LENGTH: 30
<212> TYPE: DNA
<213> ORGANISM: artificial
<220> FEATURE:
<223> OTHER INFORMATION: primer

<400> SEQUENCE: 26
atgagtgtgc tcactcaggt cctggsgttg 30

<210> SEQ ID NO 27
<211> LENGTH: 33
<212> TYPE: DNA
<213> ORGANISM: artificial
<220> FEATURE:
<223> OTHER INFORMATION: primer

<400> SEQUENCE: 27
atgaggrccc ctgctcagwt tyttggmwtc ttg 33

<210> SEQ ID NO 28
<211> LENGTH: 29
<212> TYPE: DNA
<213> ORGANISM: artificial
<220> FEATURE:
<223> OTHER INFORMATION: primer

<400> SEQUENCE: 28
atggatttwa ggtgcagatt wtcagcttc 29

<210> SEQ ID NO 29
<211> LENGTH: 27
<212> TYPE: DNA
<213> ORGANISM: artificial
<220> FEATURE:
<223> OTHER INFORMATION: primer

<400> SEQUENCE: 29
atgaggtkck ktgktsagst sctgrgg 27

<210> SEQ ID NO 30
<211> LENGTH: 31
<212> TYPE: DNA
<213> ORGANISM: artificial
<220> FEATURE:
<223> OTHER INFORMATION: primer

<400> SEQUENCE: 30
atgggcwtca agatggagtc acakwyycwg g 31

<210> SEQ ID NO 31
<211> LENGTH: 31
<212> TYPE: DNA
<213> ORGANISM: artificial
<220> FEATURE:
<223> OTHER INFORMATION: primer

<400> SEQUENCE: 31
atgtggggay ctktttycmm tttttcaatt g 31

<210> SEQ ID NO 32
<211> LENGTH: 25
<212> TYPE: DNA
<213> ORGANISM: artificial
<220> FEATURE:
<223> OTHER INFORMATION: primer

<400> SEQUENCE: 32
atggtrtccw casctcagtt ccttg 25

<210> SEQ ID NO 33
<211> LENGTH: 27
<212> TYPE: DNA
<213> ORGANISM: artificial
<220> FEATURE:
<223> OTHER INFORMATION: primer

<400> SEQUENCE: 33
atgtatatat gtttgttgtc tatttct 27

<210> SEQ ID NO 34
<211> LENGTH: 28
<212> TYPE: DNA
<213> ORGANISM: artificial
<220> FEATURE:
<223> OTHER INFORMATION: primer

<400> SEQUENCE: 34
atggaagccc cagctcagct tctcttcc 28

<210> SEQ ID NO 35
<211> LENGTH: 19
<212> TYPE: DNA
<213> ORGANISM: artificial
<220> FEATURE:
<223> OTHER INFORMATION: primer

<400> SEQUENCE: 35
tgggtatctg gtrcstgtg 19

<210> SEQ ID NO 36
<211> LENGTH: 21
<212> TYPE: DNA
<213> ORGANISM: artificial
<220> FEATURE:
<223> OTHER INFORMATION: primer

<400> SEQUENCE: 36
atggagwcag acacactsct g 21

<210> SEQ ID NO 37
<211> LENGTH: 26
<212> TYPE: DNA
<213> ORGANISM: artificial
<220> FEATURE:
<223> OTHER INFORMATION: primer

<400> SEQUENCE: 37
atgragtywc agacccaggt cttyrt 26

<210> SEQ ID NO 38
<211> LENGTH: 26
<212> TYPE: DNA
<213> ORGANISM: artificial
<220> FEATURE:
<223> OTHER INFORMATION: primer

<400> SEQUENCE: 38
atggagacac attctcaggt ctttgt 26

<210> SEQ ID NO 39
<211> LENGTH: 26
<212> TYPE: DNA
<213> ORGANISM: artificial
<220> FEATURE:
<223> OTHER INFORMATION: primer

<400> SEQUENCE: 39
atggattcac aggcccaggt tcttat 26

<210> SEQ ID NO 40
<211> LENGTH: 26
<212> TYPE: DNA
<213> ORGANISM: artificial
<220> FEATURE:
<223> OTHER INFORMATION: primer

<400> SEQUENCE: 40
atgatgagtc ctgcccagtt cctctt 26

<210> SEQ ID NO 41
<211> LENGTH: 29
<212> TYPE: DNA
<213> ORGANISM: artificial

<220> FEATURE:
<223> OTHER INFORMATION: primer

<400> SEQUENCE: 41
atgaatttgc ctgttcatct cttggtgct 29

<210> SEQ ID NO 42
<211> LENGTH: 29
<212> TYPE: DNA
<213> ORGANISM: artificial
<220> FEATURE:
<223> OTHER INFORMATION: primer

<400> SEQUENCE: 42
atggattttc aattggtcct catctcctt 29

<210> SEQ ID NO 43
<211> LENGTH: 26
<212> TYPE: DNA
<213> ORGANISM: artificial
<220> FEATURE:
<223> OTHER INFORMATION: primer

<400> SEQUENCE: 43
atgaggtgcc tarctsagtt cctgrg 26

<210> SEQ ID NO 44
<211> LENGTH: 26
<212> TYPE: DNA
<213> ORGANISM: artificial
<220> FEATURE:
<223> OTHER INFORMATION: primer

<400> SEQUENCE: 44
atgaagtact ctgctcagtt tctagg 26

<210> SEQ ID NO 45
<211> LENGTH: 26
<212> TYPE: DNA
<213> ORGANISM: artificial
<220> FEATURE:
<223> OTHER INFORMATION: primer

<400> SEQUENCE: 45
atgaggcatt ctcttcaatt cttggg 26

<210> SEQ ID NO 46
<211> LENGTH: 20
<212> TYPE: DNA
<213> ORGANISM: artificial
<220> FEATURE:
<223> OTHER INFORMATION: primer

<400> SEQUENCE: 46
actggatggt gggaagatgg 20

<210> SEQ ID NO 47
<211> LENGTH: 30
<212> TYPE: DNA
<213> ORGANISM: artificial
<220> FEATURE:
<223> OTHER INFORMATION: primer

<400> SEQUENCE: 47
gaagatctag acttactatg cagcatcagc 30

-continued

<210> SEQ ID NO 48
<211> LENGTH: 60
<212> TYPE: DNA
<213> ORGANISM: artificial
<220> FEATURE:
<223> OTHER INFORMATION: leader

<400> SEQUENCE: 48
atgtctgtgc ctacccaggt gctgggactg ctgctgctgt ggctgacaga cgcccgctgt 60

<210> SEQ ID NO 49
<211> LENGTH: 57
<212> TYPE: DNA
<213> ORGANISM: artificial
<220> FEATURE:
<223> OTHER INFORMATION: leader

<400> SEQUENCE: 49
atggaatgga gctgggtgtt cctgttcttt ctgtccgtga ccacaggcgt gcattct 57

<210> SEQ ID NO 50
<211> LENGTH: 30
<212> TYPE: DNA
<213> ORGANISM: Mus musculus

<400> SEQUENCE: 50
ggagacgcct tcacaaatta cttaatagag 30

<210> SEQ ID NO 51
<211> LENGTH: 51
<212> TYPE: DNA
<213> ORGANISM: Mus musculus

<400> SEQUENCE: 51
ctgatttatc ctgatagtgg ttacattaac tacaatgaga acttcaaggg c 51

<210> SEQ ID NO 52
<211> LENGTH: 39
<212> TYPE: DNA
<213> ORGANISM: Mus musculus

<400> SEQUENCE: 52
agatttgctt actacggtag tggctactac tttgactac 39

<210> SEQ ID NO 53
<211> LENGTH: 48
<212> TYPE: DNA
<213> ORGANISM: Mus musculus

<400> SEQUENCE: 53
agatctagtc agagccttct aaaaactaat ggaaacacct atttacat 48

<210> SEQ ID NO 54
<211> LENGTH: 21
<212> TYPE: DNA
<213> ORGANISM: Mus musculus

<400> SEQUENCE: 54
aaagtttcca accgattttc t 21

<210> SEQ ID NO 55
<211> LENGTH: 27
<212> TYPE: DNA
<213> ORGANISM: Mus musculus

<400> SEQUENCE: 55

```
tctcaaagta cacattttcc attcacg                                       27


<210> SEQ ID NO 56
<211> LENGTH: 10
<212> TYPE: PRT
<213> ORGANISM: Mus musculus

<400> SEQUENCE: 56

Gly Asp Ala Phe Thr Asn Tyr Leu Ile Glu
1               5                   10


<210> SEQ ID NO 57
<211> LENGTH: 17
<212> TYPE: PRT
<213> ORGANISM: Mus musculus

<400> SEQUENCE: 57

Leu Ile Tyr Pro Asp Ser Gly Tyr Ile Asn Tyr Asn Glu Asn Phe Lys
1               5                   10                  15

Gly


<210> SEQ ID NO 58
<211> LENGTH: 13
<212> TYPE: PRT
<213> ORGANISM: Mus musculus

<400> SEQUENCE: 58

Arg Phe Ala Tyr Tyr Gly Ser Gly Tyr Tyr Phe Asp Tyr
1               5                   10


<210> SEQ ID NO 59
<211> LENGTH: 16
<212> TYPE: PRT
<213> ORGANISM: Mus musculus

<400> SEQUENCE: 59

Arg Ser Ser Gln Ser Leu Leu Lys Thr Asn Gly Asn Thr Tyr Leu His
1               5                   10                  15


<210> SEQ ID NO 60
<211> LENGTH: 7
<212> TYPE: PRT
<213> ORGANISM: Mus musculus

<400> SEQUENCE: 60

Lys Val Ser Asn Arg Phe Ser
1               5


<210> SEQ ID NO 61
<211> LENGTH: 9
<212> TYPE: PRT
<213> ORGANISM: Mus musculus

<400> SEQUENCE: 61

Ser Gln Ser Thr His Phe Pro Phe Thr
1               5


<210> SEQ ID NO 62
<211> LENGTH: 5
<212> TYPE: PRT
<213> ORGANISM: Mus musculus

<400> SEQUENCE: 62

Asn Tyr Leu Ile Glu
```

-continued 1 5

<210> SEQ ID NO 63
<211> LENGTH: 30
<212> TYPE: DNA
<213> ORGANISM: Mus musculus

<400> SEQUENCE: 63
ggatacggct tcattaatta cttaatagag 30

<210> SEQ ID NO 64
<211> LENGTH: 51
<212> TYPE: DNA
<213> ORGANISM: Mus musculus

<400> SEQUENCE: 64
ctgattaatc ctggaagtga ttatactaac tacaatgaga acttcaaggg c 51

<210> SEQ ID NO 65
<211> LENGTH: 39
<212> TYPE: DNA
<213> ORGANISM: Mus musculus

<400> SEQUENCE: 65
agatttggtt actacggtag cggcaactac tttgactac 39

<210> SEQ ID NO 66
<211> LENGTH: 48
<212> TYPE: DNA
<213> ORGANISM: Mus musculus

<400> SEQUENCE: 66
acatctggtc agagccttgt ccacattaat ggaaacacct atttacat 48

<210> SEQ ID NO 67
<211> LENGTH: 21
<212> TYPE: DNA
<213> ORGANISM: Mus musculus

<400> SEQUENCE: 67
aaagtttcca acctattttc t 21

<210> SEQ ID NO 68
<211> LENGTH: 27
<212> TYPE: DNA
<213> ORGANISM: Mus musculus

<400> SEQUENCE: 68
tctcaaagta cacattttcc attcacg 27

<210> SEQ ID NO 69
<211> LENGTH: 10
<212> TYPE: PRT
<213> ORGANISM: Mus musculus

<400> SEQUENCE: 69

Gly Tyr Gly Phe Ile Asn Tyr Leu Ile Glu
1 5 10

<210> SEQ ID NO 70
<211> LENGTH: 17
<212> TYPE: PRT
<213> ORGANISM: Mus musculus

<400> SEQUENCE: 70

Leu Ile Asn Pro Gly Ser Asp Tyr Thr Asn Tyr Asn Glu Asn Phe Lys
1 5 10 15

Gly

<210> SEQ ID NO 71
<211> LENGTH: 13
<212> TYPE: PRT
<213> ORGANISM: Mus musculus

<400> SEQUENCE: 71

Arg Phe Gly Tyr Tyr Gly Ser Gly Asn Tyr Phe Asp Tyr
1 5 10

<210> SEQ ID NO 72
<211> LENGTH: 16
<212> TYPE: PRT
<213> ORGANISM: Mus musculus

<400> SEQUENCE: 72

Thr Ser Gly Gln Ser Leu Val His Ile Asn Gly Asn Thr Tyr Leu His
1 5 10 15

<210> SEQ ID NO 73
<211> LENGTH: 7
<212> TYPE: PRT
<213> ORGANISM: Mus musculus

<400> SEQUENCE: 73

Lys Val Ser Asn Leu Phe Ser
1 5

<210> SEQ ID NO 74
<211> LENGTH: 9
<212> TYPE: PRT
<213> ORGANISM: Mus musculus

<400> SEQUENCE: 74

Ser Gln Ser Thr His Phe Pro Phe Thr
1 5

<210> SEQ ID NO 75
<211> LENGTH: 30
<212> TYPE: DNA
<213> ORGANISM: Mus musculus

<400> SEQUENCE: 75
ggagacgcct tcactaatta cttgatcgag 30

<210> SEQ ID NO 76
<211> LENGTH: 51
<212> TYPE: DNA
<213> ORGANISM: Mus musculus

<400> SEQUENCE: 76
ctgattattc ctggaactgg ttatactaac tacaatgaga acttcaaggg c 51

<210> SEQ ID NO 77
<211> LENGTH: 39
<212> TYPE: DNA
<213> ORGANISM: Mus musculus

<400> SEQUENCE: 77
agatttggtt actacggtag tagcaactac tttgactac 39

<210> SEQ ID NO 78
<211> LENGTH: 48
<212> TYPE: DNA
<213> ORGANISM: Mus musculus

<400> SEQUENCE: 78
agatctagtc agagccttgt acacagtaat ggaaacacct atttacat 48

<210> SEQ ID NO 79
<211> LENGTH: 21
<212> TYPE: DNA
<213> ORGANISM: Mus musculus

<400> SEQUENCE: 79
aaagtttcca accgattttc t 21

<210> SEQ ID NO 80
<211> LENGTH: 27
<212> TYPE: DNA
<213> ORGANISM: Mus musculus

<400> SEQUENCE: 80
tctcaaagta cacattttcc attcact 27

<210> SEQ ID NO 81
<211> LENGTH: 10
<212> TYPE: PRT
<213> ORGANISM: Mus musculus

<400> SEQUENCE: 81

Gly Asp Ala Phe Thr Asn Tyr Leu Ile Glu
1 5 10

<210> SEQ ID NO 82
<211> LENGTH: 17
<212> TYPE: PRT
<213> ORGANISM: Mus musculus

<400> SEQUENCE: 82

Leu Ile Ile Pro Gly Thr Gly Tyr Thr Asn Tyr Asn Glu Asn Phe Lys
1 5 10 15

Gly

<210> SEQ ID NO 83
<211> LENGTH: 13
<212> TYPE: PRT
<213> ORGANISM: Mus musculus

<400> SEQUENCE: 83

Arg Phe Gly Tyr Tyr Gly Ser Ser Asn Tyr Phe Asp Tyr
1 5 10

<210> SEQ ID NO 84
<211> LENGTH: 16
<212> TYPE: PRT
<213> ORGANISM: Mus musculus

<400> SEQUENCE: 84

Arg Ser Ser Gln Ser Leu Val His Ser Asn Gly Asn Thr Tyr Leu His
1 5 10 15

<210> SEQ ID NO 85
<211> LENGTH: 7
<212> TYPE: PRT

<213> ORGANISM: Mus musculus

<400> SEQUENCE: 85

Lys Val Ser Asn Arg Phe Ser
1               5

<210> SEQ ID NO 86
<211> LENGTH: 9
<212> TYPE: PRT
<213> ORGANISM: Mus musculus

<400> SEQUENCE: 86

Ser Gln Ser Thr His Phe Pro Phe Thr
1               5

<210> SEQ ID NO 87
<211> LENGTH: 30
<212> TYPE: DNA
<213> ORGANISM: Mus musculus

<400> SEQUENCE: 87
ggagacgcct tcactaatta cttgatcgag 30

<210> SEQ ID NO 88
<211> LENGTH: 51
<212> TYPE: DNA
<213> ORGANISM: Mus musculus

<400> SEQUENCE: 88
ctgattattc ctggaactgg ttatactaac tacaatgaga acttcaaggg c 51

<210> SEQ ID NO 89
<211> LENGTH: 39
<212> TYPE: DNA
<213> ORGANISM: Mus musculus

<400> SEQUENCE: 89
agatttggtt actacggtag tggctactac tttgactac 39

<210> SEQ ID NO 90
<211> LENGTH: 48
<212> TYPE: DNA
<213> ORGANISM: Mus musculus

<400> SEQUENCE: 90
agatctagtc agagccttgt acacagtaat ggaaacacct atttacat 48

<210> SEQ ID NO 91
<211> LENGTH: 21
<212> TYPE: DNA
<213> ORGANISM: Mus musculus

<400> SEQUENCE: 91
aaagtttcca accgattttc t 21

<210> SEQ ID NO 92
<211> LENGTH: 27
<212> TYPE: DNA
<213> ORGANISM: Mus musculus

<400> SEQUENCE: 92
tctcaaagta cacattttcc attcacg 27

<210> SEQ ID NO 93

<211> LENGTH: 10
<212> TYPE: PRT
<213> ORGANISM: Mus musculus

<400> SEQUENCE: 93

Gly Asp Ala Phe Thr Asn Tyr Leu Ile Glu
1 5 10

<210> SEQ ID NO 94
<211> LENGTH: 17
<212> TYPE: PRT
<213> ORGANISM: Mus musculus

<400> SEQUENCE: 94

Leu Ile Ile Pro Gly Thr Gly Tyr Thr Asn Tyr Asn Glu Asn Phe Lys
1 5 10 15

Gly

<210> SEQ ID NO 95
<211> LENGTH: 13
<212> TYPE: PRT
<213> ORGANISM: Mus musculus

<400> SEQUENCE: 95

Arg Phe Gly Tyr Tyr Gly Ser Gly Tyr Tyr Phe Asp Tyr
1 5 10

<210> SEQ ID NO 96
<211> LENGTH: 16
<212> TYPE: PRT
<213> ORGANISM: Mus musculus

<400> SEQUENCE: 96

Arg Ser Ser Gln Ser Leu Val His Ser Asn Gly Asn Thr Tyr Leu His
1 5 10 15

<210> SEQ ID NO 97
<211> LENGTH: 7
<212> TYPE: PRT
<213> ORGANISM: Mus musculus

<400> SEQUENCE: 97

Lys Val Ser Asn Arg Phe Ser
1 5

<210> SEQ ID NO 98
<211> LENGTH: 9
<212> TYPE: PRT
<213> ORGANISM: Mus musculus

<400> SEQUENCE: 98

Ser Gln Ser Thr His Phe Pro Phe Thr
1 5

<210> SEQ ID NO 99
<211> LENGTH: 33
<212> TYPE: DNA
<213> ORGANISM: Mus musculus

<400> SEQUENCE: 99
ggcttctcca tcaccagtgg ttattactgg acc 33

<210> SEQ ID NO 100
<211> LENGTH: 48
<212> TYPE: DNA

<213> ORGANISM: Mus musculus

<400> SEQUENCE: 100
tacataggct acgatggtag caatgactcc aacccatctc tcaaaaat 48

<210> SEQ ID NO 101
<211> LENGTH: 27
<212> TYPE: DNA
<213> ORGANISM: Mus musculus

<400> SEQUENCE: 101
gcgatgttgc ggcgaggatt tgactac 27

<210> SEQ ID NO 102
<211> LENGTH: 30
<212> TYPE: DNA
<213> ORGANISM: Mus musculus

<400> SEQUENCE: 102
agtgccagct caagtttaag ttacatgcac 30

<210> SEQ ID NO 103
<211> LENGTH: 21
<212> TYPE: DNA
<213> ORGANISM: Mus musculus

<400> SEQUENCE: 103
gacacatcca aactggcttc t 21

<210> SEQ ID NO 104
<211> LENGTH: 21
<212> TYPE: DNA
<213> ORGANISM: Mus musculus

<400> SEQUENCE: 104
catcggcgga gtagttacac g 21

<210> SEQ ID NO 105
<211> LENGTH: 11
<212> TYPE: PRT
<213> ORGANISM: Mus musculus

<400> SEQUENCE: 105

Gly Phe Ser Ile Thr Ser Gly Tyr Tyr Trp Thr
1               5                   10

<210> SEQ ID NO 106
<211> LENGTH: 16
<212> TYPE: PRT
<213> ORGANISM: Mus musculus

<400> SEQUENCE: 106

Tyr Ile Gly Tyr Asp Gly Ser Asn Asp Ser Asn Pro Ser Leu Lys Asn
1               5                   10                  15

<210> SEQ ID NO 107
<211> LENGTH: 9
<212> TYPE: PRT
<213> ORGANISM: Mus musculus

<400> SEQUENCE: 107

Ala Met Leu Arg Arg Gly Phe Asp Tyr
1               5

<210> SEQ ID NO 108
<211> LENGTH: 10
<212> TYPE: PRT
<213> ORGANISM: Mus musculus

<400> SEQUENCE: 108

Ser Ala Ser Ser Ser Leu Ser Tyr Met His
1               5                   10

<210> SEQ ID NO 109
<211> LENGTH: 7
<212> TYPE: PRT
<213> ORGANISM: Mus musculus

<400> SEQUENCE: 109

Asp Thr Ser Lys Leu Ala Ser
1               5

<210> SEQ ID NO 110
<211> LENGTH: 7
<212> TYPE: PRT
<213> ORGANISM: Mus musculus

<400> SEQUENCE: 110

His Arg Arg Ser Ser Tyr Thr
1               5

<210> SEQ ID NO 111
<211> LENGTH: 6
<212> TYPE: PRT
<213> ORGANISM: Mus musculus

<400> SEQUENCE: 111

Ser Gly Tyr Tyr Trp Thr
1               5

<210> SEQ ID NO 112
<211> LENGTH: 455
<212> TYPE: DNA
<213> ORGANISM: Mus musculus

<400> SEQUENCE: 112
aagcttgccg ccaccatgga atggagctgg gtgttcctgt tctttctgtc cgtgaccaca 60
ggcgtgcatt ctcaggtcaa gctgcagcag tctggacctg agctggtaag gcctgggact 120
tcagtgaagg tgtcctgcac ggcttctgga gacgccttca caaattactt aatagagtgg 180
gtaaaacaga ggcctggaca gggccttgag tggattggac tgatttatcc tgatagtggt 240
tacattaact acaatgagaa cttcaagggc aaggcaacac tgactgcaga cagatcctcc 300
agcactgcct acatgcagct cagcagcctg acatctgagg actctgcggt ctatttctgt 360
gcaagaagat ttgcttacta cggtagtggc tactactttg actactgggg ccaaggcacc 420
actctcacag tctcctcagc ctccaccaag ggccc 455

<210> SEQ ID NO 113
<211> LENGTH: 417
<212> TYPE: DNA
<213> ORGANISM: Mus musculus

<400> SEQUENCE: 113
aagcttgccg ccaccatgtc tgtgcctacc caggtgctgg gactgctgct gctgtggctg 60
acagacgccc gctgtgatgt tgtgatgacc caaactccac tctccctgcc tgtcagtctt 120
ggagatcaag cctccatctc ttgcagatct agtcagagcc ttctaaaaac taatggaaac 180

```
acctatttac attggtacct gcagaagcca ggccagtctc caaaactcct aatcttcaaa    240

gtttccaacc gattttctgg ggtcccggac aggttcagtg gcagtggatc agggacagac    300

ttcacactca agatcagcag agtggaggct gaggatctgg gagtttattt ctgctctcaa    360

agtacacatt ttccattcac gttcggcacg gggacaaaat tggaaataaa acgtacg       417


<210> SEQ ID NO 114
<211> LENGTH: 151
<212> TYPE: PRT
<213> ORGANISM: Mus musculus

<400> SEQUENCE: 114

Lys Leu Ala Ala Thr Met Glu Trp Ser Trp Val Phe Leu Phe Phe Leu
1               5                   10                  15

Ser Val Thr Thr Gly Val His Ser Gln Val Lys Leu Gln Gln Ser Gly
            20                  25                  30

Pro Glu Leu Val Arg Pro Gly Thr Ser Val Lys Val Ser Cys Thr Ala
        35                  40                  45

Ser Gly Asp Ala Phe Thr Asn Tyr Leu Ile Glu Trp Val Lys Gln Arg
    50                  55                  60

Pro Gly Gln Gly Leu Glu Trp Ile Gly Leu Ile Tyr Pro Asp Ser Gly
65                  70                  75                  80

Tyr Ile Asn Tyr Asn Glu Asn Phe Lys Gly Lys Ala Thr Leu Thr Ala
                85                  90                  95

Asp Arg Ser Ser Ser Thr Ala Tyr Met Gln Leu Ser Ser Leu Thr Ser
            100                 105                 110

Glu Asp Ser Ala Val Tyr Phe Cys Ala Arg Arg Phe Ala Tyr Tyr Gly
        115                 120                 125

Ser Gly Tyr Tyr Phe Asp Tyr Trp Gly Gln Gly Thr Thr Leu Thr Val
    130                 135                 140

Ser Ser Ala Ser Thr Lys Gly
145                 150


<210> SEQ ID NO 115
<211> LENGTH: 139
<212> TYPE: PRT
<213> ORGANISM: Mus musculus

<400> SEQUENCE: 115

Lys Leu Ala Ala Thr Met Ser Val Pro Thr Gln Val Leu Gly Leu Leu
1               5                   10                  15

Leu Leu Trp Leu Thr Asp Ala Arg Cys Asp Val Val Met Thr Gln Thr
            20                  25                  30

Pro Leu Ser Leu Pro Val Ser Leu Gly Asp Gln Ala Ser Ile Ser Cys
        35                  40                  45

Arg Ser Ser Gln Ser Leu Leu Lys Thr Asn Gly Asn Thr Tyr Leu His
    50                  55                  60

Trp Tyr Leu Gln Lys Pro Gly Gln Ser Pro Lys Leu Leu Ile Phe Lys
65                  70                  75                  80

Val Ser Asn Arg Phe Ser Gly Val Pro Asp Arg Phe Ser Gly Ser Gly
                85                  90                  95

Ser Gly Thr Asp Phe Thr Leu Lys Ile Ser Arg Val Glu Ala Glu Asp
            100                 105                 110

Leu Gly Val Tyr Phe Cys Ser Gln Ser Thr His Phe Pro Phe Thr Phe
        115                 120                 125

Gly Thr Gly Thr Lys Leu Glu Ile Lys Arg Thr
```

130 135

<210> SEQ ID NO 116
<211> LENGTH: 455
<212> TYPE: DNA
<213> ORGANISM: Mus musculus

<400> SEQUENCE: 116
aagcttgccg ccaccatgga atggagctgg gtgttcctgt tctttctgtc cgtgaccaca 60
ggcgtgcatt ctcaggtcca actgcagcag tctggagctg agctggtaag gcctgggact 120
tcagtgaagg tgtcctgcaa ggcttctgga tacggcttca ttaattactt aatagagtgg 180
ataaaacaga ggcctggaca gggccttgag tggattggac tgattaatcc tggaagtgat 240
tatactaact acaatgagaa cttcaagggc aaggcaacac tgactgcaga caagtcctcc 300
agcactgcct acatgcacct cagcagcctg acatctgagg actctgcggt ctatttctgt 360
gcaagaagat ttggttacta cggtagcggc aactactttg actactgggg ccaaggcacc 420
actctcacag tctcctcagc ctccaccaag ggccc 455

<210> SEQ ID NO 117
<211> LENGTH: 417
<212> TYPE: DNA
<213> ORGANISM: Mus musculus

<400> SEQUENCE: 117
aagcttgccg ccaccatgtc tgtgcctacc caggtgctgg gactgctgct gctgtggctg 60
acagacgccc gctgtgatgt tgtgatgacc caaactccac tctccctgcc tgtcagtctt 120
ggagatcaag cctccatctc ttgcacatct ggtcagagcc ttgtccacat taatggaaac 180
acctatttac attggtacct gcagaagcca ggccagtctc caaagctcct catctacaaa 240
gtttccaacc tattttctgg ggtcccagac aggttcagtg gcagtggatc agggacagat 300
ttcacactca agatcagcag agtggaggct gaggatctgg gagtttattt ctgctctcaa 360
agtacacatt ttccattcac gttcggcacg gggacaaaat tggaaataaa acgtacg 417

<210> SEQ ID NO 118
<211> LENGTH: 151
<212> TYPE: PRT
<213> ORGANISM: Mus musculus

<400> SEQUENCE: 118

Lys Leu Ala Ala Thr Met Glu Trp Ser Trp Val Phe Leu Phe Phe Leu
1 5 10 15

Ser Val Thr Thr Gly Val His Ser Gln Val Gln Leu Gln Gln Ser Gly
20 25 30

Ala Glu Leu Val Arg Pro Gly Thr Ser Val Lys Val Ser Cys Lys Ala
35 40 45

Ser Gly Tyr Gly Phe Ile Asn Tyr Leu Ile Glu Trp Ile Lys Gln Arg
50 55 60

Pro Gly Gln Gly Leu Glu Trp Ile Gly Leu Ile Asn Pro Gly Ser Asp
65 70 75 80

Tyr Thr Asn Tyr Asn Glu Asn Phe Lys Gly Lys Ala Thr Leu Thr Ala
85 90 95

Asp Lys Ser Ser Ser Thr Ala Tyr Met His Leu Ser Ser Leu Thr Ser
100 105 110

Glu Asp Ser Ala Val Tyr Phe Cys Ala Arg Arg Phe Gly Tyr Tyr Gly
115 120 125

-continued

```
Ser Gly Asn Tyr Phe Asp Tyr Trp Gly Gln Gly Thr Thr Leu Thr Val
    130                 135                 140

Ser Ser Ala Ser Thr Lys Gly
145                 150


<210> SEQ ID NO 119
<211> LENGTH: 139
<212> TYPE: PRT
<213> ORGANISM: Mus musculus

<400> SEQUENCE: 119

Lys Leu Ala Ala Thr Met Ser Val Pro Thr Gln Val Leu Gly Leu Leu
1               5                   10                  15

Leu Leu Trp Leu Thr Asp Ala Arg Cys Asp Val Val Met Thr Gln Thr
            20                  25                  30

Pro Leu Ser Leu Pro Val Ser Leu Gly Asp Gln Ala Ser Ile Ser Cys
        35                  40                  45

Thr Ser Gly Gln Ser Leu Val His Ile Asn Gly Asn Thr Tyr Leu His
    50                  55                  60

Trp Tyr Leu Gln Lys Pro Gly Gln Ser Pro Lys Leu Leu Ile Tyr Lys
65                  70                  75                  80

Val Ser Asn Leu Phe Ser Gly Val Pro Asp Arg Phe Ser Gly Ser Gly
                85                  90                  95

Ser Gly Thr Asp Phe Thr Leu Lys Ile Ser Arg Val Glu Ala Glu Asp
            100                 105                 110

Leu Gly Val Tyr Phe Cys Ser Gln Ser Thr His Phe Pro Phe Thr Phe
        115                 120                 125

Gly Thr Gly Thr Lys Leu Glu Ile Lys Arg Thr
    130                 135


<210> SEQ ID NO 120
<211> LENGTH: 455
<212> TYPE: DNA
<213> ORGANISM: Mus musculus

<400> SEQUENCE: 120

aagcttgccg ccaccatgga atggagctgg gtgttcctgt tctttctgtc cgtgaccaca      60

ggcgtgcatt ctcaggtcca gctgcagcag tctggagctg agctggtcag gcctgggact     120

tcagtgaagg tgtcctgcaa ggcttctgga gacgccttca ctaattactt gatcgagtgg     180

gtaaagcaga ggcctggaca gggccttgag tggattggac tgattattcc tggaactggt     240

tatactaact acaatgagaa cttcaagggc aaggcaacac tgactgcaga caaatcctcc     300

agcactgcct acatgcagct cagcagcctg acatctgagg actctgcggt ctatttctgt     360

gcaagaagat ttggttacta cggtagtagc aactactttg actactgggg ccaaggcacc     420

actctcacag tctcctcagc ctccaccaag ggccc                                455


<210> SEQ ID NO 121
<211> LENGTH: 417
<212> TYPE: DNA
<213> ORGANISM: Mus musculus

<400> SEQUENCE: 121

aagcttgccg ccaccatgtc tgtgcctacc caggtgctgg gactgctgct gctgtggctg      60

acagacgccc gctgtgatgt tgtgatgacc caaactccac tctccctgcc tgtcagtctt     120

ggagatcaag cctccatctc ttgcagatct agtcagagcc ttgtacacag taatggaaac     180

acctatttac attggtacct gcagaagcca ggccagtctc caaagctcct gatctacaaa     240
```

```
gtttccaacc gattttctgg ggtcccagac aggttcagtg gcagtggacc agggacagat    300

ttcacactca agatcagcag agtggaggct gaggatctgg gaatttattt ctgctctcaa    360

agtacacatt ttccattcac tttcggcacg gggacaaaat tggaaataaa acgtacg       417


<210> SEQ ID NO 122
<211> LENGTH: 151
<212> TYPE: PRT
<213> ORGANISM: Mus musculus

<400> SEQUENCE: 122

Lys Leu Ala Ala Thr Met Glu Trp Ser Trp Val Phe Leu Phe Phe Leu
1               5                   10                  15

Ser Val Thr Thr Gly Val His Ser Gln Val Gln Leu Gln Gln Ser Gly
            20                  25                  30

Ala Glu Leu Val Arg Pro Gly Thr Ser Val Lys Val Ser Cys Lys Ala
        35                  40                  45

Ser Gly Asp Ala Phe Thr Asn Tyr Leu Ile Glu Trp Val Lys Gln Arg
    50                  55                  60

Pro Gly Gln Gly Leu Glu Trp Ile Gly Leu Ile Ile Pro Gly Thr Gly
65                  70                  75                  80

Tyr Thr Asn Tyr Asn Glu Asn Phe Lys Gly Lys Ala Thr Leu Thr Ala
                85                  90                  95

Asp Lys Ser Ser Ser Thr Ala Tyr Met Gln Leu Ser Ser Leu Thr Ser
            100                 105                 110

Glu Asp Ser Ala Val Tyr Phe Cys Ala Arg Arg Phe Gly Tyr Tyr Gly
        115                 120                 125

Ser Ser Asn Tyr Phe Asp Tyr Trp Gly Gln Gly Thr Thr Leu Thr Val
    130                 135                 140

Ser Ser Ala Ser Thr Lys Gly
145                 150


<210> SEQ ID NO 123
<211> LENGTH: 139
<212> TYPE: PRT
<213> ORGANISM: Mus musculus

<400> SEQUENCE: 123

Lys Leu Ala Ala Thr Met Ser Val Pro Thr Gln Val Leu Gly Leu Leu
1               5                   10                  15

Leu Leu Trp Leu Thr Asp Ala Arg Cys Asp Val Val Met Thr Gln Thr
            20                  25                  30

Pro Leu Ser Leu Pro Val Ser Leu Gly Asp Gln Ala Ser Ile Ser Cys
        35                  40                  45

Arg Ser Ser Gln Ser Leu Val His Ser Asn Gly Asn Thr Tyr Leu His
    50                  55                  60

Trp Tyr Leu Gln Lys Pro Gly Gln Ser Pro Lys Leu Leu Ile Tyr Lys
65                  70                  75                  80

Val Ser Asn Arg Phe Ser Gly Val Pro Asp Arg Phe Ser Gly Ser Gly
                85                  90                  95

Pro Gly Thr Asp Phe Thr Leu Lys Ile Ser Arg Val Glu Ala Glu Asp
            100                 105                 110

Leu Gly Ile Tyr Phe Cys Ser Gln Ser Thr His Phe Pro Phe Thr Phe
        115                 120                 125

Gly Thr Gly Thr Lys Leu Glu Ile Lys Arg Thr
    130                 135
```

<210> SEQ ID NO 124
<211> LENGTH: 455
<212> TYPE: DNA
<213> ORGANISM: Mus musculus

<400> SEQUENCE: 124
aagcttgccg ccaccatgga atggagctgg gtgttcctgt tctttctgtc cgtgaccaca 60
ggcgtgcatt ctcaggtcca gctgcagcag tctggagctg agctggtcag gcctgggact 120
tcagtgaagt tgtcctgcaa ggcttctgga gacgccttca ctaattactt gatcgagtgg 180
gtaaagcaga ggcctggaca gggccttgag tggattggac tgattattcc tggaactggt 240
tatactaact acaatgagaa cttcaagggc aaggcaacac tgactgcaga caagtcctcc 300
agcactgcct acatgcagct cagcagcctg acatctgagg actctgcggt ctatttctgt 360
gcaagaagat ttggttacta cggtagtggc tactactttg actactgggg ccaaggcacc 420
actctcacag tctcctcagc ctccaccaag ggccc 455

<210> SEQ ID NO 125
<211> LENGTH: 417
<212> TYPE: DNA
<213> ORGANISM: Mus musculus

<400> SEQUENCE: 125
aagcttgccg ccaccatgtc tgtgcctacc caggtgctgg gactgctgct gctgtggctg 60
acagacgccc gctgtgatgt tgtgatgacc caaactccac tctccctgcc tgtcagtctt 120
ggagatcaag cctccatctc ttgcagatct agtcagagcc ttgtacacag taatggaaac 180
acctatttac attggtacct gcagaagcca ggccagtctc caaagctcct gatctacaaa 240
gtttccaacc gattttctgg ggtcccagac aggttcagtg gcagtggacc agggacagat 300
ttcacactca agatcagcag agtggaggct gaggatctgg gagtttattt ctgctctcaa 360
agtacacatt ttccattcac gttcggcacg ggcacaaaat tggaaataaa acgtacg 417

<210> SEQ ID NO 126
<211> LENGTH: 151
<212> TYPE: PRT
<213> ORGANISM: Mus musculus

<400> SEQUENCE: 126

Lys Leu Ala Ala Thr Met Glu Trp Ser Trp Val Phe Leu Phe Phe Leu
1 5 10 15

Ser Val Thr Thr Gly Val His Ser Gln Val Gln Leu Gln Gln Ser Gly
20 25 30

Ala Glu Leu Val Arg Pro Gly Thr Ser Val Lys Leu Ser Cys Lys Ala
35 40 45

Ser Gly Asp Ala Phe Thr Asn Tyr Leu Ile Glu Trp Val Lys Gln Arg
50 55 60

Pro Gly Gln Gly Leu Glu Trp Ile Gly Leu Ile Ile Pro Gly Thr Gly
65 70 75 80

Tyr Thr Asn Tyr Asn Glu Asn Phe Lys Gly Lys Ala Thr Leu Thr Ala
85 90 95

Asp Lys Ser Ser Ser Thr Ala Tyr Met Gln Leu Ser Ser Leu Thr Ser
100 105 110

Glu Asp Ser Ala Val Tyr Phe Cys Ala Arg Arg Phe Gly Tyr Tyr Gly
115 120 125

Ser Gly Tyr Tyr Phe Asp Tyr Trp Gly Gln Gly Thr Thr Leu Thr Val
130 135 140

```
Ser Ser Ala Ser Thr Lys Gly
145                 150


<210> SEQ ID NO 127
<211> LENGTH: 139
<212> TYPE: PRT
<213> ORGANISM: Mus musculus

<400> SEQUENCE: 127

Lys Leu Ala Ala Thr Met Ser Val Pro Thr Gln Val Leu Gly Leu Leu
1               5                   10                  15

Leu Leu Trp Leu Thr Asp Ala Arg Cys Asp Val Val Met Thr Gln Thr
            20                  25                  30

Pro Leu Ser Leu Pro Val Ser Leu Gly Asp Gln Ala Ser Ile Ser Cys
        35                  40                  45

Arg Ser Ser Gln Ser Leu Val His Ser Asn Gly Asn Thr Tyr Leu His
    50                  55                  60

Trp Tyr Leu Gln Lys Pro Gly Gln Ser Pro Lys Leu Leu Ile Tyr Lys
65                  70                  75                  80

Val Ser Asn Arg Phe Ser Gly Val Pro Asp Arg Phe Ser Gly Ser Gly
                85                  90                  95

Pro Gly Thr Asp Phe Thr Leu Lys Ile Ser Arg Val Glu Ala Glu Asp
            100                 105                 110

Leu Gly Val Tyr Phe Cys Ser Gln Ser Thr His Phe Pro Phe Thr Phe
        115                 120                 125

Gly Thr Gly Thr Lys Leu Glu Ile Lys Arg Thr
    130                 135


<210> SEQ ID NO 128
<211> LENGTH: 443
<212> TYPE: DNA
<213> ORGANISM: Mus musculus

<400> SEQUENCE: 128

aagcttgccg ccaccatgga atggagctgg gtgttcctgt tctttctgtc cgtgaccaca      60

ggcgtgcatt ctgatataca gcttcaggag tcaggacctg gcctcgtgaa accttctcag     120

tctctgtctc tcacctgctc tgtcactggc ttctccatca ccagtggtta ttactggacc     180

tggatccggc agtttccagg aaacaaactg gagtgggtgg cctacatagg ctacgatggt     240

agcaatgact ccaacccatc tctcaaaaat cgaatctcca tcacccgtga cacatctaag     300

aaccagtttt tcctgaagtt gaattctgtg actactgagg acacagccac atattactgt     360

gcaagagcga tgttgcggcg aggatttgac tactggggcc aaggcaccac tctcacagtc     420

tcctcagcct ccaccaaggg ccc                                             443


<210> SEQ ID NO 129
<211> LENGTH: 393
<212> TYPE: DNA
<213> ORGANISM: Mus musculus

<400> SEQUENCE: 129

aagcttgccg ccaccatgtc tgtgcctacc caggtgctgg gactgctgct gctgtggctg      60

acagacgccc gctgtcaaat tgttctcacc cagtctccag caatcatgtc tgcatctcca     120

ggggagaagg tcaccatgac ctgcagtgcc agctcaagtt taagttacat gcactggtac     180

cagcagaagc caggcacctc ccccaaaaga tggatttatg acacatccaa actggcttct     240

ggagtccctg ctcgcttcag tggcagtggg tctgggacct cttattctct cacaatcagc     300
```

```
agcatggagg ctgaagatgc tgccacttat tactgccatc ggcggagtag ttacacgttc    360

ggagggggga ccaagctgga aataaaacgt acg                                 393
```

<210> SEQ ID NO 130
<211> LENGTH: 147
<212> TYPE: PRT
<213> ORGANISM: Mus musculus

<400> SEQUENCE: 130

```
Lys Leu Ala Ala Thr Met Glu Trp Ser Trp Val Phe Leu Phe Phe Leu
1               5                   10                  15

Ser Val Thr Thr Gly Val His Ser Asp Ile Gln Leu Gln Glu Ser Gly
            20                  25                  30

Pro Gly Leu Val Lys Pro Ser Gln Ser Leu Ser Leu Thr Cys Ser Val
        35                  40                  45

Thr Gly Phe Ser Ile Thr Ser Gly Tyr Tyr Trp Thr Trp Ile Arg Gln
    50                  55                  60

Phe Pro Gly Asn Lys Leu Glu Trp Val Ala Tyr Ile Gly Tyr Asp Gly
65                  70                  75                  80

Ser Asn Asp Ser Asn Pro Ser Leu Lys Asn Arg Ile Ser Ile Thr Arg
                85                  90                  95

Asp Thr Ser Lys Asn Gln Phe Phe Leu Lys Leu Asn Ser Val Thr Thr
            100                 105                 110

Glu Asp Thr Ala Thr Tyr Tyr Cys Ala Arg Ala Met Leu Arg Arg Gly
        115                 120                 125

Phe Asp Tyr Trp Gly Gln Gly Thr Thr Leu Thr Val Ser Ser Ala Ser
    130                 135                 140

Thr Lys Gly
145
```

<210> SEQ ID NO 131
<211> LENGTH: 131
<212> TYPE: PRT
<213> ORGANISM: Mus musculus

<400> SEQUENCE: 131

```
Lys Leu Ala Ala Thr Met Ser Val Pro Thr Gln Val Leu Gly Leu Leu
1               5                   10                  15

Leu Leu Trp Leu Thr Asp Ala Arg Cys Gln Ile Val Leu Thr Gln Ser
            20                  25                  30

Pro Ala Ile Met Ser Ala Ser Pro Gly Glu Lys Val Thr Met Thr Cys
        35                  40                  45

Ser Ala Ser Ser Ser Leu Ser Tyr Met His Trp Tyr Gln Gln Lys Pro
    50                  55                  60

Gly Thr Ser Pro Lys Arg Trp Ile Tyr Asp Thr Ser Lys Leu Ala Ser
65                  70                  75                  80

Gly Val Pro Ala Arg Phe Ser Gly Ser Gly Ser Gly Thr Ser Tyr Ser
                85                  90                  95

Leu Thr Ile Ser Ser Met Glu Ala Glu Asp Ala Ala Thr Tyr Tyr Cys
            100                 105                 110

His Arg Arg Ser Ser Tyr Thr Phe Gly Gly Gly Thr Lys Leu Glu Ile
        115                 120                 125

Lys Arg Thr
    130
```

<210> SEQ ID NO 132

<211> LENGTH: 122
<212> TYPE: PRT
<213> ORGANISM: Mus musculus

<400> SEQUENCE: 132

```
Gln Val Lys Leu Gln Gln Ser Gly Pro Glu Leu Val Arg Pro Gly Thr
1               5                   10                  15

Ser Val Lys Val Ser Cys Thr Ala Ser Gly Asp Ala Phe Thr Asn Tyr
            20                  25                  30

Leu Ile Glu Trp Val Lys Gln Arg Pro Gly Gln Gly Leu Glu Trp Ile
        35                  40                  45

Gly Leu Ile Tyr Pro Asp Ser Gly Tyr Ile Asn Tyr Asn Glu Asn Phe
    50                  55                  60

Lys Gly Lys Ala Thr Leu Thr Ala Asp Arg Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Arg Phe Ala Tyr Tyr Gly Ser Gly Tyr Tyr Phe Asp Tyr Trp
            100                 105                 110

Gly Gln Gly Thr Thr Leu Thr Val Ser Ser
        115                 120
```

<210> SEQ ID NO 133
<211> LENGTH: 112
<212> TYPE: PRT
<213> ORGANISM: Mus musculus

<400> SEQUENCE: 133

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Thr
            20                  25                  30

Asn Gly Asn Thr Tyr Leu His Trp Tyr Leu Gln Lys Pro Gly Gln Ser
        35                  40                  45

Pro Lys Leu Leu Ile Phe Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Phe Pro Phe Thr Phe Gly Thr Gly Thr Lys Leu Glu Ile Lys
            100                 105                 110
```

<210> SEQ ID NO 134
<211> LENGTH: 122
<212> TYPE: PRT
<213> ORGANISM: Mus musculus

<400> SEQUENCE: 134

```
Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Gly Phe Ile Asn Tyr
            20                  25                  30

Leu Ile Glu Trp Ile Lys Gln Arg Pro Gly Gln Gly Leu Glu Trp Ile
        35                  40                  45

Gly Leu Ile Asn Pro Gly Ser Asp Tyr Thr Asn Tyr Asn Glu Asn Phe
    50                  55                  60

Lys Gly Lys Ala Thr Leu Thr Ala Asp Lys Ser Ser Ser Thr Ala Tyr
```

```
65                  70                  75                  80

Met His Leu Ser Ser Leu Thr Ser Glu Asp Ser Ala Val Tyr Phe Cys
                85                  90                  95

Ala Arg Arg Phe Gly Tyr Tyr Gly Ser Gly Asn Tyr Phe Asp Tyr Trp
            100                 105                 110

Gly Gln Gly Thr Thr Leu Thr Val Ser Ser
        115                 120


<210> SEQ ID NO 135
<211> LENGTH: 112
<212> TYPE: PRT
<213> ORGANISM: Mus musculus

<400> SEQUENCE: 135

Asp Val Val Met Thr Gln Thr Pro Leu Ser Leu Pro Val Ser Leu Gly
1               5                   10                  15

Asp Gln Ala Ser Ile Ser Cys Thr Ser Gly Gln Ser Leu Val His Ile
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Leu Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Phe Pro Phe Thr Phe Gly Thr Gly Thr Lys Leu Glu Ile Lys
            100                 105                 110


<210> SEQ ID NO 136
<211> LENGTH: 122
<212> TYPE: PRT
<213> ORGANISM: Mus musculus

<400> SEQUENCE: 136

Gln Val Gln Leu Gln Gln Ser Gly Ala Glu Leu Val Arg Pro Gly Thr
1               5                   10                  15

Ser Val Lys Val Ser Cys Lys Ala Ser Gly Asp Ala Phe Thr Asn Tyr
            20                  25                  30

Leu Ile Glu Trp Val Lys Gln Arg Pro Gly Gln Gly Leu Glu Trp Ile
        35                  40                  45

Gly Leu Ile Ile Pro Gly Thr Gly Tyr Thr Asn Tyr Asn Glu Asn Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Arg Phe Gly Tyr Tyr Gly Ser Ser Asn Tyr Phe Asp Tyr Trp
            100                 105                 110

Gly Gln Gly Thr Thr Leu Thr Val Ser Ser
        115                 120


<210> SEQ ID NO 137
<211> LENGTH: 112
<212> TYPE: PRT
<213> ORGANISM: Mus musculus

<400> SEQUENCE: 137
```

Asp Val Val Met Thr Gln Thr Pro Leu Ser Leu Pro Val Ser Leu Gly
1 5 10 15

Asp Gln Ala Ser Ile Ser Cys Arg Ser Ser Gln Ser Leu Val His Ser
20 25 30

Asn Gly Asn Thr Tyr Leu His Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Pro Gly Thr Asp Phe Thr Leu Lys Ile
65 70 75 80

Ser Arg Val Glu Ala Glu Asp Leu Gly Ile Tyr Phe Cys Ser Gln Ser
85 90 95

Thr His Phe Pro Phe Thr Phe Gly Thr Gly Thr Lys Leu Glu Ile Lys
100 105 110

<210> SEQ ID NO 138
<211> LENGTH: 122
<212> TYPE: PRT
<213> ORGANISM: Mus musculus

<400> SEQUENCE: 138

Gln Val Gln Leu Gln Gln Ser Gly Ala Glu Leu Val Arg Pro Gly Thr
1 5 10 15

Ser Val Lys Leu Ser Cys Lys Ala Ser Gly Asp Ala Phe Thr Asn Tyr
20 25 30

Leu Ile Glu Trp Val Lys Gln Arg Pro Gly Gln Gly Leu Glu Trp Ile
35 40 45

Gly Leu Ile Ile Pro Gly Thr Gly Tyr Thr Asn Tyr Asn Glu Asn Phe
50 55 60

Lys Gly Lys Ala Thr Leu Thr Ala Asp Lys Ser Ser Ser Thr Ala Tyr
65 70 75 80

Met Gln Leu Ser Ser Leu Thr Ser Glu Asp Ser Ala Val Tyr Phe Cys
85 90 95

Ala Arg Arg Phe Gly Tyr Tyr Gly Ser Gly Tyr Tyr Phe Asp Tyr Trp
100 105 110

Gly Gln Gly Thr Thr Leu Thr Val Ser Ser
115 120

<210> SEQ ID NO 139
<211> LENGTH: 112
<212> TYPE: PRT
<213> ORGANISM: Mus musculus

<400> SEQUENCE: 139

Asp Val Val Met Thr Gln Thr Pro Leu Ser Leu Pro Val Ser Leu Gly
1 5 10 15

Asp Gln Ala Ser Ile Ser Cys Arg Ser Ser Gln Ser Leu Val His Ser
20 25 30

Asn Gly Asn Thr Tyr Leu His Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Pro Gly Thr Asp Phe Thr Leu Lys Ile
65 70 75 80

Ser Arg Val Glu Ala Glu Asp Leu Gly Val Tyr Phe Cys Ser Gln Ser
85 90 95

Thr His Phe Pro Phe Thr Phe Gly Thr Gly Thr Lys Leu Glu Ile Lys

-continued 100 105 110

<210> SEQ ID NO 140
<211> LENGTH: 118
<212> TYPE: PRT
<213> ORGANISM: Mus musculus

<400> SEQUENCE: 140

Asp Ile Gln Leu Gln Glu Ser Gly Pro Gly Leu Val Lys Pro Ser Gln
1 5 10 15

Ser Leu Ser Leu Thr Cys Ser Val Thr Gly Phe Ser Ile Thr Ser Gly
20 25 30

Tyr Tyr Trp Thr Trp Ile Arg Gln Phe Pro Gly Asn Lys Leu Glu Trp
35 40 45

Val Ala Tyr Ile Gly Tyr Asp Gly Ser Asn Asp Ser Asn Pro Ser Leu
50 55 60

Lys Asn Arg Ile Ser Ile Thr Arg Asp Thr Ser Lys Asn Gln Phe Phe
65 70 75 80

Leu Lys Leu Asn Ser Val Thr Thr Glu Asp Thr Ala Thr Tyr Tyr Cys
85 90 95

Ala Arg Ala Met Leu Arg Arg Gly Phe Asp Tyr Trp Gly Gln Gly Thr
100 105 110

Thr Leu Thr Val Ser Ser
115

<210> SEQ ID NO 141
<211> LENGTH: 104
<212> TYPE: PRT
<213> ORGANISM: Mus musculus

<400> SEQUENCE: 141

Gln Ile Val Leu Thr Gln Ser Pro Ala Ile Met Ser Ala Ser Pro Gly
1 5 10 15

Glu Lys Val Thr Met Thr Cys Ser Ala Ser Ser Ser Leu Ser Tyr Met
20 25 30

His Trp Tyr Gln Gln Lys Pro Gly Thr Ser Pro Lys Arg Trp Ile Tyr
35 40 45

Asp Thr Ser Lys Leu Ala Ser Gly Val Pro Ala Arg Phe Ser Gly Ser
50 55 60

Gly Ser Gly Thr Ser Tyr Ser Leu Thr Ile Ser Ser Met Glu Ala Glu
65 70 75 80

Asp Ala Ala Thr Tyr Tyr Cys His Arg Arg Ser Ser Tyr Thr Phe Gly
85 90 95

Gly Gly Thr Lys Leu Glu Ile Lys
100

<210> SEQ ID NO 142
<211> LENGTH: 366
<212> TYPE: DNA
<213> ORGANISM: Artificial
<220> FEATURE:
<223> OTHER INFORMATION: humanized antibody variant

<400> SEQUENCE: 142
gaggtgcagc tggtgcagag cggagccgag gtgaagaagc ccggcgagag cctgaagatc 60
agctgccagg ccttcggcta cggcttcatc aactacctga tcgagtggat ccggcagatg 120
cccggccagg gcctggaatg gatcggcgca atcaaccccg gcagcgacta caccaactac 180
aacgagaact tcaagggcca ggccaccctg agcgccgaca agagcagcag caccgcctac 240
ctgcagtgga gcagcctgaa ggccagcgac accgccatgt acttttgcgc caggcggttc 300
ggctactacg gcagcggcaa ctacttcgac tactggggcc agggcaccat ggtgaccgtg 360
agcagc 366

<210> SEQ ID NO 143
<211> LENGTH: 122
<212> TYPE: PRT
<213> ORGANISM: Artificial
<220> FEATURE:
<223> OTHER INFORMATION: humanized antibody variant

<400> SEQUENCE: 143

Glu Val Gln Leu Val Gln Ser Gly Ala Glu Val Lys Lys Pro Gly Glu
1 5 10 15

Ser Leu Lys Ile Ser Cys Gln Ala Phe Gly Tyr Gly Phe Ile Asn Tyr
20 25 30

Leu Ile Glu Trp Ile Arg Gln Met Pro Gly Gln Gly Leu Glu Trp Ile
35 40 45

Gly Ala Ile Asn Pro Gly Ser Asp Tyr Thr Asn Tyr Asn Glu Asn Phe
50 55 60

Lys Gly Gln Ala Thr Leu Ser Ala Asp Lys Ser Ser Ser Thr Ala Tyr
65 70 75 80

Leu Gln Trp Ser Ser Leu Lys Ala Ser Asp Thr Ala Met Tyr Phe Cys
85 90 95

Ala Arg Arg Phe Gly Tyr Tyr Gly Ser Gly Asn Tyr Phe Asp Tyr Trp
100 105 110

Gly Gln Gly Thr Met Val Thr Val Ser Ser
115 120

<210> SEQ ID NO 144
<211> LENGTH: 336
<212> TYPE: DNA
<213> ORGANISM: Artificial
<220> FEATURE:
<223> OTHER INFORMATION: humanized antibody variant

<400> SEQUENCE: 144
gacgtggtga tgacccagac ccccctgagc ctgcccgtga ccccaggcga acccgccagc 60
atcagctgta gaagctccca gtccctgctg aaaaccaacg gcaacaccta tctgcactgg 120
tatctgcaga agcccggcca gagccccaag ctgctgatct acaaggtgtc caaccggttc 180
agcggcgtgc ccgacagatt cagcggcagc ggctccggca ccgacttcac cctgaagatc 240
agccgggtgg aggccgagga cgtgggcgtg tacttctgca gccagtccac ccacttccct 300
ttcaccttcg gccagggcac aaagctggaa atcaag 336

<210> SEQ ID NO 145
<211> LENGTH: 112
<212> TYPE: PRT
<213> ORGANISM: Artificial
<220> FEATURE:
<223> OTHER INFORMATION: humanized antibody variant

<400> SEQUENCE: 145

Asp Val Val Met Thr Gln Thr Pro Leu Ser Leu Pro Val Thr Pro Gly
1 5 10 15

Glu Pro Ala Ser Ile Ser Cys Arg Ser Ser Gln Ser Leu Leu Lys Thr
20 25 30

Asn Gly Asn Thr Tyr Leu His Trp Tyr Leu Gln Lys Pro Gly Gln Ser

```
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Phe Pro Phe Thr Phe Gly Gln Gly Thr Lys Leu Glu Ile Lys
            100                 105                 110


<210> SEQ ID NO 146
<211> LENGTH: 336
<212> TYPE: DNA
<213> ORGANISM: Artificial
<220> FEATURE:
<223> OTHER INFORMATION: humanized antibody variant

<400> SEQUENCE: 146

gacgtggtga tgacccagac ccccctgagc ctgcccgtga ccccaggcga acccgccagc      60

atcagctgta gaagctccca gtccctgctg aaaaccaacg gcaacaccta tctgcactgg     120

tatctgcaga agcccggcca gagcccccag ctgctgatct acaaggtgtc caaccggttc     180

agcggcgtgc ccgacagatt cagcggcagc ggctccggca ccgacttcac cctgaagatc     240

agccgggtgg aggccgagga cgtgggcgtg tactactgca gccagtccac ccacttccct     300

ttcaccttcg gccagggcac caagctggaa atcaag                               336


<210> SEQ ID NO 147
<211> LENGTH: 112
<212> TYPE: PRT
<213> ORGANISM: Artificial
<220> FEATURE:
<223> OTHER INFORMATION: humanized antibody variant

<400> SEQUENCE: 147

Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Lys Thr
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Phe Pro Phe Thr Phe Gly Gln Gly Thr Lys Leu Glu Ile Lys
            100                 105                 110


<210> SEQ ID NO 148
<211> LENGTH: 336
<212> TYPE: DNA
<213> ORGANISM: Artificial
<220> FEATURE:
<223> OTHER INFORMATION: humanized antibody variant

<400> SEQUENCE: 148

gacgtggtga tgacccagac ccccctgagc ctgcccgtga ccccaggcga acccgccagc      60

atcagctgta gaagctccca gagcctgctg aaaaccaacg gcaacaccta tctgcactgg     120
```

-continued

```
tatctgcaga agcccggcca gagccccaag ctgctgattt tcaaggtgtc caaccggttc    180

agcggcgtgc ccgacagatt cagcggcagc ggctccggca ccgacttcac cctgaagatc    240

agccgggtgg aggccgagga cgtgggcgtg tacttctgca gccagtccac ccacttccct    300

ttcaccttcg gccagggcac aaagctggaa atcaag                              336


<210> SEQ ID NO 149
<211> LENGTH: 112
<212> TYPE: PRT
<213> ORGANISM: Artificial
<220> FEATURE:
<223> OTHER INFORMATION: humanized antibody variant

<400> SEQUENCE: 149

Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Lys Thr
            20                  25                  30

Asn Gly Asn Thr Tyr Leu His Trp Tyr Leu Gln Lys Pro Gly Gln Ser
        35                  40                  45

Pro Lys Leu Leu Ile Phe Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Phe Pro Phe Thr Phe Gly Gln Gly Thr Lys Leu Glu Ile Lys
            100                 105                 110


<210> SEQ ID NO 150
<211> LENGTH: 366
<212> TYPE: DNA
<213> ORGANISM: Artificial
<220> FEATURE:
<223> OTHER INFORMATION: humanized antibody variant

<400> SEQUENCE: 150

gaggtgcagc tggtgcagag cggagccgaa gtgaagaagc ccggcgagag cctgaagatc     60

agctgccagg ccttcggcta cggcttcatc aactacctga tcgagtggat ccggcagatg    120

cccggacagg gcctggaatg gatcggcctg atctaccccg acagcggcta catcaattac    180

aacgagaact tcaagggcca ggccaccctg agcgccgaca agagcagcag caccgcctat    240

ctgcagtgga gcagcctgaa ggccagcgac accgccatgt acttttgcgc caggcggttc    300

gcctactacg gcagcggcta ctacttcgac tactggggcc agggcacaat ggtgaccgtg    360

tctagc                                                               366


<210> SEQ ID NO 151
<211> LENGTH: 122
<212> TYPE: PRT
<213> ORGANISM: Artificial
<220> FEATURE:
<223> OTHER INFORMATION: humanized antibody variant

<400> SEQUENCE: 151

Glu Val Gln Leu Val Gln Ser Gly Ala Glu Val Lys Lys Pro Gly Glu
1               5                   10                  15

Ser Leu Lys Ile Ser Cys Gln Ala Phe Gly Tyr Gly Phe Ile Asn Tyr
            20                  25                  30
```

-continued

```
Leu Ile Glu Trp Ile Arg Gln Met Pro Gly Gln Gly Leu Glu Trp Ile
        35                  40                  45

Gly Leu Ile Tyr Pro Asp Ser Gly Tyr Ile Asn Tyr Asn Glu Asn Phe
    50                  55                  60

Lys Gly Gln Ala Thr Leu Ser Ala Asp Lys Ser Ser Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Arg Phe Ala Tyr Tyr Gly Ser Gly Tyr Tyr Phe Asp Tyr Trp
            100                 105                 110

Gly Gln Gly Thr Met Val Thr Val Ser Ser
        115                 120
```

<210> SEQ ID NO 152
<211> LENGTH: 366
<212> TYPE: DNA
<213> ORGANISM: Artificial
<220> FEATURE:
<223> OTHER INFORMATION: humanized antibody variant

<400> SEQUENCE: 152

```
gaggtgcagc tggtgcagag cggcgctgaa gtgaagaagc ccggcgagag cctgaagatc      60

agctgccagg ccttcggcta cgccttcacc aactacctga tcgagtgggt gcgccagatg     120

cccggacagg gcctggaatg gatgggcctg atctaccccg acagcggcta catcaactac     180

aacgagaact tcaagggcca ggtgaccatc agcgccgaca agagcagcag caccgcctat     240

ctgcagtgga gcagcctgaa ggccagcgac accgccatgt acttttgcgc caggcggttc     300

gcctactacg gcagcggcta ctacttcgac tactggggcc agggcacaat ggtgaccgtg     360

tccagc                                                                366
```

<210> SEQ ID NO 153
<211> LENGTH: 122
<212> TYPE: PRT
<213> ORGANISM: Artificial
<220> FEATURE:
<223> OTHER INFORMATION: humanized antibody variant

<400> SEQUENCE: 153

```
Glu Val Gln Leu Val Gln Ser Gly Ala Glu Val Lys Lys Pro Gly Glu
1               5                   10                  15

Ser Leu Lys Ile Ser Cys Gln Ala Phe Gly Tyr Ala Phe Thr Asn Tyr
            20                  25                  30

Leu Ile Glu Trp Val Arg Gln Met Pro Gly Gln Gly Leu Glu Trp Met
        35                  40                  45

Gly Leu Ile Tyr Pro Asp Ser Gly Tyr Ile Asn Tyr Asn Glu Asn Phe
    50                  55                  60

Lys Gly Gln Val Thr Ile Ser Ala Asp Lys Ser Ser Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Arg Phe Ala Tyr Tyr Gly Ser Gly Tyr Tyr Phe Asp Tyr Trp
            100                 105                 110

Gly Gln Gly Thr Met Val Thr Val Ser Ser
        115                 120
```

<210> SEQ ID NO 154
<211> LENGTH: 366
<212> TYPE: DNA

<213> ORGANISM: Artificial
<220> FEATURE:
<223> OTHER INFORMATION: humanized antibody variant

<400> SEQUENCE: 154
gaggtgcagc tggtgcagag cggcgctgaa gtgaagaagc ccggcgagag cctgaagatc 60
agctgccagg ccttcggcta cgccttcacc aactacctga tcgagtgggt gcgccagatg 120
cccggacagg gcctggaatg gatcggcctg atctaccccg acagcggcta catcaactac 180
aacgagaact tcaagggcca ggccaccctg agcgccgaca agagcagcag caccgcctat 240
ctgcagtgga gcagcctgaa ggccagcgac accgccatgt acttttgcgc caggcggttc 300
gcctactacg gcagcggcta ctacttcgac tactggggcc agggcacaat ggtgaccgtg 360
tccagc 366

<210> SEQ ID NO 155
<211> LENGTH: 122
<212> TYPE: PRT
<213> ORGANISM: Artificial
<220> FEATURE:
<223> OTHER INFORMATION: humanized antibody variant

<400> SEQUENCE: 155

Glu Val Gln Leu Val Gln Ser Gly Ala Glu Val Lys Lys Pro Gly Glu
1               5                   10                  15

Ser Leu Lys Ile Ser Cys Gln Ala Phe Gly Tyr Ala Phe Thr Asn Tyr
            20                  25                  30

Leu Ile Glu Trp Val Arg Gln Met Pro Gly Gln Gly Leu Glu Trp Ile
        35                  40                  45

Gly Leu Ile Tyr Pro Asp Ser Gly Tyr Ile Asn Tyr Asn Glu Asn Phe
    50                  55                  60

Lys Gly Gln Ala Thr Leu Ser Ala Asp Lys Ser Ser Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Arg Phe Ala Tyr Tyr Gly Ser Gly Tyr Tyr Phe Asp Tyr Trp
            100                 105                 110

Gly Gln Gly Thr Met Val Thr Val Ser Ser
        115                 120

<210> SEQ ID NO 156
<211> LENGTH: 366
<212> TYPE: DNA
<213> ORGANISM: Artificial
<220> FEATURE:
<223> OTHER INFORMATION: humanized antibody variant

<400> SEQUENCE: 156
gaggtgcagc tggtgcagag cggagccgaa gtgaagaagc ccggcgagag cctgaagatc 60
agctgccagg ccttcggcga cgccttcacc aactacctga tcgagtgggt gcgccagatg 120
cccggacagg gcctggaatg gatgggcctg atctaccccg acagcggcta catcaactac 180
aacgagaact tcaagggcca ggtgaccatc agcgccgaca gaagcagcag caccgcctat 240
ctgcagtgga gcagcctgaa ggccagcgac accgccatgt acttttgcgc caggcggttc 300
gcctactacg gcagcggcta ctacttcgac tactggggcc agggcacaat ggtgaccgtg 360
tccagc 366

<210> SEQ ID NO 157

<211> LENGTH: 122
<212> TYPE: PRT
<213> ORGANISM: Artificial
<220> FEATURE:
<223> OTHER INFORMATION: humanized antibody variant

<400> SEQUENCE: 157

Glu Val Gln Leu Val Gln Ser Gly Ala Glu Val Lys Lys Pro Gly Glu
1               5                   10                  15

Ser Leu Lys Ile Ser Cys Gln Ala Phe Gly Asp Ala Phe Thr Asn Tyr
            20                  25                  30

Leu Ile Glu Trp Val Arg Gln Met Pro Gly Gln Gly Leu Glu Trp Met
        35                  40                  45

Gly Leu Ile Tyr Pro Asp Ser Gly Tyr Ile Asn Tyr Asn Glu Asn Phe
    50                  55                  60

Lys Gly Gln Val Thr Ile Ser Ala Asp Arg Ser Ser Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Arg Phe Ala Tyr Tyr Gly Ser Gly Tyr Tyr Phe Asp Tyr Trp
            100                 105                 110

Gly Gln Gly Thr Met Val Thr Val Ser Ser
        115                 120

<210> SEQ ID NO 158
<211> LENGTH: 366
<212> TYPE: DNA
<213> ORGANISM: Artificial
<220> FEATURE:
<223> OTHER INFORMATION: humanized antibody variant

<400> SEQUENCE: 158
gaggtgcagc tggtgcagag cggagccgaa gtgaagaagc ccggcgagag cctgaagatc 60
agctgccagg ccttcggcga cgccttcacc aactacctga tcgagtgggt gcgccagatg 120
cccggacagg gcctggaatg gatcggcctg atctaccccg acagcggcta catcaactac 180
aacgagaact tcaagggcca ggccaccctg agcgccgaca gaagcagcag caccgcctat 240
ctgcagtgga gcagcctgaa ggccagcgac accgccatgt acttttgcgc caggcggttc 300
gcctactacg gcagcggcta ctacttcgac tactggggcc agggcacaat ggtgaccgtg 360
tccagc 366

<210> SEQ ID NO 159
<211> LENGTH: 122
<212> TYPE: PRT
<213> ORGANISM: Artificial
<220> FEATURE:
<223> OTHER INFORMATION: humanized antibody variant

<400> SEQUENCE: 159

Glu Val Gln Leu Val Gln Ser Gly Ala Glu Val Lys Lys Pro Gly Glu
1               5                   10                  15

Ser Leu Lys Ile Ser Cys Gln Ala Phe Gly Asp Ala Phe Thr Asn Tyr
            20                  25                  30

Leu Ile Glu Trp Val Arg Gln Met Pro Gly Gln Gly Leu Glu Trp Ile
        35                  40                  45

Gly Leu Ile Tyr Pro Asp Ser Gly Tyr Ile Asn Tyr Asn Glu Asn Phe
    50                  55                  60

Lys Gly Gln Ala Thr Leu Ser Ala Asp Arg Ser Ser Ser Thr Ala Tyr
65                  70                  75                  80

Leu Gln Trp Ser Ser Leu Lys Ala Ser Asp Thr Ala Met Tyr Phe Cys
85 90 95

Ala Arg Arg Phe Ala Tyr Tyr Gly Ser Gly Tyr Tyr Phe Asp Tyr Trp
100 105 110

Gly Gln Gly Thr Met Val Thr Val Ser Ser
115 120

<210> SEQ ID NO 160
<211> LENGTH: 112
<212> TYPE: PRT
<213> ORGANISM: Artificial
<220> FEATURE:
<223> OTHER INFORMATION: humanized antibody variant

<400> SEQUENCE: 160

Asp Val Val Met Thr Gln Thr Pro Leu Ser Leu Pro Val Ser Leu Gly
1 5 10 15

Asp Gln Ala Ser Ile Ser Cys Thr Ser Gly Gln Ser Leu Val His Ile
20 25 30

Asn Gly Asn Thr Tyr Leu His Trp Tyr Leu Gln Lys Pro Gly Gln Ser
35 40 45

Pro Lys Leu Leu Ile Tyr Lys Val Ser Asn Leu Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Phe Cys Ser Gln Ser
85 90 95

Thr His Phe Pro Phe Thr Phe Gly Thr Gly Thr Lys Leu Glu Ile Lys
100 105 110

<210> SEQ ID NO 161
<211> LENGTH: 112
<212> TYPE: PRT
<213> ORGANISM: Artificial
<220> FEATURE:
<223> OTHER INFORMATION: humanized antibody variant

<400> SEQUENCE: 161

Asp Ile Val Met Thr Gln Thr Pro Leu Ser Leu Pro Val Thr Pro Gly
1 5 10 15

Glu Pro Ala Ser Ile Ser Cys Thr Ser Gly Gln Ser Leu Val His Ile
20 25 30

Asn Gly Asn Thr Tyr Leu His Trp Tyr Leu Gln Lys Pro Gly Gln Ser
35 40 45

Pro Gln Leu Leu Ile Tyr Lys Val Ser Asn Leu Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Ser Gln Ser
85 90 95

Thr His Phe Pro Phe Thr Phe Gly Gln Gly Thr Lys Leu Glu Ile Lys
100 105 110

<210> SEQ ID NO 162
<211> LENGTH: 112
<212> TYPE: PRT
<213> ORGANISM: Artificial
<220> FEATURE:
<223> OTHER INFORMATION: humanized antibody variant

<400> SEQUENCE: 162

Asp Val Val Met Thr Gln Thr Pro Leu Ser Leu Pro Val Thr Pro Gly
1 5 10 15

Glu Pro Ala Ser Ile Ser Cys Thr Ser Gly Gln Ser Leu Val His Ile
20 25 30

Asn Gly Asn Thr Tyr Leu His Trp Tyr Leu Gln Lys Pro Gly Gln Ser
35 40 45

Pro Lys Leu Leu Ile Tyr Lys Val Ser Asn Leu Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Phe Cys Ser Gln Ser
85 90 95

Thr His Phe Pro Phe Thr Phe Gly Gln Gly Thr Lys Leu Glu Ile Lys
100 105 110

<210> SEQ ID NO 163
<211> LENGTH: 112
<212> TYPE: PRT
<213> ORGANISM: Artificial
<220> FEATURE:
<223> OTHER INFORMATION: humanized antibody variant

<400> SEQUENCE: 163

Asp Ile Val Met Thr Gln Thr Pro Leu Ser Leu Pro Val Thr Pro Gly
1 5 10 15

Glu Pro Ala Ser Ile Ser Cys Thr Ser Gly Gln Ser Leu Val His Ile
20 25 30

Asn Gly Asn Thr Tyr Leu His Trp Tyr Leu Gln Lys Pro Gly Gln Ser
35 40 45

Pro Lys Leu Leu Ile Tyr Lys Val Ser Asn Leu Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Phe Cys Ser Gln Ser
85 90 95

Thr His Phe Pro Phe Thr Phe Gly Gln Gly Thr Lys Leu Glu Ile Lys
100 105 110

<210> SEQ ID NO 164
<211> LENGTH: 112
<212> TYPE: PRT
<213> ORGANISM: Artificial
<220> FEATURE:
<223> OTHER INFORMATION: humanized antibody variant

<400> SEQUENCE: 164

Asp Val Val Met Thr Gln Thr Pro Leu Ser Leu Pro Val Thr Pro Gly
1 5 10 15

Glu Pro Ala Ser Ile Ser Cys Thr Ser Gly Gln Ser Leu Val His Ile
20 25 30

Asn Gly Asn Thr Tyr Leu His Trp Tyr Leu Gln Lys Pro Gly Gln Ser
35 40 45

Pro Gln Leu Leu Ile Tyr Lys Val Ser Asn Leu Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Phe Cys Ser Gln Ser

```
                85                  90                  95

Thr His Phe Pro Phe Thr Phe Gly Gln Gly Thr Lys Leu Glu Ile Lys
            100                 105                 110
```

```
<210> SEQ ID NO 165
<211> LENGTH: 112
<212> TYPE: PRT
<213> ORGANISM: Artificial
<220> FEATURE:
<223> OTHER INFORMATION: humanized antibody variant

<400> SEQUENCE: 165

Asp Val Val Met Thr Gln Thr Pro Leu Ser Leu Pro Val Thr Pro Gly
1               5                   10                  15

Glu Pro Ala Ser Ile Ser Cys Thr Ser Gly Gln Ser Leu Val His Ile
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Leu Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Phe Pro Phe Thr Phe Gly Gln Gly Thr Lys Leu Glu Ile Lys
            100                 105                 110
```

```
<210> SEQ ID NO 166
<211> LENGTH: 112
<212> TYPE: PRT
<213> ORGANISM: Artificial
<220> FEATURE:
<223> OTHER INFORMATION: humanized antibody variant

<400> SEQUENCE: 166

Asp Val Val Met Thr Gln Thr Pro Leu Ser Leu Pro Val Thr Pro Gly
1               5                   10                  15

Glu Pro Ala Ser Ile Ser Cys Thr Ser Gly Gln Ser Leu Val His Ile
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Leu Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Phe Pro Phe Thr Phe Gly Gln Gly Thr Lys Leu Glu Ile Lys
            100                 105                 110
```

```
<210> SEQ ID NO 167
<211> LENGTH: 112
<212> TYPE: PRT
<213> ORGANISM: Artificial
<220> FEATURE:
<223> OTHER INFORMATION: humanized antibody variant

<400> SEQUENCE: 167

Asp Val Val Met Thr Gln Thr Pro Leu Ser Leu Pro Val Thr Pro Gly
1               5                   10                  15
```

-continued

Glu Pro Ala Ser Ile Ser Cys Arg Ser Ser Gln Ser Leu Leu Lys Thr
20 25 30

Asn Gly Asn Thr Tyr Leu His Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Phe Cys Ser Gln Ser
85 90 95

Thr His Phe Pro Phe Thr Phe Gly Gln Gly Thr Lys Leu Glu Ile Lys
100 105 110

<210> SEQ ID NO 168
<211> LENGTH: 112
<212> TYPE: PRT
<213> ORGANISM: Artificial
<220> FEATURE:
<223> OTHER INFORMATION: humanized antibody variant

<400> SEQUENCE: 168

Asp Val Val Met Thr Gln Thr Pro Leu Ser Leu Pro Val Thr Pro Gly
1 5 10 15

Glu Pro Ala Ser Ile Ser Cys Arg Ser Ser Gln Ser Leu Leu Lys Thr
20 25 30

Asn Gly Asn Thr Tyr Leu His Trp Tyr Leu Gln Lys Pro Gly Gln Ser
35 40 45

Pro Gln Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Ser Gln Ser
85 90 95

Thr His Phe Pro Phe Thr Phe Gly Gln Gly Thr Lys Leu Glu Ile Lys
100 105 110

<210> SEQ ID NO 169
<211> LENGTH: 112
<212> TYPE: PRT
<213> ORGANISM: Artificial
<220> FEATURE:
<223> OTHER INFORMATION: humanized antibody variant

<400> SEQUENCE: 169

Asp Val Val Met Thr Gln Thr Pro Leu Ser Leu Pro Val Thr Pro Gly
1 5 10 15

Glu Pro Ala Ser Ile Ser Cys Arg Ser Ser Gln Ser Leu Leu Lys Thr
20 25 30

Asn Gly Asn Thr Tyr Leu His Trp Tyr Leu Gln Lys Pro Gly Gln Ser
35 40 45

Pro Lys Leu Leu Ile Phe Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Phe Cys Ser Gln Ser
85 90 95

Thr His Phe Pro Phe Thr Phe Gly Gln Gly Thr Lys Leu Glu Ile Lys
100 105 110

<210> SEQ ID NO 170
<211> LENGTH: 122
<212> TYPE: PRT
<213> ORGANISM: Artificial
<220> FEATURE:
<223> OTHER INFORMATION: humanized antibody variant

<400> SEQUENCE: 170

```
Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Gly Phe Ile Asn Tyr
            20                  25                  30

Leu Ile Glu Trp Ile Lys Gln Arg Pro Gly Gln Gly Leu Glu Trp Ile
        35                  40                  45

Gly Leu Ile Asn Pro Gly Ser Asp Tyr Thr Asn Tyr Asn Glu Asn Phe
    50                  55                  60

Lys Gly Lys Ala Thr Leu Thr Ala Asp Lys Ser Ser Ser Thr Ala Tyr
65                  70                  75                  80

Met His Leu Ser Ser Leu Thr Ser Glu Asp Ser Ala Val Tyr Phe Cys
                85                  90                  95

Ala Arg Arg Phe Gly Tyr Tyr Gly Ser Gly Asn Tyr Phe Asp Tyr Trp
            100                 105                 110

Gly Gln Gly Thr Thr Leu Thr Val Ser Ser
        115                 120
```

<210> SEQ ID NO 171
<211> LENGTH: 122
<212> TYPE: PRT
<213> ORGANISM: Artificial
<220> FEATURE:
<223> OTHER INFORMATION: humanized antibody variant

<400> SEQUENCE: 171

```
Glu Val Gln Leu Val Gln Ser Gly Ala Glu Val Lys Lys Pro Gly Glu
1               5                   10                  15

Ser Leu Lys Ile Ser Cys Gln Ser Phe Gly Tyr Ile Phe Ile Asn Tyr
            20                  25                  30

Leu Ile Glu Trp Val Arg Gln Met Pro Gly Gln Gly Leu Glu Trp Met
        35                  40                  45

Gly Leu Ile Asn Pro Gly Ser Asp Tyr Thr Asn Tyr Asn Glu Asn Phe
    50                  55                  60

Lys Gly Gln Val Thr Ile Ser Ala Asp Lys Ser Ser Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Arg Phe Gly Tyr Tyr Gly Ser Gly Asn Tyr Phe Asp Tyr Trp
            100                 105                 110

Gly Gln Gly Thr Met Val Thr Val Ser Ser
        115                 120
```

<210> SEQ ID NO 172
<211> LENGTH: 122
<212> TYPE: PRT
<213> ORGANISM: Artificial
<220> FEATURE:
<223> OTHER INFORMATION: humanized antibody variant

<400> SEQUENCE: 172

```
Glu Val Gln Leu Val Gln Ser Gly Ala Glu Val Lys Lys Pro Gly Glu
1               5                   10                  15
```

```
Ser Leu Lys Ile Ser Cys Gln Ala Phe Gly Tyr Gly Phe Ile Asn Tyr
            20                  25                  30

Leu Ile Glu Trp Ile Arg Gln Met Pro Gly Gln Gly Leu Glu Trp Ile
        35                  40                  45

Gly Leu Ile Asn Pro Gly Ser Asp Tyr Thr Asn Tyr Asn Glu Asn Phe
    50                  55                  60

Lys Gly Gln Ala Thr Leu Ser Ala Asp Lys Ser Ser Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Arg Phe Gly Tyr Tyr Gly Ser Gly Asn Tyr Phe Asp Tyr Trp
            100                 105                 110

Gly Gln Gly Thr Met Val Thr Val Ser Ser
        115                 120


<210> SEQ ID NO 173
<211> LENGTH: 122
<212> TYPE: PRT
<213> ORGANISM: Artificial
<220> FEATURE:
<223> OTHER INFORMATION: humanized antibody variant

<400> SEQUENCE: 173

Glu Val Gln Leu Val Gln Ser Gly Ala Glu Val Lys Lys Pro Gly Glu
1               5                   10                  15

Ser Leu Lys Ile Ser Cys Gln Ser Phe Gly Tyr Gly Phe Ile Asn Tyr
            20                  25                  30

Leu Ile Glu Trp Ile Arg Gln Met Pro Gly Gln Gly Leu Glu Trp Ile
        35                  40                  45

Gly Leu Ile Asn Pro Gly Ser Asp Tyr Thr Asn Tyr Asn Glu Asn Phe
    50                  55                  60

Lys Gly Gln Ala Thr Leu Ser Ala Asp Lys Ser Ser Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Arg Phe Gly Tyr Tyr Gly Ser Gly Asn Tyr Phe Asp Tyr Trp
            100                 105                 110

Gly Gln Gly Thr Met Val Thr Val Ser Ser
        115                 120


<210> SEQ ID NO 174
<211> LENGTH: 122
<212> TYPE: PRT
<213> ORGANISM: Artificial
<220> FEATURE:
<223> OTHER INFORMATION: humanized antibody variant

<400> SEQUENCE: 174

Glu Val Gln Leu Val Gln Ser Gly Ala Glu Val Lys Lys Pro Gly Glu
1               5                   10                  15

Ser Leu Lys Ile Ser Cys Gln Ala Phe Gly Tyr Ile Phe Ile Asn Tyr
            20                  25                  30

Leu Ile Glu Trp Ile Arg Gln Met Pro Gly Gln Gly Leu Glu Trp Ile
        35                  40                  45

Gly Leu Ile Asn Pro Gly Ser Asp Tyr Thr Asn Tyr Asn Glu Asn Phe
    50                  55                  60

Lys Gly Gln Ala Thr Leu Ser Ala Asp Lys Ser Ser Ser Thr Ala Tyr
65                  70                  75                  80
```

Leu Gln Trp Ser Ser Leu Lys Ala Ser Asp Thr Ala Met Tyr Phe Cys
85 90 95

Ala Arg Arg Phe Gly Tyr Tyr Gly Ser Gly Asn Tyr Phe Asp Tyr Trp
100 105 110

Gly Gln Gly Thr Met Val Thr Val Ser Ser
115 120

<210> SEQ ID NO 175
<211> LENGTH: 122
<212> TYPE: PRT
<213> ORGANISM: Artificial
<220> FEATURE:
<223> OTHER INFORMATION: humanized antibody variant

<400> SEQUENCE: 175

Glu Val Gln Leu Val Gln Ser Gly Ala Glu Val Lys Lys Pro Gly Glu
1 5 10 15

Ser Leu Lys Ile Ser Cys Gln Ala Phe Gly Tyr Gly Phe Ile Asn Tyr
20 25 30

Leu Ile Glu Trp Val Arg Gln Met Pro Gly Gln Gly Leu Glu Trp Ile
35 40 45

Gly Leu Ile Asn Pro Gly Ser Asp Tyr Thr Asn Tyr Asn Glu Asn Phe
50 55 60

Lys Gly Gln Ala Thr Leu Ser Ala Asp Lys Ser Ser Ser Thr Ala Tyr
65 70 75 80

Leu Gln Trp Ser Ser Leu Lys Ala Ser Asp Thr Ala Met Tyr Phe Cys
85 90 95

Ala Arg Arg Phe Gly Tyr Tyr Gly Ser Gly Asn Tyr Phe Asp Tyr Trp
100 105 110

Gly Gln Gly Thr Met Val Thr Val Ser Ser
115 120

<210> SEQ ID NO 176
<211> LENGTH: 122
<212> TYPE: PRT
<213> ORGANISM: Artificial
<220> FEATURE:
<223> OTHER INFORMATION: humanized antibody variant

<400> SEQUENCE: 176

Glu Val Gln Leu Val Gln Ser Gly Ala Glu Val Lys Lys Pro Gly Glu
1 5 10 15

Ser Leu Lys Ile Ser Cys Gln Ala Phe Gly Tyr Gly Phe Ile Asn Tyr
20 25 30

Leu Ile Glu Trp Ile Arg Gln Met Pro Gly Gln Gly Leu Glu Trp Met
35 40 45

Gly Leu Ile Asn Pro Gly Ser Asp Tyr Thr Asn Tyr Asn Glu Asn Phe
50 55 60

Lys Gly Gln Ala Thr Leu Ser Ala Asp Lys Ser Ser Ser Thr Ala Tyr
65 70 75 80

Leu Gln Trp Ser Ser Leu Lys Ala Ser Asp Thr Ala Met Tyr Phe Cys
85 90 95

Ala Arg Arg Phe Gly Tyr Tyr Gly Ser Gly Asn Tyr Phe Asp Tyr Trp
100 105 110

Gly Gln Gly Thr Met Val Thr Val Ser Ser
115 120

<210> SEQ ID NO 177

<211> LENGTH: 122
<212> TYPE: PRT
<213> ORGANISM: Artificial
<220> FEATURE:
<223> OTHER INFORMATION: humanized antibody variant

<400> SEQUENCE: 177

Glu Val Gln Leu Val Gln Ser Gly Ala Glu Val Lys Lys Pro Gly Glu
1               5                   10                  15

Ser Leu Lys Ile Ser Cys Gln Ala Phe Gly Tyr Gly Phe Ile Asn Tyr
            20                  25                  30

Leu Ile Glu Trp Ile Arg Gln Met Pro Gly Gln Gly Leu Glu Trp Ile
        35                  40                  45

Gly Leu Ile Asn Pro Gly Ser Asp Tyr Thr Asn Tyr Asn Glu Asn Phe
    50                  55                  60

Lys Gly Gln Val Thr Leu Ser Ala Asp Lys Ser Ser Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Arg Phe Gly Tyr Tyr Gly Ser Gly Asn Tyr Phe Asp Tyr Trp
            100                 105                 110

Gly Gln Gly Thr Met Val Thr Val Ser Ser
        115                 120

<210> SEQ ID NO 178
<211> LENGTH: 122
<212> TYPE: PRT
<213> ORGANISM: Artificial
<220> FEATURE:
<223> OTHER INFORMATION: humanized antibody variant

<400> SEQUENCE: 178

Glu Val Gln Leu Val Gln Ser Gly Ala Glu Val Lys Lys Pro Gly Glu
1               5                   10                  15

Ser Leu Lys Ile Ser Cys Gln Ala Phe Gly Tyr Gly Phe Ile Asn Tyr
            20                  25                  30

Leu Ile Glu Trp Ile Arg Gln Met Pro Gly Gln Gly Leu Glu Trp Ile
        35                  40                  45

Gly Leu Ile Asn Pro Gly Ser Asp Tyr Thr Asn Tyr Asn Glu Asn Phe
    50                  55                  60

Lys Gly Gln Ala Thr Ile Ser Ala Asp Lys Ser Ser Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Arg Phe Gly Tyr Tyr Gly Ser Gly Asn Tyr Phe Asp Tyr Trp
            100                 105                 110

Gly Gln Gly Thr Met Val Thr Val Ser Ser
        115                 120

<210> SEQ ID NO 179
<211> LENGTH: 122
<212> TYPE: PRT
<213> ORGANISM: Artificial
<220> FEATURE:
<223> OTHER INFORMATION: humanized antibody variant

<400> SEQUENCE: 179

Glu Val Gln Leu Val Gln Ser Gly Ala Glu Val Lys Lys Pro Gly Glu
1               5                   10                  15

Ser Leu Lys Ile Ser Cys Gln Ala Phe Gly Tyr Gly Phe Ile Asn Tyr

```
            20                  25                  30

Leu Ile Glu Trp Val Arg Gln Met Pro Gly Gln Gly Leu Glu Trp Ile
        35                  40                  45

Gly Leu Ile Asn Pro Gly Ser Asp Tyr Thr Asn Tyr Asn Glu Asn Phe
    50                  55                  60

Lys Gly Gln Val Thr Ile Ser Ala Asp Lys Ser Ser Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Arg Phe Gly Tyr Tyr Gly Ser Gly Asn Tyr Phe Asp Tyr Trp
            100                 105                 110

Gly Gln Gly Thr Met Val Thr Val Ser Ser
        115                 120


<210> SEQ ID NO 180
<211> LENGTH: 122
<212> TYPE: PRT
<213> ORGANISM: Artificial
<220> FEATURE:
<223> OTHER INFORMATION: humanized antibody variant

<400> SEQUENCE: 180

Glu Val Gln Leu Val Gln Ser Gly Ala Glu Val Lys Lys Pro Gly Glu
1               5                   10                  15

Ser Leu Lys Ile Ser Cys Gln Ser Phe Gly Tyr Gly Phe Ile Asn Tyr
            20                  25                  30

Leu Ile Glu Trp Val Arg Gln Met Pro Gly Gln Gly Leu Glu Trp Ile
        35                  40                  45

Gly Leu Ile Asn Pro Gly Ser Asp Tyr Thr Asn Tyr Asn Glu Asn Phe
    50                  55                  60

Lys Gly Gln Ala Thr Leu Ser Ala Asp Lys Ser Ser Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Arg Phe Gly Tyr Tyr Gly Ser Gly Asn Tyr Phe Asp Tyr Trp
            100                 105                 110

Gly Gln Gly Thr Met Val Thr Val Ser Ser
        115                 120


<210> SEQ ID NO 181
<211> LENGTH: 122
<212> TYPE: PRT
<213> ORGANISM: Artificial
<220> FEATURE:
<223> OTHER INFORMATION: humanized antibody variant

<400> SEQUENCE: 181

Glu Val Gln Leu Val Gln Ser Gly Ala Glu Val Lys Lys Pro Gly Glu
1               5                   10                  15

Ser Leu Lys Ile Ser Cys Gln Ala Phe Gly Tyr Gly Phe Ile Asn Tyr
            20                  25                  30

Leu Ile Glu Trp Ile Arg Gln Met Pro Gly Gln Gly Leu Glu Trp Ile
        35                  40                  45

Gly Leu Ile Asn Pro Gly Ser Asp Tyr Thr Asn Tyr Asn Glu Asn Phe
    50                  55                  60

Lys Gly Gln Ala Thr Leu Ser Ala Asp Lys Ser Ser Ser Thr Ala Tyr
65                  70                  75                  80

Leu Gln Trp Ser Ser Leu Lys Ala Ser Asp Thr Ala Met Tyr Phe Cys
```

```
                85                  90                  95

Ala Arg Arg Phe Gly Tyr Tyr Gly Ser Gly Asn Tyr Phe Asp Tyr Trp
            100                 105                 110

Gly Gln Gly Thr Met Val Thr Val Ser Ser
        115                 120


<210> SEQ ID NO 182
<211> LENGTH: 122
<212> TYPE: PRT
<213> ORGANISM: Artificial
<220> FEATURE:
<223> OTHER INFORMATION: humanized antibody variant

<400> SEQUENCE: 182

Glu Val Gln Leu Val Gln Ser Gly Ala Glu Val Lys Lys Pro Gly Glu
1               5                   10                  15

Ser Leu Lys Ile Ser Cys Gln Ala Phe Gly Tyr Gly Phe Ile Asn Tyr
            20                  25                  30

Leu Ile Glu Trp Ile Arg Gln Met Pro Gly Gln Gly Leu Glu Trp Ile
        35                  40                  45

Gly Leu Ile Asn Pro Gly Ser Asp Tyr Thr Asn Tyr Asn Glu Asn Phe
    50                  55                  60

Lys Gly Gln Ala Thr Leu Ser Ala Asp Lys Ser Ser Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Arg Phe Gly Tyr Tyr Gly Ser Gly Asn Tyr Phe Asp Tyr Trp
            100                 105                 110

Gly Gln Gly Thr Met Val Thr Val Ser Ser
        115                 120


<210> SEQ ID NO 183
<211> LENGTH: 122
<212> TYPE: PRT
<213> ORGANISM: Artificial
<220> FEATURE:
<223> OTHER INFORMATION: humanized antibody variant

<400> SEQUENCE: 183

Glu Val Gln Leu Val Gln Ser Gly Ala Glu Val Lys Lys Pro Gly Glu
1               5                   10                  15

Ser Leu Lys Ile Ser Cys Gln Ala Phe Gly Tyr Gly Phe Ile Asn Tyr
            20                  25                  30

Leu Ile Glu Trp Ile Arg Gln Met Pro Gly Gln Gly Leu Glu Trp Ile
        35                  40                  45

Gly Leu Ile Asn Pro Gly Ser Asp Tyr Thr Asn Tyr Asn Glu Asn Phe
    50                  55                  60

Lys Gly Gln Ala Thr Leu Ser Ala Asp Lys Ser Ser Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Arg Phe Gly Tyr Tyr Gly Ser Gly Asn Tyr Phe Asp Tyr Trp
            100                 105                 110

Gly Gln Gly Thr Met Val Thr Val Ser Ser
        115                 120


<210> SEQ ID NO 184
<211> LENGTH: 122
<212> TYPE: PRT
```

<213> ORGANISM: Artificial
<220> FEATURE:
<223> OTHER INFORMATION: humanized antibody variant

<400> SEQUENCE: 184

Glu Val Gln Leu Val Gln Ser Gly Ala Glu Val Lys Lys Pro Gly Glu
1 5 10 15

Ser Leu Lys Ile Ser Cys Gln Ala Phe Gly Tyr Gly Phe Ile Asn Tyr
20 25 30

Leu Ile Glu Trp Ile Arg Gln Met Pro Gly Gln Gly Leu Glu Trp Ile
35 40 45

Gly Ala Ile Asn Pro Gly Ser Asp Tyr Thr Asn Tyr Asn Glu Asn Phe
50 55 60

Lys Gly Gln Ala Thr Leu Ser Ala Asp Lys Ser Ser Ser Thr Ala Tyr
65 70 75 80

Leu Gln Trp Ser Ser Leu Lys Ala Ser Asp Thr Ala Met Tyr Phe Cys
85 90 95

Ala Arg Arg Phe Gly Tyr Tyr Gly Ser Gly Asn Tyr Phe Asp Tyr Trp
100 105 110

Gly Gln Gly Thr Met Val Thr Val Ser Ser
115 120

<210> SEQ ID NO 185
<211> LENGTH: 122
<212> TYPE: PRT
<213> ORGANISM: Artificial
<220> FEATURE:
<223> OTHER INFORMATION: humanized antibody variant

<400> SEQUENCE: 185

Glu Val Gln Leu Val Gln Ser Gly Ala Glu Val Lys Lys Pro Gly Glu
1 5 10 15

Ser Leu Lys Ile Ser Cys Gln Ala Phe Gly Tyr Gly Phe Ile Asn Tyr
20 25 30

Leu Ile Glu Trp Ile Arg Gln Met Pro Gly Gln Gly Leu Glu Trp Ile
35 40 45

Gly Leu Ile Tyr Pro Asp Ser Gly Tyr Ile Asn Tyr Asn Glu Asn Phe
50 55 60

Lys Gly Gln Ala Thr Leu Ser Ala Asp Lys Ser Ser Ser Thr Ala Tyr
65 70 75 80

Leu Gln Trp Ser Ser Leu Lys Ala Ser Asp Thr Ala Met Tyr Phe Cys
85 90 95

Ala Arg Arg Phe Ala Tyr Tyr Gly Ser Gly Tyr Tyr Phe Asp Tyr Trp
100 105 110

Gly Gln Gly Thr Met Val Thr Val Ser Ser
115 120

<210> SEQ ID NO 186
<211> LENGTH: 122
<212> TYPE: PRT
<213> ORGANISM: Artificial
<220> FEATURE:
<223> OTHER INFORMATION: humanized antibody variant

<400> SEQUENCE: 186

Glu Val Gln Leu Val Gln Ser Gly Ala Glu Val Lys Lys Pro Gly Glu
1 5 10 15

Ser Leu Lys Ile Ser Cys Gln Ala Phe Gly Tyr Ala Phe Thr Asn Tyr
20 25 30

```
Leu Ile Glu Trp Val Arg Gln Met Pro Gly Gln Gly Leu Glu Trp Met
        35                  40                  45

Gly Leu Ile Tyr Pro Asp Ser Gly Tyr Ile Asn Tyr Asn Glu Asn Phe
    50                  55                  60

Lys Gly Gln Val Thr Ile Ser Ala Asp Lys Ser Ser Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Arg Phe Ala Tyr Tyr Gly Ser Gly Tyr Tyr Phe Asp Tyr Trp
            100                 105                 110

Gly Gln Gly Thr Met Val Thr Val Ser Ser
        115                 120


<210> SEQ ID NO 187
<211> LENGTH: 122
<212> TYPE: PRT
<213> ORGANISM: Artificial
<220> FEATURE:
<223> OTHER INFORMATION: humanized antibody variant

<400> SEQUENCE: 187

Glu Val Gln Leu Val Gln Ser Gly Ala Glu Val Lys Lys Pro Gly Glu
1               5                   10                  15

Ser Leu Lys Ile Ser Cys Gln Ala Phe Gly Tyr Ala Phe Thr Asn Tyr
            20                  25                  30

Leu Ile Glu Trp Val Arg Gln Met Pro Gly Gln Gly Leu Glu Trp Ile
        35                  40                  45

Gly Leu Ile Tyr Pro Asp Ser Gly Tyr Ile Asn Tyr Asn Glu Asn Phe
    50                  55                  60

Lys Gly Gln Ala Thr Leu Ser Ala Asp Lys Ser Ser Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Arg Phe Ala Tyr Tyr Gly Ser Gly Tyr Tyr Phe Asp Tyr Trp
            100                 105                 110

Gly Gln Gly Thr Met Val Thr Val Ser Ser
        115                 120


<210> SEQ ID NO 188
<211> LENGTH: 122
<212> TYPE: PRT
<213> ORGANISM: Artificial
<220> FEATURE:
<223> OTHER INFORMATION: humanized antibody variant

<400> SEQUENCE: 188

Glu Val Gln Leu Val Gln Ser Gly Ala Glu Val Lys Lys Pro Gly Glu
1               5                   10                  15

Ser Leu Lys Ile Ser Cys Gln Ala Phe Gly Asp Ala Phe Thr Asn Tyr
            20                  25                  30

Leu Ile Glu Trp Val Arg Gln Met Pro Gly Gln Gly Leu Glu Trp Met
        35                  40                  45

Gly Leu Ile Tyr Pro Asp Ser Gly Tyr Ile Asn Tyr Asn Glu Asn Phe
    50                  55                  60

Lys Gly Gln Val Thr Ile Ser Ala Asp Arg Ser Ser Ser Thr Ala Tyr
65                  70                  75                  80

Leu Gln Trp Ser Ser Leu Lys Ala Ser Asp Thr Ala Met Tyr Phe Cys
                85                  90                  95
```

-continued

```
Ala Arg Arg Phe Ala Tyr Tyr Gly Ser Gly Tyr Tyr Phe Asp Tyr Trp
            100                 105                 110

Gly Gln Gly Thr Met Val Thr Val Ser Ser
        115                 120


<210> SEQ ID NO 189
<211> LENGTH: 122
<212> TYPE: PRT
<213> ORGANISM: Artificial
<220> FEATURE:
<223> OTHER INFORMATION: humanized antibody variant

<400> SEQUENCE: 189

Glu Val Gln Leu Val Gln Ser Gly Ala Glu Val Lys Lys Pro Gly Glu
1               5                   10                  15

Ser Leu Lys Ile Ser Cys Gln Ala Phe Gly Asp Ala Phe Thr Asn Tyr
            20                  25                  30

Leu Ile Glu Trp Val Arg Gln Met Pro Gly Gln Gly Leu Glu Trp Ile
        35                  40                  45

Gly Leu Ile Tyr Pro Asp Ser Gly Tyr Ile Asn Tyr Asn Glu Asn Phe
    50                  55                  60

Lys Gly Gln Ala Thr Leu Ser Ala Asp Arg Ser Ser Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Arg Phe Ala Tyr Tyr Gly Ser Gly Tyr Tyr Phe Asp Tyr Trp
            100                 105                 110

Gly Gln Gly Thr Met Val Thr Val Ser Ser
        115                 120
```